(12) United States Patent
Anderson et al.

(10) Patent No.: US 11,845,950 B2
(45) Date of Patent: *Dec. 19, 2023

(54) CIRCULAR RNA FOR TRANSLATION IN EUKARYOTIC CELLS

(71) Applicant: Massachusetts Institute of Technology, Cambridge, MA (US)

(72) Inventors: Daniel G. Anderson, Framingham, MA (US); Robert Alexander Wesselhoeft, Boston, MA (US); Piotr S. Kowalski, Cork (IE)

(73) Assignee: MASSACHUSETTS INSTITUTE OF TECHNOLOGY, Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/894,141

(22) Filed: Aug. 23, 2022

(65) Prior Publication Data

US 2023/0050306 A1 Feb. 16, 2023

Related U.S. Application Data

(60) Continuation of application No. 17/492,512, filed on Oct. 1, 2021, now Pat. No. 11,447,796, which is a division of application No. 17/191,697, filed on Mar. 3, 2021, now Pat. No. 11,203,767, which is a continuation of application No. 16/432,177, filed on Jun. 5, 2019.

(60) Provisional application No. 62/851,548, filed on May 22, 2019, provisional application No. 62/791,028, filed on Jan. 10, 2019, provisional application No. 62/681,617, filed on Jun. 6, 2018.

(51) Int. Cl.
| | |
|---|---|
| C12N 15/79 | (2006.01) |
| C07H 21/02 | (2006.01) |
| C07H 21/04 | (2006.01) |
| C12N 15/85 | (2006.01) |
| C07K 16/28 | (2006.01) |
| C12N 15/11 | (2006.01) |

(52) U.S. Cl.
CPC .......... *C12N 15/85* (2013.01); *C07K 16/2803* (2013.01); *C12N 15/11* (2013.01); *C07K 2317/31* (2013.01); *C12N 2015/859* (2013.01); *C12N 2015/8518* (2013.01); *C12N 2800/107* (2013.01); *C12N 2800/202* (2013.01); *C12N 2800/70* (2013.01); *C12N 2840/203* (2013.01); *C12N 2840/55* (2013.01); *C12N 2840/60* (2013.01); *C12N 2999/007* (2013.01)

(58) Field of Classification Search
CPC ........ C12N 15/79; C12N 15/85; C12N 15/86; C12N 15/11; C12N 2015/8518; C12N 2840/203; C07H 21/02; C07H 21/04

See application file for complete search history.

(56) References Cited

U.S. PATENT DOCUMENTS

| | | |
|---|---|---|
| 4,323,689 A | 4/1982 | Vogel et al. |
| 4,661,450 A | 4/1987 | Kempe et al. |
| 5,434,261 A | 7/1995 | Schoen et al. |
| 5,580,859 A | 12/1996 | Felgner et al. |
| 5,591,737 A | 1/1997 | Doherty et al. |
| 5,625,047 A | 4/1997 | Been et al. |
| 5,629,304 A | 5/1997 | Murakata et al. |
| 5,656,606 A | 8/1997 | Nargund et al. |
| 5,672,596 A | 9/1997 | Wyvratt et al. |
| 5,712,128 A | 1/1998 | Been et al. |
| 5,747,485 A | 5/1998 | Doherty et al. |
| 5,766,903 A | 6/1998 | Sarnow et al. |
| 5,773,244 A | 6/1998 | Ares et al. |
| 5,972,964 A | 10/1999 | Perregaard |
| 6,043,026 A | 3/2000 | Patchett et al. |
| 6,210,931 B1 | 4/2001 | Feldstein et al. |
| 6,211,174 B1 | 4/2001 | Devita et al. |
| 6,368,802 B1 | 4/2002 | Kool |

(Continued)

FOREIGN PATENT DOCUMENTS

| | | |
|---|---|---|
| CN | 101016264 A | 8/2007 |
| CN | 105176981 A | 12/2015 |

(Continued)

OTHER PUBLICATIONS

Zhang et al., Jan. 18, 2018, Oncogene, 37: 1805-1814.*
Badelt, S. et al., "Computational Design of a Circular RNA with Prionlike Behavior," Artificial Life, vol. 22; 172-184 (2016).
Barrett, S.P. and Salzman, J., "Circular RNAs: analysis, expression and potential functions," Development, vol. 143; No. 11; 1838-1847 (2016).

(Continued)

*Primary Examiner* — Shin Lin Chen
(74) *Attorney, Agent, or Firm* — Hamilton, Brook, Smith & Reynolds, P.C.

(57) ABSTRACT

Methods and constructs for engineering circular RNA are disclosed. In some embodiments, the methods and constructs comprise a vector for making circular RNA, the vector comprising the following elements operably connected to each other and arranged in the following sequence: a.) a 5' homology arm, b.) a 3' group I intron fragment containing a 3' splice site dinucleotide, c.) optionally, a 5' spacer sequence, d.) a protein coding or noncoding region, e.) optionally, a 3' spacer sequence, f) a 5' Group I intron fragment containing a 5' splice site dinucleotide, and g.) a 3' homology arm, the vector allowing production of a circular RNA that is translatable or biologically active inside eukaryotic cells. Methods for purifying the circular RNA produced by the vector and the use of nucleoside modifications in circular RNA produced by the vector are also disclosed.

19 Claims, 58 Drawing Sheets
(44 of 58 Drawing Sheet(s) Filed in Color)
Specification includes a Sequence Listing.

(56) References Cited

U.S. PATENT DOCUMENTS

| | | |
|---|---|---|
| 6,576,628 B1 | 6/2003 | Grams et al. |
| 6,620,597 B1 | 9/2003 | Chen et al. |
| 8,829,170 B2 | 9/2014 | Dale et al. |
| 11,203,767 B2 | 12/2021 | Anderson et al. |
| 11,352,640 B2 | 6/2022 | Anderson et al. |
| 11,352,641 B2 | 6/2022 | Anderson et al. |
| 11,447,796 B2 | 9/2022 | Anderson et al. |
| 11,603,396 B2 | 3/2023 | Wesselhoeft et al. |
| 11,679,120 B2 | 6/2023 | Horhota et al. |
| 2006/0199851 A1 | 9/2006 | Kempf et al. |
| 2010/0137407 A1 | 6/2010 | Abe et al. |
| 2011/0019782 A1 | 1/2011 | Kobayashi et al. |
| 2015/0079630 A1 | 3/2015 | Hiroshi et al. |
| 2016/0083747 A1 | 3/2016 | Kruse |
| 2016/0194368 A1 | 7/2016 | Hoge et al. |
| 2018/0010175 A1 | 1/2018 | Cheng |
| 2018/0311343 A1 | 11/2018 | Huang et al. |
| 2018/0326045 A1 | 11/2018 | Ciaramella et al. |
| 2019/0290694 A1 | 9/2019 | Gautron et al. |
| 2020/0040370 A1 | 2/2020 | Eber et al. |
| 2020/0080106 A1 | 3/2020 | Anderson et al. |
| 2021/0085719 A1 | 3/2021 | Jensen |
| 2021/0198688 A1 | 7/2021 | Anderson et al. |
| 2021/0363540 A1 | 11/2021 | Anderson et al. |
| 2021/0371494 A1 | 12/2021 | Wesselhoeft et al. |
| 2021/0403944 A1 | 12/2021 | Anderson et al. |
| 2022/0025395 A1 | 1/2022 | Anderson et al. |
| 2022/0106259 A1 | 4/2022 | Benenato et al. |
| 2022/0177540 A1 | 6/2022 | Anderson et al. |
| 2022/0323480 A1 | 10/2022 | Goodman et al. |
| 2023/0058784 A1 | 2/2023 | Goodman et al. |
| 2023/0062665 A1 | 3/2023 | Goodman et al. |

FOREIGN PATENT DOCUMENTS

| | | |
|---|---|---|
| CN | 106801050 A | 6/2017 |
| EP | 2 819 377 A1 | 12/2014 |
| EP | 3 630 966 A1 | 4/2020 |
| EP | 3 819 377 A1 | 5/2021 |
| GB | 2308064 A | 6/1997 |
| JP | 2016-521133 A | 7/2016 |
| JP | 2017-043556 A | 3/2017 |
| JP | 62-84181 B2 | 2/2018 |
| KR | 2011/0095439 A | 8/2011 |
| WO | WO 1995/011029 A1 | 4/1995 |
| WO | WO 1995/024207 A1 | 9/1995 |
| WO | WO 2005/044201 A2 | 5/2005 |
| WO | WO 2005/079803 A1 | 9/2005 |
| WO | WO 2006/138380 A2 | 12/2006 |
| WO | WO 2007/044627 A2 | 4/2007 |
| WO | WO 2009/035541 A1 | 3/2009 |
| WO | WO 2010/084371 A1 | 7/2010 |
| WO | WO 2010/138652 A1 | 12/2010 |
| WO | WO 2010/138659 A1 | 12/2010 |
| WO | WO 2010/138685 A1 | 12/2010 |
| WO | WO 2010/138695 A1 | 12/2010 |
| WO | WO 2010/138706 A1 | 12/2010 |
| WO | WO 2010/138758 A1 | 12/2010 |
| WO | WO 2013/076509 A1 | 5/2013 |
| WO | WO 2013/118878 A1 | 8/2013 |
| WO | WO 2014/144871 A1 | 9/2014 |
| WO | 2014/186334 A1 | 11/2014 |
| WO | WO 2014/186334 A1 | 11/2014 |
| WO | WO 2014/193857 A1 | 12/2014 |
| WO | WO 2015/034925 A1 | 3/2015 |
| WO | WO 2015/095340 A1 | 6/2015 |
| WO | WO 2016/020373 A1 | 2/2016 |
| WO | WO 2016/197121 A1 | 12/2016 |
| WO | WO 2017/046203 A1 | 3/2017 |
| WO | WO 2017/049245 A2 | 3/2017 |
| WO | WO 2017/055487 A2 | 4/2017 |
| WO | WO 2017/059357 A1 | 4/2017 |
| WO | WO 2017/118734 A1 | 7/2017 |
| WO | WO 2017/172698 A1 * | 10/2017 |
| WO | WO 2017/201332 A1 | 11/2017 |
| WO | WO 2017/201333 A1 | 11/2017 |
| WO | WO 2017/201340 A2 | 11/2017 |
| WO | WO 2017/201342 A1 | 11/2017 |
| WO | WO 2017/201346 A1 | 11/2017 |
| WO | WO 2017/201348 A1 | 11/2017 |
| WO | WO 2017/201349 A1 | 11/2017 |
| WO | WO 2017/201350 A1 | 11/2017 |
| WO | WO 2017/222911 A1 * | 12/2017 |
| WO | WO 2018/144775 A1 | 8/2018 |
| WO | WO 2018/157009 A1 | 8/2018 |
| WO | WO 2018/170260 A1 | 9/2018 |
| WO | WO 2018/170306 A1 | 9/2018 |
| WO | WO 2018/191722 A1 | 10/2018 |
| WO | WO 2018/237372 A1 | 12/2018 |
| WO | WO 2019/118919 A1 | 6/2019 |
| WO | WO 2019/213308 A1 | 11/2019 |
| WO | WO 2019/222275 A2 | 11/2019 |
| WO | WO 2019/236673 A1 | 12/2019 |
| WO | WO 2020/010242 A1 | 1/2020 |
| WO | WO 2020/035070 A1 | 2/2020 |
| WO | WO 2020/061367 A1 | 3/2020 |
| WO | WO 2020/198403 A2 | 10/2020 |
| WO | WO 2020/237227 A1 | 11/2020 |
| WO | WO 2020/252436 A1 | 12/2020 |
| WO | WO 2021/041541 A1 | 3/2021 |
| WO | WO 2021/055849 A1 | 3/2021 |
| WO | WO 2021/113777 A2 | 6/2021 |

OTHER PUBLICATIONS

Bohanjen, P. R. et al., "A small circular TAR RNA decoy specifically inhibits Tat-activated HIV-1 transcription,", Nucleic Acids Res., vol. 24; No. 19; 3733-3738 (1996).

Bohjanen, P. R., et al., "TAR RNA decoys inhibit Tat-activated HIV-1 transcription after preinitiation complex formation", Nucleic Acids Res., vol. 25; 4481-4486 (1997).

Borchardt, E.K. et al., "Inducing circular RNA formation using the CRISPR endoribonuclease Csy4," RNA, vol. 23; No. 5; 619-627 (2017).

Branch, A.D. et al., "Unusual properties of two branched RNA's with circular and linear components," Nucleic Acids Research, vol. 13; No. 13; 4889-4903 (1985).

Cech, T.R., "Self-Splicing of Group 1 Introns," Ann. Rev. Biochem., vol. 59; 543-568 (1990).

Chen, C. and Sarnow, P., "Initiation of protein synthesis by the eukaryotic translational apparatus on circular RNAs," America Association for the Advancement of Science, Abstract 268.5209; p. 415 (1995).

Chen, Y.G. et al., "Sensing Self and Foreign Circular RNAs by Intron Identity," Molecular Cell, vol. 67; 228-238 (2017).

Chen, G. et al., "Promising diagnostic and therapeutic circRNAs for skeletal and chondral disorders," International Journal of Biological Sciences, vol. 17; 1428-1439 (2021).

Costello, A. et al., "Reinventing the Wheel: Synthetic Circular RNAs for Mammalian Cell Engineering," Trends in Biotechnology, vol. 38; No. 2; 217-230 (2020).

Dahlman, J.E., et al., "Barcoded nanoparticles for high throughput in vivo discovery of targeted therapeutics," PNAS, vol. 114; No. 8; 2060-2065 (2017).

Devaux, Y. et al., "Circular RNAs in heart failure", European Journal of Heart Failure, vol. 19; 701-709 (2017).

Durymanov, M. and Reineke, J., "Non-viral Delivery of Nucleic Acids: Insight Into Mechanisms of Overcoming Intrecellular Barriers," Frontiers in Pharmacology, vol. 9; Article 971; 15 pages (2018).

Fenton et al., "Customizable Lipid Nanoparticle Materials for the Delivery of siRNAs and mRNAs," Angew Chem Int Ed Engl. 57(41):13582-86 (2018).

Foster, et al., "Purification of mRNA Encoding Chimeric Antigen Receptor is Critical for Generation of a Robust T-Cell Response," Hum Gene Ther, vol. 30; No. 2; 168-178 (2019).

Greene, J. et al., "Circular RNAs: Biogenesis, Function and Role in Human Diseases", Frontiers in Molecular Biosciences, vol. 4; Article 38; 11 pages (2017).

(56) References Cited

OTHER PUBLICATIONS

He, J. et al., "Cicular RNAs and cancer", Cancer Letters, vol. 396, 138-144 (2017).
Holdt, L.M. et al., "Circular RNAs as Therapeutic Agents and Targets," Frontiers in Physiology, vol. 9; Article 1262; 16 pages (2018).
Jeck, W.R. and Sharpless, N.E., "Detecting and characterizing circular RNAs," Nat Biotechnol., vol. 32; No. 5; 453-461 (2014).
Kaczmarek, J.C. et al., "Advances in the delivery of RNA therapeutics: from concept to clinical reality," Genome Medicine, vol. 9; No. 1, 16 pages (2017).
Kariko, K. et al., "Incorporation of Pseudouridine Into mRNA Yields Superior Nonimmunogenic Vector With Increased Translational Capacity and Biological Stability," Molecular Therapy, vol. 16; No. 11; 1833-1840 (2008).
Kariko, K. et al., "Generating the optimal mRNA for therapy: HPLC purification eliminates immune activation and improves translation of nucleoside-modified, protein-encoding mRNA", Nucleic Acids Research, vol. 39; No. 21; e142, 10 pages (2011).
Kauffman, K.J. et al., "Efficacy and Immunogenicity of Unmodified and Pseudouridine-Modified mRNA Delivered Systemically with Lipid Nanoparticles in Vivo," Biomaterials, vol. 109; 78-87 (2016).
Kauffman, K.J., "Optimization and analysis of lipid nanoparticles for in vivo mRNA delivery," Ph.D. Thesis, Massachusetts Institute of Technology, Department of Chemical Engineering; 167 pages (2017).
Kauffman, K.J. et al., "Rapid, Single-cell Analysis and Discovery of Vectored mRNA Transfection in Vivo with a loxP-Flanked tdTomato Reporter Mouse," Molecular Therapy: Nucleic Acids, vol. 10; 55-63 (2018).
Kotterman, M.A. and Schaffer, D.V., "Engineering adeno-associated viruses for clinical gene therapy," Nature Reviews, vol. 15; 445-451 (2014).
Legnini, I. et al., "Circ-ZNF609 Is a Circular RNA that Can Be Translated and Functions in Myogenesis," Molecular Cell, vol. 66; No. 1; 22-37 (2017).
Lenzi et al., "Gene Transfer Research: The Evolution of the Clinical Science," NCBI Bookshelf, A Service of the National Library of Medicine, National Institutes of Health, 16 pages (2014).
Li, X. et al., "The Biogenesis, Functions, and Challenges of Circular RNAs," Molecular Cell Review, vol. 71; 428-442 (2018).
Litke, J.L. and Jaffrey, S.R., "Trans ligation of RNAs to generate hybrid circular RNAs using highly efficient autocatalytic transcripts," Methods, 9 pages (2021).
Mao, X. et al., "Biological roles and therapeutic potential of circular RNAs in osteoarthritis," Molecular Therapy Nucleic Acids, vol. 24; 856-867 (2021).
Meganck, R.M. et al., "Engineering highly efficient backsplicing and translation of synthetic circRNAs," Molecular Therapy Nucleic Acids, vol. 23; 821-834 (2021).
Memczak, S. et al., "Circular RNAs and a large class of animal RNAs with regulatory potency," Nature, vol. 495; 333-338 (2013).
Mu, X. et al., "An origin of the immunogenicity of in vitro transcribed RNA," Nucleic Acids Research, vol. 46; No. 10; 5239-5249 (2018).
Nakamoto, K. and Abe, H., "Chemical Synthesis of Circular RNAs with Phosphoramidate Linkages for Rolling-Circle Translation," Current Protcol., vol. 1; e43; 11 pages (2021).
Obi, P. and Chen, Y.G., "The design and synthesis of circular RNAs," Methods, 19 pages (2021).
Ochi, A., et al., Nucleic Acids Symp. Ser. vol. 53, pp. 275-276 (2009).
Pamudurti, N.R. et al., "Translation of CircRNAs," Molecular Cell, vol. 66; No. 1; 9-21 (2017).
Petkovic, S. et al., "RNA circularization strategies in vivo and in vitro," Nucleic Acids Research, vol. 43; No. 4; 2454-2465 (2015).
Puttaraju, M. et al., "Group I permuted intron—exon (PIE) sequences self-splice to produce circular exons," Nucleic Acids Research, vol. 20; No. 20; 5357-5364 (1992).
Puttaraju, M. and Been, M. D., Circular Ribozymes Generated in *Escherichia coli* Using Group I Self-splicing Permuted Intron-Exon Sequences, J. Biol. Chem., vol. 271, pp. 26081-26087 (1996).
Rausch, J.W. et al., "Characterizing and circumventing sequence restrictions for synthesis of circular RNA in vitro," Nucleic Acids Research, vol. 49; No. 6; e35 13 pages (2021).
Sahin, U. et al., "mRNA-based therapeutics—developing a new class of drugs," Nature Reviews, vol. 13; 759-780 (2014).
Shim, G. et al., "Nonviral Delivery Systems for Cancer Gene Therapy: Strategies and Challenges," Current Gene Therapy, vol. 17; 18 pages (2017).
Sullenger, et al., "From the RNA world to the clinic," Science, vol. 352; No. 6292; 1417-1420 (2016).
Umekage, S. and Kikuchi, Y., "In vivo circular RNA production using a constitutive promoter for high-level expression," Journal of Bioscience and Bioengineering, vol. 108; No. 4; 354-356 (2009).
Umekage, U. et al., In Vivo Circular RNA Expression by the Permuted Intron-Exon Method, Innovations in Biotechnology, Chapter 4, 17 pages (2012).
Valdmanis, P.N. and Kay, M.A., "The Expanding Repertoire of Circular RNAs," The American Society of Gene and Cell Therapy, vol. 21; No. 6; 1112-1114 (2013).
Wang, Y. and Wang, Z., "Efficient backsplicing produces translatable circular mRNAs," RNA, vol. 21; No. 2; 172-179 (2014).
Wesselhoeft, R.A. et al., "Engineering circular RNA for potent and stable translation in eukaryotic cells," Nature Communications, vol. 9; No. 1; 10 pages (2018).
Wesselhoeft, R.A. et al., "RNA Circularization Diminished Immunogenicity and Can Extend Translation Duration in Vivo," Molecular Cell, vol. 74; 508-520 (2019).
Wiesinger, et al., "Clinical-Scale Production of CAR-T Cells for the Treatment of Melanoma Patients by mRNA Transfection of a CSPG4-Specific CAR under Full GMP Compliance," Cancers (Basel), vol. 11; No. 8; 1198 (2019).
Xue, et al., "Lipid-based nanocarriers for RNA delivery," Curr Pharm Des, vol. 21; No. 22; 3140-3147 (2015).
Yang, E. et al., "Decay Rates of Human mRNAs: Correlation with Functional Characteristics and Sequence Attributes," Genome Research, vol. 13; 1863-1872 (2003).
Yang, Q. et al., "Circular RNAs: Expression, localization, and therapeutic potentials," Molecular Therapy, vol. 29; No. 5; 1683-1702 (2021).
Zeng et al., "A Circular RNA Binds to and Activates AKT Phosphorylation and Nuclear Localization Reducing Apoptosis and Enhancing Cardiac Repair," Theranostics 7(16):3842-3855 (2017).
International Preliminary Report on Patentability for International Application No. PCT/US2019/035531, entitled: "Circular RNA For Translation In Eukaryotic Cells," dated Dec. 17, 2020 (9 pages).
International Search Report and Written Opinion for International Application No. PCT/US2019/035531, entitled: "Circular RNA For Translation In Eukaryotic Cells," dated Sep. 27, 2019 (17 pages).
Final Office Action for U.S. Appl. No. 17/191,697, dated Sep. 30, 2021.
Non-Final Office Action for U.S. Appl. No. 17/191,697, dated Jun. 18, 2021.
Non-Final Office Action for U.S. Appl. No. 17/374,497, dated Dec. 7, 2021.
Non-Final Office Action for U.S. Appl. No. 17/468,100, dated Dec. 8, 2021.
Non-Final Office Action for U.S. Appl. No. 17/492,512, dated Mar. 1, 2022.
Notice of Allowance for U.S. Appl. No. 17/191,697, dated Nov. 2, 2021.
Unpublished U.S. Appl. No. 17/202,223, entitled: "Circular RNA Compositions and Methods," filed Mar. 15, 2021; Inventors: Brian Goodman, Alexander Wesselhoeft, Allen T. Horhota, Jung-hoon Yang, and Kristen Ott.
Unpublished U.S. Appl. No. 17/374,497, entitled: "Circular RNA for Translation in Eukaryotic Cells," filed Jul. 13, 2021, Inventors: Daniel G. Anderson, Robert Alexander Wesselhoeft, and Piotr S. Kowalski.
Unpublished U.S. Appl. No. 17/384,460, entitled: "Circular RNA Compositions and Methods," filed Jul. 23, 2021; Inventors: Alex-

(56) References Cited

OTHER PUBLICATIONS ander Wesselhoeft, Daniel G. Anderson, Shinichiro Fuse, Brian Goodman, Allen Horhota, and Raffaella Squilloni.
Unpublished U.S. Appl. No. 17/468,100, entitled: "Circular RNA for Translation in Eukaryotic Cells," filed Sep. 7, 2021, Inventors: Daniel G. Anderson, Robert Alexander Wesselhoeft, and Piotr S. Kowalski.
Unpublished U.S. Appl. No. 17/492,512, entitled: "Circular RNA For Translation In Eukaryotic Cells," filed Oct. 1, 2021, Inventors: Daniel G. Anderson, Robert Alexander Wesselhoeft, and Piotr S. Kowalski.
Unpublished U.S. Appl. No. 17/548,247, entitled: "Circular RNA Compositions and Methods," filed Dec. 10, 2021; Inventors: Alexander Wesselhoeft, Daniel G. Anderson, Shinichiro Fuse, Brian Goodman, Allen Horhota, and Raffaella Squilloni.
Notice of Allowance for U.S. Appl. No. 17/374,497, dated Apr. 13, 2022.
Notice of Allowance for U.S. Appl. No. 17/468,100, dated Apr. 8, 2022.
Notice of Allowance for U.S. Appl. No. 17/492,512, dated Apr. 26, 2022.
Benenato, Ciaramella, and Huang. "Structures of Lipids," 2022, 28 pages.
Koos et al. "Influence of structure on antimicrobial activity of some heterocycles. IV. 1-(3-alkylamino-2-hydroxypropyl)-2-methyl-5-nitroimidazoles," Chem Papers. 1994, 48(1):54-57.
Liang et al. "Short intronic repeat sequences facilitate circular RNA production," Genes & Development, 2014, 28:2233-2247.
Liang et al. "The Output of Protein-Coding Genes Shifts to Circular RNAs When the Pre-mRNA Processing Machinery Is Limiting," Molecular Cell, 2017, 68:940-954.
Starke et al. "Exon Circularization Requires Canonical Splice Signals," Cell Reports, 2015, 10:103-111.
STN Registry Database Entry for 1333432-38-4 entered STN Sep. 27, 2011.
STN Registry Database Entry for 1333626-46-2 entered STN Sep. 28, 2011.
STN Registry Database Entry for 156811-31-3 entered STN Aug. 5, 1994.
STN Registry Database Entry for 157493-54-4 entered STN Sep. 7, 1994.
STN Registry Database Entry for 1609534-48-6 entered STN Jun. 4, 2014.
STN Registry Database Entry for 2086785-24-0 entered STN Mar. 17, 2017.
STN Registry Database Entry for 2086785-25-1 entered STN Mar. 17, 2017.
STN Registry Database Entry for 2086785-26-2 entered STN Mar. 17, 2017.
STN Registry Database Entry for 2086785-27-3 entered STN Mar. 17, 2017.
STN Registry Database Entry for 2086785-32-0 entered STN Mar. 17, 2017.
STN Registry Database Entry for 2086785-33-1 entered STN Mar. 17, 2017.
STN Registry Database Entry for 2089251-16-9 entered STN Apr. 10, 2017.
STN Registry Database Entry for 79111-60-7 entered STN Nov. 16, 1984.
Van Esch et al. "Aggregation behavior and copper-binding properties of surfactants containing imidazole and pyrazole ligands," Recl Trav Chim Pays-Bas. 1994, 113(4):186-193.
Wang et al. "Combinatorially designed lipid-like nanoparticles for intracellular delivery of cytotoxic protein for cancer therapy," Angew Chem Int Ed Engl. 2014, 53(11):2893-2898.
Non-Final Office Action for U.S. Appl. No. 16/432,177, dated Oct. 3, 2022.
Unpublished U.S. Appl. No. 17/853,576, entitled "Circular RNA Vectors Encoding Chimeric Antigen Receptors Targeting BCMA," filed Jun. 29, 2022; Inventors: Robert Alexander Wesselhoeft, Kristen Ott, Thomas Barnes, Gregory Motz, Amy M. Becker, Allen T. Horhota, and Brian Goodman.
Unpublished U.S. Appl. No. 17/503,208, entitled: "Circular RNA Compositions and Methods," filed Oct. 15, 2021; Inventors: Brian Goodman, Alexander Wesselhoeft, Allen T. Horhota, Jung-hoon Yang, and Kristen Ott.
Unpublished U.S. Appl. No. 18/069,621, entitled: "Circular RNA Compositions and Methods," filed Dec. 21, 2022; Inventors: Brian Goodman, Alexander Wesselhoeft, Allen T. Horhota, Jung-hoon Yang, and Kristen Ott.
Final Office Action for U.S. Appl. No. 16/432,177, dated Apr. 25, 2023.
Corrected Notice of Allowability for U.S. Appl. No. 17/202,223, dated Mar. 2, 2023.
Final Office Action for U.S. Appl. No. 17/202,223, dated Mar. 7, 2022.
Final Office Action for U.S. Appl. No. 17/202,223, dated Nov. 2, 2022.
Non-Final Office Action for U.S. Appl. No. 17/202,223, dated Aug. 20, 2021.
Non-Final Office Action for U.S. Appl. No. 17/202,223, dated Apr. 18, 2022.
Notice of Allowance for U.S. Appl. No. 17/202,223, dated Nov. 16, 2022.
Final Office Action for U.S. Appl. No. 17/384,460, dated Jul. 22, 2022.
Non-Final Office Action for U.S. Appl. No. 17/384,460, dated Mar. 24, 2022.
Non-Final Office Action for U.S. Appl. No. 17/384,460, dated Dec. 23, 2022.
Notice of Allowance for U.S. Appl. No. 17/384,460 dated Jun. 13, 2023.
Non-Final Office Action for U.S. Appl. No. 17/503,208, dated May 5, 2022.
Notice of Allowance for U.S. Appl. No. 17/503,208, dated Jan. 19, 2023.
Final Office Action for U.S. Appl. No. 17/503,208, dated Aug. 30, 2022.
Final Office Action for U.S. Appl. No. 17/548,241, dated Sep. 28, 2022.
Non-Final Office Action for U.S. Appl. No. 17/548,241, dated May 24, 2022.
Notice of Allowance for U.S. Appl. No. 17/548,241, dated Feb. 27, 2023.
Corrected Notice of Allowability for U.S. Appl. No. 17/548,241, dated Mar. 31, 2023.
Corrected Notice of Allowability for U.S. Appl. No. 17/548,241, dated May 22, 2023.
Non-Final Office Action for U.S. Appl. No. 17/548,247, dated Apr. 1, 2022.
Notice of Allowance for U.S. Appl. No. 17/548,247, dated Jul. 22, 2022.
Notice of Allowance for U.S. Appl. No. 17/548,247, dated Nov. 14, 2022.
Carmona, Ellese Marie. 2019. Circular RNA: Design Criteria for Optimal Therapeutical Utility. Doctoral dissertation, Harvard University, Graduate School of Arts & Sciences.

\* cited by examiner (-) No Spacer  (D) Disruptive Spacer  (P1) Permissive Spacer 1  (P2) Permissive Spacer 2

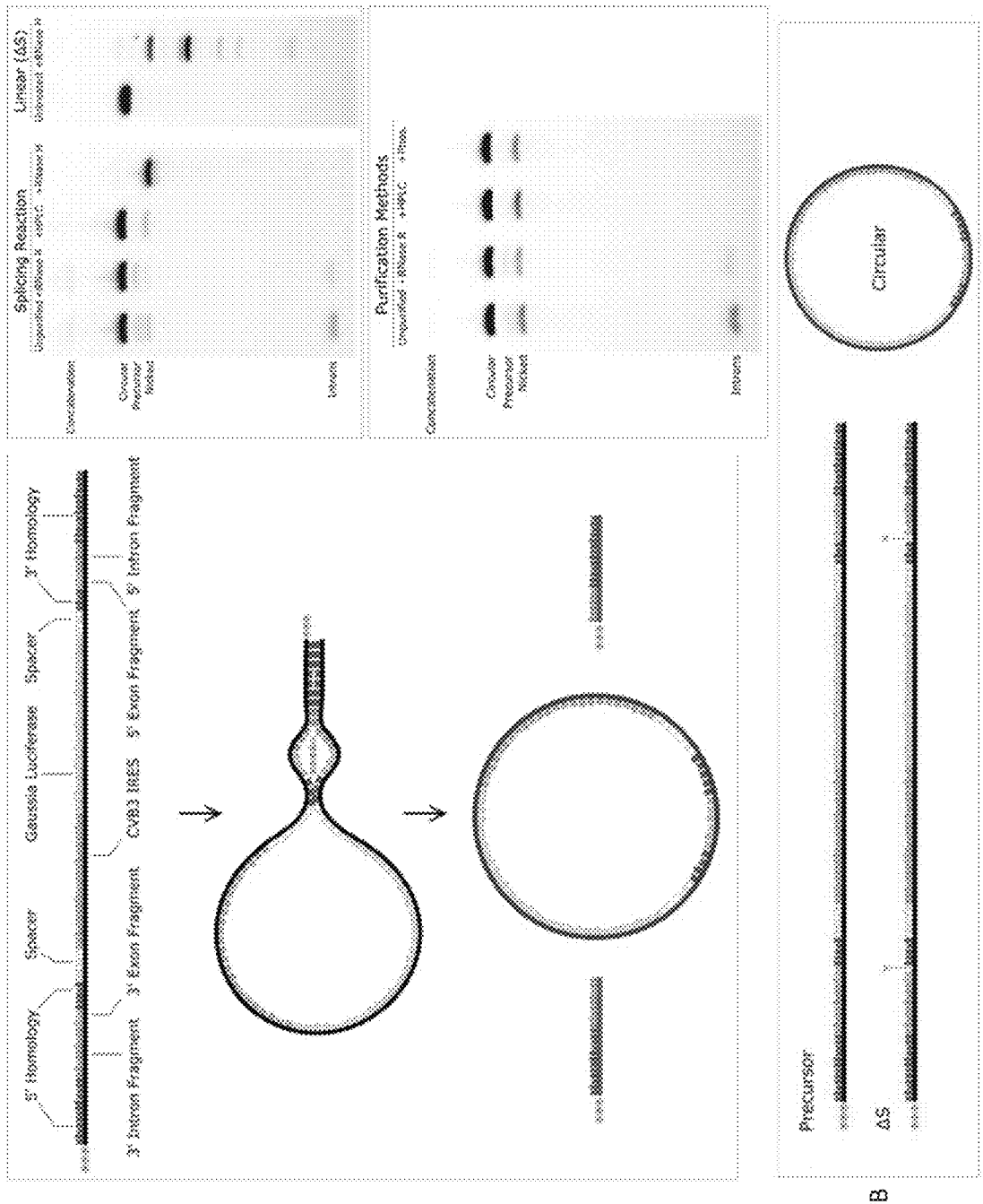

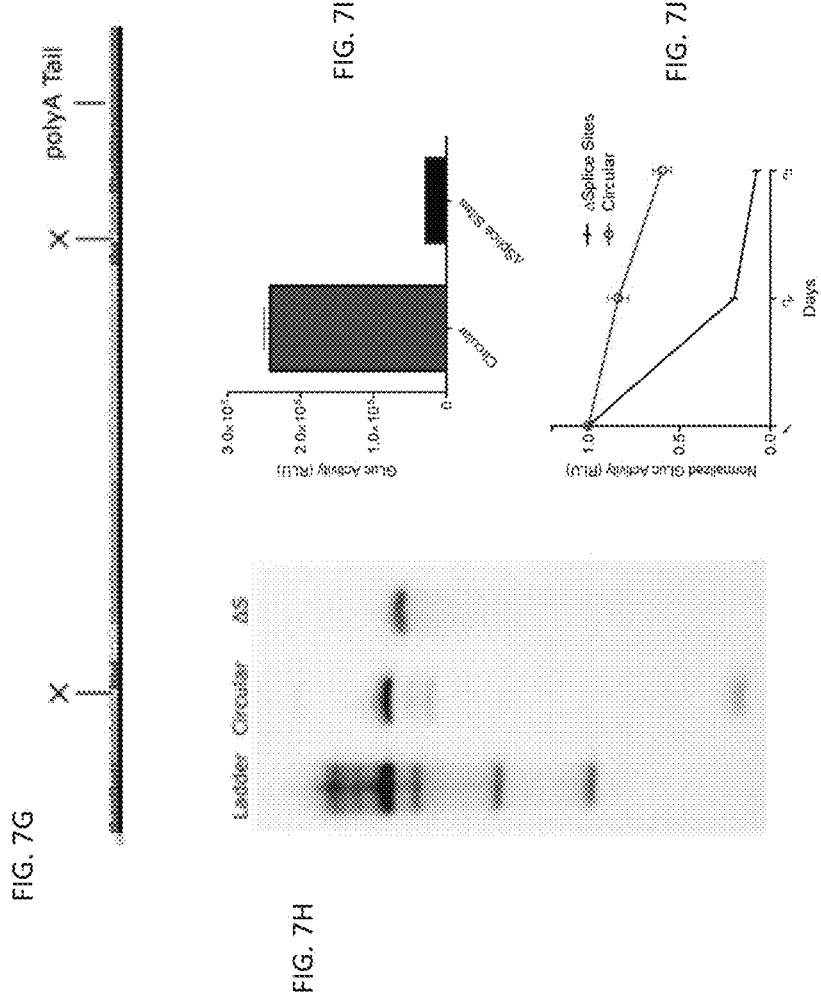

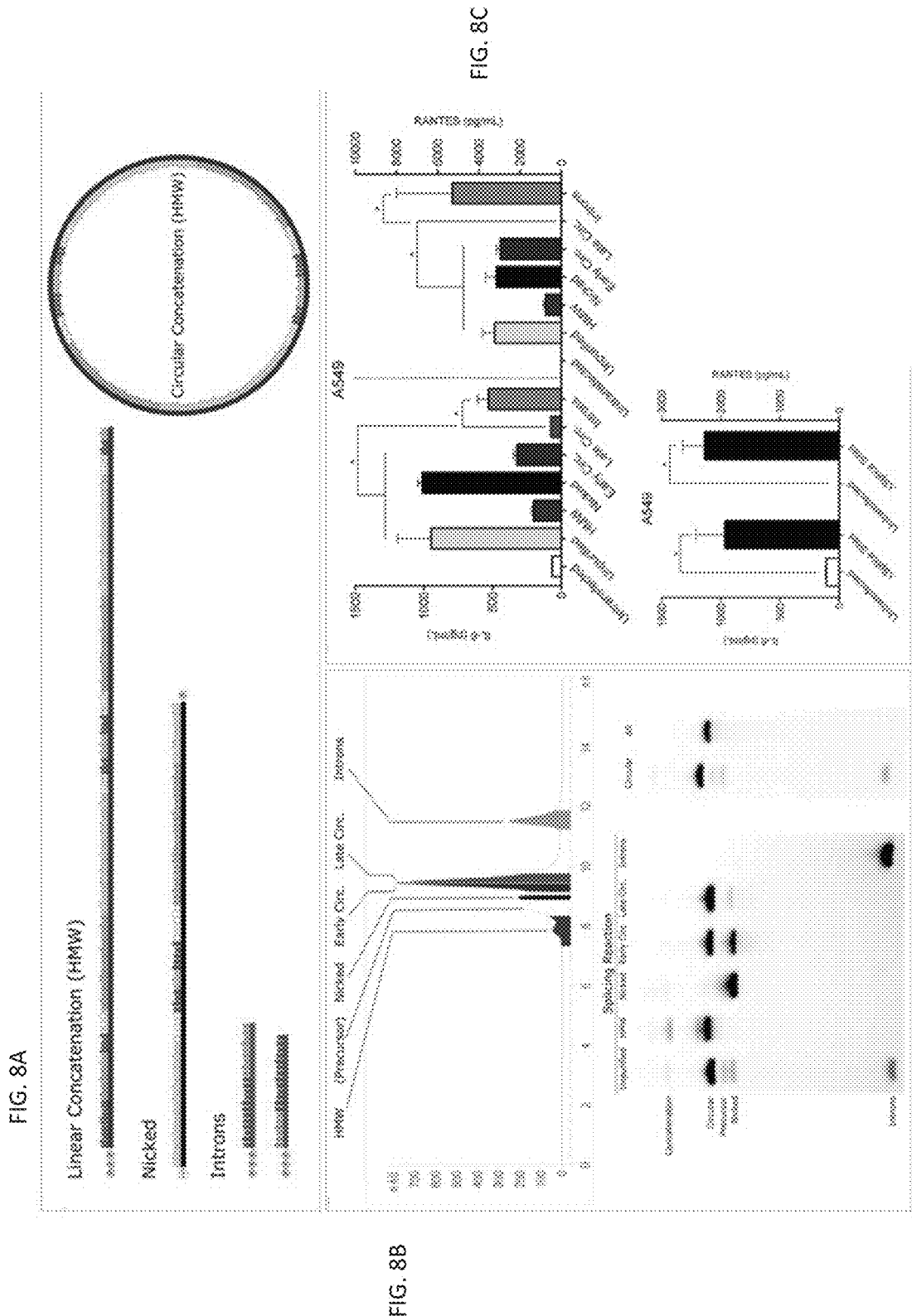

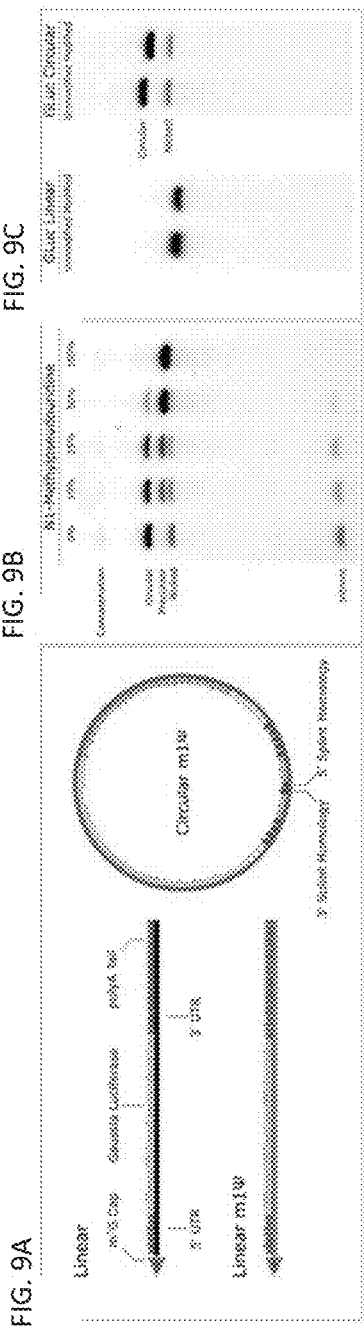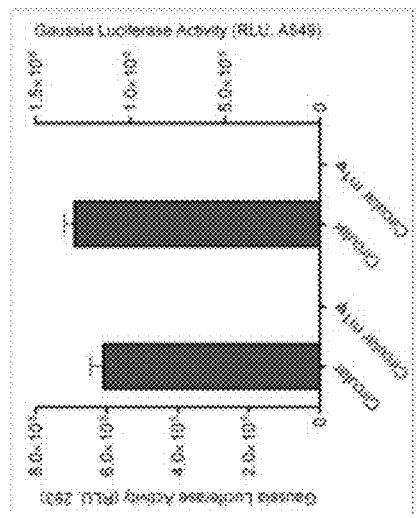

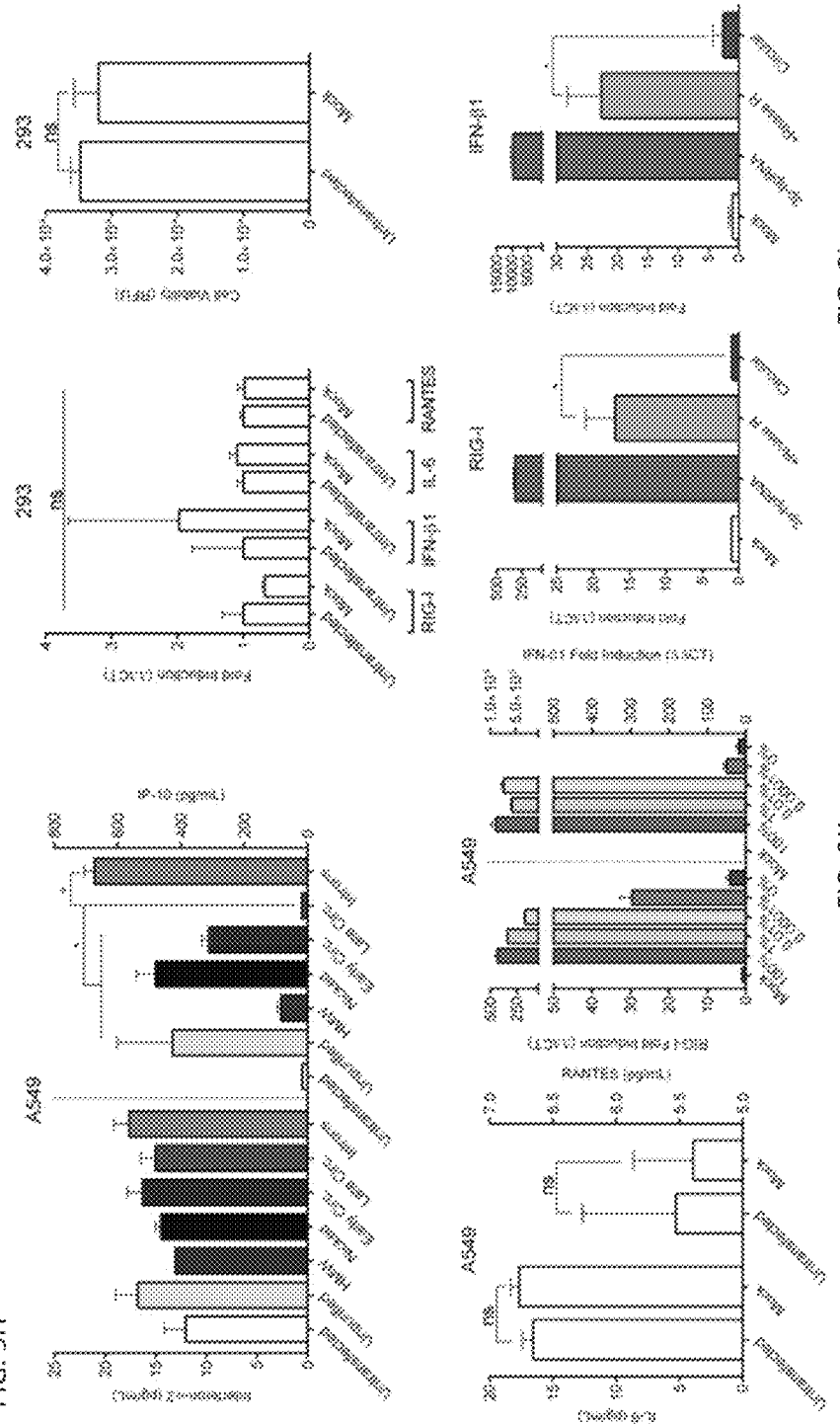

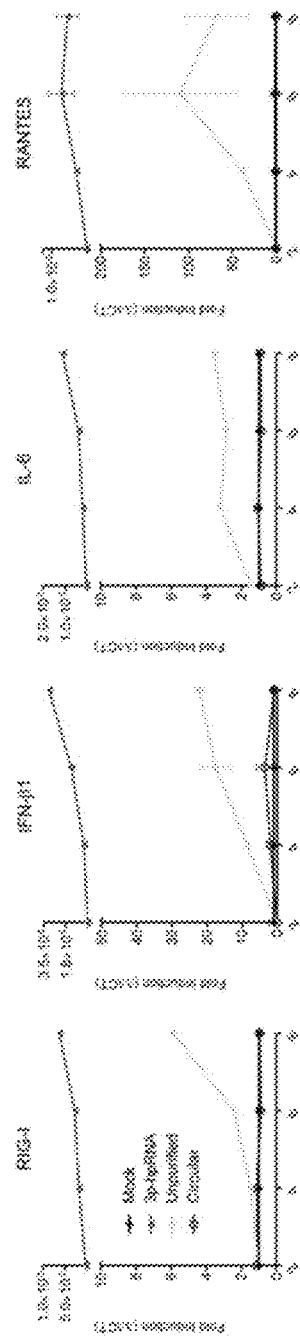
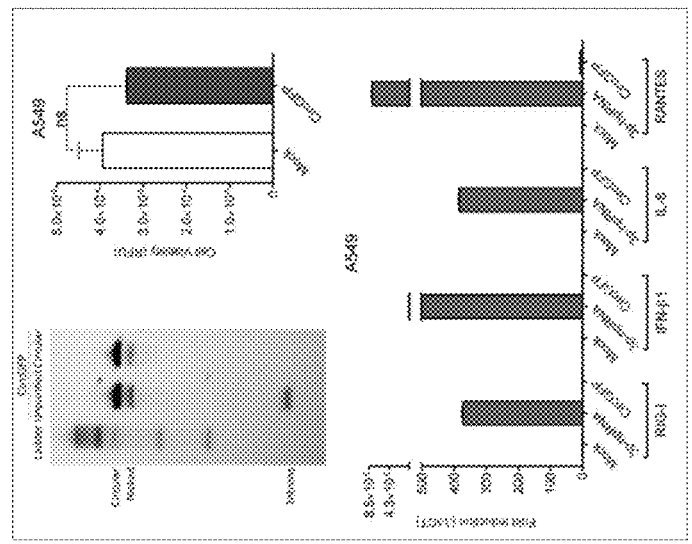
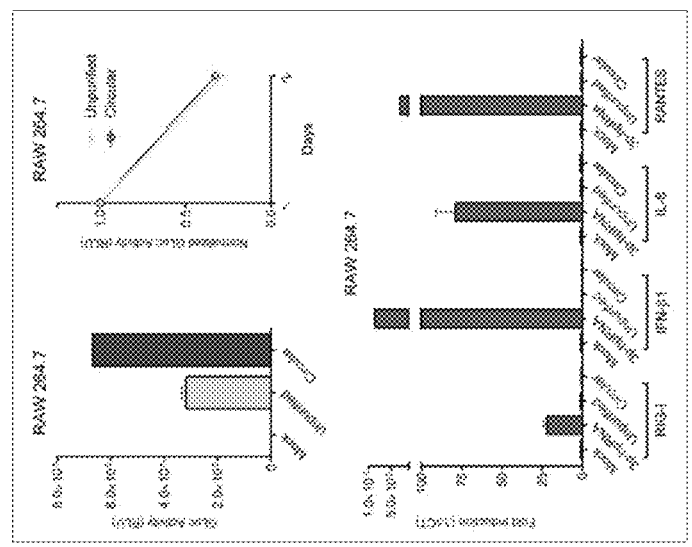
FIG. 9M
FIG. 9N
FIG. 9O

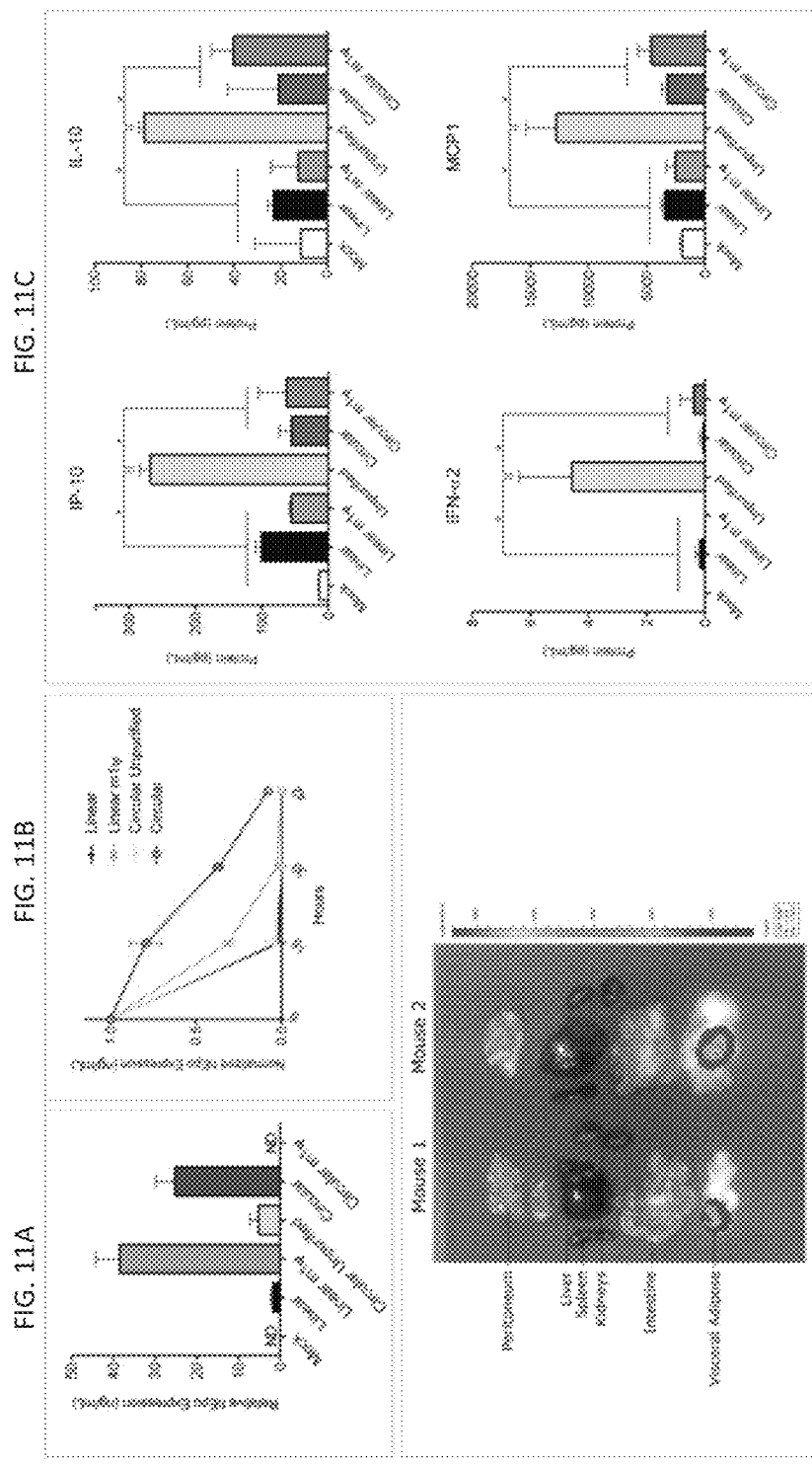

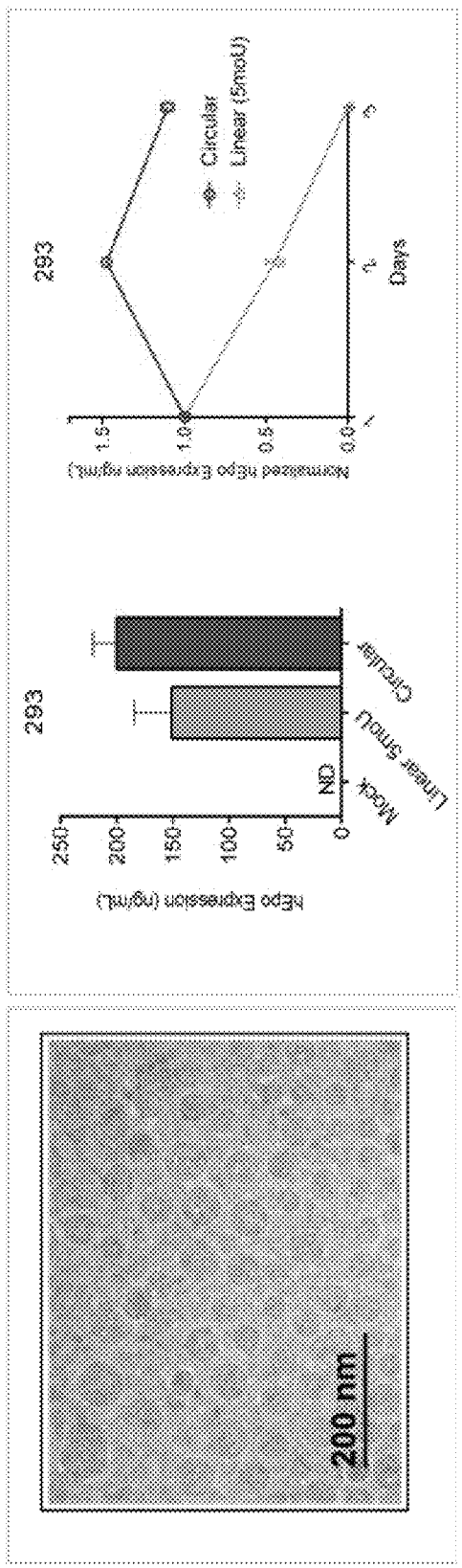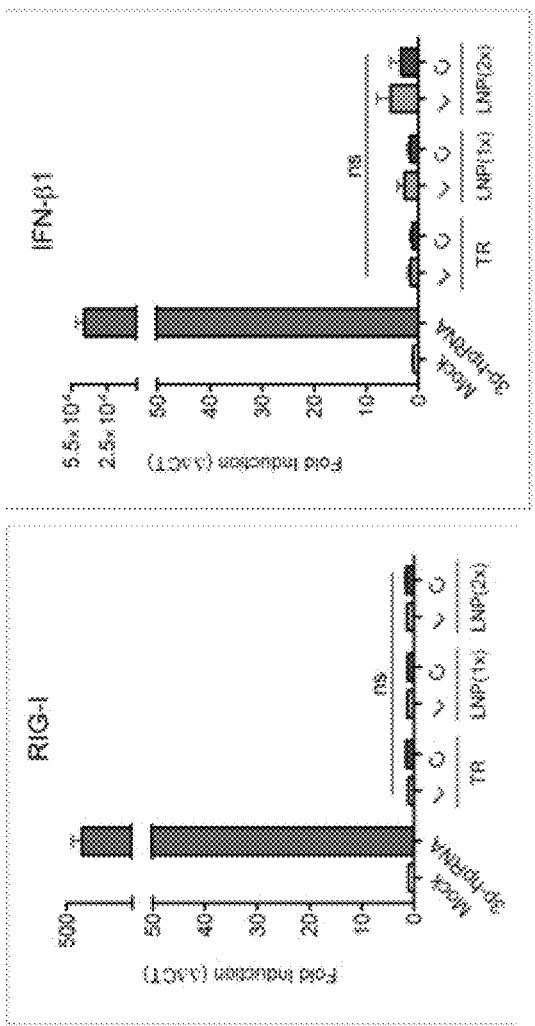
FIG. 12A
FIG. 12B
FIG. 12C

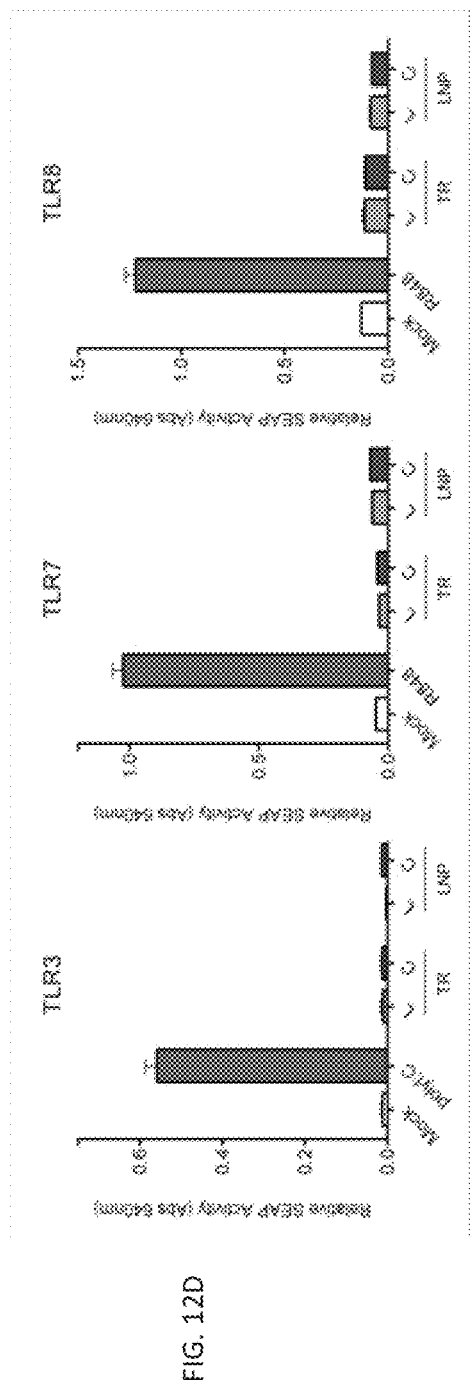
FIG. 12D
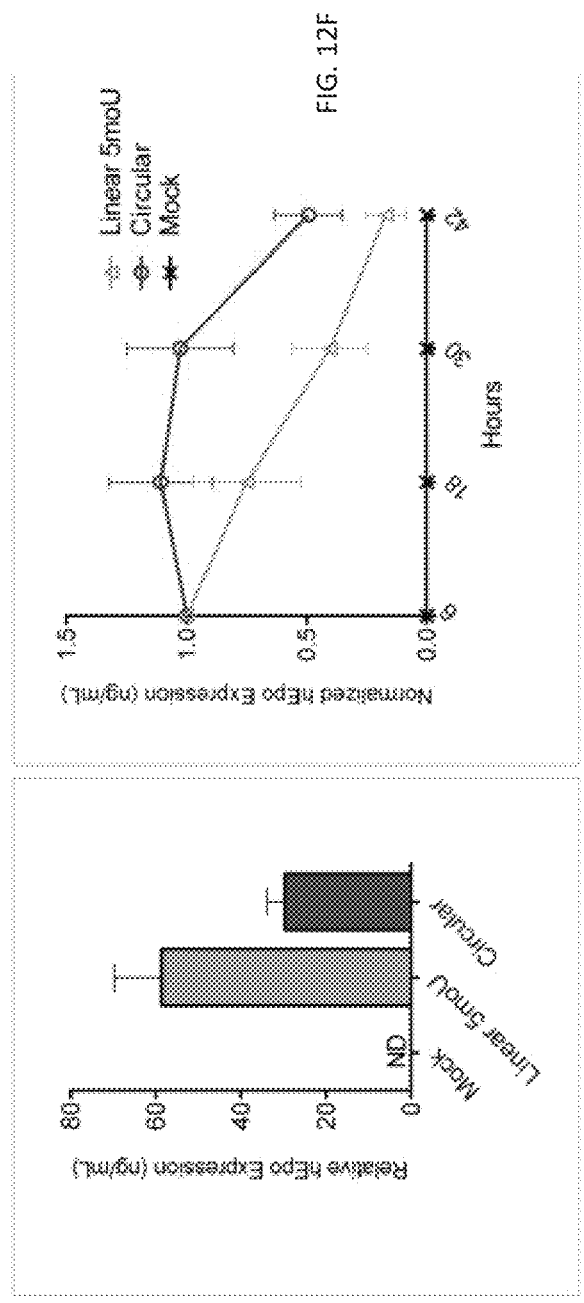
FIG. 12E
FIG. 12F

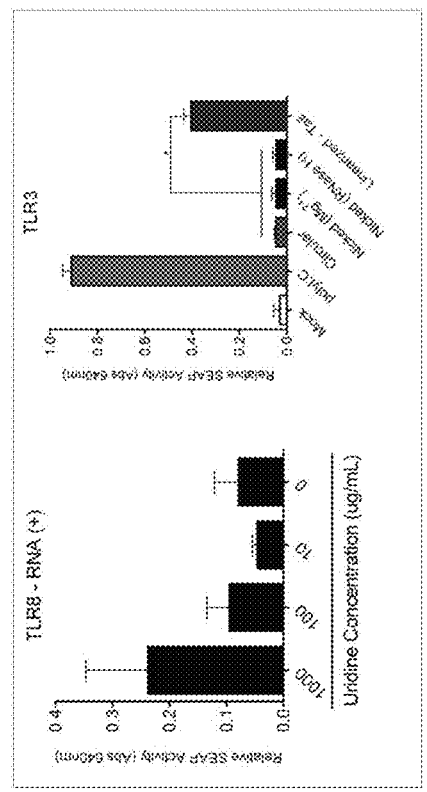
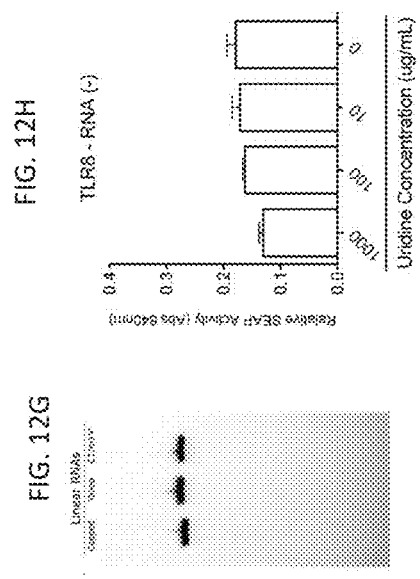
FIG. 12G
FIG. 12H
FIG. 12I

```
                         SEQUENCE LISTING

Sequence total quantity: 79
SEQ ID NO: 1            moltype = DNA  length = 1465
FEATURE                 Location/Qualifiers
misc_feature            1..1465
                        note = Full T4 intron-based circRNA construct with EMCV
                         IRES and GLuccoding region
source                  1..1465
                        mol_type = other DNA
                        organism = synthetic construct
SEQUENCE: 1
gggagaccct cgagcctaac gactatccct ttggggagta gggtcaagtg actcgaaacg   60
atagacaact tgctttaaca agttggagat atagtctgct ctgcatggtg acatgcagct  120
ggatataatt ccggggtaag attaacgacc ttatctgaac ataatgctac cgtttaatat  180
tgcgtcaccc ccctctccct cccccctaa cgttactgcg cgaagccgct tggaataagg   240
ccggtgtgcg tttgtctata tgttattttc caccatattg ccgtctttg gcaatgtgag   300
ggcccggaaa cctggccctg tcttcttgac gagcattcct aggggtcttt ccctctcgc   360
caaaggaatg caaggtctgt tgaatgtcgt gaaggaagca gttcctctgg aagcttcttg  420
aagacaaaca acgtctgtag cgacccttg caggcagcgg aaccccccac ctggcgacag   480
gtgcctctgc ggccaaaagc cacgtgtata agatacacct gcaaaggcgg cacaacccca  540
gtgccacgtt gtgagttgga tagttgtgga aagagtcaaa tggctctcct caagcgtatt  600
caacaagggg ctgaaggatg cccagaaggt accccattgt atgggatctg atctgggcc   660
tcggtgcaca tgctttacat gtgtttagtc gaggttaaaa aacgtctagg ccccccgaac  720
cacggggacg tggttttcct ttgaaaaaca cgatgataat atggccacaa ccatgggagt  780
caaagttctg tttgccctga tctgcatcgc tgtggccgag gccaagccca ccgagaacaa  840
cgaagacttc aacatcgtgg ccgtggccag caacttcgcg accacggatc tcgatgctga  900
ccgcgggaag ttgcccggca agaagctgcc gctggaggtg ctcaaagaga tggaagccaa  960
tgcccggaaa gctggctgca ccaggggctg tctgatctgc ctgtcccaca tcaagtgcac 1020
gcccaagatg aagaagttca tcccaggacg ctgccacacc tacgaaggcg acaaagagtc 1080
cgcacagggc ggcataggcg aggcgatcgt cgacattcct gagattcctg ggttcaagga 1140
cttggagccc atggagcagt tcatcgcaca ggtcgatctg tgtgtggact gcacaactgg 1200
ctgcctcaaa gggcttgcca acgtgcagtg ttctgacctg ctcaagaagt ggctgccgca 1260
acgctgtgcg acctttgcca gcaagatcca gggccaggtg gacaagatca aggggccgg   1320
tggtgactaa cagagatgtt ttcttgggtt aattgaggcc tgagtataag gtgacttata 1380
cttgtaatct atctaaacgg ggaacctctc tagtagacaa tcccgtgcta aattgtagga 1440
ctaattccat ttatcagatt tctag                                       1465

SEQ ID NO: 2            moltype = DNA  length = 180
FEATURE                 Location/Qualifiers
misc_feature            1..180
                        note = Intron fragment with designed homology arm
source                  1..180
                        mol_type = other DNA
                        organism = synthetic construct
SEQUENCE: 2
gggagaccct cgaggttcta cataaatgcc taacgactat ccctttgggg agtagggtca   60
agtgactcga aacgatagac aacttgcttt aacaagttgg agatatagtc tgctctgcat  120
ggtgacatgc agctggatat aattccgggg taagattaac gaccttatct gaacataatg  180

SEQ ID NO: 3            moltype = DNA  length = 116
FEATURE                 Location/Qualifiers
misc_feature            1..116
                        note = Intron fragment with designed homology arm
source                  1..116
                        mol_type = other DNA
                        organism = synthetic construct
SEQUENCE: 3
taattgaggc ctgagtataa ggtgacttat acttgtaatc tatctaaacg gggaacctct   60
ctagtagaca atcccgtgct aaattgtagg actaattcca tttatcagat ttctag      116

SEQ ID NO: 4            moltype = DNA  length = 188
FEATURE                 Location/Qualifiers
misc_feature            1..188
                        note = Intron fragment with designed homology arm
source                  1..188
                        mol_type = other DNA
                        organism = synthetic construct
```

```
SEQUENCE: 4
gggagaccct cgaatggaat tggttctaca taaatgccta acgactatcc ctttggggag    60
tagggtcaag tgactcgaaa cgatagacaa cttgctttaa caagttggag atatagtctg   120
ctctgcatgg tgcatgcag ctggatataa ttccggggta agattaacga ccttatctga    180
acataatg                                                            188

SEQ ID NO: 5              moltype = DNA   length = 116
FEATURE                   Location/Qualifiers
misc_feature              1..116
                          note = Intron fragment with designed homology arm
source                    1..116
                          mol_type = other DNA
                          organism = synthetic construct
SEQUENCE: 5
taattgaggc ctgagtataa ggtgacttat acttgtaatc tatctaaacg gggaacctct    60
ctagtagaca atcccgtgct aaattgtagg actaattcca tttatcagat ttctag       116

SEQ ID NO: 6              moltype = DNA   length = 41
FEATURE                   Location/Qualifiers
misc_feature              1..41
                          note = Designed spacer sequence
source                    1..41
                          mol_type = other DNA
                          organism = synthetic construct
SEQUENCE: 6
actgcaagtt gtctatcgtt acggtaagtc accttatttc a                        41

SEQ ID NO: 7              moltype = DNA   length = 35
FEATURE                   Location/Qualifiers
misc_feature              1..35
                          note = Designed spacer sequence
source                    1..35
                          mol_type = other DNA
                          organism = synthetic construct
SEQUENCE: 7
ggtagtggtg ctactaactt cagcctgctg aagca                               35

SEQ ID NO: 8              moltype = DNA   length = 34
FEATURE                   Location/Qualifiers
misc_feature              1..34
                          note = Designed spacer sequence
source                    1..34
                          mol_type = other DNA
                          organism = synthetic construct
SEQUENCE: 8
ggtagtaaac tactaactac aacctgctga agca                                34

SEQ ID NO: 9              moltype = DNA   length = 2721
FEATURE                   Location/Qualifiers
misc_feature              1..2721
                          note = Construct for testing maximum length of
                          circularization
source                    1..2721
                          mol_type = other DNA
                          organism = synthetic construct
SEQUENCE: 9
gggagaccct cgaatggaat tggttctaca taaatgccta acgactatcc ctttggggag    60
tagggtcaag tgactcgaaa cgatagacaa cttgctttaa caagttggag atatagtctg   120
ctctgcatgg tgcatgcag ctggatataa ttccggggta agattaacga ccttatctga    180
acataatgct accgtttaat attgcgtcag gtagtaaact actaactaca acctgctgaa   240
gcaccccct ctcccctccc ccctaacgtt actggccgaa gccgcttgga ataaggccgg    300
tgtgcgtttg tctatatgtt attttccacc atattgccgt cttttggcaa tgtgagggcc   360
cggaaacctg gccctgtctt cttgacgagc attcctaggg gtctttcccc tctcgccaaa   420
ggaatgcaag gtctgttgaa tgtcgtgaag gaagcagttc ctctggaagc ttcttgaaga   480
caaacaacgt ctgtagcgac cctttgcagg cagcggaacc ccccacctgg cgacaggtgc   540
ctctgcggcc aaaagccacg tgtataagat acacctgcaa aggcggcaca ccccagtgc   600
cacgttgtga gttggatagt tgtggaaaga gtcaaatggc tctcctcaag cgtattcaac   660
aaggggctga aggatgccca aaggtaccc cattgtatgg gatctgatct ggggcctcgg   720
tgcacatgct ttacatgtgt ttagtcgagg ttaaaaaacg tctaggcccc ccgaaccacg   780
gggacgtggt tttcctttga aaaacacgat gataatatgg ccacaaccat ggaagacgcc   840
aaaaacataa agaaaggccc ggcgccattc tatccgctgg aagatggaac cgctggagag   900
caactgcata aggctatgaa gagatacgcc ctggttcctg gaacaattgc ttttacagat   960
gcacatatcg aggtggacat cacttacgct gagtacttcg aaatgtccgt tcggttggca  1020
gaagctatga aacgatatgg gctgaataca aatcacagaa tcgtcgtatg cagtgaaaac  1080
tctcttcaat tctttatgcc ggtgttgggc gcgttattta tcggagttgc agttgcgccc  1140
gcgaacgaca tttataatga acgtgaattg ctcaacagta tgggcatttc gcagcctacc  1200
gtggtgttcg tttccaaaaa ggggttgcaa aaattttga acgtgcaaaa aaagctccca  1260
atcatccaaa aaattattat catggattct aaaacggatt accagggatt tcagtcgatg  1320
tacacgttcg tcacatctca tctacctccc ggttttaatg aatacgattt tgtgccagag  1380
```

```
tccttcgata gggacaagac aattgcactg atcatgaact cctctggatc tactggtctg    1440
cctaaaggtg tcgctctgcc tcatagaact gcctgcgtga gattctcgca tgccagagat    1500
cctatttttg gcaatcaaat cattccggat actgcgattt taagtgttgt tccattccat    1560
cacggttttg gaatgtttac tacactcgga tatttgatat gtggatttcg agtcgtctta    1620
atgtatagat ttgaagaaga gctgtttctg aggagccttc aggattacaa gattcaaagt    1680
gcgctgctgg tgccaaccct attctccttc ttcgccaaaa gcactctgat tgacaaatac    1740
gatttatcta atttacacga aattgcttct ggtggcgctc ccctctctaa ggaagtcggg    1800
gaagcggttg ccaagaggtt ccatctgcca ggtatcaggc aaggatatgg gctcactgag    1860
actacatcag ctattctgat tacacccgag ggggatgata aaccgggcgc ggtcggtaaa    1920
gttgttccat ttttgaagc gaaggttgtg gatctggata ccgggaaaac gctgggcgtt     1980
aatcaaagag gcgaactgtg tgtgagaggt cctatgatta tgtccggtat gggagtcaaa    2040
gttctgtttg ccctgatctg catcgctgtg gccgaggcca agcccaccga gaacaacgaa    2100
gacttcaaca tcgtggccgt ggccagcaac ttcgcgacca cggatctcga tgctgaccgc    2160
gggaagttgc ccggcaagaa gctgccgctg gaggtgctca aagagatgga agccaatgcc    2220
cggaaagctg gctgcaccag gggctgtctg atctgcctgt cccacatcaa gtgcacgccc    2280
aagatgaaga agttcatccc aggacgctgc cacacctacg aaggcgacaa agagtccgca    2340
cagggcggca taggcgaggc gatcgtcgac attcctgaga ttcctgggtt caaggacttg    2400
gagcccatgg agcagttcat cgcacaggtc gatctgtgtg tggactgcac aactggctgc    2460
ctcaaagggc ttgccaacgt gcagtgttct gacctgctca agaagtggct gccgcaacgc    2520
tgtgcgacct ttgccagcaa gatccagggc caggtggaca agatcaaggg ggccggtggt    2580
gactaacaga atgttttct tgggttaatt gaggcctgag tataaggtga cttatacttg      2640
taatctatct aaacggggaa cctctctagt agacaatccc gtgctaaatt gtaggactaa    2700
ttccatttat cagatttcta g                                               2721

SEQ ID NO: 10          moltype = DNA   length = 5121
FEATURE                Location/Qualifiers
misc_feature           1..5121
                       note = Construct for testing maximum length of
                       circularization
source                 1..5121
                       mol_type = other DNA
                       organism = synthetic construct
SEQUENCE: 10
gggagaccct cgaatggaat tggttctaca taaatgccta acgactatcc ctttggggag     60
tagggtcaag tgactcgaaa cgatagacaa cttgctttaa caagttggag atatagtctg    120
ctctgcatgg tgacatgcag ctggatataa ttccggggta agattaacga ccttatctga    180
acataatgct accgtttaat attgcgtcag gtagtaaact actaactaca acctgctgaa    240
gcaccccct ctccctcccc cctaacgtt actggccgaa gccgcttgga ataaggccgg       300
tgtgcgttta tctatatgtt attttccacc atattgccgt cttttggcaa tgtgagggc      360
cggaaacctg gccctgtctt cttgacgagc attcctaggg gtctttcccc tctcgccaaa    420
ggaatgcaag gtctgttgaa tgtcgtgaag gaagcagttc tctgcttgaagc ttcttgaaga  480
caaacaacgt ctgtagcgac cctttgcagg cagcggaacc cccaccctgg cgacaggtgc    540
ctctgcgcc aaaagccacg tgtataagat acacctgcaa aggcggcaca accccagtgc     600
cacgttgtga gttggatagt tgtggaaaga gtcaaatggc tctcctcaag cgtattcaac    660
aaggggctga aggatgccca gaaggtaccc cattgtatgg gatctgatct ggggcctcgg    720
tgcacatgct ttacatgtgt ttagtcgagg ttaaaaaacg tctaggcccc ccgaaccacg     780
gggacgtggt tttcctttga aaaacacgat gataatatgg ccacaaccat ggaagacgcc    840
aaaaacataa agaaaggccc ggcgccattc tatccgctgg aagatggaac cgctggagag    900
caactgcata aggctatgaa gagatacgcc ctggttcctg gaacaattgc ttttacagat    960
gcacatatcg aggtggacat cacttacgct gagtacttcg aaatgtccgt tcggttggca   1020
gaagctatga aacgatatgg gctgaataca aatcacagaa tcgtcgtatg cagtgaaaac   1080
tctcttcaat tctttatgcc ggtgttgggc gcgttattta tcggagttgc agttgcgccc   1140
gcgaacgaca tttataatga acgtgaattg ctcaacagta tgggcatttc gcagcctacc   1200
gtggtgttca tttccaaaaa ggggttgcaa aaaattttga acgtgcaaaa aaagctccca   1260
atcatccaaa aaattattat catggattct aaaacggatt accagtcgatg gtcagtcgatg 1320
tacacgttcg tcacatctca tctacctccc ggttttaatg aatacgattt tgtgccagag   1380
tccttcgata gggacaagac aattgcactg atcatgaact cctctggatc tactggtctg   1440
cctaaaggtg tcgctctgcc tcatagaact gcctgcgtga gattctcgca tgccagagat   1500
cctatttttg gcaatcaaat cattccggat actgcgattt taagtgttgt tccattccat   1560
cacggttttg gaatgtttac tacactcgga tatttgatat gtggatttcg agtcgtctta   1620
atgtatagat ttgaagaaga gctgtttctg aggagccttc aggattacaa gattcaaagt   1680
gcgctgctgg tgccaaccct attctccttc ttcgccaaaa gcactctgat tgacaaatac   1740
gatttatcta atttacacga aattgcttct ggtggcgctc ccctctctaa ggaagtcggg   1800
gaagcggttg ccaagaggtt ccatctgcca ggtatcaggc aaggatatgg gctcactgag   1860
actacatcag ctattctgat tacacccgag ggggatgata aaccgggcgc ggtcggtaaa   1920
gttgttccat tttttgaagc gaaggttgtg gatctggata ccgggaaaac gctgggcgtt   1980
aatcaaagag gcgaactgtg tgtgagaggt cctatgatta tgtccggtag gtctcatatc   2040
accttggctt tcgccgtatt cacatgctgg aacacatcat gctagcattta acatcgggga   2100
gttacgatcc gtgaaaagac ggatatattg cccttgtaca tctatatta ccggagggat     2160
tagaatttat agttggagag cttcatacccc cactgagctt tcactgtat gctagtaatt     2220
atacttcatt tgctcgttgg gtagatgcgt tcttctcgca caagccgatg atttccgagt   2280
ttcttttcag cggccgtaaa gcctcgacac gtgacgcact gtgaaccgca cccgtatacc     2340
taatagaggc agttaacttc attcagccac ataaggggtg ataacaccga ctgcccaagt   2400
acggaattaa gaaaatggat aatgaagatt atgagatcgc cgctacatta gcaacgcttg   2460
gtgctttaat tggcatgtat gaccaatcta caacctgggg ggagggtacc tctttgagat   2520
gtacgatgca gcctaaaggg taacgttatg caagtggtca agagcctagc atgcttatgc   2580
ggtttatcaa aatgtatcgc actttatgct aggtaatgtg tgttctccac ggtatccata   2640
agcttgccta aatactgaag tctacagaaa aactatggga tatttgtgca tatattcccc   2700
atagttatcc tggagcagtc cgttcccacg tagaatgtag cgaattgcgt ggctggcttc   2760
```

```
aaacatagca ccgaacagta gatctagttg cgccccttcc aagtttacag ttaggtaaac   2820
cttcacgata gaaagttggg aacaaggccg cattcaacct ttacgatcac ttccagaaag   2880
ggattgtggg taggagacac cacgccctca gatcacgtcg atcacttgtt ataaggtcaa   2940
atgtgagaaa cgcgtcagaa gggagttggt gcttgcttat ttcttttcca gactcgtcgt   3000
tggatcaacc tatctcatga ccctagctct agtatgtctg gtggtaaagg agctgcgctg   3060
gatgcattta ttctgctggg agaaataatc gcggatatta tccttttca aagagacgcc    3120
gaactaatga cttgtcgaga ggaatcggca tggtttcgta ccttgccagc attcccaatt   3180
ttttttattt tgcttgggtc ttataaagga aatcgacaat ttgggtaaaa tggtgcaaag   3240
aatctacccg ttggaatatt ttactggagt caccggggga gcttcgagga cacacctacc   3300
tggtctaacc cagcctactt gtaagatatg ttaacgtcgg caccgtcatt gtagttatct   3360
tatttaaggc gacacgagac gtgagaactt ttgcattgca tatgtaacgg tcaatgtcgt   3420
acatgcgaca ccattggatc gctaccgtaa aagtacacgt tacggggggta gctggtgtac   3480
ctaagcgcga cccggaacac ctacacccgc tagtttagct tgtgaaagtg cggcgctgcc   3540
tgtgattcac gcgttgtatg gacaacgttg taccattcgt agcagacttt gatcaatgat   3600
gtagttatgc catgcccgaa acaaactata gacattttcg aaaacgttcc actgagttaa   3660
tccttaagcc atgcaatttt atgaaaattt attaggctag cggaaattac gttccaagtt   3720
ctggaacccct tatatcgatc aaggctgcag acctaatggc ttgtgttcct gaaacatgtt   3780
acgttgccat taactcggga gtcgagtacg tgccatgtgt tgtgatggga ggtactcgtt   3840
tgcggaaagg catctgccca aaaacacatt aggtcattaa cgtcccgtta cggtagatat   3900
ggccacggtc cacataaacc gctcatgggt aaaaaggatt cctataccta acggctagat   3960
ggccaggtat gtgcaatttg gcaggatcc cgttggacgt gacatctcaa tggcctgaga   4020
ggtctgagac ccccgatgga gatagtttaa tcaaactttt gaaatgccaa ggcacagcta   4080
gatttagata gtcaacgcca tcgactttgc attttcgaca tatactcttg ccattatgag   4140
agtgacgcgg ataagaggta gggatgcatg agtaaaagag agcggttta cgttcaaatt    4200
gtggaaggat gctctagccg ggagtgagga cactaaacgc ttgtcatgca cagttactgt   4260
gcggcgtatt gttagggatg cggttgtagt agtcaaacgg ccagaaaatg tgtctcattt   4320
tgaattcgcg atctcagatc tccgtgaaat gatcttcgga attcaactct catcgggaca   4380
gcaggacgcg tgctaactta gggcgtttca actgtgatcc gaatacgtat gggagtcaaa   4440
gttctgtttg ccctgatctg catcgctgtg gccgaggcca agcccaccga gaacaacgaa   4500
gacttcaaca tcgtggccgt ggccagcaac ttcgcgacca cggatctcga tgctgaccgc   4560
gggaagttgc ccggcaagaa gctgcgcgct gaggtgctca aagagatgga agccaatgcc   4620
cggaaagctg gctgcaccag gggctgtctg atctgcctgt cccacatcaa gtgcacgccc   4680
aagatgaaga agttcatccc aggacgctgc cacacctacg aaggcgacaa agagtccgca   4740
cagggcgagc taggcgaggc gatcgtcgac attcctgact tcctgggtt caaggacttg   4800
gagcccatgg agcagttcat cgcacaggtc gatctgtgtg tggactgcac aactggctgc   4860
ctcaaagggc ttgccaacgt gcagtgttct gacctgctca agaagtggct gccgcaacgc   4920
tgtgcgacct tgccagcaa gatccagggc caggtggaca agatcaaggg ggccggtggt    4980
gactaacaga gatgttttct tgggttaatt gaggcctgag tataaggtga cttatacttg   5040
taatctatct aaacgggaa cctctctagt agacaatccc gtgctaaatt gtaggactaa    5100
ttccatttat cagatttcta g                                             5121
```

SEQ ID NO: 11    moltype = DNA length = 1555
FEATURE      Location/Qualifiers
misc_feature    1..1555
          note = Full anabaena intron-based circRNA construct with
          IRES and GLuccoding region
source       1..1555
          mol_type = other DNA
          organism = synthetic construct
SEQUENCE: 11

```
gggagaccct cgaccgtcga ttgtccactg gtcaacaata gatgacttac aactaatcgg     60
aaggtgcaga gactcgacgg gagctaccct aacgtcaaga cgagggtaaa gagagagtcc    120
aattctcaaa gccaataggc agtagcgaaa gctgcaagag aatgaaaatc cgttgacctt    180
aaacggtcgt gtgggttcaa gtccctccac ccccagaaac caactttatt actatattcc    240
ccacaacccc cctctcccctc cccccctaac gttactgccc gaagccgctt ggaataaggc    300
cggtgtgcgt ttgtctatat gttatttttcc accatattgc cgtcttttgg caatgtgagg    360
gcccggaaac ctggccctgt cttcttgacg agcattccta ggggtctttc cctctcgcc     420
aaaggaatgc aaggtctgtt gaatgtcgtg aaggaagcag ttcctctgga gcttcttga     480
agacaaacaa cgtctgtagc gacccttttgc aggcagcgga acccccacc tggcgacagg    540
tgcctctgcg gccaaaagcc acgtgtataa gatacacctg caaaggcggc acaacccag    600
tgccacgttg tgagttggat agttgtggaa agagtcaaat ggctctcctc aagcgtattc    660
aacaaggggc tgaaggatgc ccagaaggta cccccattgta tgggatctga tctgggccct   720
cggtgcacat gctttacatg tgtttagtcg aggttaaaaa acgtctaggc cccccgaacc    780
acggggacgt ggttttcctt tgaaaaacac gatgataata tggccacaac catgggagtc    840
aaagttctgt ttgccctgat ctgcatcgct gtggccgagg ccagcccac cgagaacaac   900
gaagacttca acatcgtggc cgtggccagc aacttcgcga ccacggatc cgatgctgac    960
cgcgggaagt tgcccggcaa gaagctgcgc ctgagggtgc tcaaagagat ggaagccaat   1020
gcccggaaag ctggctgcac caggggctgt ctgatctgcc tgtcccacat caagtgcacg   1080
cccaagatga gaagttcat cccaggacgc tgccacacct acgaaggcga caaagagtcc   1140
gcacagggcg cataggcga ggcgatcgtc gacattcctg agattcctgg gttcaaggac    1200
ttggagccca tggagcagtt catcgcacag gtcgatctgt gtgtggactg cacaactggc   1260
tgcctcaaag gcttgccaa cgtgcagtgt tctgacctgc tcaagaagtg gctgccgcaa    1320
cgctgtgcga ccttttgccag caagatccag ggccaggtgg acaagatcaa gggggccggt   1380
ggtgactaaa gacgctacgg acttaaataa ttgagcctta aagaagaaat ctttaagtg    1440
gatgctctca aactcaggga aacctaaatc tagttataga caaggcaatc ctgagccaag   1500
ccgaagtagt aattagtaag accagtggac aatcgacgga taacagcata tctag        1555
```

```
SEQ ID NO: 12            moltype = DNA  length = 1561
FEATURE                  Location/Qualifiers
misc_feature             1..1561
                         note = Full anabaena intron-based circRNA construct with
                         IRES and GLuccoding region
source                   1..1561
                         mol_type = other DNA
                         organism = synthetic construct
SEQUENCE: 12
gggagaccct cgaccgtcga ttgtccactg gtcaacaata gatgacttac aactaatcgg   60
aaggtgcaga gactcgacgg gagctaccct aacgtcaaga cgagggtaaa gagagagtcc  120
aattctcaaa gccaataggc agtagcgaaa gctgcaagag aatgaaaatc cgttgacctt  180
aaacggtcgt gtgggttcaa gtccctccac ccccatgatc tgaaaccaac tttattacta  240
tattccccac aaccccccctc tccctccccc cctaacgtta ctggccgaag ccgcttggaa  300
taaggccggt gtgcgtttgt ctatatgtta ttttccacca tattgccgtc ttttggcaat  360
gtgagggccc ggaaacctgg ccctgtcttc ttgacgagca ttcctagggg tctttcccct  420
ctcgccaaag gaatgcaagg tctgttgaat gtcgtgaagg aagcagttcc tctgaagct  480
tcttgaagac aaacaacgtc tgtagcgacc ctttgcaggc agcggaaccc cccacctggc  540
gacaggtgcc tctgcggcca aaagccacgt gtataagata cacctgcaaa ggcggcacaa  600
ccccagtgcc acgttgtgag ttggatagtt gtggaaagag tcaaatggct ctcctcaagc  660
gtattcaaca aggggctgaa ggatgcccag aaggtacccc attgtatggg atctgatctg  720
gggcctcggt gcacatgctt tacatgtgtt tagtcgaggt taaaaaacgt ctaggccccc  780
cgaaccacgg ggacgtggtt ttccctttgaa aaacacgatg ataatatggc cacaaccatg  840
ggagtcaaag ttctgtttgc cctgatctgc atcgctgtgg ccgaggccaa gcccaccgag  900
aacaacgaag acttcaacat cgtggccgtg gccagcaact cgcgaccac ggatctcgat  960
gctgaccgcg ggaagttgcc cggcaagaag ctgccgctgg aggtgctcaa agagatggaa 1020
gccaatgccc ggaaagctgg ctgcaccagg ggctgtctga tctgcctgtc ccacatcaag 1080
tgcacgccca agatgaagaa gttcatccca ggacgctgcc acacctacga aggcgacaaa 1140
gagtccgcac agggcggcat aggcgaggcg atcgtcgaca ttcctgagat tcctgggttc 1200
aaggacttgg agcccatgga gcagttcatc gcacaggtcg atctgtgtgt ggactgcaca 1260
actggctgcc tcaaagggct tgccaacgtg cagtgttctg acctgctcaa gaagtggctg 1320
ccgcaacgct gtgcgacctt tgccagcaag atccaggcc aggtggacaa gatcaagggg 1380
gccggtggtg actaaagacg ctacggactt aaataattga gccttaaaga agaaattctt 1440
taagtggatg ctctcaaact cagggaaacc taaatctagt tatagacaag gcaatcctga 1500
gccaagccga agtagtaatt agtaagacca gtggacaatc gacggataac agcatatcta 1560
g                                                                1561

SEQ ID NO: 13            moltype = DNA  length = 1604
FEATURE                  Location/Qualifiers
misc_feature             1..1604
                         note = Full anabaena intron-based circRNA construct with
                         IRES and GLuccoding region
source                   1..1604
                         mol_type = other DNA
                         organism = synthetic construct
SEQUENCE: 13
gggagaccct cgaccgtcga ttgtccactg gtcaacaata gatgacttac aactaatcgg   60
aaggtgcaga gactcgacgg gagctaccct aacgtcaaga cgagggtaaa gagagagtcc  120
aattctcaaa gccaataggc agtagcgaaa gctgcaagag aatgaaaatc cgttgacctt  180
aaacggtcgt gtgggttcaa gtccctccac ccccacgccg gaaacgcaat agccgaaaaa  240
caaaaaacaa aaaaaccccc ctctccctcc ccccctaacg ttactggccg aagccgcttg  300
gaataaggcc ggtgtgcgtt tgtctatatg ttatttttcca ccatattgcc gtcttttgca  360
aatgtgaggg cccggaaacc tggccctgtc ttcttgacga gcattcctag gggtctttcc  420
cctctcgcca aaggaatgca aggtctgttg aatgtcgtga aggaagcagt tcctctggaa  480
gcttcttgaa gacaaacaac gtctgtagcg acccttttgca ggcagcggaa ccccccacct  540
ggcgacaggt gcctctgcgg ccaaaagcca cgtgtataag atacacctgc aaaggcggca  600
caaccccagt gccacgttgt gagttggata gttgtgaaa gagtcaaatg ctctcctca  660
agcgtattca acaaggggct gaaggatgcc cagaaggtac cccattgtat gggatctgat  720
ctggggcctc ggtgcacatg ctttacatgt gtttagtcgg ttaaaaaa cgtctaggcc  780
ccccgaaccac ggggacgtg gttttccttt gaaaaacacg atgataata tggcacaacc  840
atgggagtca aagttctgtt tgccctgatc tgcatcgctg tggccgaggc caagcccacc  900
gagaacaacg aagacttcaa catcgtggcc gtggccagca acttcgcgac cacggatctc  960
gatgctgacc gcgggaagtt gcccggcaag aagctgccgc tggaggtgct caaagagatg 1020
gaagccaatg cccggaaagc tggctgcacc aggggctgtc tgatctgcct gtcccacatc 1080
aagtgcacgc ccaagatgaa gaagttcatc ccaggacgct gccacaccta cgaaggcgac 1140
aaagagtccg cacagggcgg cataggcgag gcgatcgtcg acattcctga gattcctgga 1200
ttcaaggact tggagcccat ggagcagttc atcgcacagg tcgatctgtg tgtggactgc 1260
acaactggct gcctcaaagg gcttgccaac gtgcagtgtt ctgacctgct caagaagtgg 1320
ctgccgcaac gctgtgcgac ctttgccagc aagatccagg ccaggtggga caagatcaag 1380
ggggccggtg tgactaaaaa aaacaaaaa acaaaacggc tattatgcgt taccggcgag 1440
acgctacgga cttaaataat tgagccttaa agaagaaatt cttttaagtgg atgctctcaa 1500
actcaggga acctaaatct agttatagac aaggcaatcc tgagccaagc cgaagtagta 1560
attagtaaga ccagtggaca atcgacggat aacagcatat ctag                 1604
```

```
SEQ ID NO: 14            moltype = DNA   length = 582
FEATURE                  Location/Qualifiers
misc_feature             1..582
                         note = hEpo coding region inserted into circularization
                          backbone
source                   1..582
                         mol_type = other DNA
                         organism = synthetic construct
SEQUENCE: 14
atgggagtgc atgaatgtcc tgcctggctg tggcttctcc tgtcactgct gtctctccct   60
ctgggcctcc cagtgctggg cgcaccacca agactcatct gtgacagcag agtgctggag  120
aggtatctct tggaggccaa ggaggctgag aacattacca caggctgtgc tgaacactgc  180
agcttgaatg agaatatcac tgtcccagac accaaagtta atttctatgc ctggaagagg  240
atggaggttg gcaacaagc agttgaagtg tggcaaggcc tggccctgct gtctgaagct   300
gtcctgaggg gccaggcact gttggtcaac tcttcccagc cttgggagcc cctgcaactg  360
catgtggata aagcagtgag tggccttaga agcctcacca ctctgcttcg ggctctggga  420
gcacagaagg aagccatctc ccctccagat gcagcctcag cagctccact cagaacaatt  480
actgctgaca ctttttagaaa actctttagg gtgtactcca atttcctccg ggggaaagctg  540
aagctgtaca caggtgaggc atgtaggaca ggggacagat aa                     582

SEQ ID NO: 15            moltype = DNA   length = 720
FEATURE                  Location/Qualifiers
misc_feature             1..720
                         note = EGFP coding region inserted into circularization
                          backbone
source                   1..720
                         mol_type = other DNA
                         organism = synthetic construct
SEQUENCE: 15
atggtgagca agggcgagga gctgttcacc ggggtggtgc ccatcctggt cgagctggac   60
ggcgacgtaa acggccacaa gttcagcgtg tctggcgagg gcgagggcga tgccacctac  120
ggcaagctga ccctgaagtt catctgcacc accggcaagc tgcccgtgcc ctggcccacc  180
ctcgtgacca ccctgaccta cggcgtgcag tgcttcagcc gctaccccga ccacatgaag  240
cagcacgact tcttcaagtc cgccatgccc gaaggctacg tccaggagcg caccatcttc  300
ttcaaggacg acggcaacta caagacccgc gccgaggtga agttcgaggg cgacaccctg  360
gtgaaccgca tcgagctgaa gggcatcgac ttcaaggagg acggcaacat cctggggcac  420
aagctggagt acaactacaa cagccacaac gtctatatca tggccgacaa gcagaagaac  480
ggcatcaagg cgaacttcaa gatccgccac aacatcgagg acggcagcgt gcagctcgcc  540
gaccactacc agcagaacac ccccatcggc gacggccccg tgctgctgcc cgacaaccac  600
tacctgagca cccagtccgc cctgagcaaa gaccccaacg agaagcgcga tcacatggtc  660
ctgctggagt tcgtgaccgc cgccgggatc actctcggca tggacgagct gtacaagtaa  720

SEQ ID NO: 16            moltype = DNA   length = 1653
FEATURE                  Location/Qualifiers
misc_feature             1..1653
                         note = FLuc coding region inserted into circularization
                          backbone
source                   1..1653
                         mol_type = other DNA
                         organism = synthetic construct
SEQUENCE: 16
atggaagacg ccaaaaacat aaagaaaggc ccggcgccat tctatccgct ggaagatgga   60
accgctggag agcaactgca taaggctatg aagagatacg cccctggttcc tggaacaatt  120
gcttttacag atgcacatat cgaggtggac atcacttacg ctgagtactt cgaaatgtcc  180
gttcggttgg cagaagctat gaaacgatat gggctgaata caaatcacag aatcgtcgta  240
tgcagtgaaa actctcttca attctttatg ccggtgttgg gcgcgttatt tatcggagtt  300
gcagttgcgc ccgcgaacga catttataat gaacgtgaat tgctcaacag tatgggcatt  360
tcgcagccta ccgtggtgtt cgtttccaaa aggggttgc aaaaaatttt gaacgtgcaa   420
aaaaagctcc caatcatcca aaaaattatt atcatggatt ctaaaacgga ttaccaggga  480
tttcagtcga tgtacacgtt cgtcacatct catctacctc ccggttttaa tgaatacgat  540
tttgtgccag agtccttcga tagggacaag acaattgcac tgatcatgaa ctcctctgga  600
tctactggtc tgcctaaagg tgtcgctctg cctcatagaa ctgcctgcgt gagattctcg  660
catgccagag atcctatttt tggcaatcaa atcattccgg atactgcgat tttaagtgtt  720
gttccattcc atcacggttt tggaatgttt actacactcg atatttgat atgtggattt   780
cgagtcgtct taatgtatag atttgaagaa gagctgtttc tgaggagcct tcaggattac  840
aagattcaaa gtgcgctgct ggtgccaacc ctattctctt tcttcgccaa aagcactctg  900
attgacaaat acgatttatc taatttacac gaaattgctt ctggtggcgc tcccctctct  960
aaggaagtcg gggaagcggt tgccaagagg ttccatctgc aggtatcag gcaaggatat  1020
gggctcactg agactacatc agctattctg attacacccg agggggatga taaaccgggc  1080
gcggtcggta aagttgttcc attttttgaa gcgaaggttg tggatctgga taccgggaaa  1140
acgctgggcg ttaatcaaag aggcgaactg tgtgtgagag gtcctatgat tatgtccggt  1200
tatgtaaaca atccggaagc gaccaacgcc ttgattgaca aggatggatg gctacattct  1260
ggagacatag cttactggga cgaagacgaa cacttcttca tcgttgaccg cctgaagtct  1320
ctgattaagt acaaaggcta tcaggtggct cccgctgaat tggaatccat cttgctccaa  1380
caccccaaca tcttcgacgc aggtgtcgca ggtcttcccg acgatgacgc cggtgaactt  1440
cccgccgccg ttgttgtttt ggagcacgga aagacgatga cggaaaaaga gatcgtggat  1500
```

```
tacgtcgcca gtcaagtaac aaccgcgaaa aagttgcgcg gaggagttgt gtttgtggac  1560
gaagtaccga aagtcttac cggaaaactc gacgcaagaa aaatcagaga gatcctcata   1620
aaggccaaga agggcggaaa gatcgccgtg taa                                1653
```

| SEQ ID NO: 17 | moltype = DNA   length = 4203 |
|---|---|
| FEATURE | Location/Qualifiers |
| misc_feature | 1..4203 |
| | note = Cas9 coding region inserted into circularization backbone |
| source | 1..4203 |
| | mol_type = other DNA |
| | organism = synthetic construct |

SEQUENCE: 17

```
atggccccaa agaagaagcg gaaggtcggt atccacggag tcccagcagc cgacaagaag   60
tacagcatcg gcctggacat cggcaccaac tctgtgggct gggccgtgat caccgacgag  120
tacaaggtgc ccagcaagaa attcaaggtg ctgggcaaca ccgaccggca cagcatcaag  180
aagaacctga tcggagccct gctgttcgac agcggcgaaa cagccgaggc cacccggctg  240
aagagaaccg ccagaagaag atacaccaga cggaagaacc ggatcctgct tctgcaagag  300
atcttcagca acgagatggc caaggtggac gacagcttct ccacagact ggaagagtcc   360
ttcctggtgg aagaggataa gaagcacgag cggcacccca tcttcggcaa catcgtggac  420
gaggtggcct accacgagaa gtaccccacc atctaccacc tgagaaagaa actggtggac  480
agcaccgaca aggccgacct gcggctgatc tatctggccc tggcccacat gatcaagttc  540
cggggccact tcctgatcga gggcgacctg aaccccgaca cagcgacgt ggacaagctg   600
ttcatccagc tggtgcagac ctacaaccag ctgttcgagg aaaacccat caacgccagc    660
ggcgtggacg ccaaggccat cctgtctgcc agactgagca gagcagacg gctggaaaat   720
ctgatcgccc agctgcccgg cgagaagaag aatggcctgt tcggaaacct gattgccctg  780
agcctgggcc tgacccccaa cttcaagagc aacttcgacc tggccgagga tgccaaactg  840
cagctgagca aggacaccta cgacgacgac ctggacaacc tgctggccca gatcggcgac  900
cagtacgccg acctgttcct ggccgccaag aacctgtccg acgccatcct gctgagcgac  960
atcctgagag tgaacaccga gatcaccaag gcccccctga gcgcctctat gatcaagaga 1020
tacgacgagc accaccagga cctgaccctg ctgaaagctc tcgtgcggca gcagctgcct 1080
gagaagtaca agagattt cttcgaccag agcaagaacg gctacgccgg ctacattgac  1140
ggcggagcca gccaggaaga gttctacaag ttcatcaagc ccatcctgga aaagatggac 1200
ggcaccgagg aactgctcgt gaagctgaac agagaggacc tgctgcggaa gcagcggacc 1260
ttcgacaacg gcagcatccc ccaccagatc acctgggag agctgcacgc cattctgcgg 1320
cggcaggaag attttacc attcctgaag gacaacggg aaaagatcga aagatcctg    1380
accttccgca tcccctacta cgtgggccct ctggccaggg aaacagcag attcgcctgg 1440
atgaccagaa agagcgagga aaccatcacc cctggaactc tcgaggaagt ggtggacaag 1500
ggcgcttccg cccagagctt catcgagcgg atgaccaact tcgataagaa cctgcccaac 1560
gagaaggtgc tgcccaagca cagcctgctg tacgagtact tcaccgtgta taacgagctg 1620
accaaagtga aatacgtgac cgagggaatg agaaagcccg ccttcctgag cggcgagcag 1680
aaaaaggcca tcgtggacct gctgttcaag accaaccgga aagtgaccgt gaagcagctg 1740
aaagagctt acttcaagaa aatcgagtgc ttcgactcg tggaaatctc cggcgtggaa  1800
gatcggttca acgcctccct gggcacatac cacgatctgc tgaaaattat caaggacaag 1860
gacttcctgg acaatgagga aaacgaggac attctggaag atatcgtgct gaccctgaca 1920
ctgtttgagg acagagagat gatcgaggaa cggctgaaaa cctatgccca cctgttcgac 1980
gacaaagtga tgaagcagct gaagcggcgg agatacaccg gttggggcag gctgagccgg 2040
aagctgatca acggcatccg ggacaagcag tccggcaaga caatcctgga tttcctgaag 2100
tccgacggct tcgccaacag aaacttcatg cagctgatcc acgacgacag cctgaccttt 2160
aaagaggaca tccagaaagc ccaggtgtcc ggccagggcg atagcctgca cgagcacatt 2220
gccaatctgg ccggcagccc cgccattaag aagggcatct tgcagacagt gaaggtgctg 2280
gacgagctcg tgaaagtgat gggccggcac aagcccgaga acatcgtgat cgaaatggcc 2340
agagagaacc agaccaccca gaagggacag aagaacagcc gcgagagaat gaagcggatc 2400
gaagagggca tcaaagagct gggcagccag atcctgaaag aacacccgt ggaaaacacc 2460
cagctgcaga acgagaagct gtacctgtac tacctgcaga atgggcggga tatgtacgtg 2520
gaccaggaac tggacatcaa ccggctgtcc gactacgatg tggaccatat cgtgcctcag 2580
agctttctga ggacgactc catcgacaac aaggtgctga caagaagcga caagaaccgg 2640
ggcaagagcg acaacgtgcc ctccgaagag gtcgtgaaga gatgaagaa ctactggcgg  2700
cagctgctga acgccaagct gattacccag agaaagttcg acaatctgac aaaggccgac 2760
agaggcggcc tgagcgaact ggataaggcc ggcttcatca gagacagct ggtggaaacc  2820
cggcagatca caaagcacgt ggcacagatc ctggactccc ggatgaacac taagtacgac 2880
gagaatgaca agctgatccg ggaagtgaaa gtgatcaccc tgaagtccaa gctggtgtcc 2940
gatttccgga aggatttcca gttttacaaa gtgcgcgaga tcaacaacta ccaccacgcc 3000
cacgacgcct acctgaacgc cgtcgtggga accgccctga tcaaaaagta ccctaagctg 3060
gaaagcgagt tcgtgtacgg cgactacaag gtgtacgacg tgcggaagat gatcgccaag 3120
agcgagcagg aaatcggcaa ggctaccgcc aagtacttct ctacagcaa catcatgaac 3180
tttttcaaga ccgagattac cctggccaac ggcgagatcc ggaagcggcc tctgatcgag 3240
acaaacggcg aaaccgggga tcgtgtgg gataagggcc gggattttgc caccgtgcgg 3300
aaagtgctga gcatgcccca agtgaatatc gtgaaaaga cgaggtgca gcaggcgga   3360
ttcagcaaag agtctatcct gcccaagagg aacagcgata gctgatcgc cagaaagaag 3420
gactgggacc ctaagaagta cggcggcttc gacagcccca ccgtggccta ttctgtgctg 3480
gtggtggcca agtggaaaa gggcaagtcc aagaaactga gagtgtgaa agagctgctg  3540
gggatcacca tcatggaaag aagcagcttc gagaagaatc catcgactt tctggaagcc 3600
aagggctaca aggaagtgaa aaaggacctg atcatcaagc tgccctgttc 3660
gagctgaaa acggcggaaa gagaatgctg gcctctgccg gcgaactgca aaaggggaaac 3720
gaactggccc tgccctccaa atatgtgaac ttcctgtacc tggccagcca ctatgagaag 3780
ctgaagggct cccccgagga taatgagcag aaacagctgt tgtggaaca gcacaagcac 3840
tacctggacg agatcatcga gcagatcagc gagttctcca gagagtgat cctggccgac 3900
gctaatctgg acaaagtgct gtccgcctac aacaagcacc gggataagcc catcagagag 3960
```

-continued

```
caggccgaga atatcatcca cctgtttacc ctgaccaatc tgggagcccc tgccgccttc  4020
aagtactttg acaccaccat cgaccggaag aggtacacca gcaccaaaga ggtgctggac  4080
gccaccctga tccaccagag catcaccggc ctgtacgaga cacggatcga cctgtctcag  4140
ctggaggcg acaaaaggcc ggcggccacg aaaaaggccg gccaggcaaa aagaaaaag    4200
taa                                                                4203

SEQ ID NO: 18          moltype = RNA   length = 102
FEATURE                Location/Qualifiers
misc_feature           1..102
                       note = sgRNA used to guide Cas9 to GFP
source                 1..102
                       mol_type = other RNA
                       organism = synthetic construct
SEQUENCE: 18
gggcgaggag cgcaccgggg gttttagagc tagaaatagc aagttaaaat aaggctagtc  60
cgttatcaac ttgaaaaagt ggcaccgagt cggtgctttt tt                     102

SEQ ID NO: 19          moltype = DNA   length = 25
FEATURE                Location/Qualifiers
misc_feature           1..25
                       note = Primer used to guide RNase H to a specific RNA
                       digestion site
source                 1..25
                       mol_type = other DNA
                       organism = synthetic construct
SEQUENCE: 19
catggttgtg gccatattat catcg                                        25

SEQ ID NO: 20          moltype = DNA   length = 20
FEATURE                Location/Qualifiers
misc_feature           1..20
                       note = Primer used to sequence across the splice junction
                       and confirmcircularity
source                 1..20
                       mol_type = other DNA
                       organism = synthetic construct
SEQUENCE: 20
cgatcgtcga cattcctgag                                              20

SEQ ID NO: 21          moltype = DNA   length = 20
FEATURE                Location/Qualifiers
misc_feature           1..20
                       note = Primer used to sequence across the splice junction
                       and confirmcircularity
source                 1..20
                       mol_type = other DNA
                       organism = synthetic construct
SEQUENCE: 21
atgctcgtca agaagacagg                                              20

SEQ ID NO: 22          moltype = DNA   length = 213
FEATURE                Location/Qualifiers
misc_feature           1..213
                       note = IRES sequence inserted into circularization backbone
source                 1..213
                       mol_type = other DNA
                       organism = synthetic construct
SEQUENCE: 22
tttgggaatc gcaacacaac atggttaccc atagattgag gaaatttcca ataaactcaa  60
tcttaaggct tgttgtgttg gacaaggtgc cctatttagg gtgaggagcc ttgctggcag  120
ccccagtgaa tcctctattg gataggaaca gctatattgg gtagttgtag cagttgtatt  180
caaacgaatg cagcgttccg aaataccata cct                               213

SEQ ID NO: 23          moltype = DNA   length = 373
FEATURE                Location/Qualifiers
misc_feature           1..373
                       note = IRES sequence inserted into circularization backbone
source                 1..373
                       mol_type = other DNA
                       organism = synthetic construct
SEQUENCE: 23
gtatacgagg ttagttcatt ctcgtataca cgattggaca aatcaaaatt ataatttggt  60
tcagggcctc cctccagcga cggccgaact gggctagcca tgcccatagt aggactagca  120
aacggaggga ctagcctag tggcgagctc cctgggtggt ctaagtcctg agtacaggac   180
agtcgtcagt agttcgacgt gagcagaagc ccacctcgag atgctacgtg gacgagggca  240
tgcccaagac acaccttaac cctagcgggg gtcgctaggg tgaaatcaca ccacgtgatg  300
ggagtacgac ctgatagggc gctgcagagg cccactatta ggctagtata aaatctctg   360
ctgtacatgg cac                                                     373
```

```
SEQ ID NO: 24              moltype = DNA   length = 741
FEATURE                    Location/Qualifiers
misc_feature               1..741
                           note = IRES sequence inserted into circularization backbone
source                     1..741
                           mol_type = other DNA
                           organism = synthetic construct
SEQUENCE: 24
ttaaaacagc ctgtgggttg atcccaccca caggcccatt gggcgctagc actctggtat    60
cacggtacct ttgtgcgcct gttttatacc ccctccccca actgtaactt agaagtaaca   120
cacaccgatc aacagtcagc gtggcacacc agccacgttt tgatcaagca cttctgttac   180
cccggactga gtatcaatag actgctcacg cggttgaagg agaaagcgtt cgttatccgg   240
ccaactactt cgaaaaacct agtaacaccg tggaagttgc agagtgtttc gctcagcact   300
accccagtgt agatcaggtc gatgagtcac cgcattcccc acgggcgacc gtggcggtgg   360
ctgcgttggc ggcctgccca tggggaaacc catgggacgc tctaatacag acatggtgcg   420
aagagtctat tgagctagtt ggtagtcctc cggcccctga atgcggctaa tcctaactgc   480
ggagcacaca ccctcaagcc agagggcagt gtgtcgtaac gggcaactct gcagcggaac   540
cgactacttt gggtgtccgt gttcattttt attcctatac tggctgctta tggtgacaat   600
tgagagatcg ttaccatata gctattggat tggccatccg gtgactaata gagctattat   660
atatcccttt gttgggttta taccacttag cttgaaagag gttaaaacat tacaattcat   720
tgttaagttg aatacagcaa a                                             741

SEQ ID NO: 25              moltype = DNA   length = 696
FEATURE                    Location/Qualifiers
misc_feature               1..696
                           note = IRES sequence inserted into circularization backbone
source                     1..696
                           mol_type = other DNA
                           organism = synthetic construct
SEQUENCE: 25
ttgccagtct gctcgatatc gcaggctggg tccgtgacta cccactcccc ctttcaacgt    60
gaaggctacg atagtgccag ggcgggtact gccgtaagtg ccaccccaaa caacaacaac   120
aaaacaaact cccctcccc ccccttacta tactggccga agccacttgg aataaggccg   180
gtgtgcgttt gtctacatgc tattttctac cgcattaccg tcttatggta atgtgagggt   240
ccagaacctg accctgtctt cttgacgaac actcctaggg gtctttcccc tctcgacaaa   300
ggagtgtaag gtctgttgaa tgtcgtgaag gaagcagttc ctctggaagc ttcttaaaga   360
caaacaacgt ctgtagcgac cctttgcagg cagcggaacc cccaccctgg tgacaggtgc   420
ctctgcggcc aaaagccacg tgtataagat acacctgcaa aggcggcaca accccagtgc   480
cacgttgtga gttggatagt tgtggaaaga gtcaaatggc tctcctcaag cgtattcaac   540
aagggctga aggatgccca gaaggtaccc cattgtatgg gatctgatct ggggcctcgg   600
tgcacgtgct ttacacgtgt tgagtcgagg tgaaaaaacg tctaggcccc ccgaaccacg   660
gggacgtggt tttcctttga aaccacgat tacaat                             696

SEQ ID NO: 26              moltype = DNA   length = 743
FEATURE                    Location/Qualifiers
misc_feature               1..743
                           note = IRES sequence inserted into circularization backbone
source                     1..743
                           mol_type = other DNA
                           organism = synthetic construct
SEQUENCE: 26
ttaaaacagc tgtgggttgt cacccaccca cagggtccac tgggcgctag tacactggta    60
tctcggtacc tttgtacgcc tgttttatac ccctccctg atttgcaact agaagcaac    120
gcaaaccaga tcaatagtag gtgtgacata ccagtcgcat cttgatcaag cacttctgta   180
tccccggacc gagtatcaat agactgtgca cacggttgaa ggagaaaacg tccgttaccc   240
ggctaactac ttcgagaagc ctagtaacgc cattgaagtt gcagagtgtt tcgctcagca   300
ctccccccgt gtagatcagg tcgatgagtc accgcattcc ccacgggcga ccgtggcggt   360
ggctgcgttg gcggcctgcc tatggggtaa cccataggac gctctaatac ggacatggcg   420
tgaagagtct attgagctag ttagtagtcc tccggcccct gaatgcggct aatcctaact   480
gcggagcaca taccccttaat ccaaagggca gtgtgtcgta acgggcaact ctgcagcact   540
accgactact ttgggtgtcc gtgtttcttt ttattcttgt attggctgct tatggtgaca   600
attaaagaat tgttaccata tagctattgg attggccatc cagtgtcaaa cagagctatt   660
gtatatctct ttgttggatt cacacctctc actcttgaaa cgttacacac cctcaattac   720
attatactgc tgaacacgaa gcg                                           743

SEQ ID NO: 27              moltype = DNA   length = 733
FEATURE                    Location/Qualifiers
misc_feature               1..733
                           note = IRES sequence inserted into circularization backbone
source                     1..733
                           mol_type = other DNA
                           organism = synthetic construct
SEQUENCE: 27
ttcaagaggg gtttccggag tttttccgga gccccctctt gg aagtccatgg tgaggggact    60
tgatacctca ccgccgtttg cctaggctat aggctaaatt tccctttccc tgtccttccc   120
ttatttccct ttatcctgtt tgtaaatatt aattcctgca ggtcagggt tctttaatct   180
gtttctctat aagaacactc aattttcacg ctttctgtct tctttcttcc agggctctcc   240
ccttgcccta ggctctggcc gttgcgcccg cggggtcaa ctccatgatt agcatggagc   300
tgtaggagtc taaattgggg acgcagatgt ttggacgtc gccttgcagt gttaacttgg   360
```

```
ctctcatgaa cctctttgat cttcacaag gggtaggcta cgggtgaaac cccttaggct    420
aatacttcta tgaagagatg ccttggatag ggtaacagcg gcggatattg gtgagttgtt    480
aagacaaaaa ccattcaacg ccggaggact ggctctcatc cagtggatgc attgagtgaa    540
ttgattgtca gggctgtctt taggtttaat ctcagacctc tctgtgctta gggcaaacac    600
tatttggcct taaatgggat cctgtgagag ggggtccctc cattgacagc tggactgttc    660
tttggggcct tatgtagtgt ttgcctctga ggtactcagg ggcatttagg tttttcctca    720
ctcttaaaca ata                                                       733
```

```
SEQ ID NO: 28         moltype = DNA  length = 614
FEATURE               Location/Qualifiers
misc_feature          1..614
                      note = IRES sequence inserted into circularization backbone
source                1..614
                      mol_type = other DNA
                      organism = synthetic construct
SEQUENCE: 28
ttaaaactgg atccaggttg ttcccacctg gatttcccac agggagtggt actctgttat    60
tacggtaact ttgtacgcca gttttatctc ccttcccca tgtaacttag aagttttca    120
caaagaccaa tagccggtaa tcagccagat tactgaaggt caagcacttc tgtttccccg    180
gtcaatgttg atatgctcca acagggcaaa acaactgcg atcgttaacc gcaaagcgcc    240
tacgcaaagc ttagtagcat ctttgaaatc gtttggctgg tcgatccgcc atttcccctg    300
gtagacctgg cagatgaggc tagaaatacc ccactggcca cagtgttcta gcctgcgtgg    360
ctgcctgcac accctatggg tgtgaagcca aacaatggac aaggtgtgaa gagcccgtg    420
tgctcgcttt gagtcctccg gcccctgaat gtggctaacc ttaaccctgc agctagagca    480
cgtaacccaa tgtgtatcta gtcgtaatga gcaattgcgg gatgggacca actactttgg    540
gtgtccgtgt ttcactttt ccttatatt tgcttatggt gacaatatat acaatatata    600
tattggcacc atgg                                                      614
```

```
SEQ ID NO: 29         moltype = DNA  length = 449
FEATURE               Location/Qualifiers
misc_feature          1..449
                      note = IRES sequence inserted into circularization backbone
source                1..449
                      mol_type = other DNA
                      organism = synthetic construct
SEQUENCE: 29
ggctcgcatc tctccttcac gcgcccgccg ccctacctga ggccgccatc cacgccggtt    60
gagtcgcgtt ctgccgcctc ccgcctgtgg tgcctcctga actgcgtccg ccgtctaggt    120
aagttagag ctcaggtcga gaccgggcct ttgtccggcg gcctacctag    180
actcagccgg ctctccacgc tttgcctgac cctgcttgtt caactctgcg tctttgtttc    240
gttttctgtt ctgcgccgct acagatcgaa agttccaccc cttcccttt cattcacgac    300
tgactgccgg cttggcccac ggccaagtac cggcgactcc gttggctcgg agccagcgac    360
agcccatcct atagcactct ccaggagaga aacttagtac acagttgggg gctcgtccgg    420
gatacgagcg ccccttatt ccctaggca                                       449
```

```
SEQ ID NO: 30         moltype = DNA  length = 742
FEATURE               Location/Qualifiers
misc_feature          1..742
                      note = IRES sequence inserted into circularization backbone
source                1..742
                      mol_type = other DNA
                      organism = synthetic construct
SEQUENCE: 30
ttaaaacagc tctggggttg tacccacccc agaggcccac gtggcggcta gtactccggt    60
attgcggtac ccttgtacgc ctgttttata ctcccttccc gtaacttaga cgcacaaaac    120
caagttcaat agaaggggggt acaaaccagt accaccacga caagcactt ctgtttcccc    180
ggtgatgtcg tatagactgc ttgcgtggtt gaaagcgacg gatccgttat ccgcttatgt    240
acttcgagaa gcccagtacc acctcggaat cttcgatgcg ttgcgctcag cactcaaccc    300
cagagtgtag cttaggctga tgagtctgga catccctcca cggttgacggt ggtccaggct    360
gcgttggctg cctacctatg gctaacgcca tgggacgcta gttgtgaaca aggtgtgaag    420
agcctattga gctacataag aatcctccgg cccctgaatg cggctaatcc caacctcgga    480
gcaggtggtc acaaaccagt gattggcctg tcgtaacgcg caagtccgtg gcggaaccga    540
ctactttggg tgtccgtgtt tccttttatt ttattgtggc tgcttatggt gacaatcaca    600
gattgttatc ataaagcgaa ttggattggc catccggtga aagtgagact cattatctat    660
ctgtttgctg gatccgctcc attgagtgtg tttactctaa gtacaatttc aacagttatt    720
tcaatcagac aattgtatca ta                                             742
```

```
SEQ ID NO: 31         moltype = DNA  length = 1790
FEATURE               Location/Qualifiers
misc_feature          1..1790
                      note = Optimized anabaena intron-based circRNA construct
                      with CVB3 IRES,GLuc coding region, and pAC tract
source                1..1790
                      mol_type = other DNA
                      organism = synthetic construct
SEQUENCE: 31
gggagaccct cgaccgtcga ttgtccactg gtcaacaata gatgacttac aactaatcgg    60
aaggtgcaga gactcgacgg gagctaccct aacgtcaaga cgagggtaaa gagagagtcc    120
aattctcaaa gccaataggc agtagcgaaa gctgcaagag aatgaaaatc cgttgacctt    180
```

```
aaacggtcgt gtgggttcaa gtccctccac ccccacgccg gaaacgcaat agccgaaaaa  240
caaaaaacaa aaaaaacaaa aaaaaaacca aaaaaacaaa acacattaaa acagcctgtg  300
ggttgatccc acccacaggc ccattgggcg ctagcactct ggtatcacgg tacctttgtg  360
cgcctgtttt ataccccctc ccccaactgt aacttagaag taacacacac cgatcaacag  420
tcagcgtggc acaccagcca cgttttgatc aagcacttct gttaccccgg actgagtatc  480
aatagactgc tcacgcggtt gaaggagaaa gcgttcgtta tccggccaac tacttcgaaa  540
aacctagtaa caccgtggaa gttgcagagt gtttcgctca gcactacccc agtgtagatc  600
aggtcgatga gtcaccgcat tccccacggg cgaccgtggc ggtggctgcg ttggcggcct  660
gcccatgggg aaacccatgg gacgctctaa tacagacatg gtgcgaagag tctattgagc  720
tagttggtag tcctccggcc cctgaatgcg gctaatccta actgcggagc acacaccctc  780
aagccagagg gcagtgtgtc gtaacgggca actctgcagc ggaaccgact actttgggtg  840
tccgtgtttc attttattcc tatactggct gcttatggtg acaattgaga gatcgttacc  900
atatagctat tggattggcc atccggtgac taatagagct attatatatc cctttgttgg  960
gtttatacca cttagcttga aagaggttaa aacattacaa ttcattgtta agttgaaatac 1020
agcaaaatgg gagtcaaagt tctgtttgcc ctgatctgca tcgctgtggc cgaggccaag 1080
cccaccgaga caacgaaga cttcaacatc gtggccgtgg ccagcaactt cgcgaccacg 1140
gatctcgatg ctgaccgcgg gaagttgccc ggcaagaagc tgccgctgga ggtgctcaaa 1200
gagatggaag ccaatgcccg gaaagctggc tgcaccaggg gctgtctgat ctgcctgtcc 1260
cacatcaagt gcacgcccaa gatgaagaag ttcatcccag gacgctgcca cacctacgaa 1320
ggcgacaaaa gtccgcaca gggcggcata ggcgaggcga tcgtcgacat tcctgagatt 1380
cctgggttca aggacttgga gcccatggag cagttcatcg cacaggtcga tctgtgtgtg 1440
gactgcacaa ctggctgcct caagggctt gccaacgtgc agtgttctga cctgctcaag 1500
aagtggctgc cgcaacgctg tgcgaccttt gccagcaaga tccagggcca ggtggacaag 1560
atcaagggg ccggtggtga ctaaaaaaaa caaaaaacaa aacggctatt atgcgttacc 1620
ggcgagacgc tacggactta aataattgag ccttaaagaa gaaattcttt aagtggatgc 1680
tctcaaactc agggaaaacct aaatctagtt atagacaagg caatcctgag ccaagccgaa 1740
gtagtaatta gtaagaccag tggacaatcg acgataaca gcatatctag            1790

SEQ ID NO: 32          moltype = DNA   length = 576
FEATURE                Location/Qualifiers
misc_feature           1..576
                       note = Linear control construct
source                 1..576
                       mol_type = other DNA
                       organism = synthetic construct
SEQUENCE: 32
gggagaccct cgaatgggag tcaaagttct gtttgccctg atctgcatcg ctgtggccga   60
ggccaagccc accgagaaca cgaagactt caacatcgtg gccgtggcca gcaacttcgc  120
gaccacggat ctcgatgctg accgcggaa gttgcccggc aagaagctgc cgctggaggt  180
gctcaaagag atggaagcca atgcccgaa agctggctgc accaggggct gtctgatctg  240
cctgtcccac atcaagtgca cgcccaagat gaagaagttc atcccaggac gctgccacac  300
ctacgaaggc gacaaagagt ccgcacaggg cggcataggc gaggcgatcg tcgacattcc  360
tgagattcct gggttcaagg acttggagcc catggagcag ttcatcgcac aggtcgatct  420
gtgtgtggac tgcacaactg gctgcctcaa agggcttgcc aacgtgcagt gttctgacct  480
gctcaagaag tggctgccgc aacgctgtgc gacctttgcc agcaagatcc agggccaggt  540
ggacaagatc aagggggccg gtggtgacta atctag                          576

SEQ ID NO: 33          moltype = DNA   length = 42
FEATURE                Location/Qualifiers
misc_feature           1..42
                       note = Optimized splint
source                 1..42
                       mol_type = other DNA
                       organism = synthetic construct
SEQUENCE: 33
gtttgtggtt cgtgcgtctc cgtgctgttc tgttggtgtg gg                     42

SEQ ID NO: 34          moltype = DNA   length = 20
FEATURE                Location/Qualifiers
misc_feature           1..20
                       note = Probe
source                 1..20
                       mol_type = other DNA
                       organism = synthetic construct
SEQUENCE: 34
ttgaacccag gaatctcagg                                              20

SEQ ID NO: 35          moltype = DNA   length = 258
FEATURE                Location/Qualifiers
misc_feature           1..258
                       note = IRES Sequence HCV
source                 1..258
                       mol_type = other DNA
                       organism = synthetic construct
```

```
SEQUENCE: 35
gccagccccc tgatgggggc gacactccac catgaatcac tccctgtga ggaactactg    60
tcttcacgca gaaagcgtct agccatggcg ttagtatgag tgtcgtgcag cctccaggac   120
cccccctccc gggagagcca tagtggtctg cggaaccggt gagtacaccg gaattgccag   180
gacgaccggg tcctttcttg gataaacccg ctcaatgcct ggagatttgg gcgtgccccc   240
gcaagactgc tagccgag                                                 258

SEQ ID NO: 36          moltype = DNA   length = 264
FEATURE                Location/Qualifiers
misc_feature           1..264
                       note = IRES Sequence EMCV
source                 1..264
                       mol_type = other DNA
                       organism = synthetic construct
SEQUENCE: 36
cccccctctc cctcccccc taacgttact ggccgaagcc gcttggaata aggccggtgt    60
gcgtttgtct atatgttatt ttccaccata ttgccgtctt ttggcaatgt gagggcccgg   120
aaacctggcc ctgtcttctt gacgagcatt cctaggggtc tttcccctct cgccaaagga   180
atgcaaggtc tgttgaatgt cgtgaaggaa gcagttcctc tggaagcttc ttgaagacaa   240
acaacgtctg tagcgaccct ttgc                                          264

SEQ ID NO: 37          moltype = DNA   length = 201
FEATURE                Location/Qualifiers
misc_feature           1..201
                       note = IRES Sequence NRF
source                 1..201
                       mol_type = other DNA
                       organism = synthetic construct
SEQUENCE: 37
cagagtaatg acatggttcc ttccatcctc caaggtgac caataatagt ttgtaagtat    60
cattatgaac taatgaattt tcaacatatt tgatatattt caatccattg ccatcattgt   120
tcttatcgat atttgagttg gctcactttg ccagtaagag tctattcaaa ttggcttctg   180
agtccatttg acacaacacc t                                             201

SEQ ID NO: 38          moltype = DNA   length = 199
FEATURE                Location/Qualifiers
misc_feature           1..199
                       note = IRES Sequence CRPV
source                 1..199
                       mol_type = other DNA
                       organism = synthetic construct
SEQUENCE: 38
aaagcaaaaa tgtgatcttg cttgtaaata caattttgag aggttaataa attacaagta    60
gtgctatttt tgtatttagg ttagctattt agctttacgt tccaggatgc ctagtggcag   120
ccccacaata tccaggaagc cctctctgcg gttttttcaga ttaggtagtc gaaaacctta   180
agaaatttac ctgctacat                                                199

SEQ ID NO: 39          moltype = DNA   length = 170
FEATURE                Location/Qualifiers
misc_feature           1..170
                       note = IRES Sequence GTX
source                 1..170
                       mol_type = other DNA
                       organism = synthetic construct
SEQUENCE: 39
ttctgacatc cggcgggtat ttcagaaccg gcgggtagta ctgtaccggc gggtttctga    60
catccggcgg gttacagtca tccgcgggt tactacagtc cggcgggtta ctcagaaccg   120
gcgggttaga attcctccgg cgggtgactc acaaccccag aaacagagcc               170

SEQ ID NO: 40          moltype = DNA   length = 43
FEATURE                Location/Qualifiers
misc_feature           1..43
                       note = IRES Sequence Rbm3
source                 1..43
                       mol_type = other DNA
                       organism = synthetic construct
SEQUENCE: 40
tttataattt cttcttccag aagaatttgt tggtaaagcc acc                      43

SEQ ID NO: 41          moltype = DNA   length = 174
FEATURE                Location/Qualifiers
misc_feature           1..174
                       note = IRES Sequence TMEV
source                 1..174
                       mol_type = other DNA
                       organism = synthetic construct
```

```
SEQUENCE: 41
caatctttga tgtcgtctgc ggtgaatacg ctaatcgtgt tttcaccatc cttggcaaag    60
agaacggtct cctgactgtt gaacaagccg tgcttggctt gccgggtatg gatcccatgg   120
agaaagacac ctcccctgga ttgccctaca cccaacaagg actcagacga actg         174

SEQ ID NO: 42            moltype = DNA   length = 197
FEATURE                  Location/Qualifiers
misc_feature             1..197
                         note = IRES Sequence PPV
source                   1..197
                         mol_type = other DNA
                         organism = synthetic construct
SEQUENCE: 42
ctagggcgcg ccagtcctcc aaacactcaa cacacagacc cggaggctgt cgcttcaggt    60
gtgtcatcta tcacaggtcc catgtcgaca tttatggcat cacccactgt tgaggaactt   120
gccggagaca catcagatag gttgttccag ctaattgcag gtaactcatc ccttattacc   180
caggagtcag cacgact                                                  197

SEQ ID NO: 43            moltype = DNA   length = 31
FEATURE                  Location/Qualifiers
misc_feature             1..31
                         note = Ana1 5 Prime Spacer
source                   1..31
                         mol_type = other DNA
                         organism = synthetic construct
SEQUENCE: 43
gaaaccaact ttattactat attccccaca a                                   31

SEQ ID NO: 44            moltype = DNA   length = 40
FEATURE                  Location/Qualifiers
misc_feature             1..40
                         note = Ana2 5 Prime Spacer
source                   1..40
                         mol_type = other DNA
                         organism = synthetic construct
SEQUENCE: 44
cgccggaaac gcaatagccg aaaaacaaaa aacaaaaaaa                          40

SEQ ID NO: 45            moltype = DNA   length = 40
FEATURE                  Location/Qualifiers
misc_feature             1..40
                         note = Ana2 3 Prime Spacer
source                   1..40
                         mol_type = other DNA
                         organism = synthetic construct
SEQUENCE: 45
aaaaaacaaa aaacaaaacg gctattatgc gttaccggcg                          40

SEQ ID NO: 46            moltype = DNA   length = 70
FEATURE                  Location/Qualifiers
misc_feature             1..70
                         note = Ana3 5 Prime Spacer
source                   1..70
                         mol_type = other DNA
                         organism = synthetic construct
SEQUENCE: 46
cgccggaaac gcaatagccg aaaaacaaaa aacaaaaaaa acaaaaaaaa aaccaaaaaa    60
acaaaacaca                                                           70

SEQ ID NO: 47            moltype = DNA   length = 70
FEATURE                  Location/Qualifiers
misc_feature             1..70
                         note = Ana4 5 Prime Spacer
source                   1..70
                         mol_type = other DNA
                         organism = synthetic construct
SEQUENCE: 47
cgccggaaac gcaatagccg aaaaacaaaa aacaaaaaaa aaaaaaaaaa aaaaaaaaaa    60
aaaaaaaaaa                                                           70

SEQ ID NO: 48            moltype = DNA   length = 37
FEATURE                  Location/Qualifiers
misc_feature             1..37
                         note = Ana5 5 Prime Spacer
source                   1..37
                         mol_type = other DNA
                         organism = synthetic construct
```

```
SEQUENCE: 48
tgatctgaaa ccaactttat tactatattc cccacaa                              37

SEQ ID NO: 49           moltype = DNA   length = 31
FEATURE                 Location/Qualifiers
misc_feature            1..31
                        note = Ana6 5 Prime Spacer
source                  1..31
                        mol_type = other DNA
                        organism = synthetic construct
SEQUENCE: 49
gaaaccaact ttattactat attcctctta a                                    31

SEQ ID NO: 50           moltype = DNA   length = 37
FEATURE                 Location/Qualifiers
misc_feature            1..37
                        note = Ana7 5 Prime Spacer
source                  1..37
                        mol_type = other DNA
                        organism = synthetic construct
SEQUENCE: 50
gaaaccaact ttattactgg catatccgtc cccacaa                              37

SEQ ID NO: 51           moltype = DNA   length = 33
FEATURE                 Location/Qualifiers
misc_feature            1..33
                        note = Ana pA 5 Prime Spacer
source                  1..33
                        mol_type = other DNA
                        organism = synthetic construct
SEQUENCE: 51
aaaaaaaaaa aaaaaaaaaa aaaaaaaaaa aaa                                  33

SEQ ID NO: 52           moltype = DNA   length = 33
FEATURE                 Location/Qualifiers
misc_feature            1..33
                        note = Ana pA 3 Prime Spacer
source                  1..33
                        mol_type = other DNA
                        organism = synthetic construct
SEQUENCE: 52
aaaaaaaaaa aaaaaaaaaa aaaaaaaaaa aaa                                  33

SEQ ID NO: 53           moltype = DNA   length = 30
FEATURE                 Location/Qualifiers
misc_feature            1..30
                        note = Ana pAC 5 Prime Spacer
source                  1..30
                        mol_type = other DNA
                        organism = synthetic construct
SEQUENCE: 53
acaaaaaaaa aaccaaaaaa acaaaacaca                                      30

SEQ ID NO: 54           moltype = DNA   length = 33
FEATURE                 Location/Qualifiers
misc_feature            1..33
                        note = Ana pT 5 Prime Spacer
source                  1..33
                        mol_type = other DNA
                        organism = synthetic construct
SEQUENCE: 54
tttttttttt tttttttttt tttttttttt ttt                                  33

SEQ ID NO: 55           moltype = DNA   length = 33
FEATURE                 Location/Qualifiers
misc_feature            1..33
                        note = Ana pT 3 Prime Spacer
source                  1..33
                        mol_type = other DNA
                        organism = synthetic construct
SEQUENCE: 55
tttttttttt tttttttttt tttttttttt ttt                                  33
```

```
SEQ ID NO: 56            moltype = DNA   length = 33
FEATURE                  Location/Qualifiers
misc_feature             1..33
                         note = Ana pC 5 Prime Spacer
source                   1..33
                         mol_type = other DNA
                         organism = synthetic construct
SEQUENCE: 56
cccccccccc cccccccccc cccccccccc ccc                                         33

SEQ ID NO: 57            moltype = DNA   length = 33
FEATURE                  Location/Qualifiers
misc_feature             1..33
                         note = Ana pC 3 Prime Spacer
source                   1..33
                         mol_type = other DNA
                         organism = synthetic construct
SEQUENCE: 57
cccccccccc cccccccccc cccccccccc ccc                                         33

SEQ ID NO: 58            moltype = DNA   length = 33
FEATURE                  Location/Qualifiers
misc_feature             1..33
                         note = Ana pG 3 Prime Spacer
source                   1..33
                         mol_type = other DNA
                         organism = synthetic construct
SEQUENCE: 58
gggggggggg gggggggggg gggggggggg ggg                                         33

SEQ ID NO: 59            moltype = DNA   length = 50
FEATURE                  Location/Qualifiers
misc_feature             1..50
                         note = BG 5 Prime UTR
source                   1..50
                         mol_type = other DNA
                         organism = synthetic construct
SEQUENCE: 59
acatttgctt ctgacacaac tgtgttcact agcaacctca aacagacacc                       50

SEQ ID NO: 60            moltype = DNA   length = 132
FEATURE                  Location/Qualifiers
misc_feature             1..132
                         note = BG 3 Prime UTR
source                   1..132
                         mol_type = other DNA
                         organism = synthetic construct
SEQUENCE: 60
gctcgctttc ttgctgtcca atttctatta aaggttcctt tgttccctaa gtccaactac            60
taaactgggg gatattatga agggccttga gcatctggat tctgcctaat aaaaaacatt           120
tattttcatt gc                                                               132

SEQ ID NO: 61            moltype = DNA   length = 140
FEATURE                  Location/Qualifiers
misc_feature             1..140
                         note = 5 Prime HHV UTR
source                   1..140
                         mol_type = other DNA
                         organism = synthetic construct
SEQUENCE: 61
ggacagatcg cctggagacg ccatccacgc tgttttgacc tccatagaag acaccgggac            60
cgatccagcc tccgcggccg ggaacggtgc attggaacgc ggattccccg tgccaagagt           120
gactcaccgt ccttgacacg                                                       140

SEQ ID NO: 62            moltype = DNA   length = 105
FEATURE                  Location/Qualifiers
misc_feature             1..105
                         note = 3 Prime HGH UTR
source                   1..105
                         mol_type = other DNA
                         organism = synthetic construct
SEQUENCE: 62
cgggtggcat ccctgtgacc cctccccagt gcctctcctg gccctggaag ttgccactcc            60
agtgcccacc agccttgtcc taataaaatt aagttgcatc aagct                           105
```

```
SEQ ID NO: 63            moltype = DNA  length = 41
FEATURE                  Location/Qualifiers
misc_feature             1..41
                         note = AL 5 Prime UTR
source                   1..41
                         mol_type = other DNA
                         organism = synthetic construct
SEQUENCE: 63
ctagcttttc tcttctgtca accccacacg cctttggcac a                          41

SEQ ID NO: 64            moltype = DNA  length = 186
FEATURE                  Location/Qualifiers
misc_feature             1..186
                         note = AL 3 Prime UTR
source                   1..186
                         mol_type = other DNA
                         organism = synthetic construct
SEQUENCE: 64
catcacattt aaaagcatct cagcctacca tgagaataag agaaagaaaa tgaagatcaa       60
aagcttattc atctgttttt cttttcgtt ggtgtaaagc caacaccctg tctaaaaaac      120
ataaatttct ttaatcattt tgcctctttt ctctgtgctt caattaataa aaaatggaaa    180
gaatcg                                                                186

SEQ ID NO: 65            moltype = DNA  length = 20
FEATURE                  Location/Qualifiers
misc_feature             1..20
                         note = Ana1 5 Prime Homology Arm
source                   1..20
                         mol_type = other DNA
                         organism = synthetic construct
SEQUENCE: 65
ccgtcgattg tccactggtc                                                  20

SEQ ID NO: 66            moltype = DNA  length = 20
FEATURE                  Location/Qualifiers
misc_feature             1..20
                         note = Ana1 3 Prime Homology Arm
source                   1..20
                         mol_type = other DNA
                         organism = synthetic construct
SEQUENCE: 66
gaccagtgga caatcgacgg                                                  20

SEQ ID NO: 67            moltype = DNA  length = 12
FEATURE                  Location/Qualifiers
misc_feature             1..12
                         note = T4 5 Prime inherent Homology Arm
source                   1..12
                         mol_type = other DNA
                         organism = synthetic construct
SEQUENCE: 67
aatctgataa at                                                          12

SEQ ID NO: 68            moltype = DNA  length = 12
FEATURE                  Location/Qualifiers
misc_feature             1..12
                         note = T4 3 Prime inherent Homology Arm
source                   1..12
                         mol_type = other DNA
                         organism = synthetic construct
SEQUENCE: 68
atttatcaga tt                                                          12

SEQ ID NO: 69            moltype = DNA  length = 37
FEATURE                  Location/Qualifiers
misc_feature             1..37
                         note = T41 5 Prime Homology Arm
source                   1..37
                         mol_type = other DNA
                         organism = synthetic construct
SEQUENCE: 69
agcctacgat cgggctaaca gctcgaatct gataaat                               37
```

```
SEQ ID NO: 70            moltype = DNA   length = 37
FEATURE                  Location/Qualifiers
misc_feature             1..37
                         note = T41 3 Prime Homology Arm
source                   1..37
                         mol_type = other DNA
                         organism = synthetic construct
SEQUENCE: 70
atttatcaga ttcgagctgt tagcccgatc gtaggct                              37

SEQ ID NO: 71            moltype = DNA   length = 19
FEATURE                  Location/Qualifiers
misc_feature             1..19
                         note = T42 5 Prime Homology Arm
source                   1..19
                         mol_type = other DNA
                         organism = synthetic construct
SEQUENCE: 71
gaatggaatt ggttctaca                                                  19

SEQ ID NO: 72            moltype = DNA   length = 19
FEATURE                  Location/Qualifiers
misc_feature             1..19
                         note = T42 3 Prime Homology Arm
source                   1..19
                         mol_type = other DNA
                         organism = synthetic construct
SEQUENCE: 72
tgtaggacta attccattt                                                  19

SEQ ID NO: 73            moltype =    length =
SEQUENCE: 73
000

SEQ ID NO: 74            moltype =    length =
SEQUENCE: 74
000

SEQ ID NO: 75            moltype = DNA   length = 29
FEATURE                  Location/Qualifiers
misc_feature             1..29
                         note = Ana2 5 Prime Homology Arm
source                   1..29
                         mol_type = other DNA
                         organism = synthetic construct
SEQUENCE: 75
ggtaactgtc cgtcgattgt ccactggtc                                       29

SEQ ID NO: 76            moltype = DNA   length = 29
FEATURE                  Location/Qualifiers
misc_feature             1..29
                         note = Ana2 3 Prime Homology Arm
source                   1..29
                         mol_type = other DNA
                         organism = synthetic construct
SEQUENCE: 76
gaccagtgga caatcgacgg acagttacc                                       29

SEQ ID NO: 77            moltype = DNA   length = 17
FEATURE                  Location/Qualifiers
misc_feature             1..17
                         note = 5 prime exon at splice junction
source                   1..17
                         mol_type = other DNA
                         organism = synthetic construct
SEQUENCE: 77
gagacgtttt cttgggt                                                    17

SEQ ID NO: 78            moltype = DNA   length = 20
FEATURE                  Location/Qualifiers
misc_feature             1..20
                         note = 3 prime exon at splice junction
source                   1..20
                         mol_type = other DNA
                         organism = synthetic construct
SEQUENCE: 78
ctaccgttta atattgcgtc                                                 20
```

```
SEQ ID NO: 79          moltype = DNA  length = 37
FEATURE                Location/Qualifiers
misc_feature           1..37
                       note = exon sequence at splice junction
source                 1..37
                       mol_type = other DNA
                       organism = synthetic construct
SEQUENCE: 79
gagacgtttt cttgggtcta ccgtttaata ttgcgtc                                37
```

CIRCULAR RNA FOR TRANSLATION IN EUKARYOTIC CELLS

RELATED APPLICATION(S)

This application is a Continuation of U.S. application Ser. No. 17/492,512, filed Oct. 1, 2021, which is a Divisional of U.S. application Ser. No. 17/191,697, filed Mar. 3, 2021, now U.S. Pat. No. 11,203,767, which is a Continuation of U.S. application Ser. No. 16/432,177, filed Jun. 5, 2019, which claims the benefit of U.S. Provisional Application No. 62/851,548, filed on May 22, 2019, U.S. Provisional Application No. 62/791,028, filed on Jan. 10, 2019 and U.S. Provisional Application No. 62/681,617, filed on Jun. 6, 2018. The entire teachings of the above applications are incorporated herein by reference.

GOVERNMENT SUPPORT

This invention was made with government support under W32P4Q-13-1-0011 from Defense Advanced Research Projects Agency and under 5R01HL125428 from National Institutes of Health. The government has certain rights in the invention.

INCORPORATION BY REFERENCE OF MATERIAL IN XML

This application incorporates by reference the Sequence Listing contained in the following eXtensible Markup Language (XML) file being submitted concurrently herewith:
  a) File name: 00502311020 Sequence Listing.xml; created Sep. 1, 2022, 131, 396 Bytes in size.

BACKGROUND

Messenger RNA (mRNA) has broad potential for a range of therapeutic and engineering applications. However, one fundamental limitation to its use is its relatively short half-life in biological systems. Thus, there is a need to extend the duration of protein expression from full-length RNA messages.

SUMMARY

In certain aspects, provided herein is a vector for making circular RNA(circRNA).

In some embodiments, the vector comprises the following elements operably connected to each other and, in some embodiments, arranged in the following sequence: a.) a 5' homology arm, b.) a 3' group I intron fragment containing a 3' splice site dinucleotide, c.) a protein coding or noncoding region, d.) a 5' group I intron fragment containing a 5' splice site dinucleotide, and e.) a 3' homology arm. In certain embodiments said vector allows production of a circular RNA that is translatable and/or biologically active inside eukaryotic cells. In some embodiments, the biologically active RNA is, for example, an miRNA sponge, or long non-coding RNA.

In some embodiments, said vector comprises the following elements operably connected to each other and arranged in the following sequence: a.) a 5' homology arm, b.) a 3' group I intron fragment containing a 3' splice site dinucleotide, c.) optionally, a 5' spacer sequence, d.) optionally, an internal ribosome entry site (IRES), e.) a protein coding or noncoding region, f) optionally, a 3' spacer sequence, g.) a 5' group I intron fragment containing a 5' splice site dinucleotide, and h.) a 3' homology arm. In certain embodiments, said vector allows production of a circular RNA that is translatable and/or biologically active inside eukaryotic cells.

In some embodiments, the vector comprises the following elements operably connected to each other and arranged in the following sequence: a.) a 5' homology arm, b.) a 3' group I intron fragment containing a 3' splice site dinucleotide, c.) a 5' spacer sequence, d.) an internal ribosome entry site (IRES), e.) a protein coding or noncoding region, f.) a 5' group I intron fragment containing a 5' splice site dinucleotide, and g.) a 3' homology arm. In some embodiments, said vector allows production of a circular RNA that is translatable and/or biologically active inside eukaryotic cells.

In some embodiments, the vector comprises the following elements operably connected to each other and arranged in the following sequence: a.) a 5' homology arm, b.) a 3' group I intron fragment containing a 3' splice site dinucleotide, c.) a 5' spacer sequence, d.) a protein coding or noncoding region, e.) a 3' spacer sequence, f.) a 5' group I intron fragment containing a 5' splice site dinucleotide, and g.) a 3' homology arm. In some embodiments, said vector allows production of a circular RNA that is translatable and/or biologically active inside eukaryotic cells.

In some embodiments, said vector comprises the following elements operably connected to each other and arranged in the following sequence: a.) a 5' homology arm, b.) a 3' group I intron fragment containing a 3' splice site dinucleotide, c.) an internal ribosome entry site (IRES), d.) a protein coding or noncoding region, e.) a 3' spacer sequence, f) a 5' group I intron fragment containing a 5' splice site dinucleotide, and g.) a 3' homology arm. In some embodiments, said vector allows production of a circular RNA that is translatable and/or biologically active inside eukaryotic cells.

In some embodiments, said vector comprises the following elements operably connected to each other and arranged in the following sequence: a.) a 5' homology arm, b.) a 3' group I intron fragment containing a 3' splice site dinucleotide, c.) a protein coding or noncoding region, d.) a 3' spacer sequence, e.) a 5' group I intron fragment containing a 5' splice site dinucleotide, and f.) a 3' homology arm. In some embodiments, said vector allows production of a circular RNA that is translatable and/or biologically active inside eukaryotic cells.

In some embodiments, said vector comprises the following elements operably connected to each other and arranged in the following sequence: a.) a 5' homology arm, b.) a 3' group I intron fragment containing a 3' splice site dinucleotide, c.) a 5' spacer sequence, d.) a protein coding or noncoding region, e.) a 5' group I intron fragment containing a 5' splice site dinucleotide, and f.) a 3' homology arm. In some embodiments, said vector allows production of a circular RNA that is translatable and/or biologically active inside eukaryotic cells.

In some embodiments, said vector comprises the following elements operably connected to each other and arranged in the following sequence: a.) a 5' homology arm, b.) a 3' group I intron fragment containing a 3' splice site dinucleotide, c.) an internal ribosome entry site (IRES), d.) a protein coding or noncoding region, e.) a 5' group I intron fragment containing a 5' splice site dinucleotide, and f) a 3' homology arm. In some embodiments, said vector allows production of a circular RNA that is translatable and/or biologically active inside eukaryotic cells.

In some embodiments, the vector comprises the following elements operably connected to each other and arranged in the following sequence: a.) a 5' homology arm, b.) a 3' group I intron fragment containing a 3' splice site dinucleotide, c.) a 5' spacer sequence, d.) an internal ribosome entry site (IRES), e.) a protein coding or noncoding region, f) a 3' spacer sequence, g.) a 5' group I intron fragment containing a 5' splice site dinucleotide, and h.) a 3' homology arm. In some embodiments, said vector allowing production of a circular RNA that is translatable and/or biologically active inside eukaryotic cells.

In one embodiment, the 3' group I intron fragment and/or the 5' group I intron fragment is from a *Cyanobacterium Anabaena* sp. pre-tRNA-Leu gene or T4 phage Td gene.

In one embodiment, the 3' group I intron fragment and/or the 5' group I intron fragment is from a *Cyanobacterium Anabaena* sp. pre-tRNA-Leu gene.

In another embodiment, if present, the IRES sequence is an IRES sequence of *Taura* syndrome virus, *Triatoma* virus, Theiler's encephalomyelitis virus, simian Virus 40, *Solenopsis invicta* virus 1, *Rhopalosiphum padi* virus, Reticuloendotheliosis virus, fuman poliovirus 1, *Plautia stali* intestine virus, Kashmir bee virus, Human rhinovirus 2, *Homalodisca coagulata* virus-1, Human Immunodeficiency Virus type 1, *Homalodisca coagulata* virus—1, Himetobi P virus, Hepatitis C virus, Hepatitis A virus, Hepatitis GB virus, foot and mouth disease virus, Human enterovirus 71, Equine rhinitis virus, *Ectropis obliqua* picorna-like virus, Encephalomyocarditis virus (EMCV), *Drosophila* C Virus, Crucifer tobamo virus, Cricket paralysis virus, Bovine viral diarrhea virus 1, Black Queen Cell Virus, Aphid lethal paralysis virus, Avian encephalomyelitis virus, Acute bee paralysis virus, Hibiscus chlorotic ringspot virus, Classical swine fever virus, Human FGF2, Human SFTPA1, Human AML1/RUNX1, *Drosophila* antennapedia, Human AQP4, Human AT1R, Human BAG-1, Human BCL2, Human BiP, Human c-IAP1, Human c-myc, Human eIF4G, Mouse NDST4L, Human LEF1, Mouse HIF1 alpha, Human n.myc, Mouse Gtx, Human p27kip1, Human PDGF2/c-sis, Human p53, Human Pim-1, Mouse Rbm3, *Drosophila* reaper, Canine Scamper, *Drosophila* Ubx, Human UNR, Mouse UtrA, Human VEGF-A, Human XIAP, Salivirus, Cosavirus, Parechovirus, *Drosophila* hairless, *S. cerevisiae* TFIID, *S. cerevisiae* YAP1, Human c-src, Human FGF-1, Simian picomavirus, Turnip crinkle virus, an aptamer to eIF4G, Coxsackievirus B3 (CVB3) or Coxsackievirus A (CVB1/2). In yet another embodiment, the IRES is an IRES sequence of Coxsackievirus B3 (CVB3). In a further embodiment, the IRES is an IRES sequence of Encephalomyocarditis virus.

In one embodiment, the protein coding region encodes a protein of eukaryotic or prokaryotic origin. In another embodiment, the protein coding region encodes human protein or non-human protein. In some embodiments, the protein coding region encodes one or more antibodies. For example, in some embodiments, the protein coding region encodes human antibodies. In one embodiment, the protein coding region encodes a protein selected from hFIX, SP-B, VEGF-A, human methylmalonyl-CoA mutase (hMUT), CFTR, cancer self-antigens, and additional gene editing enzymes like Cpf1, zinc finger nucleases (ZFNs) and transcription activator-like effector nucleases (TALENs). In another embodiment, the protein coding region encodes a protein for therapeutic use. In one embodiment, the human antibody encoded by the protein coding region is an anti-HIV antibody. In one embodiment, the antibody encoded by the protein coding region is a bispecific antibody. In one embodiment, the bispecific antibody is specific for CD19 and CD22. In another embodiment, the bispecific antibody is specific for CD3 and CLDN6. In one embodiment, the protein coding region encodes a protein for diagnostic use.

In one embodiment, the protein coding region encodes *Gaussia* luciferase (Gluc), Firefly luciferase (Fluc), enhanced green fluorescent protein (eGFP), human erythropoietin (hEPO), or Cas9 endonuclease.

In one embodiment, the 5' homology arm is about 5-50 nucleotides in length. In another embodiment, the 5' homology arm is about 9-19 nucleotides in length. In some embodiments, the 5' homology arm is at least 5, 6, 7, 8, 9, 10, 11, 12, 13, 14, 15, 16, 17, 18 or 19 nucleotides in length. In some embodiments, the 5' homology arm is no more than 50, 45, 40, 35, 30, 25 or 20 nucleotides in length. In some embodiments, the 5' homology arm is 5, 6, 7, 8, 9, 10, 11, 12, 13, 14, 15, 16, 17, 18 or 19 nucleotides in length.

In one embodiment, the 3' homology arm is about 5-50 nucleotides in length. In another embodiment, the 3' homology arm is about 9-19 nucleotides in length. In some embodiments, the 3' homology arm is at least 5, 6, 7, 8, 9, 10, 11, 12, 13, 14, 15, 16, 17, 18 or 19 nucleotides in length. In some embodiments, the 3' homology arm is no more than 50, 45, 40, 35, 30, 25 or 20 nucleotides in length. In some embodiments, the 3' homology arm is 5, 6, 7, 8, 9, 10, 11, 12, 13, 14, 15, 16, 17, 18 or 19 nucleotides in length.

In one embodiment, the 5' spacer sequence is at least 10 nucleotides in length. In another embodiment, the 5' spacer sequence is at least 15 nucleotides in length. In a further embodiment, the 5' spacer sequence is at least 30 nucleotides in length. In some embodiments, the 5' spacer sequence is at least 7, 8, 9, 10, 11, 12, 13, 14, 15, 16, 17, 18, 19, 20, 25 or 30 nucleotides in length. In some embodiments, the 5' spacer sequence is no more than 100, 90, 80, 70, 60, 50, 45, 40, 35 or 30 nucleotides in length. In some embodiments the 5' spacer sequence is between 20 and 50 nucleotides in length. In certain embodiments, the 5' spacer sequence is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides in length. In one embodiment, the 5' spacer sequence is a polyA sequence. In another embodiment, the 5' spacer sequence is a polyA-C sequence.

In one embodiment, the 3' spacer sequence is at least 10 nucleotides in length. In another embodiment, the 3' spacer sequence is at least 15 nucleotides in length. In a further embodiment, the 3' spacer sequence is at least 30 nucleotides in length. In some embodiments, the 3' spacer sequence is at least 7, 8, 9, 10, 11, 12, 13, 14, 15, 16, 17, 18, 19, 20, 25 or 30 nucleotides in length. In some embodiments, the 3' spacer sequence is no more than 100, 90, 80, 70, 60, 50, 45, 40, 35 or 30 nucleotides in length. In some embodiments the 3' spacer sequence is between 20 and 50 nucleotides in length. In certain embodiments, the 3' spacer sequence is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides in length. In one embodiment, the 3' spacer sequence is a polyA sequence. In another embodiment, the 5' spacer sequence is a polyA-C sequence.

In one embodiment, the vector further comprises an RNA polymerase promoter. In another embodiment, the RNA polymerase promoter is a T7 virus RNA polymerase promoter, T6 virus RNA polymerase promoter, SP6 virus RNA polymerase promoter, T3 virus RNA polymerase promoter, or T4 virus RNA polymerase promoter.

In one embodiment, the vector is used to transcribe circular RNA with the size range of about 500 to about 10,000 nucleotides. In some embodiments, the circular RNA is at least 500, 550, 600, 650, 700, 750, 800, 850, 900, 950, 1,000, 1,100, 1,200, 1,300, 1,400, 1,500, 1,600, 1,700, 1,800, 1,900, 2,000, 2,500, 3,000, 3,500, 4,000, 4,500 or 5,000 nucleotides in size. In some embodiments, the circular RNA is no more than 10,000, 9,000, 8,000, 7,000, 6,000, 5,000 or 4,000 nucleotides in size.

In another embodiment, the IRES is an IRES sequence from Coxsackievirus B3 (CVB3), the protein coding region encodes Guassia luciferase (Gluc) and the spacer sequences are polyA-C.

In some embodiments, the IRES, if present, is at least about 50 nucleotides in length. In one embodiment, the vector comprises an IRES that comprises a natural sequence. In one embodiment, the vector comprises an IRES that comprises a synthetic sequence.

In one embodiment, the invention is directed to a vector for making circular RNA, said vector comprising the following elements operably connected to each other and arranged in the following sequence: a.) a 5' homology arm, b.) a 3' group I intron fragment containing a 3' splice site dinucleotide, c.) a 5' spacer sequence, d.) an internal ribosome entry site (IRES), e.) a protein coding or noncoding region, f.) a 5' group I intron fragment containing a 5' splice site dinucleotide, and g.) a 3' homology arm. In some embodiments, said vector allows production of a circular RNA that is translatable and/or biologically active inside eukaryotic cells.

In one embodiment, the invention is directed to a vector for making circular RNA, said vector comprising the following elements operably connected to each other and arranged in the following sequence: a.) a 5' homology arm, b.) a 3' group I intron fragment containing a 3' splice site dinucleotide, c.) an internal ribosome entry site (IRES), d.) a protein coding or noncoding region, e.) a spacer (e.g., second spacer) sequence, f.) a 5' group I intron fragment containing a 5' splice site dinucleotide, and g.) a 3' homology arm. In some embodiments, said vector allows production of a circular RNA that is translatable and/or biologically active inside cells, e.g., eukaryotic cells.

In certain embodiments, the vectors provided herein do not comprise a multi cloning site (MCS).

In one embodiment, the invention is directed to a circular RNA. In certain embodiments, the circular RNA is a circular RNA produced by a vector provided herein. In some embodiments, the circular RNA comprises, in the following sequence: a.) a 5' spacer sequence, b.) an internal ribosome entry site (IRES), c.) a protein coding or noncoding region, and d.) a 3' spacer sequence. In some embodiments, the circular RNA further comprises the portion of the 3' group I intron fragment that is 3' of the 3' splice site dinucleotide. In some embodiments, the circular RNA further comprises the portion of the 5' group I intron fragment that is 5' of the 5' splice site dinucleotide. In some embodiments, the circular RNA is at least 500, 600, 700, 800, 900, 1000, 1500, 2000, 2500, 3000, 3500, 4000 or 4500 nucleotides. In one embodiment, the circular RNA is at least about 10 nt. In one embodiment, the circular RNA is about 500 nt or less than 500 nt. In one embodiment, the circular RNA is at least about 1 kb. The circular RNA can be unmodified, partially modified or completely modified. In one embodiment, the circular RNA contains at least one nucleoside modification. In one embodiment, up to 100% of the nucleosides of the circular RNA are modified. In one embodiment, at least one nucleoside modification is a uridine modification or an adenosine modification. In one embodiment, at least one nucleoside modification is selected from N6-methyladenosine (m6A), pseudouridine (ψ), $N^1$-methylpseudouridine (m1ψ), and 5-methoxyuridine (5moU). In one embodiment, the precursor RNA is modified with methylpseudouridine (m1ψ).

In another embodiment, the invention is directed to a method of expressing protein in a cell, said method comprising transfecting the circular RNA into the cell. In one embodiment, the method comprises transfecting using lipofection or electroporation. In another embodiment, the circular RNA is transfected into a cell using a nanocarrier. In yet another embodiment, the nanocarrier is a lipid, polymer or a lipo-polymeric hybrid. In one embodiment, the circular RNA comprises coxsackievirus B3 IRES.

In one embodiment, the invention is directed to a method of purifying circular RNA, comprising running the RNA through a size-exclusion column in tris-EDTA or citrate buffer in a high performance liquid chromatography (HPLC) system. In another embodiment, the RNA is run through the size-exclusion column in tris-EDTA or citrate buffer at pH in the range of about 4-7 at a flow rate of about 0.01-5 mL/minute. In one embodiment, the HPLC removes one or more of: intron fragments, nicked linear RNA, linear and circular concatenations, and impurities resulting from the in vitro transcription and splicing reactions.

In one embodiment, provided herein is a precursor RNA. In certain embodiments, the precursor RNA is a circular RNA produced by in vitro transcription of a vector provided herein. In some embodiments, the precursor RNA comprises, in the following sequence, a.) a 5' homology arm, b.) a 3' group I intron fragment containing a 3' splice site dinucleotide, c.) a 5' spacer sequence, d.) an internal ribosome entry site (IRES), e.) a protein coding or noncoding region, f) a 3' spacer sequence, f.) a 5' group I intron fragment containing a 5' splice site dinucleotide, and g.) a 3' homology arm. The precursor RNA can be unmodified, partially modified or completely modified. In one embodiment, the precursor RNA contains at least one nucleoside modification. In one embodiment, up to 100% of the nucleosides of the precursor RNA are modified. In one embodiment, at least one nucleoside modification is a uridine modification or an adenosine modification. In one embodiment, at least one nucleoside modification is selected from $N^6$-methyladenosine (m6A), pseudouridine (ψ), $N^1$-methylpseudouridine (m1ψ), and 5-methoxyuridine (5moU). In one embodiment, the precursor RNA is modified with methylpseudouridine (m1ψ).

In another embodiment, the invention is directed to a method of purifying circular RNA, said method comprising: running circular RNA (e.g., circular RNA provided herein) through a size-exclusion column in tris-EDTA or citrate buffer in a high-performance liquid chromatography (HPLC) system, and treating the circular RNA with phosphatase after running the circular RNA through the size-exclusion column, thereby producing purified circular RNA. In one embodiment, the phosphatase treatment is followed by RNase R treatment. In one embodiment, the purified circular RNA is formulated into nanoparticles. In one embodiment, the circular RNA is run through the size-exclusion column at a pH in the range of about 4-8. In one embodiment, the circular RNA is run through the size-exclusion column at a flow rate of about 0.01-5.0 mL/minute.

In some embodiments, the HPLC as utilized in the methods herein can include an aqueous buffer that includes a salt, such as phosphate buffer, having a pH of between about 4 and about 7.5.

In yet another embodiment, the invention is directed to a method of making circular RNA from precursor RNA, said method comprising using a vector provided herein. In some embodiments, the method comprises a.) synthesizing precursor RNA by in vitro transcription of the vector, and b.) incubating the precursor RNA in the presence of magnesium ions and quanosine nucleotide or nucleoside at a temperature at which RNA circularization occurs (e.g., between 20° C. and 60° C.). In some embodiments the vector comprises the following elements operably connected to each other and arranged in the following sequence: a) a 5' homology arm, b) a 3' group I intron fragment containing a 3' splice site dinucleotide, c) a 5' spacer sequence, d) a protein coding or noncoding region, e) a 3' spacer sequence, f) a 5' group I intron fragment containing a 5' splice site dinucleotide, and g) a 3' homology arm, said vector allowing production of a circular RNA that is translatable inside eukaryotic cells. In one embodiment, the method further comprises an internal ribosome entry site (IRES) between the 5' spacer sequence and the protein coding region.

In one embodiment, the invention is directed to a method for making circular RNA from precursor RNA generated by in vitro transcription of a vector provided herein. In some embodiments, the method includes incubating the precursor RNA in the presence of magnesium ions and quanosine nucleotide or nucleoside at a temperature at which RNA circularization occurs (e.g., between 20° C. and 60° C.). In some embodiments, the nucleosides of the precursor RNA are unmodified. The precursor RNA can be unmodified, partially modified or completely modified. In one embodiment, the precursor RNA can be naturally occurring. In one embodiment, the precursor RNA contains at least one nucleoside modification. In one embodiment, up to 100% of the nucleosides of the precursor RNA are modified. In one embodiment, at least one nucleoside modification is a uridine modification or an adenosine modification. In one embodiment, at least one nucleoside modification is selected from $N^6$-methyladenosine (m6A), pseudouridine ($\psi$), $N^1$-methylpseudouridine (m1$\psi$), and 5-methoxyuridine (5moU). In one embodiment, the precursor RNA is modified with methylpseudouridine (m1$\psi$).

In one embodiment, the invention is directed to a circular RNA produced by a vector and/or a method disclosed herein. In one embodiment, the invention is directed to a composition, e.g., a pharmaceutical composition, comprising a circular RNA provided herein (e.g., a circular RNA produced by a vector, precursor RNA and/or a method disclosed herein).

In one embodiment, the invention is directed to a method of expressing protein in a cell, said method comprising transfecting a circular RNA provided herein into the cell.

As used herein, "precursor RNA" refers to a linear RNA molecule created by in vitro transcription (e.g., from a vector provided herein). This precursor RNA molecule contains the entirety of the circRNA sequence, plus splicing sequences (intron fragments and homology arms) necessary to circularize the RNA. These splicing sequences (intron fragments and homology arms) are removed from the precursor RNA during circularization, yielding circRNA plus two intron/homology arm linear RNA fragments. Precursor RNA can be unmodified, partially modified or completely modified. In one embodiment, the precursor RNA contains only naturally occurring nucleotides.

In one embodiment, the invention is directed to a method of making circular RNA with enhanced translation efficiency, said method comprising incorporating artificial nucleosides into a precursor RNA during transcription of a vector encoding the precursor RNA and circularizing the precursor RNA to form the circular RNA.

In another embodiment, the invention is directed to a method of making circular RNA with enhanced protein expression stability, said method comprising incorporating artificial nucleosides into a precursor RNA during transcription of a vector encoding the precursor RNA and circularizing the precursor RNA to form the circular RNA.

In yet another embodiment, the invention is directed to a method of making circular RNA with reduced immunogenicity said method comprising incorporating artificial nucleosides into a precursor RNA during transcription of a vector encoding the precursor RNA and circularizing the precursor RNA to form the circular RNA.

In some embodiments, a vector provided herein can be used to transcribe a precursor RNA that will self-splice into a circRNA under the right conditions (e.g., conditions provided herein). In one embodiment, the length of this circRNA is between about 200 and about 10,000 nucleotides long.

In one embodiment, the vectors provided herein comprise an RNA polymerase promoter upstream of the region that encodes the precursor RNA (e.g., upstream of the 5' homology arm). In some embodiments, the promoter can be recognized by the T7 phage RNA polymerase enzyme.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIGS. 7A-7J. FIGS. 7A-F show an example of the design, synthesis, and purification of circRNA. FIG. 7A) Precursor RNA design and self-splicing overview. Colors denote different regions of the RNAs used. FIG. 7B) Schematics of RNAs introduced and used in this figure. ΔSplice Sites (ΔS) is identical to the precursor RNA except for small deletions encompassing both splice sites. FIG. 7C) Agarose gel showing precursor RNA after splicing, RNase R digestion, HPLC purification, and oligonucleotide-guided RNase H digestion. Circular RNA is digested by RNase H into one major band, while ΔS is digested into two major bands, confirming circularity. FIG. 7D) Agarose gel showing cumulative purification methods applied to circRNA. + RNase R: unpurified circRNA digested with RNase R only. +HPLC: unpurified circRNA HPLC purified, and then digested with RNase R. +Phos: unpurified circRNA HPLC purified, then treated with a phosphatase, and then digested with RNase R. FIG. 7E) Cell viability, GLuc expression stability, and cytokine release from 293 cells transfected with different circRNA preparations as described in FIG. 7D). Cell viability was assessed 3 days after transfection. Cytokine release was assessed 24 hours after transfection (data presented as mean+SD, n=3, ns=not significant p<0.05, ND=not detected). FIG. 7F) Cell viability, circRNA expression stability, and cytokine release from A549 cells transfected with different circRNA preparations described in FIG. 7D). Cell viability was assessed 3 days after transfection. Cytokine release was assessed 24 hours after transfection (data presented as mean+SD, n=3, ND=not detected, *p<0.05). FIGS. 7G-J show ΔSplice Sites (ΔS) characterization. FIG. 7G) Schematic of the RNA introduced and used in this figure. ΔS is the linear circRNA precursor with deleted splice sites (marked by x). ΔS is polyadenylated and treated with phosphatase. FIG. 7H) Agarose gel showing ladder used to assign molecular weights and bands. ΔS does not detectably circularize. FIG. 7I) GLuc expression 24 hours after transfection of 293 cells with circRNA or ΔS (data presented as mean+SD, n=3). FIG. 7J) GLuc protein production stability over 3 days after transfection of 293 cells with circRNA or ΔS (data presented as mean+SD, n=3).

FIGS. 8A-G. FIGS. 8A-F show splicing reaction fractionation and assessment of immunogenicity. FIG. 8A) Schematics of RNAs introduced and used in this figure. HMW: High Molecular Weight; this fraction contains linear and circular concatenations. FIG. 8B) Above: HPLC chromatogram of an unpurified splicing reaction. Below: agarose gel of purified fractions. Adequate separation of precursor RNA was difficult, and therefore ΔS was used instead. FIG. 8C) Cytokine release 24 hours after transfection of A549 cells with different HPLC fractions as described in FIG. 8B) (data presented as mean+SD, n=3, *p<0.05). FIG. 8D) Cell viability 36 hours after transfection of A549 cells with different HPLC fractions as described in b) (data presented as mean+SD, n=3, *p<0.05). FIG. 8E) RIG-I and IFN-β1 transcript induction 18 hours after transfection of A549 cells with the indicated RNAs. 3p-hpRNA is 5' triphosphate hairpin RNA and a specific agonist of RIG-I (data presented as mean+SD, n=3, *p<0.05). FIG. 8F) RIG-I and IFN-β1 transcript induction 18 hours after transfection of A549 cells with RNase R digested splicing reactions or the late circRNA fraction (data presented as mean+SD, n=3, *p<0.05). FIG. 8G shows additional cytokines assessed in culture media after transfection of A549 (left) and 293 (right) cells with different circRNA preparations as described in FIG. 7D (data presented as mean+SD, n=3). In most cases, these analytes were detected at extremely low levels, precluding the observance of significant differences.

FIGS. 9A-O. FIGS. 9A-F show determination of circRNA immunogenicity in relation to linear mRNA. FIG. 9A) Schematics of RNAs introduced and used in this figure. Linear mRNAs do not contain an IRES or other structured features that may provoke a structure-specific immune response. FIG. 9B) Agarose gel showing progressive modification of circRNA precursor with m1ψ. FIG. 9C) Agarose gel showing purified unmodified and modified RNAs. Modification with m1ψ reduces apparent molecular weight. FIG. 9D) GLuc expression 24 hours after transfection of 293 or A549 cells with unmodified circRNA or m1ψ-circRNA (data presented as mean+SD, n=3). FIG. 9E) Cell viability, GLuc expression stability, and cytokine release from 293 cells transfected with unmodified or m1ψ linear mRNA or circRNA. Cell viability was assessed 3 days after transfection. Cytokine release was assessed 24 hours after transfection (data presented as mean+SD, n=3, ns=not significant p<0.05, ND=not detected).

FIG. 9F) Cell viability, GLuc expression stability, and cytokine release from A549 cells transfected with unmodified or m1ψ linear mRNA or circRNA. Cell viability was assessed 3 days after transfection. Cytokine release was assessed 24 hours after transfection (data presented as mean+SD, n=3, ND=not detected, *p<0.05). FIG. 9H) Additional cytokines assessed in culture media after transfection of A549 cells with different HPLC fractions as shown in FIG. 9H (data presented as mean+SD, n=3, *p<0.05). FIG. 9I Cell viability 36 hours after mock transfection or no transfection of 293 cells (left) and transcript induction 24 hours after mock transfection or no transfection of 293 cells (right; fold induction relative to untransfected; data presented as mean+SD, n=2, ns=not significant). FIG. 9J) IL-6 and RANTES secretion by A549 cells 24 hours after mock transfection with MessengerMax, or without transfection (data presented as mean+SD, n=3). FIG. 9K) RIG-I and IFN-β1 transcript induction 24 hours after transfection of A549 cells with purified circRNA containing a synthetic RIG-I ligand (3p-hpRNA) as a percentage of total RNA transfected (data presented as mean+SD, n=3, *p<0.05). FIG. 9L) RIG-I and IFN-β1 transcript induction 24 hours after transfection of HeLa cells with the indicated RNAs (data presented as mean+SD, n=3, *p<0.05). FIG. 9M) Time course of transcript induction 2-8 hours after transfection of 150,000 A549 cells with 20 ng of the indicated RNAs (data presented as mean+SD, n=2). FIG. 9N) GLuc expression 24 hours after transfection of RAW264.7 cells at 80% confluence with the indicated RNAs (left). GLuc expression stability over 2 days (right; data presented as mean+SD, n=3). Transcript induction 24 hours after transfection of RAW264.7 cells with the indicated RNAs (data presented as mean+SD, n=2). FIG. 9O) Analysis of a circular RNA containing an EMCV IRES and coding for GFP (circGFP). Agarose gel showing circGFP circularization and purified circGFP (left). A549 cell viability 36 hours after reverse transfection of 20,000 A549 cells with 40 ng of circRNA (right). Transcript induction 24 hours after reverse transfection of A549 cells with the indicated RNAs (bottom; data presented as mean+SD, n=2, ns=not significant).

FIGS. 10A-F show CircRNA evasion of TLRs. FIG. 10A) Schematics of RNAs introduced and used for TLR experiments. Linearized circRNAs contain all of the same sequence elements as spliced circRNA due to deletions encompassing both the introns and homology arms. FIG. 10B) SEAP expression 36 hours after transfection of TLR reporter cells with the indicated RNAs relative to null controls (data presented as mean+SD, n=3, ns=not significant, *p<0.05). FIG. 10C) SEAP expression 36 hours after transfection of TLR8 reporter cells with the late circRNA fraction relative to the null control. (−): media contains no nucleoside. C: media contains cytidine (3.5 mM). U: media contains uridine (3.5 mM); (data presented as mean+SD, n=3, ns=not significant, *p<0.05). FIG. 10D) Schematic of RNAs introduced and used for TLR nicked RNA experiments. FIG. 10E) Agarose gel showing alternative circRNA nicking strategies. FIG. 10F) SEAP expression 36 hours after transfection of TLR reporter cells with the indicated RNAs relative to null controls (data presented as mean+SD, n=3, *p<0.05). FIGS. 10G-I show splint ligation optimization. FIG. 10G) Splint ligation precursor RNA design and splicing overview. FIG. 10H) Different splints used for ligation. Of note, these optimizations were conducted with a plasmid containing an NaeI restriction cut site for linearization, leading to unwanted RNA side products (seen as extraneous bands in Ligase(−) and Splint(−) conditions) forming during in vitro transcription. This site was changed to XbaI for the GLuc and hEpo splint ligations used in FIG. 9A-F and FIG. 10A-F. OH: overhang (5',3'); Tm: melting temperature. FIG. 10I) shows optimization of circularization conditions.

FIGS. 11A-F. FIGS. 11A-D show hEpo circRNA characterization in vivo. FIG. 11A) Serum hEpo expression 6 hours after injection of 350 ng of unmodified or m1ψ linear mRNA or circRNA complexed with MessengerMax into visceral adipose tissue (data presented relative to molecular weight, mean+SD, n=3). FIG. 11B) Relative hEpo expression in serum over 42 hours (data presented as mean+SD, n=3). FIG. 11C) Cytokines detected in serum 6 hours after injection of 350 ng of the indicated RNAs into visceral adipose (data presented as mean+SD, n=3, *p<0.05). FIG. 11D) Injection site demonstrated by injection of modified firefly luciferase mRNA complexed with MessengerMax. FIG. 11E shows Cell viability, GLuc expression stability, and cytokine release from 293 cells transfected with unmodified or m1ψ linear mRNA or circRNA. Cell viability was assessed 3 days after transfection. Cytokine release was assessed 24 hours after transfection (data presented as mean+SD, n=3, ns=not significant p<0.05, ND=not detected). FIG. 11F shows additional cytokines assessed in culture media after transfection of 293 and A549 cells with unmodified or m1ψ linear mRNA or circRNA (see FIG. 9E,9F; data presented as mean+SD, n=3). In most cases, these analytes were detected at extremely low levels, precluding the observance of significant differences.

FIGS. 12A-I. FIGS. 12A-F show LNP-circRNA characterization. FIG. 12A) Cryo-TEM image of LNP-circRNA. FIG. 12B) hEpo expression 24 hours after transfection of 293 cells with equimolar quantities of LNP-5moU-mRNA or unmodified LNP-circRNA (left) and hEpo protein expression stability over 3 days (right; data presented as mean+SD, n=3). FIG. 12C) RIG-I and IFN-β1 transcript induction 24 hours after transfection of A549 cells with LNP-5moU-mRNA or unmodified LNP-circRNA. TR: transfection reagent plus 200 ng RNA (MessengerMax); LNP(1×): 200 ng LNP-RNA; LNP(2×): 400 ng LNP-RNA; L: 5moU-mRNA; C: circRNA (data presented as mean+SD, n=3, ns=not significant, p<0.05). FIG. 12D) SEAP expression 48 hours after transfection of TLR reporter cells with the RNAs indicated in c), relative to null controls (data presented as mean+SD, n=3). FIG. 12E) Serum hEpo expression 6 hours after injection of 1.5 picomoles of LNP-5moU-mRNA or unmodified LNP-circRNA into visceral adipose (data presented as mean+SD, n=5 Linear 5moU, Circular; n=3 Mock). FIG. 12F) Relative hEpo expression in serum over 42 hours after injection with LNP-RNAs (data presented as mean+SD, n=5 Linear 5moU, Circular; n=3 Mock). FIG. 12G) Agarose gel of the linear RNAs depicted in FIG. 9G. FIG. 12H) SEAP expression 36 hours after transfection of TLR8 reporter cells with the tailed linear RNA shown in a) relative to null controls in the presence or absence of varying concentrations of uridine (data presented as mean+SD, n=2). FIG. 12I) Complete data from FIG. 10F including an additional positive control.

FIG. 14A) Agarose gel showing purified unmodified and modified RNAs. FIG. 14B) hEpo expression 24 hours after transfection of 293 cells with equimolar quantities of m1ψ-mRNA or unmodified circRNA (data presented as mean+SD, n=3). FIG. 14C) Cell viability, hEpo protein production stability, and 24 hour protein expression from 293 cells transfected with equal weights of unmodified or m1ψ linear mRNA or circRNA. Cell viability was assessed 36 hours after transfection (data presented as mean+SD, n=3). FIG. 14D) Cell viability, hEpo protein production stability, and 24 hour protein expression from A549 cells transfected with equal weights of unmodified or m1ψ linear mRNA or circRNA. Cell viability was assessed 36 hours after transfection (data presented as mean+SD, n=3).

FIG. 16A) Physicochemical properties of LNP-RNAs (data presented as mean±SD, n=3). FIG. 16B) Injection site demonstrated by injection of modified firefly luciferase mRNA formulated into cKK-E12 LNPs. Luminescence detected at 6 and 24 hours shows local delivery to visceral adipose. FIG. 16C) Cytokines detected in serum 6 hours after intraperitoneal injection of 750 ng of the indicated RNAs formulated into cKK-E12 LNPs (data presented as mean+SD, n=3). FIG. 16D) Transcript induction in visceral adipose tissue 24 hours after intraperitoneal injection of 750 ng of the indicated RNAs formulated into cKK-E12 LNPs (data presented as mean+SD, n=3).

FIG. 18A shows circularization of precursor RNA containing a T4 or *Anabaena* permuted intron, EMCV IRES, GLuc reading frame, strong homology arms, and a 5' spacer at different GTP concentrations. FIG. 18B shows circularization of the precursor RNAs described in FIG. 18A at different concentrations of RNA. FIG. 18C shows gel extraction of major top and bottom bands resulting from complete splicing using three alternative protocols to rule out interconversion of species.

FIG. 20A) Stability and expression of GLuc from EMCV-circRNA without spacers and with or without UTRs over 144h in HeLa cells. FIG. 20B) Stability and expression of GLuc from EMCV-circRNA without spacers and with or without UTRs over 144h in 293 cells. FIG. 20C) Expression of GLuc from CVB3-circRNA with a 5' spacer and with or without different UTRs. Trilink: 5mC/pseudo-modified linear mRNA purchased from Trilink.

FIG. 20D) Circularization of precursor RNA containing a T4 permuted intron, EMCV IRES, GLuc reading frame, strong homology arms, a 5' spacer with or without different UTRs. R: RNase R digestion.

FIGS. 21A-21D) Expression of GLuc from circRNA with a 5' spacer and with different IRES sequences in 293 and HeLa cells. 21E-21F) Expression of GLuc from circRNA with a 5' spacer and with different IRES sequences or UTRs in 293 and HeLa cells. CircRNAs contain a CVB3 IRES unless otherwise stated. Trilink: 5mC/pseudo-modified linear mRNA purchased from Trilink. 21G) Comparison of StemFect transfection reagent and lipid nanoparticle (LNP) delivery of different RNA species in 293 cells.

FIGS. 22A-22B) Expression of GLuc from CVB3-circRNA with an *Anabaena* permuted intron, a 5' spacer, and with or without different polyN sequences in 293 and HeLa cells.

FIG. 23A) Comparison of the effects of permuted intron sequence context on the expression of GLuc from circRNA with a 5' spacer and the indicated IRES in 293 cells. FIG. 23B) Serum expression of GLuc from circRNA containing a T4 permuted intron, a 5' spacer, and different IRES sequences, or linear mRNA. RNA was formulated into liver-homing LNPs and injected intravenously. Serum was collected 6 hours after injection.

FIG. 25A) Circularization of precursor RNA containing an *Anabaena* permuted intron, GLuc reading frame, strong homology arms, 5' and 3' spacers, and the indicated IRES. FIG. 25B) Circularization of precursor RNA containing an *Anabaena* permuted intron, FLuc reading frame, strong homology arms, 5' and 3' spacers, and the indicated IRES.

FIG. 26A) HeLa cells. FIG. 26B) A594 cells. RIG-I and IFNB1 fold induction after transfection of indicated circRNA preparations. All preparations contain circRNA with an *Anabaena* permuted intron, GLuc reading frame, strong homology arms, 5' and 3' spacers, and a CVB3 IRES. Unpurified: total splicing reaction. GMP: CircRNA precursors transcribed in the presence of 12.5-fold GMP over GTP. 3phpRNA: triphosphate hairpin RNA positive control.

DETAILED DESCRIPTION

Figure 1A:
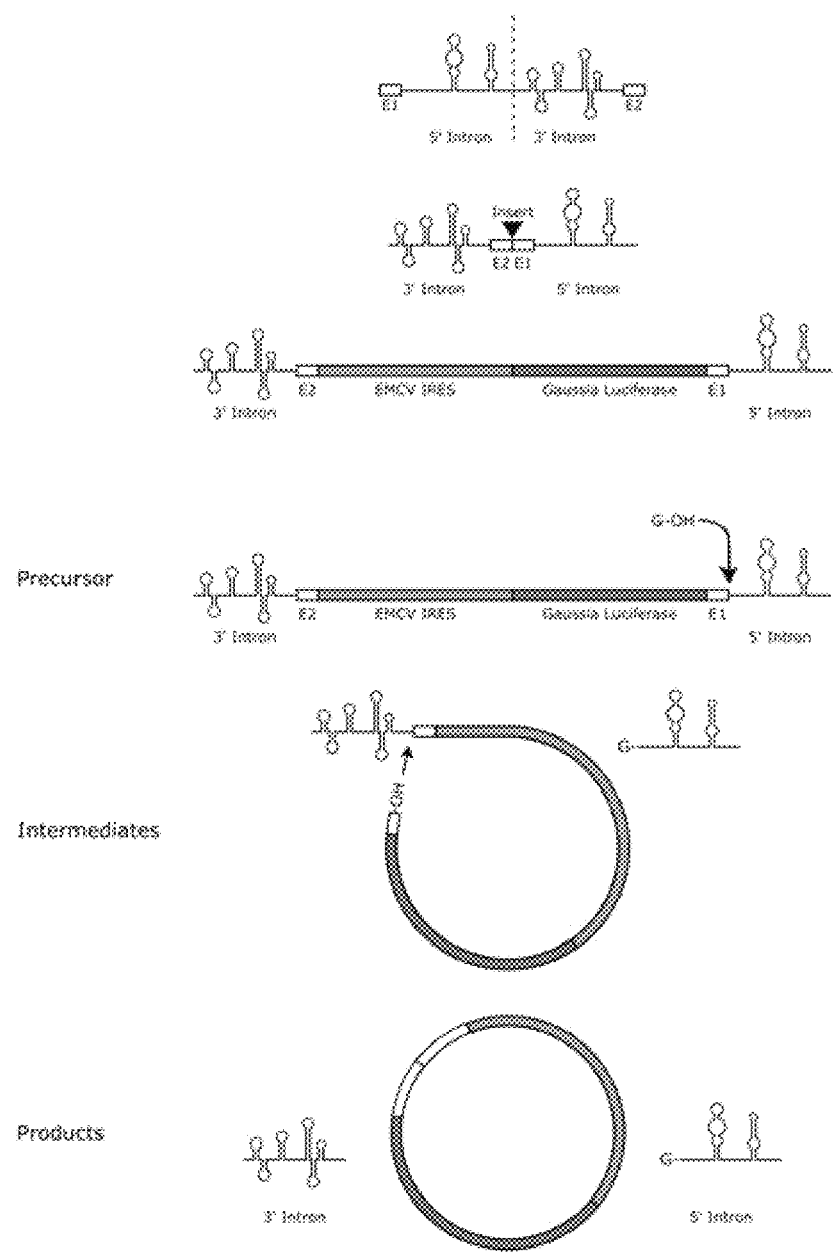
FIG. 1A is a schematic diagram showing an example of a permuted intron-exon construct design and mechanism of splicing. The group I catalytic intron of the T4 phage Td gene is bisected in such a way as to preserve structural elements critical for ribozyme folding. Exon fragment 2 (E2) is ligated upstream of exon fragment 1 (E1), and a coding region approximately 1.1 kb in length is inserted at the exon-exon junction. During splicing, the 3' hydroxyl group of a guanosine nucleotide engages in a transesterification reaction at the 5' splice site. The 5' intron fragment is excised, and the freed hydroxyl group at the end of the intermediate engages in a second transesterification at the 3' splice site, resulting in circularization of the intervening region and excision of the 3' intron.

A description of example embodiments follows.

As described herein, exogenous circRNA was developed to extend the duration of protein expression from full-length RNA messages. First, a self-splicing intron was engineered to circularize efficiently a wide range of RNAs in vitro, coding for proteins such as Cas9, by rationally designing ubiquitous accessory sequences that aid in splicing. Functional protein was produced from these circRNAs in eukaryotic cells and translation incorporating different internal ribosome entry sites (IRES) and internal polyadenosine tracts was maximized. Engineered circRNA purified by high performance liquid chromatography displayed exceptional protein production qualities in terms of both quantity of protein produced and stability of production. Provided herein are methods and compositions that facilitate the use of exogenous circRNA for robust and stable protein expression in eukaryotic cells, rendering circRNA a promising alternative to linear mRNA.

Circular RNAs (circRNAs) endogenous to eukaryotic cells have drawn increasing interest due to their prevalence and range of potential biological functions (Barrett, S. P. & Salzman, J., "Circular RNAs: analysis, expression and potential functions," *Development*, 143(11):1838-1847 (2016)). Most circRNAs are generated through backsplicing and appear to fulfill noncoding roles (Barrett, S. P. & Salzman, J., "Circular RNAs: analysis, expression and potential functions," *Development*, 143(11):1838-1847 (2016); Chen, L. & Yang, L., "Regulation of circRNA biogenesis," *RNA Biology*, 12(4):381-388 (2015); Jeck, W. R. and Sharpless, N. E., "Detecting and characterizing circular RNAs," *Nat. Biotechnol.*, 32:453-461 (2014); Wang, Y. & Wang, Z., "Efficient backsplicing produces translatable circular mRNAs," *RNA*, 21(2):172-179 (2014); Hansen, T. B. et al., "Natural RNA circles function as efficient microRNA sponges," *Nature*, 495(7441):384-388 (2013); Li, Z. et al., "Exon-intron circular RNAs regulate transcription in the nucleus," *Nature Structural & Molecular Biology*, 22(3):256-264 (2015)). However, it has been suggested that some circRNAs endogenous to *Drosophila* may be translated into protein (Legnini, I. et al., "Circ-ZNF609 Is a Circular RNA that Can Be Translated and Functions in Myogenesis," *Molecular Cell*, 66(1):22-37.e9 (2017); Pamudurti, N. R. et al., "Translation of CircRNAs," *Molecular Cell*, 66(1) (2017)).

In addition to having protein-coding potential, endogenous circRNAs lack the free ends necessary for exonuclease-mediated degradation, rendering them resistant to several mechanisms of RNA turnover and granting them extended lifespans as compared to their linear mRNA counterparts (Chen, L. & Yang, L., "Regulation of circRNA biogenesis," *RNA Biology*, 12(4):381-388 (2015); Enuka, Y. et al., "Circular RNAs are long-lived and display only minimal early alterations in response to a growth factor," *Nucleic Acids Research,* 44(3):1370-1383 (2015)). For this reason, circularization may allow for the stabilization of mRNAs that generally suffer from short half lives and may therefore improve the overall efficacy of exogenous mRNA in a variety of applications (Kaczmarek, J. C. et al., "Advances in the delivery of RNA therapeutics: from concept to clinical reality," *Genome Medicine,* 9(1) (2017); Fink, M. et al., "Improved translation efficiency of injected mRNA during early embryonic development," *Developmental Dynamics,* 235(12):3370-3378 (2006); Ferizi, M., et al., "Stability analysis of chemically modified mRNA using micropattern-based single-cell arrays," *Lab Chip,* 15(17): 3561-3571 (2015)). However, the efficient circularization of long in vitro transcribed (IVT) RNA, the purification of circRNA, and the adequate expression of protein from circRNA are significant obstacles that must be overcome before their protein-coding potential can be realized. As described herein, in one embodiment, an engineering approach is presented to generate exogenous circRNAs for potent and durable protein expression in cells, e.g., eukaryotic cells.

Abbreviations

GFP Green fluorescent protein
ORF Open reading frame
IRES Internal ribosome entry site
UTR Untranslated region
HEK Human embryonic kidney
IRES Internal Ribosome Entry Site
EMCV Encephalomyocarditis virus, a picornavirus
PIE permutated intron-exon splice site In one embodiment, the present invention is directed to a vector for making circular RNA, said vector comprising the following elements operably connected to each other and arranged in the following sequence: a.) a 5' homology arm, b.) a 3' group I intron fragment containing a 3' splice site dinucleotide, c.) optionally, a 5' spacer sequence, d.) optionally, an internal ribosome entry site (IRES), e.) a protein coding or noncoding region, f) optionally, a 3' spacer sequence, g.) a 5' group I intron fragment containing a 5' splice site dinucleotide, and h.) a 3' homology arm, said vector allowing production of a circular RNA that is translatable and/or biologically active inside eukaryotic cells.

As used herein, the lettering of the elements (e.g., "a.)—h.)") are used solely for clarity purposes. In addition, it is understood that in alternative embodiments, it is possible that the elements can be arranged in a different sequence, and/or that one or more elements may be omitted.

As used herein, the elements of a vector are "operably connected" if they are positioned on the vector such that they can be transcribed to form a precursor RNA that can then be circularized into a circular RNA using the methods provided herein.

In one embodiment, the present invention is directed to a vector (e.g., a plasmid) for making circRNA, said vector comprising the following elements operably connected to each other and arranged in the following sequence: a.) a 5' homology arm, b.) a 3' group I intron fragment, c.) an optional 5' spacer sequence, d.) an optional internal ribosome entry site (IRES), e.) a protein coding or noncoding region, f.) an optional 3' spacer sequence, g.) a 5' group I intron fragment containing a 5' splice site dinucleotide, and h.) a 3' homology arm, said vector allowing production of a circRNA that is translatable or biologically active inside eukaryotic cells.

As used herein, a "homology arm" is any contiguous sequence that is 1) predicted to form base pairs with at least about 75% (e.g., at least about 80%, at least about 85%, at least about 90%, at least about 95%, about 100%) of another sequence in the RNA, such as another homology arm 2) at least 7 nt long and no longer than 250 nt 3) located before and adjacent to, or included within, the 3' intron fragment and/or after and adjacent to, or included within, the 5' intron fragment and, optionally, 4) predicted to have less than 50% (e.g., less than 45%, less than 40%, less than 35%, less than 30%, less than 25%) base pairing with unintended sequences in the RNA (e.g., non-homology arm sequences). A "strong homology arm" refers to a homology arm with a Tm of greater than 50 degrees Celsius when base paired with another homology arm in the RNA.

As used herein, a 3' group I intron fragment is a contiguous sequence that is at least 75% (e.g., at least 80%, at least 85%, at least 90%, at least 95%, 100%) homologous to a 3' proximal fragment of a natural group I intron, including the 3' splice site dinucleotide, and, optionally, the adjacent exon sequence at least 1 nucleotide in length (e.g., at least 5 nucleotides in length, at least 10 nucleotides in length, at least 15 nucleotides in length, at least 20 nucleotides in length, at least 25 nucleotides in length, at least 50 nucleotides in length). In one embodiment, the included adjacent exon sequence is about the length of the natural exon. In some embodiments, a 5' group I intron fragment is a contiguous sequence that is at least 75% (e.g., at least 80%, at least 85%, at least 90%, at least 95%, 100%) homologous to a 5' proximal fragment of a natural group I intron, including the 5' splice site dinucleotide and, optionally, the adjacent exon sequence at least 1 nucleotide in length (e.g., at least 5 nucleotides in length, at least 10 nucleotides in length, at least 15 nucleotides in length, at least 20 nucleotides in length, at least 25 nucleotides in length, at least 50 nucleotides in length). In one embodiment, the included adjacent exon sequence is about the length of the natural exon.

As used herein, a "spacer" refers to any contiguous nucleotide sequence that is 1) predicted to avoid interfering with proximal structures, for example, from the IRES, coding or noncoding region, or intron 2) at least 7 nucleotides long (and optionally no longer than 100 nucleotides) 3) located downstream of and adjacent to the 3' intron fragment and/or upstream of and adjacent to the 5' intron fragment and/or 4) contains one or more of the following: a) an unstructured region at least 5 nt long b) a region predicted base pairing at least 5 nt long to a distal (i.e., non-adjacent) sequence, including another spacer, and/or c) a structured region at least 7 nt long limited in scope to the sequence of the spacer.

As used herein, "interfering" with regard to sequences refers to sequence(s) predicted or empirically determined to alter the folding of other structures in the RNA, such as the IRES or group I intron-derived sequences.

As used herein, "unstructured" with regard to RNA refers to an RNA sequence that is not predicted by the RNAFold software or similar predictive tools to form a structure (e.g., a hairpin loop) with itself or other sequences in the same RNA molecule.

As used herein, "structured" with regard to RNA refers to an RNA sequence that is predicted by the RNAFold software or similar predictive tools to form a structure (e.g., a hairpin loop) with itself or other sequences in the same RNA molecule.

In some embodiments, the spacer sequence can be, for example, at least 10 nucleotides in length, at least 15 nucleotides in length, or at least 30 nucleotides in length. In some embodiments, the spacer sequence is at least 7, 8, 9, 10, 11, 12, 13, 14, 15, 16, 17, 18, 19, 20, 25 or 30 nucleotides in length. In some embodiments, the spacer sequence is no more than 100, 90, 80, 70, 60, 50, 45, 40, 35 or 30 nucleotides in length. In some embodiments the spacer sequence is between 20 and 50 nucleotides in length. In certain embodiments, the spacer sequence is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides in length.

The spacer sequences can be polyA sequences, polyA-C sequences, polyC sequences, or poly-U sequences, or the spacer sequences can be specifically engineered depending on the IRES. Spacer sequences as described herein can have two functions: (1) promote circularization and (2) promote functionality by allowing the introns and IRES to fold correctly. More specifically, the spacer sequences as described herein were engineered with three priorities: 1) to be inert with regards to the folding of proximal intron and IRES structures; 2) to sufficiently separate intron and IRES secondary structures; and 3) to contain a region of spacer-spacer complementarity to promote the formation of a 'splicing bubble'. In one embodiment, the vectors are compatible with many possible IRES and coding or noncoding regions and two spacer sequences.

In some embodiments, an RNA folding computer software, such as RNAFold, can be utilized to guide designs of the various elements of the vector, including the spacers.

In some embodiments, one or more elements in the vector for making circular RNA comprise at least 75% sequence identity with natural sequences, including e.g., the IRES and intron fragment elements. In some embodiments, the protein coding regions or noncoding regions are not naturally occurring nucleotide sequences. In some embodiments, the protein coding regions encode natural or synthetic proteins.

In some embodiments, the coding or noncoding regions can be natural or synthetic sequences. In some embodiments, the coding regions can encode chimeric antigen receptors, immunomodulatory proteins, and/or transcription factors. In some embodiments, the noncoding regions can encode sequences can alter cellular behavior, such as e.g., lymphocyte behavior. In some embodiments, the noncoding sequences are antisense to cellular RNA sequences.

In one embodiment, the vector can comprise a 5' spacer sequence, but not a 3' spacer sequence. In another embodiment, the vector can comprise a 3' spacer sequence, but not a 5' spacer sequence. In another embodiment, the vector can comprise neither a 5' spacer sequence, nor a 3' spacer sequence. In another embodiment, the vector does not comprise an IRES sequence. In a further embodiment, the vector does not comprise an IRES sequence, a 5' spacer sequence or a 3' spacer sequence.

As used herein, a "vector" means a piece of DNA, that is synthesized (e.g., using PCR), or that is taken from a virus, plasmid, or cell of a higher organism into which a foreign DNA fragment can be or has been inserted for cloning and/or expression purposes. In some embodiments, a vector can be stably maintained in an organism. A vector can comprise, for example, an origin of replication, a selectable marker or reporter gene, such as antibiotic resistance or GFP, and/or a multiple cloning site (MCS). The term includes linear DNA fragments (e.g., PCR products, linearized plasmid fragments), plasmid vectors, viral vectors, cosmids, bacterial artificial chromosomes (BACs), yeast artificial chromosomes (YACs), and the like. In one embodiment, the vectors provided herein comprise a multiple cloning site (MCS). In another embodiment, the vectors provided herein do not comprise a MCS.

Examples of Group I intron self-splicing sequences include, but are not limited to, self-splicing permuted intron-exon sequences derived from T4 bacteriophage gene td or *Cyanobacterium Anabaena* sp. pre-tRNA-Leu gene.

The protein coding region can encode a protein of eukaryotic or prokaryotic origin. In some embodiments, the protein can be any protein for therapeutic use or diagnostic use. For example, the protein coding region can encode human protein or antibodies. In some embodiments, the protein can be selected from, but not limited to, hFIX, SP-B, VEGF-A, human methylmalonyl-CoA mutase (hMUT), CFTR, cancer self-antigens, and additional gene editing enzymes like Cpf1, zinc finger nucleases (ZFNs) and transcription activator-like effector nucleases (TALENs). In some embodiments, the vector or circRNA lacks a protein coding sequence. In some embodiments, the precursor RNA is a necessary intermediate between plasmid and circRNA.

The 5' and 3' homology arms can be synthetic sequences and are distinct from the internal homology regions but similar in function. The homology arms can be, e.g., about 5-50 nucleotides in length, about 9-19 nucleotides in length, for example, about 5, about 10 about 20, about 30, about 40, or about 50 nucleotides in length. In another embodiment, the homology arms can be 9 nucleotides in length. In a further embodiment, the homology arms can be 19 nucleotides in length. In some embodiments, the homology arms are at least 5, 6, 7, 8, 9, 10, 11, 12, 13, 14, 15, 16, 17, 18 or 19 nucleotides in length. In some embodiments, the homology arms are no more than 50, 45, 40, 35, 30, 25 or 20 nucleotides in length. In some embodiments, the homology arms are 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides in length.

In some embodiments, the vector comprises an IRES sequence. The IRES sequence can be selected from, but not limited to, an IRES sequence of a *Taura* syndrome virus, *Triatoma* virus, Theiler's encephalomyelitis virus, simian Virus 40, *Solenopsis invicta* virus 1, *Rhopalosiphum padi* virus, Reticuloendotheliosis virus, fuman poliovirus 1, *Plautia stali* intestine virus, Kashmir bee virus, Human rhinovirus 2, *Homalodisca coagulata* virus—1, Human Immunodeficiency Virus type 1, *Homalodisca coagulata* virus—1, Himetobi P virus, Hepatitis C virus, Hepatitis A virus, Hepatitis GB virus, foot and mouth disease virus, Human enterovirus 71, Equine rhinitis virus, *Ectropis obliqua* picorna-like virus, Encephalomyocarditis virus (EMCV), *Drosophila* C Virus, Crucifer tobamo virus, Cricket paralysis virus, Bovine viral diarrhea virus 1, Black Queen Cell Virus, Aphid lethal paralysis virus, Avian encephalomyelitis virus, Acute bee paralysis virus, Hibiscus chlorotic ringspot virus, Classical swine fever virus, Human FGF2, Human SFTPA1, Human AML1/RUNX1, *Drosophila* antennapedia, Human AQP4, Human AT1R, Human BAG-1, Human BCL2, Human BiP, Human c-IAP1, Human c-myc, Human eIF4G, Mouse NDST4L, Human LEF1, Mouse HIF1 alpha, Human n.myc, Mouse Gtx, Human p27kip1, Human PDGF2/c-sis, Human p53, Human Pim-1, Mouse Rbm3, *Drosophila* reaper, Canine Scamper, *Drosophila* Ubx, Human UNR, Mouse UtrA, Human VEGF-A, Human XIAP, *Drosophila* hairless, *S. cerevisiae* TFIID, *S. cerevisiae* YAP1, Human c-src, Human FGF-1, Simian picomavirus, Turnip crinkle virus, an aptamer to eIF4G, Coxsackievirus B3 (CVB3) or Coxsackievirus A (CVB1/2). Wild-type IRES sequences can also be modified and be effective in the invention. In some embodiments, the IRES sequence is about 50 nucleotides in length.

In some embodiments, in order to express protein in a cell, the circular RNA can be transfected into the cell using, for example, lipofection or electroporation. In another embodiment, the circular RNA is transfected into a cell using a nanocarrier. The nanocarrier can be, for example, a lipid, polymer or a lipo-polymeric hybrid.

The circular RNA can be purified by the method of running the RNA through a size-exclusion column in tris-EDTA or citrate buffer in a high-performance liquid chromatography (HPLC) system. In one embodiment, the RNA is run through the size-exclusion column in tris-EDTA or citrate buffer at pH in the range of about 4-7 at a flow rate of about 0.01-5 mL/minute.

In certain embodiments, provided herein is a method of generating precursor RNA by performing in vitro transcription using a vector provided herein as a template (e.g., a vector provided herein with a RNA polymerase promoter positioned upstream of the 5' homology arm).

In some embodiments, the use of a nucleotide, nucleoside, or a chemically modified nucleotide or nucleoside in the in vitro transcription reactions described herein is at an excess concentration relative to the analogous nucleotide triphosphate. "Excess concentration" is defined as greater than the concentration of the analogous nucleotide triphosphate, with the purpose of changing the 5' end nucleotide, specifically to reduce the immunogenicity of circRNA preparations by preventing the inclusion of a 5' triphosphate motif or to allow for the enzymatic circularization of precursor molecules by including the necessary 5' monophosphate motif.

In some embodiments, the nucleotide used in excess is guanosine monophosphate (GMP). In other embodiments, the nucleotide used in excess is GDP, ADP, CDP, UDP, AMP, CMP, UMP, guanosine, adenosine, cytidine, uridine, or any chemically modified nucleotide or nucleoside. In some embodiments, the excess is about a 10-fold excess. In some embodiments, the excess is about a 12.5-fold excess.

In one embodiment, the nucleotide, nucleoside, or a chemically modified nucleotide or nucleoside is used at concentrations at least about 10× in excess of the analogous nucleotide triphosphate in the in vitro transcription reaction.

In some embodiments, the circRNA that results from precursor RNA synthesized in the presence of a nucleotide, nucleoside, or a chemically modified nucleotide or nucleoside at least about 10× in excess of the analogous nucleotide triphosphate in the in vitro transcription reaction is then purified by HPLC to achieve minimal immunogenicity.

Pharmaceutical Compositions/Administration

In embodiments of the present disclosure, the circRNA products described herein and/or produced using the vectors and/or methods described herein, may be provided in compositions, e.g., pharmaceutical compositions.

Therefore, in some embodiments, the invention also relates to compositions, e.g., compositions comprising a circRNA (circRNA product) and a pharmaceutically acceptable carrier. In one aspect, the present disclosure provides pharmaceutical compositions comprising an effective amount of a circRNA described herein and a pharmaceutically acceptable excipient. Pharmaceutical compositions of the present disclosure may comprise a circRNA as described herein, in combination with one or more pharmaceutically or physiologically acceptable carriers, excipients or diluents. In some embodiments, pharmaceutical compositions of the present disclosure may comprise a circRNA expressing cell, e.g., a plurality of circRNA-expressing cells, as described herein, in combination with one or more pharmaceutically or physiologically acceptable carriers, excipients or diluents.

In some embodiments, a pharmaceutically acceptable carrier can be an ingredient in a pharmaceutical composition, other than an active ingredient, which is nontoxic to the subject.

A pharmaceutically acceptable carrier can include, but is not limited to, a buffer, excipient, stabilizer, or preservative. Examples of pharmaceutically acceptable carriers are solvents, dispersion media, coatings, antibacterial and antifungal agents, isotonic and absorption delaying agents, and the like that are physiologically compatible, such as salts, buffers, saccharides, antioxidants, aqueous or non-aqueous carriers, preservatives, wetting agents, surfactants or emulsifying agents, or combinations thereof. The amounts of pharmaceutically acceptable carrier(s) in the pharmaceutical compositions may be determined experimentally based on the activities of the carrier(s) and the desired characteristics of the formulation, such as stability and/or minimal oxidation.

In some embodiments, such compositions may comprise buffers such as acetic acid, citric acid, histidine, boric acid, formic acid, succinic acid, phosphoric acid, carbonic acid, malic acid, aspartic acid, Tris buffers, HEPPSO, HEPES, neutral buffered saline, phosphate buffered saline and the like; carbohydrates such as glucose, sucrose, mannose, or dextrans, mannitol; proteins; polypeptides or amino acids such as glycine; antioxidants; chelating agents such as EDTA or glutathione; adjuvants (e.g., aluminum hydroxide); antibacterial and antifungal agents; and preservatives.

In certain embodiments, compositions of the present disclosure can be formulated for a variety of means of parenteral or non-parenteral administration. In one embodiment, the compositions can be formulated for infusion or intravenous administration. Compositions disclosed herein can be provided, for example, as sterile liquid preparations, e.g., isotonic aqueous solutions, emulsions, suspensions, dispersions, or viscous compositions, which may be buffered to a desirable pH. Formulations suitable for oral administration can include liquid solutions, capsules, sachets, tablets, lozenges, and troches, powders liquid suspensions in an appropriate liquid and emulsions.

In one aspect, the disclosure relates to administering a therapeutically effective amount of a composition comprising a circRNA described herein for the treatment of a subject having, or at risk of developing, a disease or disorder, e.g., cancer. In another aspect, the disclosure relates to administering a therapeutically effective amount of a composition comprising a circRNA described herein for the treatment of a subject having a disease involving loss of a functional gene.

In some embodiments, the treatment aims to prolong translation from the circRNA to a protein.

Pharmaceutical compositions of the present disclosure may be administered in a manner appropriate to the disease to be treated (or prevented). The quantity and frequency of administration will be determined by such factors as the condition of the subject, and the type and severity of the subject's disease, although appropriate dosages may be determined by clinical trials.

The terms "treat" or "treatment" refer to therapeutic treatment wherein the object is to slow down (lessen) an undesired physiological change or disease, or provide a beneficial or desired clinical outcome during treatment. Beneficial or desired clinical outcomes include alleviation of symptoms, diminishment of extent of disease, stabilized (i.e., not worsening) state of disease, delay or slowing of disease progression, amelioration or palliation of the disease state, and/or remission (whether partial or total), whether detectable or undetectable. "Treatment" can also mean prolonging survival as compared to expected survival if a subject was not receiving treatment. Those in need of treatment include those subjects already with the undesired physiological change or disease as well as those subjects prone to have the physiological change or disease.

A "therapeutically effective amount" or "effective amount", used interchangeably herein, refers to an amount effective, at dosages and for periods of time necessary, to achieve a desired therapeutic result. A therapeutically effective amount may vary according to factors such as the disease state, age, sex, and weight of the individual, and the ability of a therapeutic or a combination of therapeutics to elicit a desired response in the individual. Example indicators of an effective therapeutic or combination of therapeutics that include, for example, improved well-being of the patient, reduction of disease burden, arrested or slowed progression of disease, and/or absence of progression of disease to other locations in the body.

As used herein, the term "subject" refers to an animal. The terms "subject" and "patient" may be used interchangeably herein. As such, a "subject" includes a human that is being treated for a disease, or prevention of a disease, such as a patient.

As used herein, the term "splice site dinucleotide" refers to the two nucleotides that border a splice site.

In some embodiments, the method described herein may be used to treat an animal subject belonging to any classification. Examples of such animals include mammals, such as mice, hamsters, rabbits. cats, dogs, cows, pigs or horses). The mammals may be of monkeys, humans and apes. In one embodiment, the mammal is a human.

Delivery systems useful in the context of embodiments of the invention may include time-released, delayed release, and sustained release delivery systems such that the delivery of the compositions occurs prior to, and with sufficient time to cause, sensitization of the site to be treated. The composition can be used in conjunction with other therapeutic agents or therapies. Such systems can avoid repeated administrations of the composition, thereby increasing convenience to the subject and the physician, and may be particularly suitable for certain composition embodiments of the invention.

Release delivery systems include polymer base systems such as poly(lactide-glycolide), copolyoxalates, polyesteramides, polyorthoesters, polycaprolactones, polyhydroxybutyric acid, and polyanhydrides. Microcapsules of the foregoing polymers containing drugs are described in, for example, U.S. Pat. No. 5,075,109. Delivery systems also include non-polymer systems that are lipids including sterols such as cholesterol, cholesterol esters, and fatty acids or neutral fats such as mono-di- and tri-glycerides; sylastic systems; peptide based systems; hydrogel release systems; wax coatings; compressed tablets using conventional binders and excipients; partially fused implants; and the like. In some embodiments, lipid nanoparticles or polymers are used as delivery vehicles for therapeutic circRNAs described herein, including delivery of RNA to tissues.

In certain embodiments, the administration of the compositions may be carried out in any manner, e.g., by parenteral or nonparenteral administration, including by aerosol inhalation, injection, infusions, ingestion, transfusion, implantation or transplantation. For example, the compositions described herein may be administered to a patient trans-arterially, intradermally, subcutaneously, intratumorally, intramedullary, intranodally, intramuscularly, by intravenous (i.v.) injection, intranasally, intrathecally or intraperitoneally. In one aspect, the compositions of the present disclosure are administered intravenously. In one aspect, the compositions of the present disclosure are administered to a subject by intradermal or subcutaneous injection. The compositions may be injected, for instance, directly into a tumor, lymph node, tissue, organ, or site of infection.

In one embodiment, administration may be repeated after one day, two days, three days, four days, five days, six days, one week, two weeks, three weeks, one month, five weeks, six weeks, seven weeks, two months, three months, four months, five months, six months or longer. Repeated courses of treatment are also possible, as is chronic administration. The repeated administration may be at the same dose or at a different dose.

In some embodiments, the compositions may be administered in the methods of the invention by maintenance therapy, such as, e.g., once a week for a period of 6 months or more.

In one embodiment, cells can transiently express the circRNA described herein for 4, 5, 6, 7, 8, 9, 10, 11, 12, 13, 14, 15 days after introduction. Transient expression of the circRNA can be affected by the method of delivery. In one embodiment, the circRNA is transduced into the cell by electroporation. In one embodiment, the circRNA is introduced into the cell by lipid transfection methods known in the art.

In some embodiments, a circRNA as described herein may be used in combination with other known agents and therapies. Administered "in combination", as used herein, means that two (or more) different treatments are delivered to the subject during the course of the subject's treatment e.g., the two or more treatments are delivered after the subject has been diagnosed with the disease and before the disease has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

In further embodiments, a composition described herein may be used in a treatment regimen in combination with surgery, radiation, chemotherapy, antibodies, or other agents.

EXAMPLES

Example 1

Figure 1B:
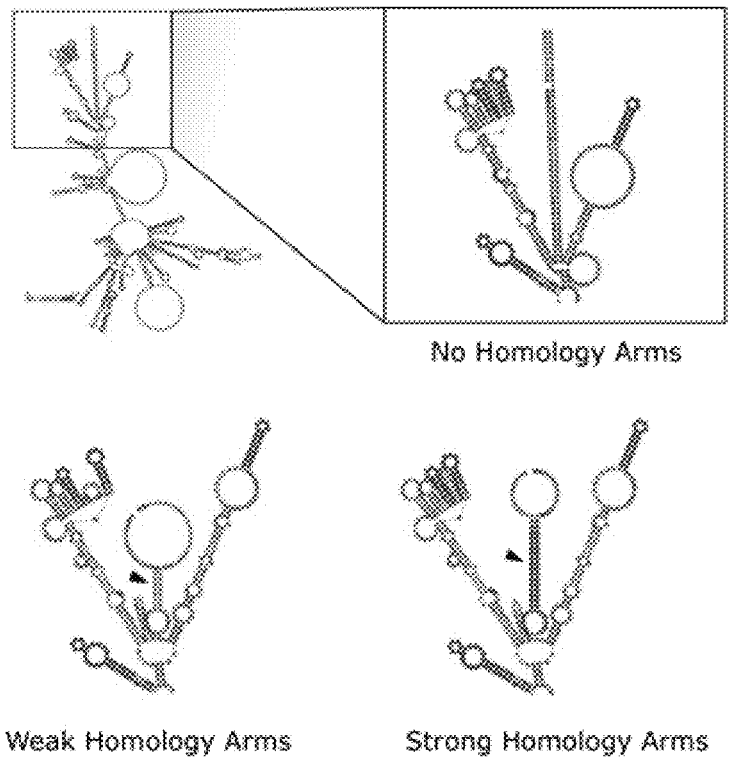
FIG. 1B shows RNA Fold predictions of precursor RNA secondary structure for homology arm design. Colors denote base pairing probability, with red indicating higher probability. Without homology arms, no base pairing is predicted to occur between the ends of the precursor molecule. The arrows point to the added homology arms.
Figure 1C:
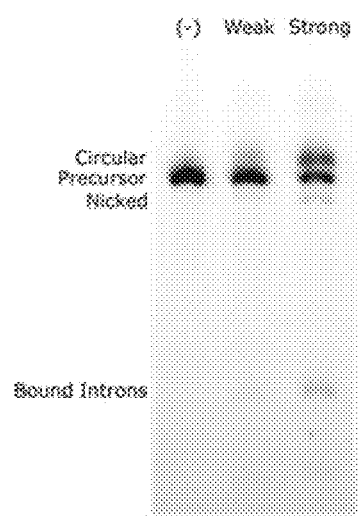
FIG. 1C shows an agarose gel demonstrating the effect of homology arms on splicing. Putative circRNA runs at a higher molecular weight than heavier precursor RNA, as indicated. (−): no homology arms. Weak: weak homology arms, 9 nt. Strong: strong homology arms, 19 nt.
Figure 1D:
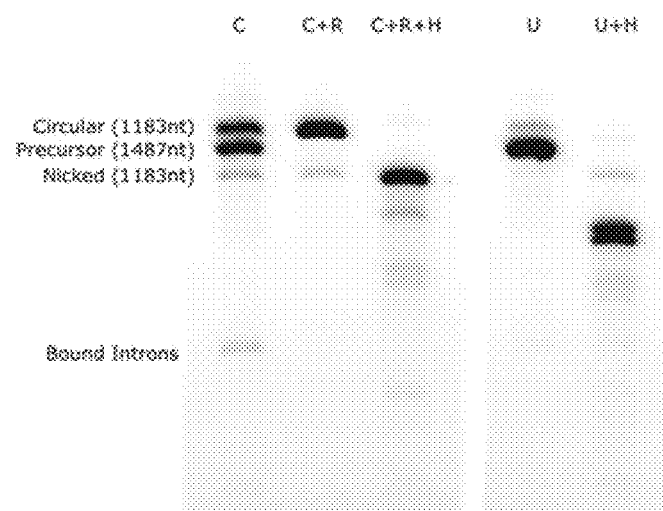
FIG. 1D shows agarose gel confirmation of precursor RNA circularization. C: precursor RNA (with strong homology arms) subjected to circularization conditions. C+R: Lane C, digested with RNase R. C+R+H: Lane C+R, digested with oligonucleotide-guided RNase H. U: precursor RNA not subjected to circularization conditions. U+H: Lane U, digested with oligonucleotide-guided RNase H.
Figure 1E:
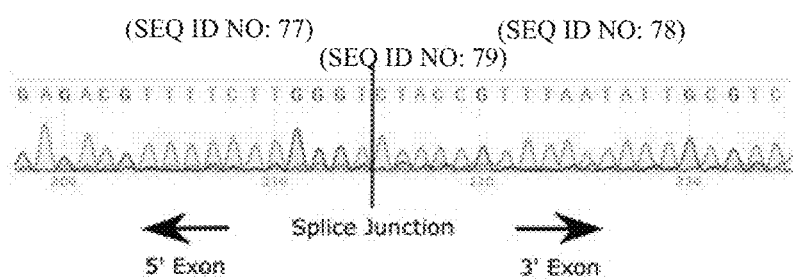
FIG. 1E shows sanger sequencing output of RT-PCR across the splice junction of the sample depicted in lane C+R from FIG. 1D.

There are three general strategies for exogenous RNA circularization: chemical methods using cyanogen bromide or a similar condensing agent, enzymatic methods using RNA or DNA ligases, and ribozymatic methods using self-splicing introns (Petkovic, S. & Muller, S., "RNA circularization strategies in vivo and in vitro," *Nucleic Acids Research*, 43(4):2454-2465 (2015); Beaudury, D. & Perreault, J., "An efficient strategy for the synthesis of circular RNA molecules," *Nucleic Acids Research*, 23(15):3064-3066 (1995); Micura, R., "Cyclic Oligoribonucleotides (RNA) by Solid-Phase Synthesis," *Chemistry—A European Journal*, 5(7):2077-2082 (1999)). A ribozymatic method utilizing a permuted group I catalytic intron has been reported to be more applicable to long RNA circularization and requires only the addition of GTP and Mg2+ as cofactors (Petkovic, S. & Muller, S., "RNA circularization strategies in vivo and in vitro," *Nucleic Acids Research*, 43(4):2454-2465 (2015)). This permuted intron-exon (PIE) splicing strategy consists of fused partial exons flanked by half-intron sequences (Puttaraju, M. & Been, M., "Group I permuted intron-exon (PIE) sequences self-splice to produce circular exons," *Nucleic Acids Research*, 20(20):5357-5364 (1992)). In vitro, these constructs undergo the double trans-esterification reactions characteristic of group I catalytic introns, but because the exons are already fused they are excised as covalently 5' to 3' linked circles (FIG. 1A) (Petkovic, S. & Muller, S., "RNA circularization strategies in vivo and in vitro," *Nucleic Acids Research*, 43(4):2454-2465 (2015)). Using this strategy as a starting point for creating a protein coding circular RNA, a 1.1 kb sequence containing a full-length encephalomyocarditis virus (EMCV) IRES, a *Gaussia* luciferase (GLuc) message, and two short regions corresponding to exon fragments (E1 and E2) of the PIE construct between the 3' and 5' introns of the permuted group I catalytic intron in the thymidylate synthase (Td) gene of the T4 phage were inserted (FIG. 1A, Table 1) (Ford, E. & Ares, M., "Synthesis of circular RNA in bacteria and yeast using RNA cyclase ribozymes derived from a group I intron of phage T4," *Proceedings of the National Academy of Sciences*, 91(8):3117-3121 (1994)). Precursor RNA was synthesized by run-off transcription and then heated in the presence of magnesium ions and GTP to promote circularization, essentially as described previously for the circularization of shorter RNAs (Ford, E. & Ares, M., "Synthesis of circular RNA in bacteria and yeast using RNA cyclase ribozymes derived from a group I intron of phage T4," *Proceedings of the National Academy of Sciences*, 91(8):3117-3121 (1994)). However, splicing products were not obtained. It was speculated that long intervening regions between splice sites may reduce the ability of the splice sites to interact with one another and form a stable complex, thus reducing splicing efficiency. Indeed, the intervening region between the 5' and 3' splice sites of native group I introns is on average 300-500 nucleotides long, while the intervening region of the engineered RNA that we constructed was two to four-fold longer (Vicens, Q., et al., "Toward predicting self-splicing and protein-facilitated splicing of group I introns," *RNA*, 14(10):2013-2029 (2008)). Therefore, perfectly complementary 'homology arms' 9 (weak) or 19 (strong) nucleotides in length were designed and placed at the 5' and 3' ends of the precursor RNA with the aim of bringing the 5' and 3' splice sites into proximity of one another (FIG. 1B, Table 1). Addition of these homology arms increased splicing efficiency from 0% to 16% for weak homology arms and to 48% for strong homology arms as assessed by disappearance of the precursor RNA band (FIG. 1C). To ensure that the major splicing product was circular, the splicing reaction was treated with RNase R (FIG. 1D). Sequencing across the putative splice junction of RNase R-treated splicing reactions revealed ligated exons, and digestion of the RNase R-treated splicing reaction with oligonucleotide-targeted RNase H produced a single band in contrast to two bands yielded by RNase H-digested linear precursor (FIG. 1D and FIG. 1E). These data show that circRNA is a major product of these splicing reactions and that agarose gel electrophoresis allows for simple and effective separation of circular splicing products from linear precursor molecules, nicked circles, splicing intermediates, and excised introns.

Figure 1F:
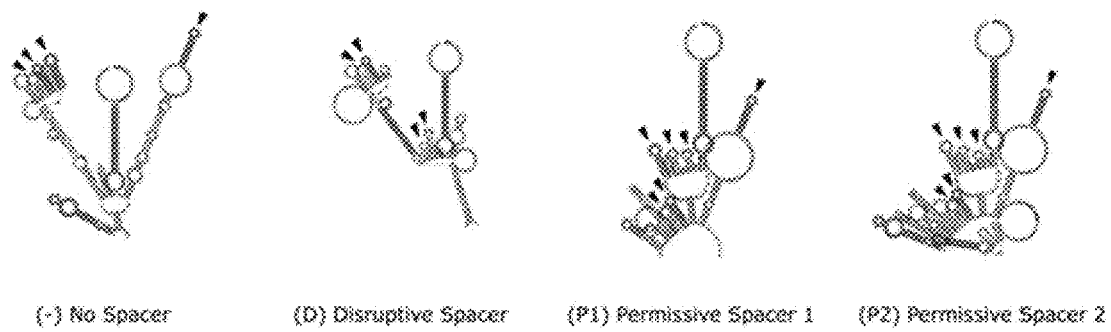
FIG. 1F shows RNAFold predictions of precursor RNA secondary structure in the context of designed spacers. Secondary structures potentially important for ribozyme function are identified by black arrows.
Figure 1G:
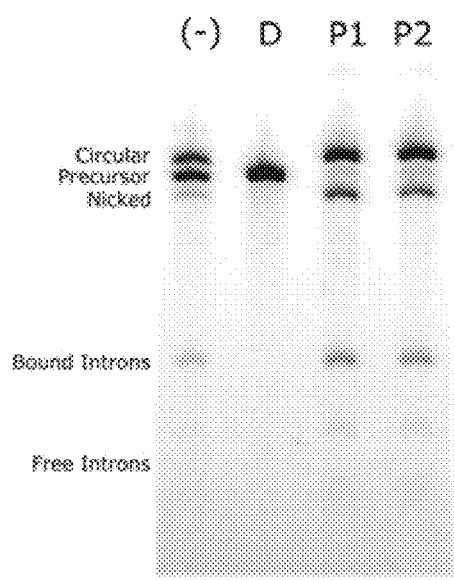
FIG. 1G shows an agarose gel demonstrating the effect of spacers on splicing. (−): no spacer. D: disruptive spacer. P1: permissive spacer 1. P2: permissive spacer 2.
Figure 1H:
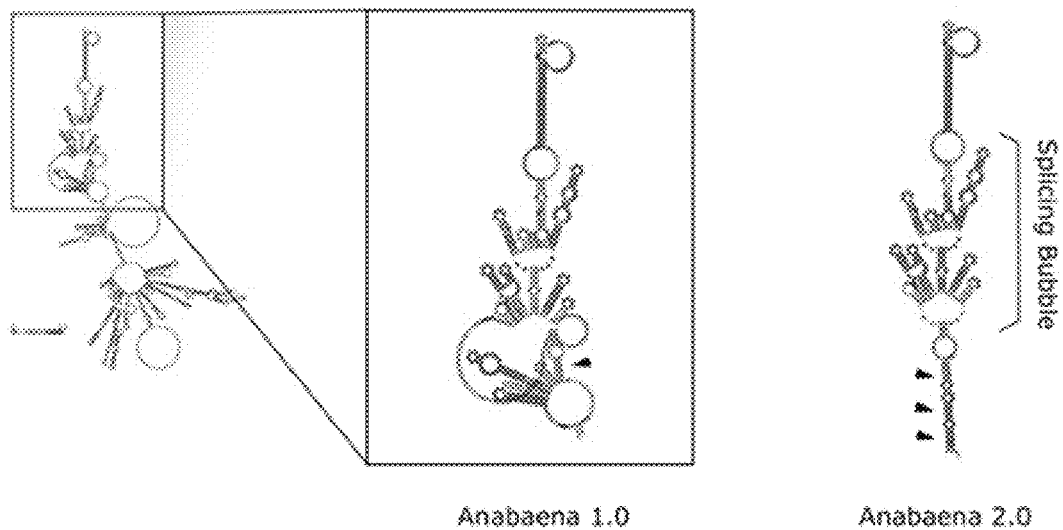
FIG. 1H shows RNAFold predictions of precursor RNA secondary structure for internal homology region design. Lack of significant internal homology (*Anabaena* 1.0) and introduced internal homology (*Anabaena* 2.0) indicated by black arrows. 'Splicing bubble' indicated as the region between homology arms and internal homology regions that contains the splicing ribozyme.
Figure 1I:
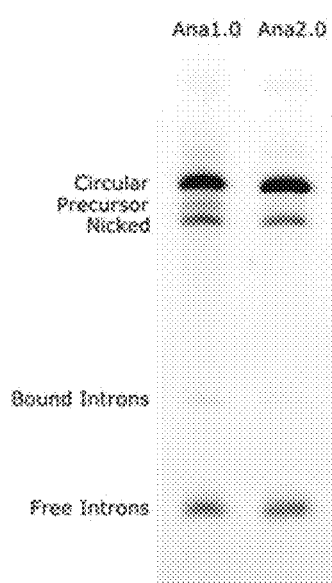
FIG. 1I shows an agarose gel demonstrating the effect of internal homology on splicing.
Figure 1J:
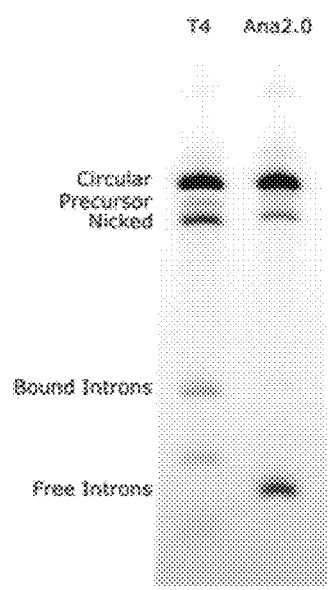
FIG. 1J shows an agarose gel comparing the optimized T4 phage splicing reaction to the optimized *Anabaena* splicing reaction. *Anabaena* intron halves are of roughly equal lengths, and are less likely to remain associated after splicing in comparison to the T4 phage intron halves despite stronger homology arms.
Figure 4A:
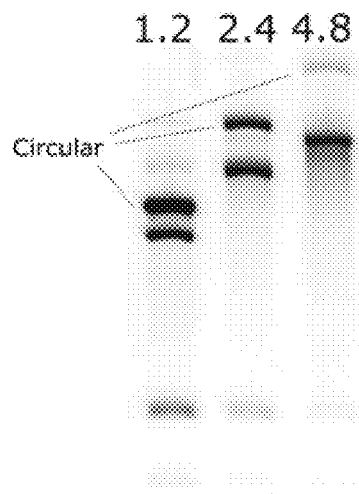
FIG. 4A shows the effect of insert length on RNA circularization efficiency using a permuted group I intron containing optimized spacers and homology arms. 1.2: 1200 nt circRNA. 2.4: 2400 nt circRNA. 4.8: 4800 nt circRNA.
Figure 4B:
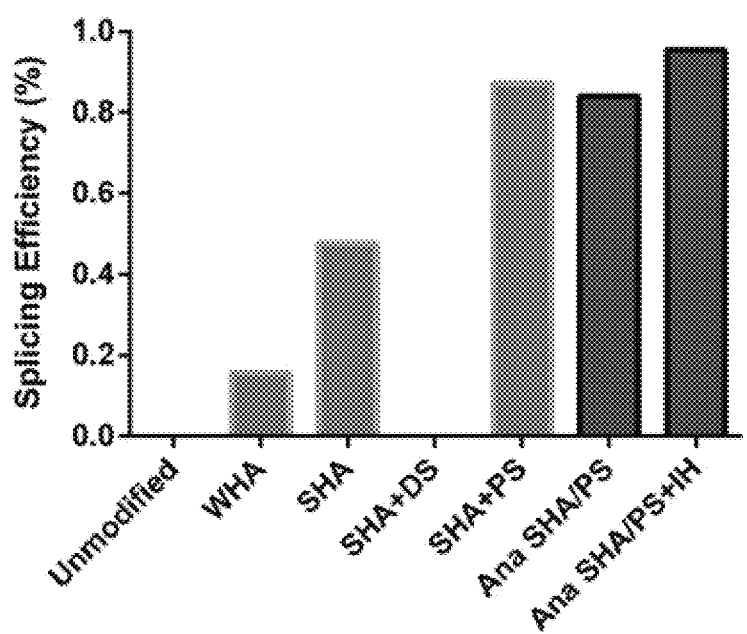
FIG. 4B is a bar graph showing gel quantification of splicing efficiency of precursor molecules containing different engineered sequences. WHA: weak homology arms. SHA: strong homology arms. DS: disruptive spacer. PS: permissive spacer. Ana: *Anabaena* base. IH: internal homology.

In order to further improve the efficiency of circRNA generation from the self-splicing precursor RNA, other factors that may influence successful circularization were considered. The 3' PIE splice site is proximal to the IRES, and because both sequences are highly structured it was hypothesized that sequences within the IRES may interfere with the folding of the splicing ribozyme, either proximally at the 3' splice site or distally at the 5' splice site through long-distance contacts. In order to allow these structures to fold independently, a series of spacers between the 3' PIE splice site and the IRES were designed and it was predicted would either permit or disrupt splicing (FIG. 1F, Table 1). Permissive spacers were designed to conserve secondary structures present within intron sequences that may be important for ribozyme activity, while the disruptive spacer was designed to disrupt sequences in both intron halves, especially the 5' half. The addition of spacer sequences predicted to permit splicing increased splicing efficiency from 46% to 87% (P1 and P2), while the addition of a disruptive spacer sequence completely abrogated splicing (FIG. 1G). This improved construct, containing both homology arms and rationally designed spacers, was able to circularize RNA approaching 5 kb in length (FIG. 4). The use of an alternative group I catalytic intron from the *Anabaena* pre-tRNA was also explored (Puttaraju, M. & Been, M., "Group I permuted intron-exon (PIE) sequences self-splice to produce circular exons," *Nucleic Acids Research*, 20(20):5357-5364 (1992)). The same optimization techniques used to increase the efficiency of the permuted T4 phage intron splicing reaction were applied. Interestingly, during our optimizations it was noted that switching from the T4 catalytic intron to the *Anabaena* catalytic intron may have resulted in the weakening of a short stretch of internal homology between the IRES and the 3' end of the coding region, which may have aided in the formation of an isolated 'splicing bubble' (FIG. 1H). Strengthening this internal homology further increased splicing efficiency from 84% to 95% using the permuted *Anabaena* catalytic intron (FIG. 1H and FIG. 1I, Table 1). The use of the *Anabaena* catalytic intron resulted in a 37% reduction in circRNA nicking compared to the T4 catalytic intron (FIG. 1I and FIG. 1J). Due to increased splicing efficiency and intact circRNA output, the engineered *Anabaena* PIE system proved to be overall superior to the engineered T4 PIE system (FIG. 1J).

Figure 2A:
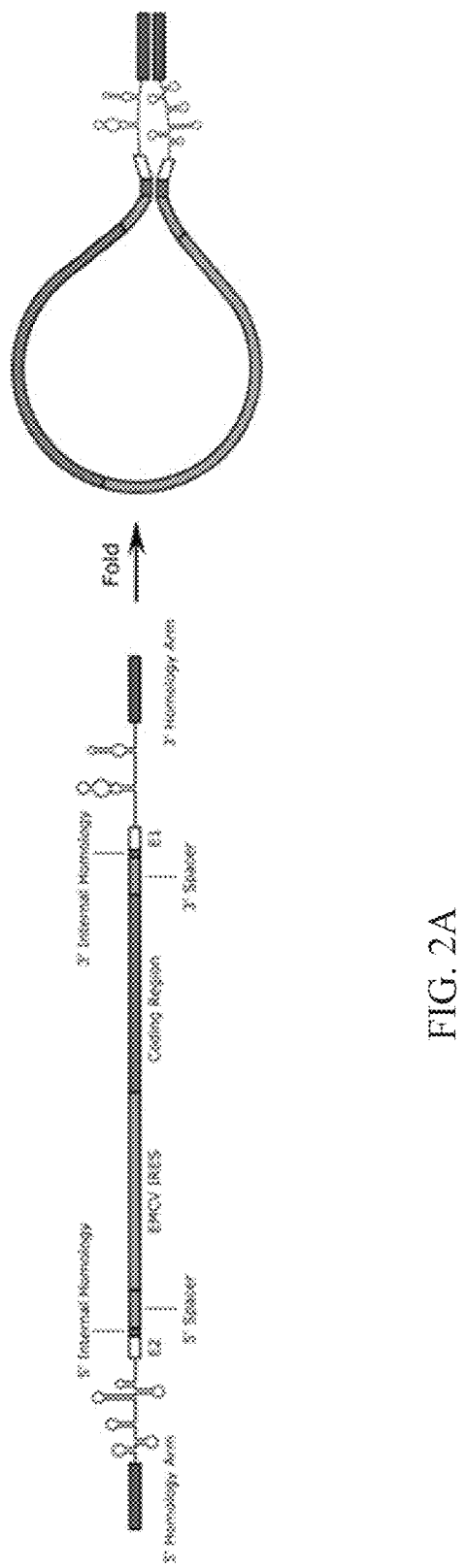
FIG. 2A is a schematic diagram showing elements of an example engineered self-splicing precursor RNA design. Evaluation of circularization efficacy and translation for a range of protein-coding circRNAs generated from de-novo engineered precursor RNA.
Figure 2B:
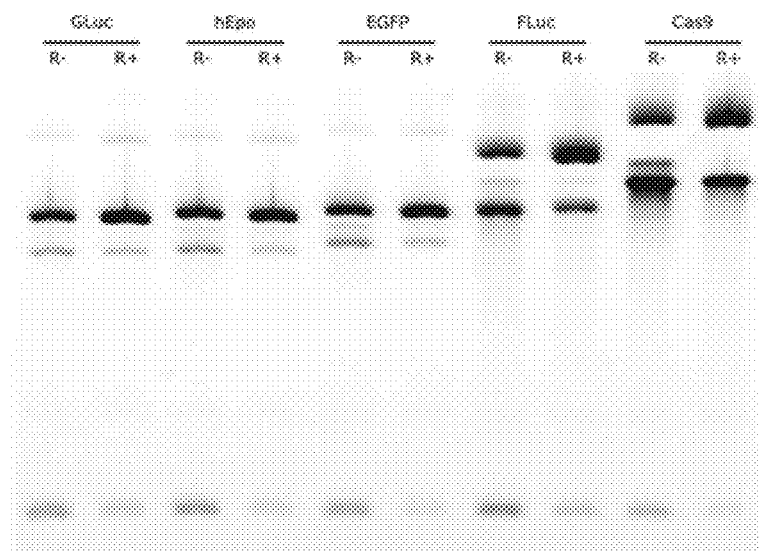
FIG. 2B shows an agarose gel of precursor RNA containing an EMCV IRES and a variable insert including *Gaussia* luciferase (GLuc), human erythropoietin (hEpo), EGFP, Firefly luciferase (FLuc), or Cas9 coding regions after circularization and recirculization (R−). CircRNA was enriched by RNase R degradation (R+).
Figure 2C:
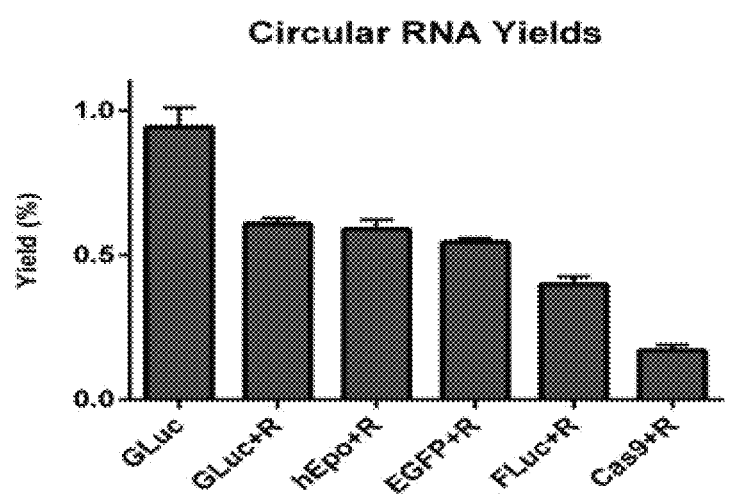
FIG. 2C is a bar graph showing approximate circRNA yields from treatment of 20 μg of splicing reaction with RNase R, as assessed by spectrophotometry (data presented as mean+SD, n=3).
Figure 5A:
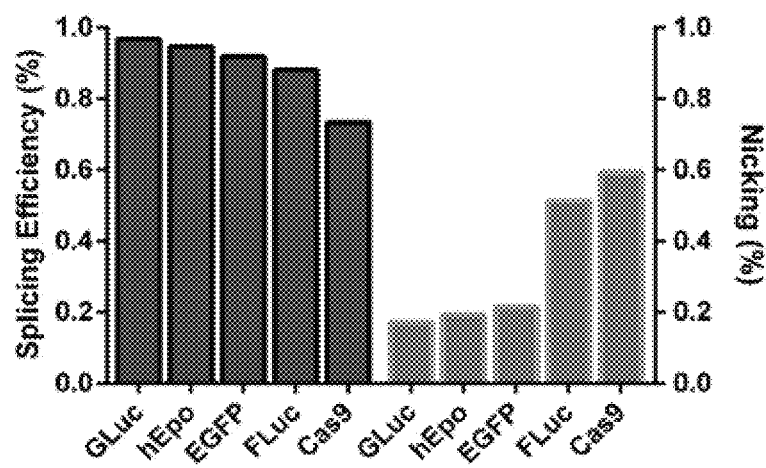
FIG. 5A is a bar graph showing gel quantification (ImageJ) of splicing efficiency and nicking in circRNA containing different intervening coding regions, arranged by length. Splicing efficiency presented as ratio of non-precursor (circular, nicked) to precursor RNA. Nicking presented as ratio of nicked RNA to non-nicked long RNA (precursor, circular).

Internal homology between exon 2 and the GLuc coding sequence rendered the optimized *Anabaena* PIE system incompatible with non-GLuc intervening regions. To adapt the circRNA construct for efficient circularization of a variety of long intervening RNA sequences, a pair of spacer sequences were de novo designed based on the understanding of the parameters that affect permuted catalytic group I intron splicing efficacy. These spacer sequences were engineered with three priorities: 1) to be inert with regards to the folding of proximal intron and IRES structures; 2) to sufficiently separate intron and IRES secondary structures; and 3) to contain a region of spacer-spacer complementarity to promote the formation of a 'splicing bubble' (FIG. 2A, Table 1). Homology arms at the 5' and 3' ends of the precursor molecule were also included. Between these sequences an EMCV IRES was inserted as well as coding regions for five different proteins, including *Gaussia* luciferase, Firefly luciferase, eGFP, human erythropoietin, and Cas9 endonuclease. Circularization of all five RNA sequences was achieved (FIG. 2B, Table 1); circularization efficiency matched that of the stepwise-designed construct (FIG. 1J) and was highly reproducible between inserts but was also dependent on size, with long RNAs less efficiently circularized (FIG. 5A). In addition, it was found that long circRNAs were more prone to nicking in the presence of magnesium ions, resulting in accumulation of nicked circRNA during and after in vitro transcription and RNase R digestion which reduced the overall yields and the purity of the RNase R-treated sample (FIG. 2B and FIG. 2C, FIG. 5A). RNase R did not fully digest resistant *Anabaena* introns (FIG. 2B, bottom bands) or circular concatenations (FIG. 2B, top bands).

Figure 2D:
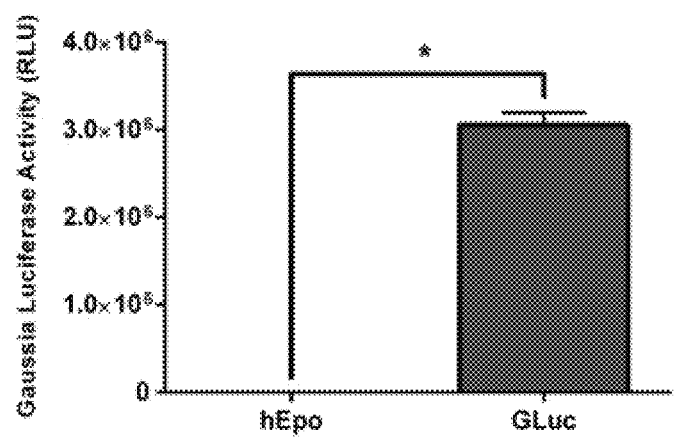
FIG. 2D is a bar graph showing luminescence in the supernatant of HEK293 cells 24 hours after transfection with circRNA coding for GLuc (data presented as mean+SD, n=4, *p<0.05).
Figure 2E:
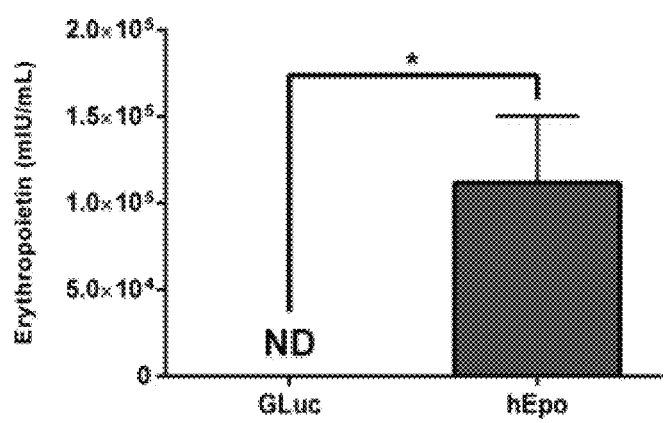
FIG. 2E is a bar graph showing the expression of human erythropoietin in the supernatant of HEK293 cells 24 hours after transfection with circRNA coding for hEpo (data presented as mean+SD, n=4, *p<0.05).
Figure 2F:
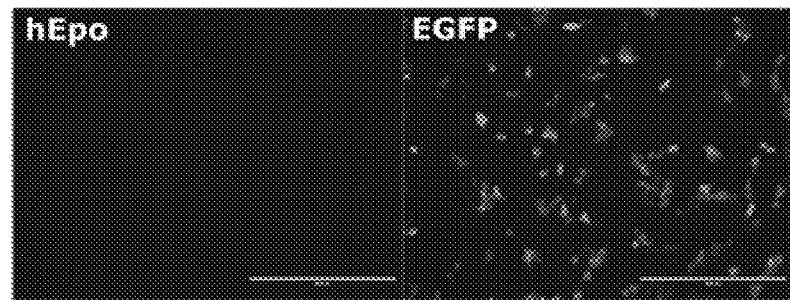
FIG. 2F shows GFP fluorescence in HEK293 cells 24 hours after transfection with circRNA coding for EGFP.
Figure 2G:
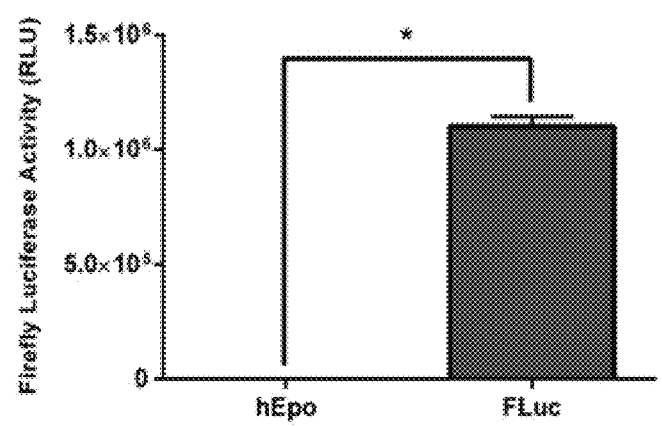
FIG. 2G is a bar graph showing luminescence in the lysate of HEK293 cells 24 hours after transfection with circRNA coding for FLuc (data presented as mean+SD, n=4, *p<0.05).
Figure 2H:
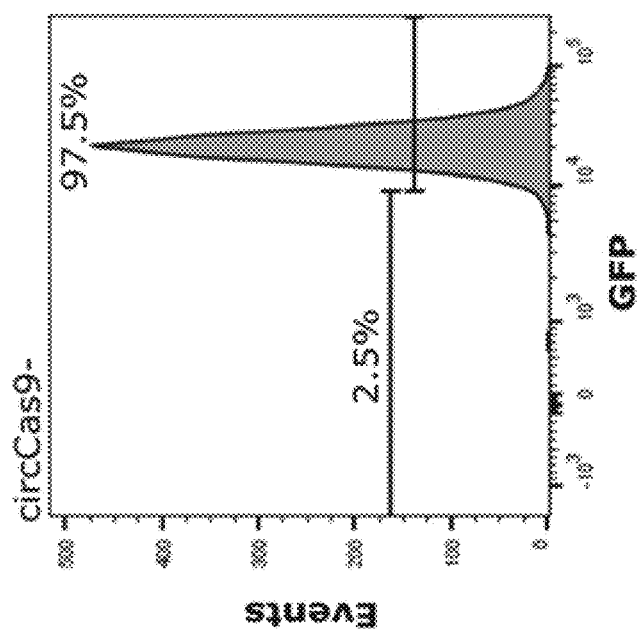
FIG. 2H is a graph showing FACS analysis demonstrating GFP ablation in HEK293-EF1a-GFP cells 4 days after transfection with sgGFP alone (circCas9−) indicated by the appearance of a GFP-negative cell population.
Figure 2I:
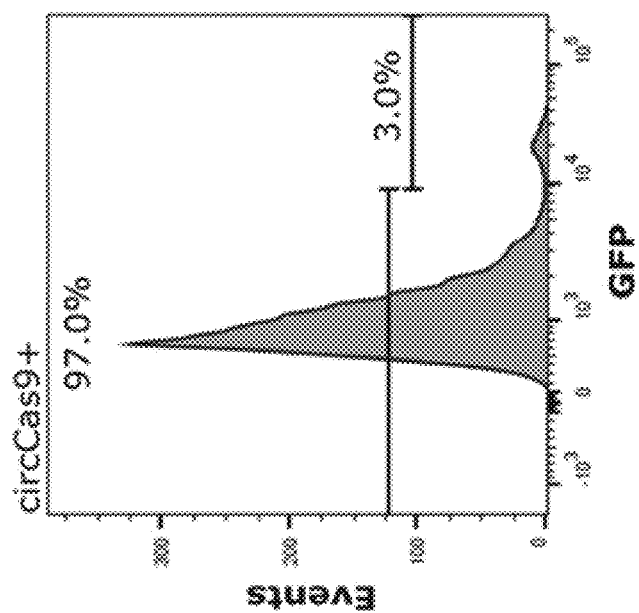
FIG. 2I is a graph showing FACS analysis demonstrating GFP ablation in HEK293-EF1a-GFP cells 4 days after transfection with circRNA coding for Cas9 (circCas9+), indicated by the appearance of a GFP-negative cell population.
Figure 5B:
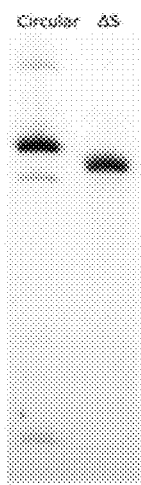
FIG. 5B shows agarose gel demonstrating the effect of small deletions encompassing the 5' and 3' splice sites on splicing.
Figure 5C:
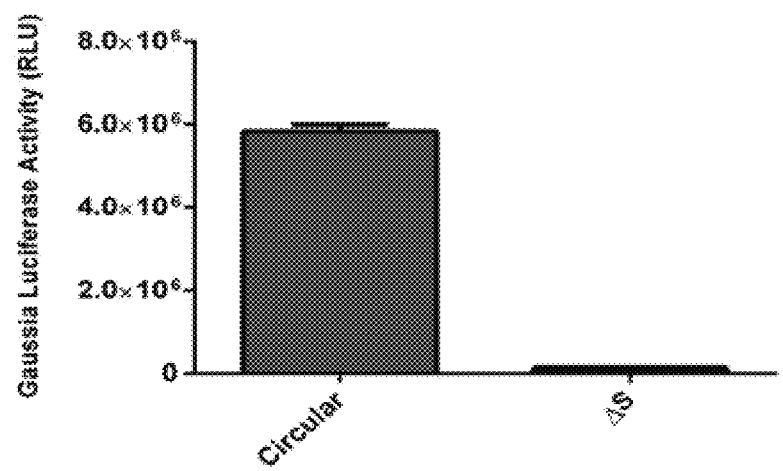
FIG. 5C is a bar graph showing luminescence in the supernatant of HEK293 cells 24 hours after transfection with circRNA coding for GLuc and containing an EMCV IRES or the same precursor RNA with deleted splice sites (data presented as mean+SD, n=4).

It has been demonstrated that endogenous circRNA may produce small quantities of protein (Legnini, I. et al., "CircZNF609 Is a Circular RNA that Can Be Translated and Functions in Myogenesis," *Molecular Cell*, 66(1):22-37.e9 (2017)). As a means of assessing the ability of engineered circRNAs to produce protein, RNase R-digested splicing reactions of each construct was transfected into human embryonic kidney cells (HEK293). Transfection of *Gaussia* or Firefly luciferase circRNA resulted in robust production of functional protein as measured by luminescence (FIG. 2D and FIG. 2G). Likewise, human erythropoietin was detected in cell culture media from transfection of erythropoietin circRNA, and EGFP fluorescence was observed from transfection of EGFP circRNA (FIG. 2E and FIG. 2F). Co-transfection of Cas9 circRNA with sgRNA directed against GFP into HEK293 cells constitutively expressing GFP resulted in ablated fluorescence in up to 97% of cells in comparison to an sgRNA-only control (FIG. 2H and FIG. 2I). Because RNase R digestion of splicing reactions is not always complete and precursor RNA contains a functional IRES, a splice site deletion mutant of the GLuc construct was created to measure the potential contribution of impurities to protein expression. When transfected at equal weight quantities to RNase-R digested splicing reactions, this splice site deletion mutant produced a barely detectable level of protein (FIG. 5B and FIG. 5C).

Figure 3A:
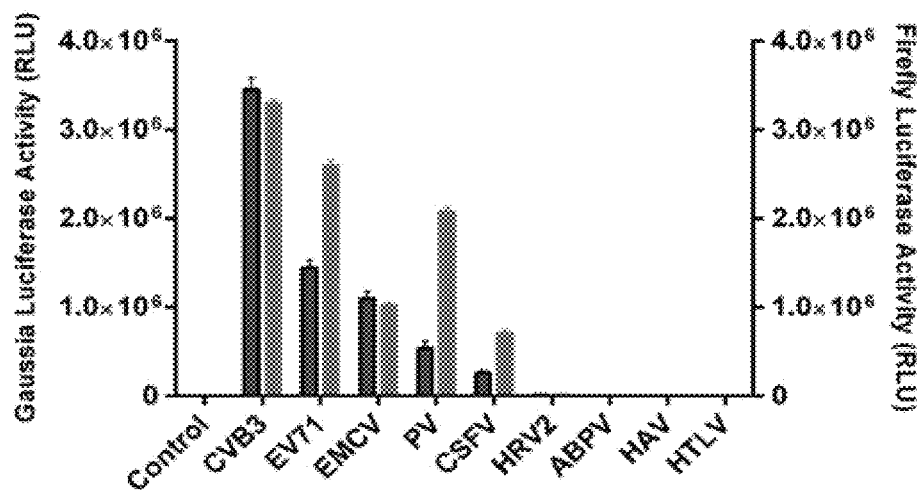
FIG. 3A is a bar graph showing luminescence in the supernatant of HEK293 cells 24 hours after transfection with circRNA containing a panel of viral 5' UTR IRES sequences in GLuc (left bars, black) and FLuc (right bars, gray) contexts (data presented as mean+SD, n=4).
Figure 3B:
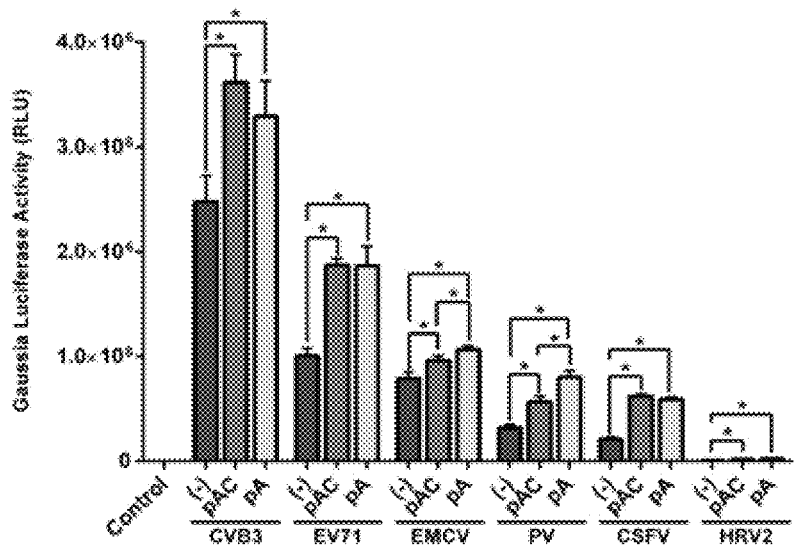
FIG. 3B is a bar graph showing luminescence in the supernatant of HEK293 cells 24 hours after transfection with circRNA containing a GLuc coding region and a functional IRES. The effect of adding a polyA(30) or polyAC(30) spacer sequence separating the IRES from the splice junction is measured. (−): no spacer. pAC: 30 nt spacer consisting of adenosines and cytosines. pA: 30 nt spacer consisting of adenosines (data presented as mean+SD, n=4, *p<0.05).
Figure 3C:
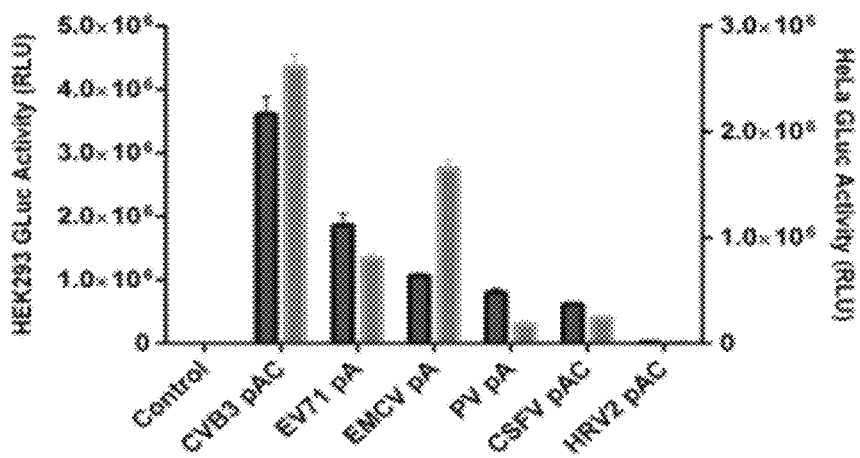
FIG. 3C is a bar graph showing luminescence in the supernatant of HEK293 (left, black) and HeLa (right, gray) cells 24 hours after transfection with the most effective circRNAs by IRES in b) (data presented as mean+SD, n=4).
Figure 6A:
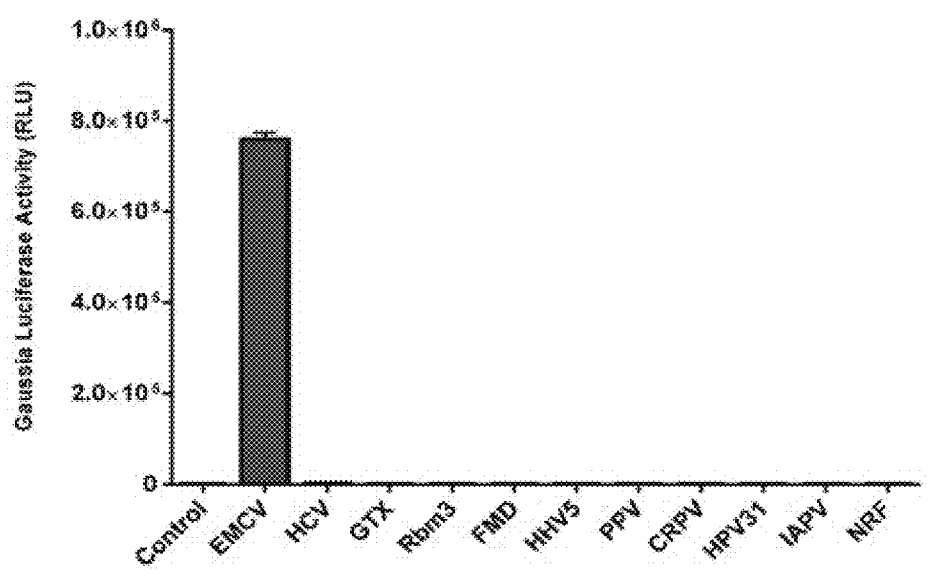
FIG. 6A is a bar graph showing additional IRES sequences and putative IRES sequences tested for functionality in the context of circRNA.
Figure 6B:
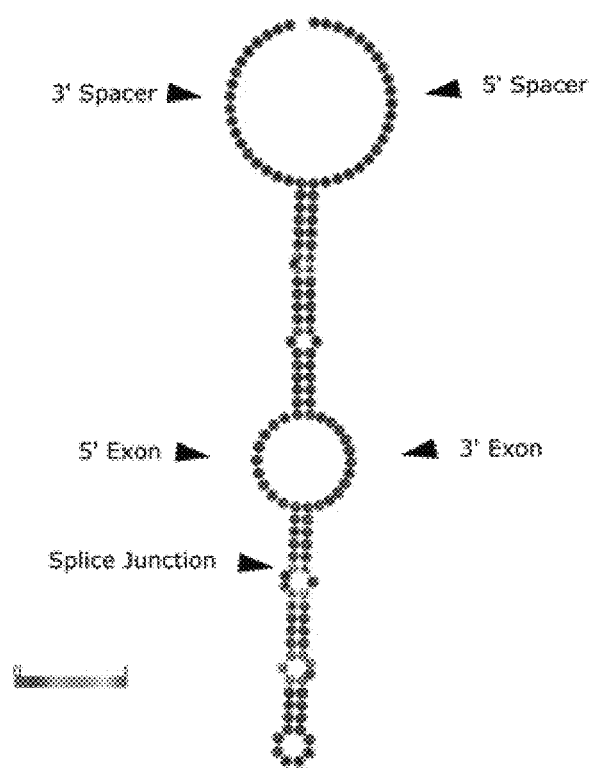
FIG. 6B is a schematic diagram of an RNAFold prediction of precursor RNA secondary structure at the splice junction. IRES, coding region, and introns are excluded.
Figure 6C:
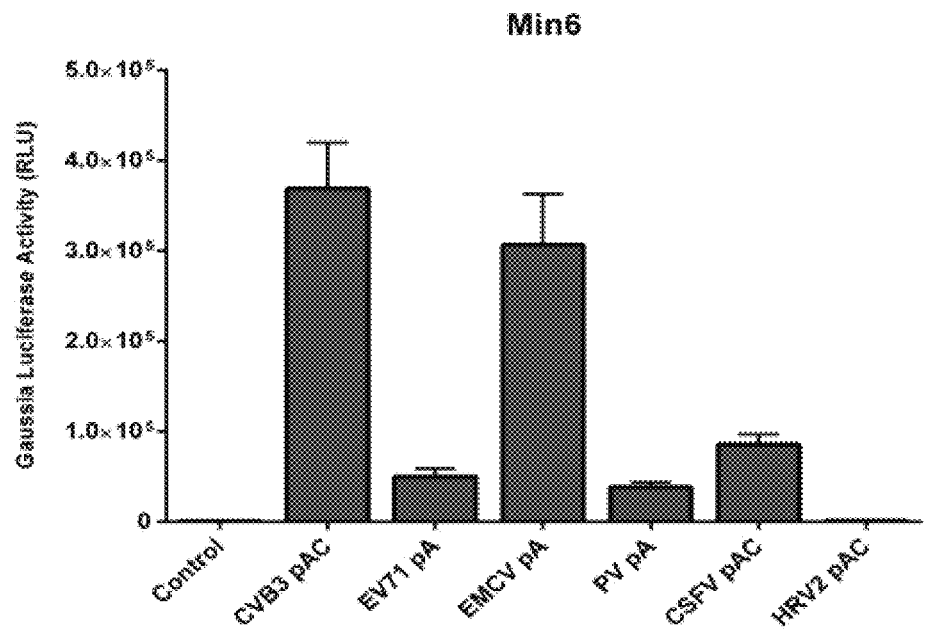
FIG. 6C is a bar graph showing luminescence in the supernatant of Min6 cells 24 hours after transfection with the most effective circRNAs by IRES in FIG. 3B (data presented as mean+SD, n=4).
Figure 6D:
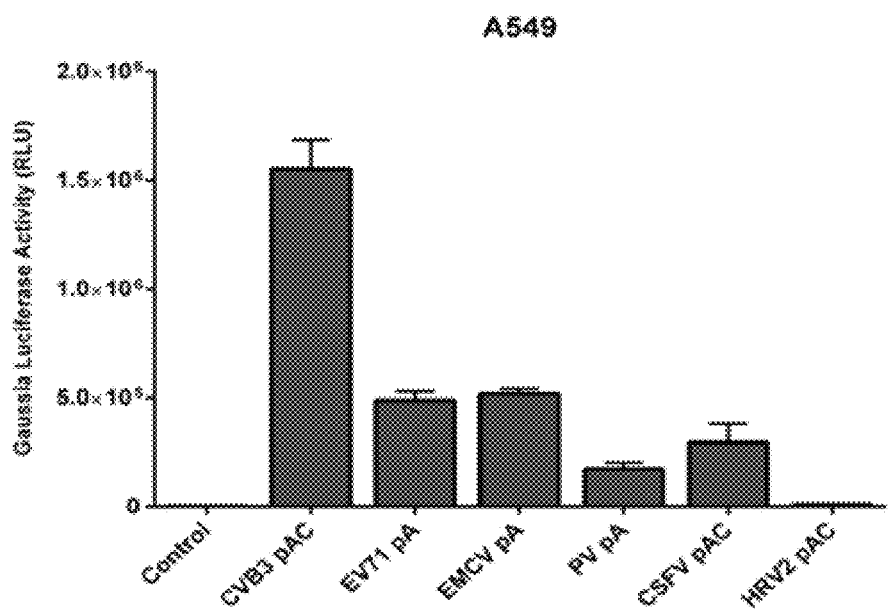
FIG. 6D is a bar graph showing luminescence in the supernatant of A549 cells 24 hours after transfection with the most effective circRNAs by IRES in FIG. 3B (data presented as mean+SD, n=4).

To establish exogenous circRNA as a reliable alternative to existing linear mRNA technology it is desirable to maximize protein expression. Cap-independent translation mediated by an IRES can exhibit varying levels of efficiency depending on cell context and is generally considered less efficient than cap-dependent translation when included in bicistronic linear mRNA (Borman, A. M. et al., "Comparison of Picornaviral IRES-Driven Internal Initiation of Translation in Cultured Cells of Different Origins," *Nucleic Acids Research*, 25(5):925-932 (1997)). Similarly, the polyA tail stabilizes and improves translation initiation efficiency in linear mRNA through the actions of polyadenylate binding proteins (Imataka, H., "A newly identified N-terminal amino acid sequence of human eIF4G binds poly(A)-binding protein and functions in poly(A)-dependent translation," *The EMBO Journal*, 17.24:7480-489 (1998); Kahvejian, A. et al., "Mammalian poly(A)-binding protein is a eukaryotic translation initiation factor, which acts via multiple mechanisms," *Genes & Development*, 19(1):104-113 (2005)). However, the efficiency of different IRES sequences and the inclusion of a polyA tract within the context of circRNA has not been investigated. The EMCV IRES was replaced with 5' UTR sequences from several viral transcripts that contain known or putative IRESs, as well as several other putative IRES sequences (Table 1, FIG. 6A) (Weingarten-Gabbay, S. et al., "Systematic discovery of cap-independent translation sequences in human and viral genomes," *Science*, 351(6270) (2016)). It was found that the IRES from Coxsackievirus B3 (CVB3) was 1.5-fold more effective than the commonly adopted EMCV IRES in HEK293 cells (FIG. 3A). Because secondary structures proximal to the IRES, including within the coding region that directly follows the IRES, have the potential to disrupt IRES folding and translation initiation, selected viral IRES sequences were tested in the context of Firefly luciferase. While the CVB3 IRES was still superior to all others, the efficacy of several other IRESs, most notably the Poliovirus IRES, was dramatically altered (FIG. 3B). The addition of an internal polyA sequence or a polyAC spacer control to IRES sequences was tested and showed the ability to drive protein production above background levels from engineered circRNA would alter protein expression. It was found that both sequences improved expression in all constructs, possibly due to greater unstructured separation between the beginning of the IRES sequence and the exon-exon splice junction, which is predicted to maintain stable structure (FIG. 3B, FIG. 6B). This greater degree of unstructured separation may reduce steric hindrance occluding initiation factor binding to IRES structures. In the case of EMCV and Poliovirus IRESs, polyA sequences improved expression beyond the improvement seen with an unstructured polyAC spacer. This may suggest that the association of polyadenylate binding proteins may enhance IRES efficiency. After selecting the most effective polyA or polyAC construct for each IRES, IRES efficacy in different cell types was explored, including human cervical adenocarcinoma (HeLa), human lung carcinoma (A549), and immortalized mouse pancreatic beta cells (Minh). jIRES efficacy varied depending on type, but the CVB3 IRES was superior in all types tested (FIG. 3C, FIG. 6C and FIG. 6D).

Figure 3D:
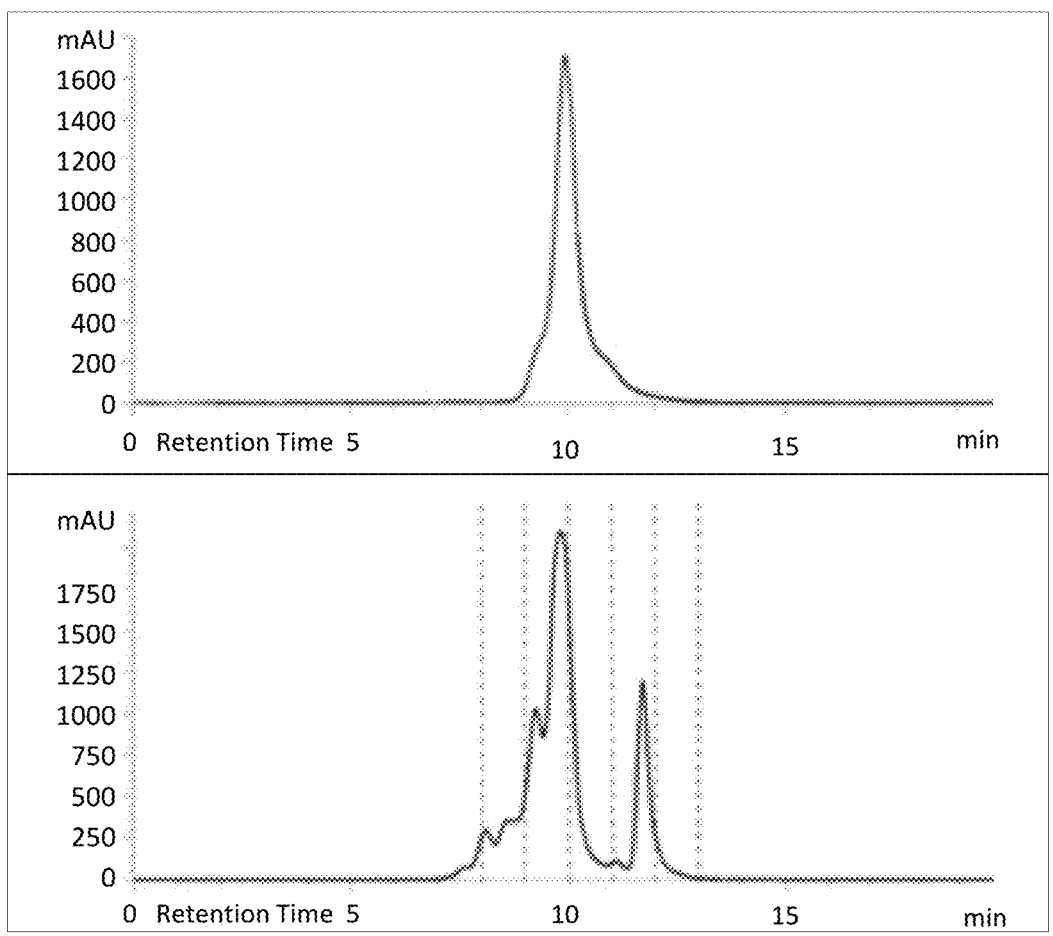
FIG. 3D is a graph showing HPLC chromatogram of linear GLuc RNA (top) and a CVB3-GLuc-pAC splicing reaction (bottom).
Figure 3E:
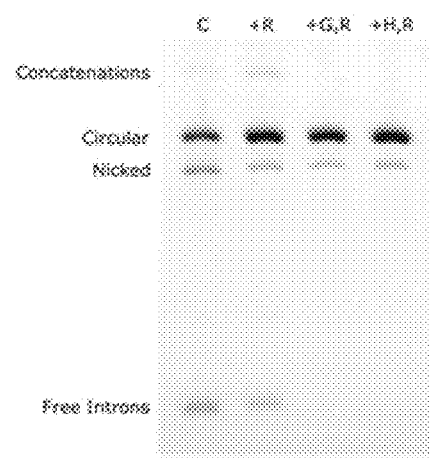
FIG. 3E shows agarose gel of CVB3-GLuc-pAC purified by different methods. C: splicing reaction. +R: splicing reaction treated with RNase R. +G,R: splicing reaction gel extracted, and then treated with RNase R. +H,R: splicing reaction HPLC purified, and then treated with RNase R.
Figures 3F, 3G:
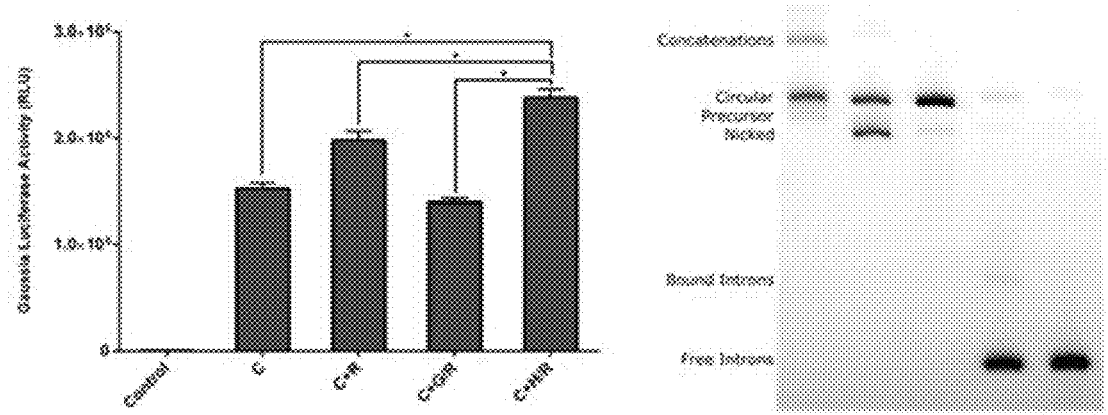
FIG. 3F shows luminescence in the supernatant of HEK293 cells 24 hours after transfection with the CVB3-GLuc-pAC splicing reactions purified by different methods as noted in FIG. 3E (data presented as mean+SD, n=4, *p<0.05).
FIG. 3G shows an agarose gel of HPLC fractions for the data in FIG. 3D. From left to right: Fraction 1, 2, 3, 4, 5.

Purity of circRNA preparations is another factor essential for maximizing protein production from circRNA and for avoiding innate cellular immune responses. It has been shown that removal of dsRNA by HPLC eliminates immune activation and improves translation of linear nucleoside-modified IVT mRNA (Karikó, K. et al., "Generating the optimal mRNA for therapy: HPLC purification eliminates immune activation and improves translation of nucleoside-modified, protein-encoding mRNA," *Nucleic Acids Research*, 39(21):e142-e142 (2011)). However, no scalable methods have been reported for purification of circRNA from byproducts of IVT and circularization reactions, which include dsRNA and triphosphate-RNA that may engage RNA sensors and induce a cellular immune response (Karikó, K. et al., "Generating the optimal mRNA for therapy: HPLC purification eliminates immune activation and improves translation of nucleoside-modified, protein-encoding mRNA," *Nucleic Acids Research*, 39(21):e142-e142 (2011)). While the complete avoidance of nicked circRNA was untenable due to mild degradation during processing, substantially pure (90% circular, 10% nicked) circRNA was obtained using gel extraction for small quantities and size exclusion HPLC for larger quantities of splicing reaction starting material (FIG. 3D and FIG. 3E). In both cases, purification was followed with RNase R treatment to eliminate the majority of degraded RNA. When comparing the protein expression of gel extracted or HPLC purified circRNA to RNase-R digested splicing reactions, HPLC purification was found to be a superior method of purification that surpassed RNAse-R digestion alone (FIG. 3E and FIG. 3F).

Figure 3H:
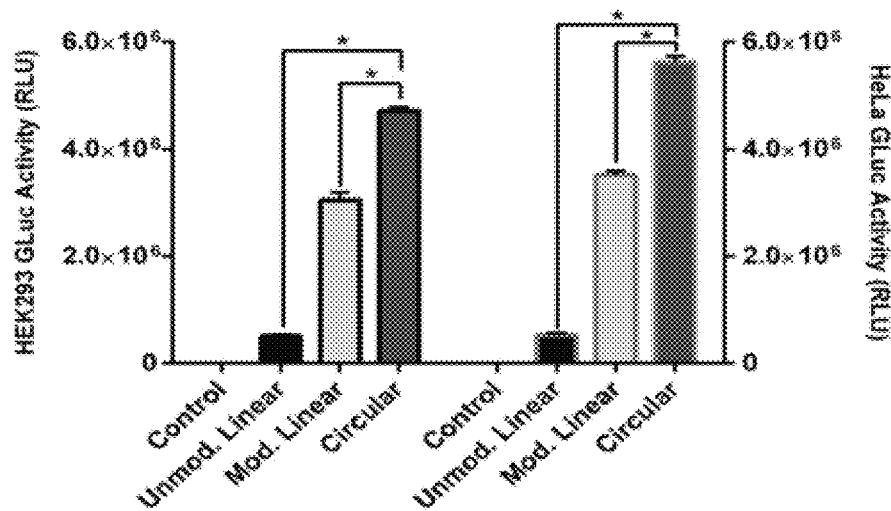
FIG. 3H is a bar graph showing luminescence in the supernatant of HEK293 (left) and HeLa (right) cells 24 hours after transfection with CVB3-GLuc-pAC circRNA or modified or unmodified linear GLuc mRNA (data presented as mean+SD, n=4 HEK293, n=3 HeLa, *p<0.05).
Figure 3I:
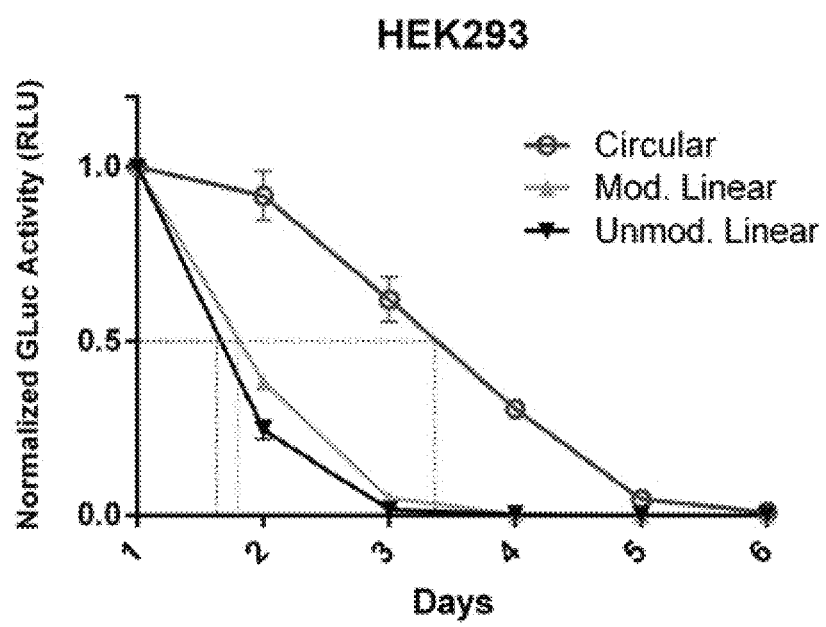
FIG. 3I is a graph showing luminescence in the supernatant of HEK293 cells starting 24 hours after transfection with CVB3-GLuc-pAC circRNA or modified or unmodified linear GLuc mRNA and continuing for 6 days (data presented as mean+SD, n=4 HEK293).
Figure 3K:
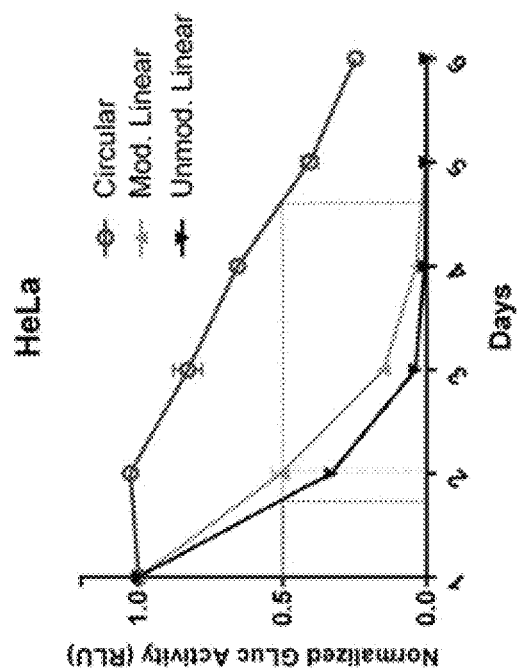
FIG. 3K is a graph showing luminescence in the supernatant of HeLa cells starting 24 hours after transfection with CVB3-GLuc-pAC circRNA or modified or unmodified linear GLuc mRNA and continuing for 6 days (data presented as mean+SD, n=3 HeLa).
Figure 3J:
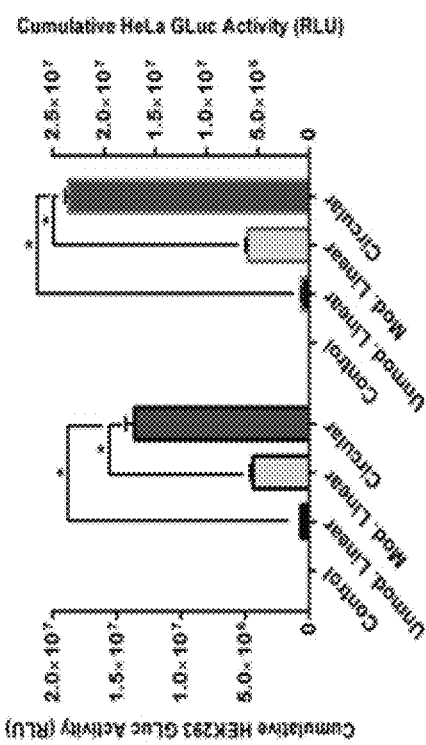
FIG. 3J is a graph showing relative cumulative luminescence produced over 6 days by HEK293 (left) and HeLa (right) cells transfected with CVB3-GLuc-pAC circRNA or modified or unmodified linear GLuc mRNA (data presented as mean+SD, n=4 HEK293, n=3 HeLa, *p<0.05).

It is unknown whether exogenous circRNA translation efficiency is comparable to that of linear mRNA, and whether circRNA protein production exhibits differences in stability. Using HPLC-purified engineered circRNA, the stability and efficacy of *Gaussia* luciferase-coding circRNA (CVB3-GLuc-pAC) was compared to equimolar quantities of a canonical unmodified 5' methylguanosine-capped and 3' polyA-tailed linear GLuc mRNA as well as a commercially available nucleoside modified linear GLuc mRNA (Trilink). Protein production assessed by luminescence 24 hours post-transfection revealed that circRNA produced 811.2% more protein than unmodified linear mRNA at this early time point in HEK293 cells (FIG. 3H). Interestingly, circRNA also produced 54.5% more protein than modified mRNA, demonstrating that nucleoside modifications are not necessary for robust protein production from circRNA. Similar results were obtained in HeLa cells (FIG. 3H). Luminescence data collected over six days showed that protein production from circRNA was extended relative to that from linear mRNA in HEK293 cells, with circRNA exhibiting a protein production half-life of 80 hours, while the half-lives of protein production from unmodified and modified linear mRNA were approximately 43 and 45 hours respectively (FIG. 3I). Due to increased expression or stability, circRNA also produced substantially more protein than both unmodified and modified linear mRNAs over its lifetime (FIG. 3J and FIG. 3K). In HeLa cells, circRNA exhibited a protein production half-life of 116 hours, while the half-lives of protein production from unmodified and modified linear mRNA were approximately 44 and 49 hours respectively (FIG. 3I). This again resulted in substantially more protein production from circRNA over its lifetime compared to both unmodified and modified linear mRNAs (FIG. 3J and FIG. 3K).

Obtaining stable protein production from exogenous mRNA has been a longstanding goal of mRNA biotechnology. The possibility of adapting circular RNA for this purpose has been stifled by low circRNA production efficiency, difficulty of purification, and weak protein expression. Indeed, these obstacles must be overcome before the stability of protein production from circRNA can be fully assessed. The modular permuted group 1 catalytic intron-based system using a vector that included homology arms and spacers as described herein permits the efficient circularization of a wide range of long RNAs. In addition, it was shown that optimized circRNA is capable of producing large quantities of protein and that it can be effectively purified by HPLC. Finally, it was shown that circRNA can produce greater quantities of protein for a longer duration than unmodified and modified linear RNA, providing evidence that circRNA holds potential as an alternative to mRNA for the stable expression of therapeutic proteins.

Figure 17:
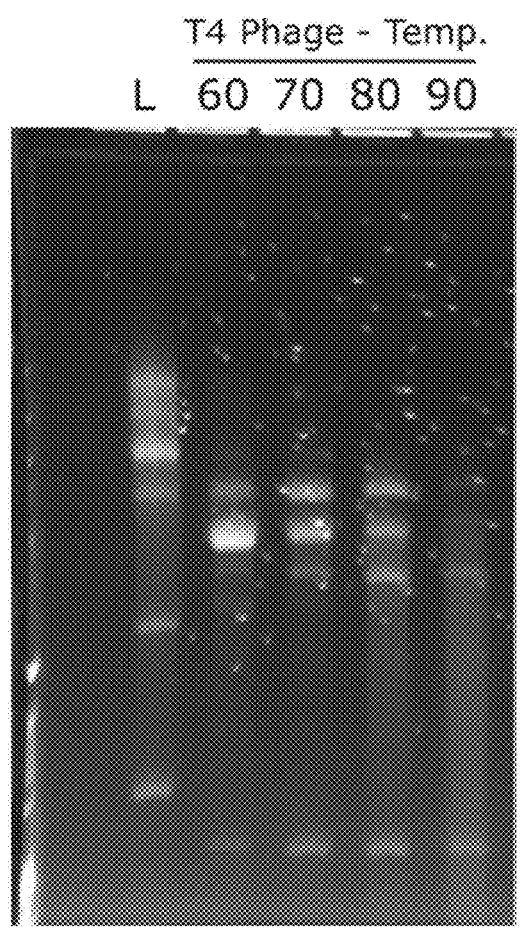
FIG. 17 shows circularization of precursor RNA containing a T4 phage permuted intron, EMCV IRES, GLuc reading frame, and strong homology arms directly after in vitro transcription. Precursor RNA was heated at the indicated temperatures, cooled on ice, and then spliced at 55 degrees Celsius.

The results for FIG. 17 show that RNA circularization with a suboptimal construct can be promoted by increased temperature, but at the cost of increased degradation.

Figure 18A:
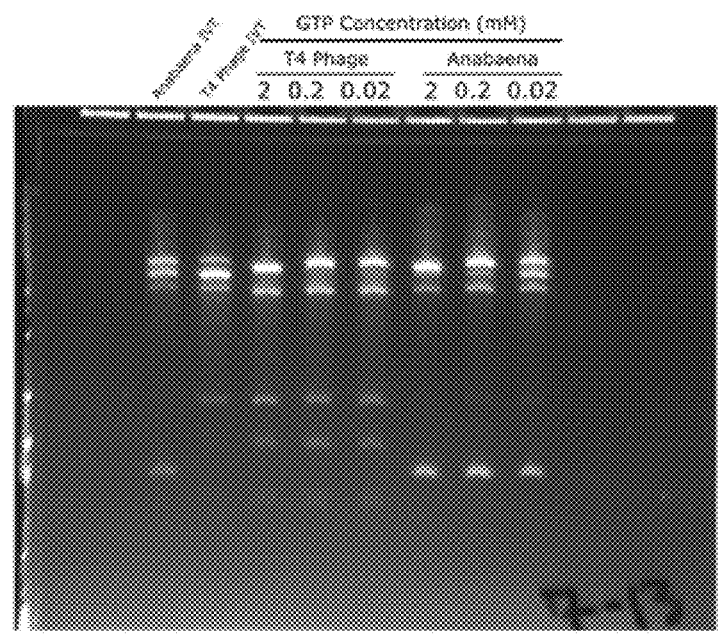
FIGS. 18A-18C show circularization of precursor RNA.
Figure 18B:
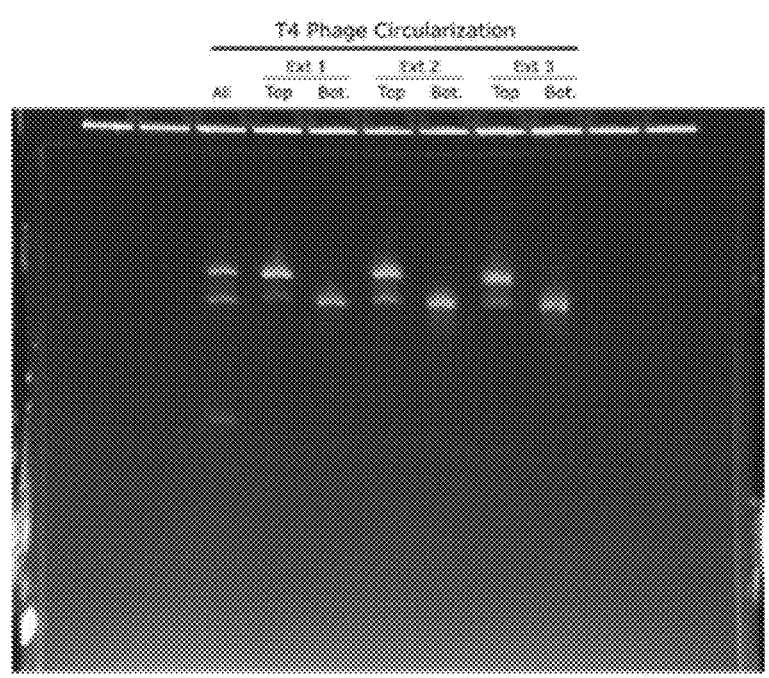
Figure 18C:
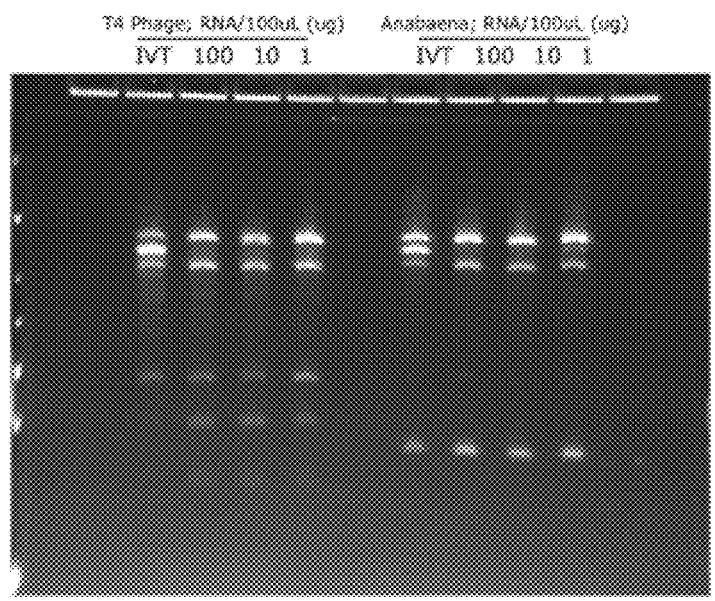

The results for FIGS. 18A-C show that circularization is sensitive to GTP concentration, insensitive to RNA concentration, and the two bands on the gel don't interchange (A, B, C respectively); this is also an example of strong homology arm/5' spacer circularization.

Figure 19:
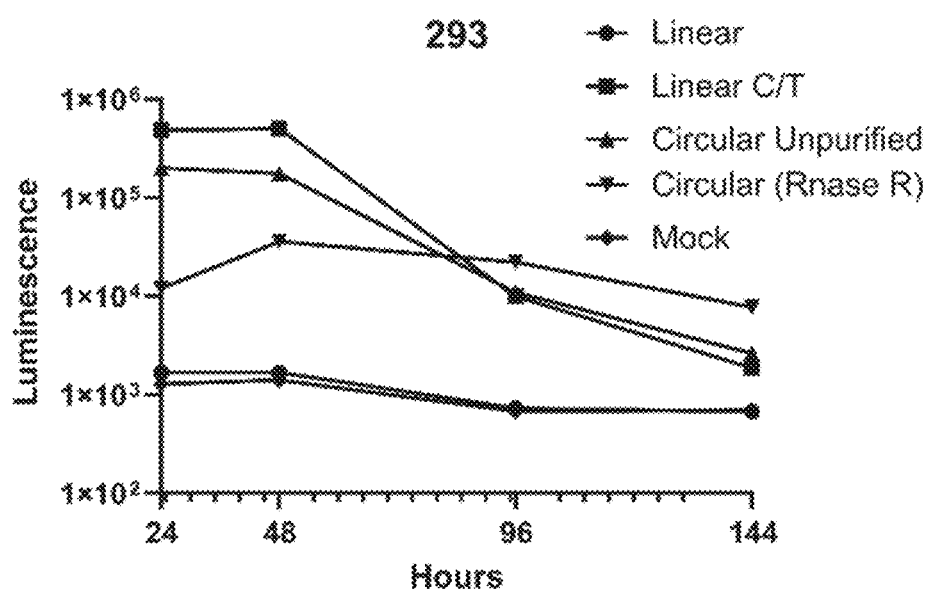
FIG. 19 shows a graph of stability and expression of GLuc from EMCV-circRNA without spacers or linear mRNA over 144h in 293 cells.

The results for FIG. 19 show that low protein expression from unoptimized circRNA construct—no spacers, strong homology arms; demonstration of the importance of purification on circRNA expression/stability.

Figure 20A:
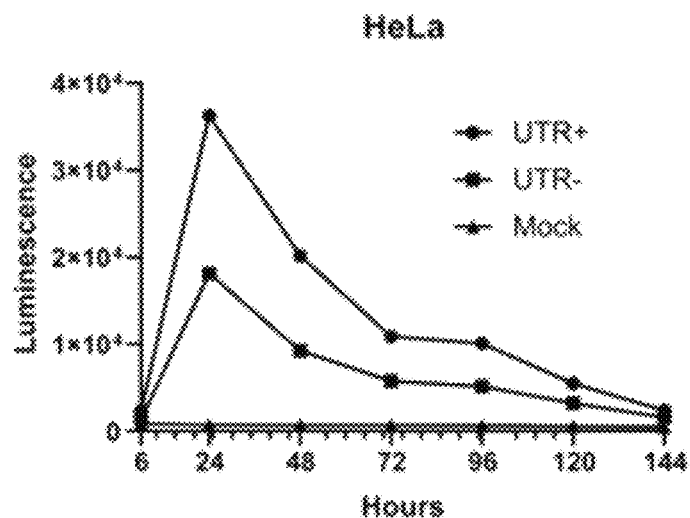
FIGS. 20A-20D.
Figure 20B:
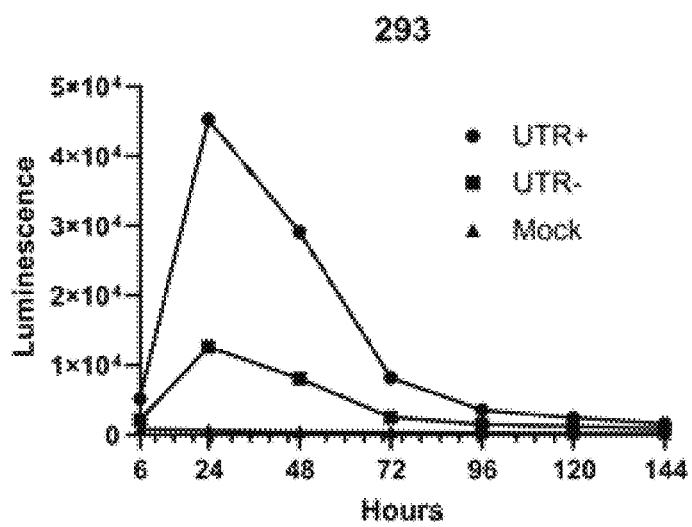
Figure 20C:
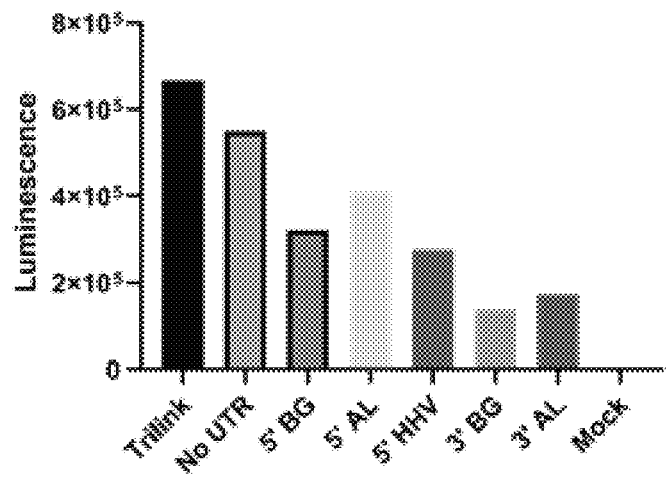
Figure 20D:
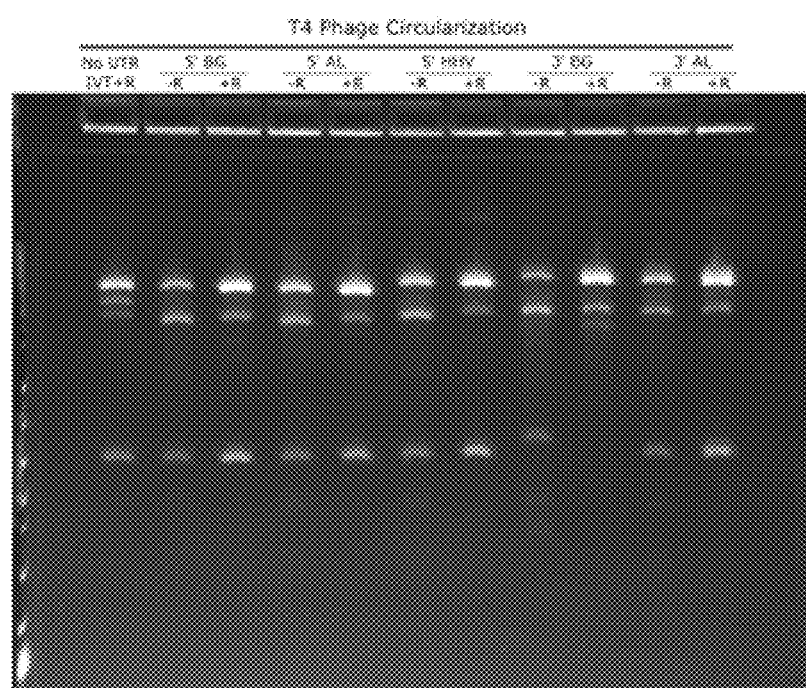
Figure 21A:
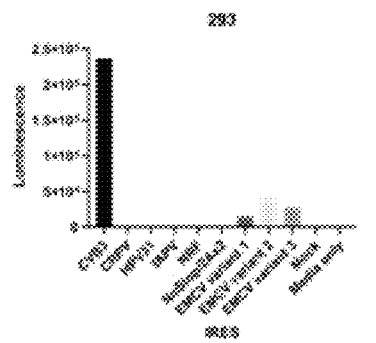
FIGS. 21A-21G.
Figure 21B:
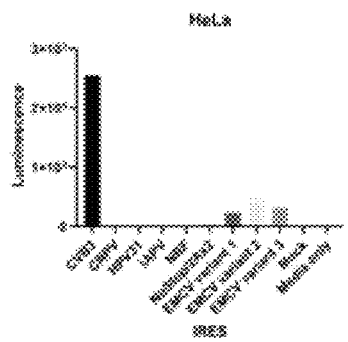
Figure 21C:
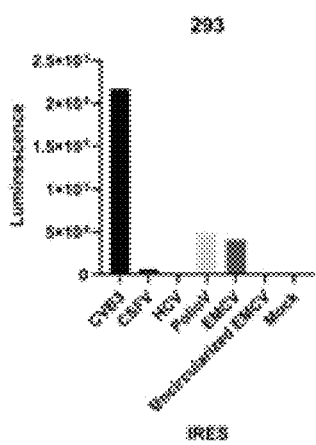
Figure 21D:
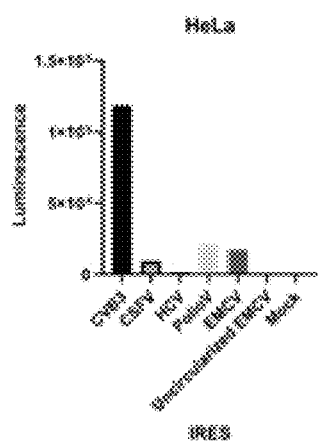
Figure 21E:
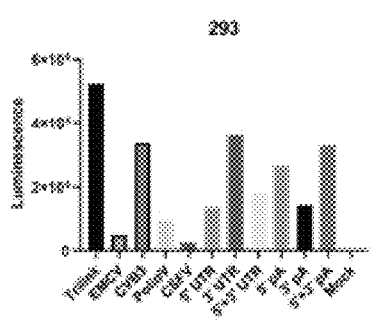
Figure 21F:
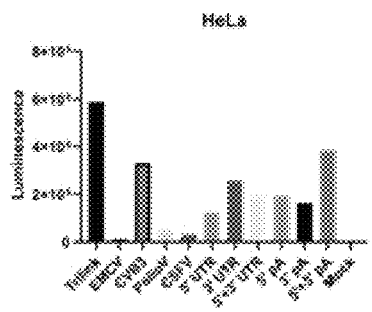
Figure 21G:
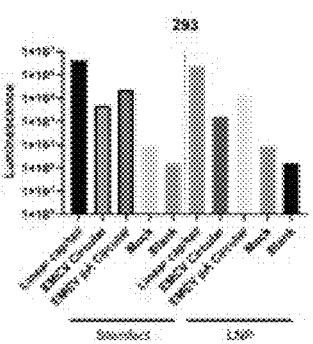

The results for FIGS. 20A and B show that UTRs can improve expression from circRNA. The results for FIG. 20C show that when used in combination with a 5' spacer, the expression benefits of adding UTRs disappear, suggesting that UTRs can act as spacers. The results for FIG. 20D show that efficient circularization of UTR-containing constructs, all using the same spacers/homology arms.

The results for FIGS. 21A-G show expression assays using different IRES or spacer sequences. pA/UTR conditions in FIGS. E and F use the EMCV IRES and are able to improve expression to the level of the CVB3 IRES in some cases. FIG. G shows comparison of transfection reagent and nanoparticles; doesn't appear to be a difference here.

Figure 22A:
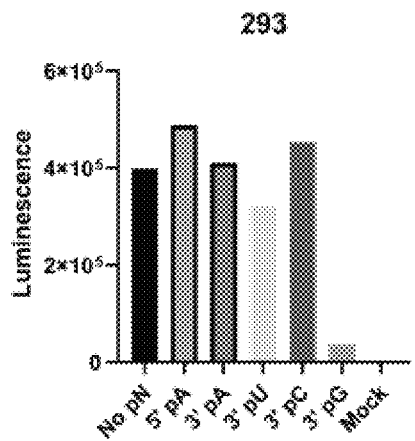
FIGS. 22A-22B.
Figure 22B:
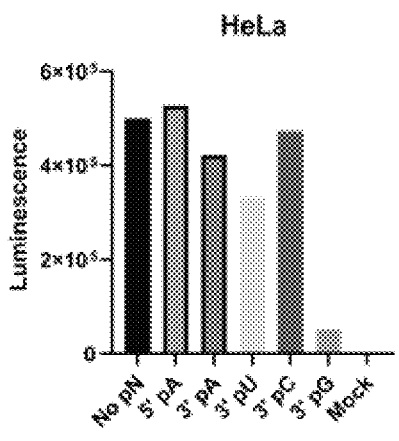

The results for FIGS. 22A and B show that addition of different 5' or 3' spacers (in addition to an existing, designed spacer) can modulate expression.

Figure 23A:
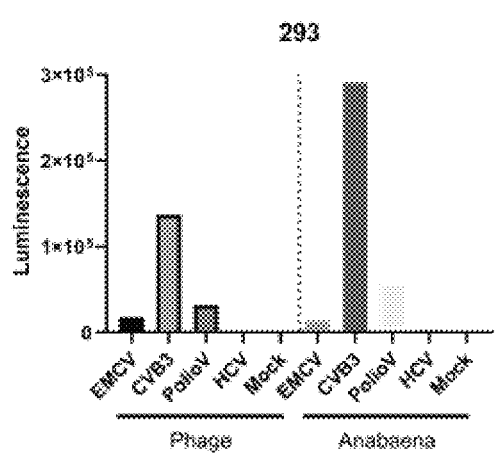
FIGS. 23A-23B.
Figure 23B:
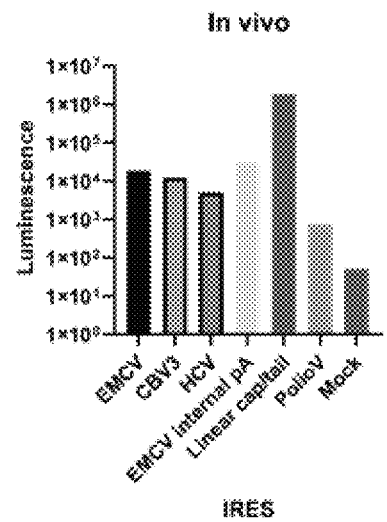

The results for FIGS. 23A and B show that introns can interfere with translation from different IRES sequences to different degrees; *Anabaena* interferes less with CVB3/polioV IRESes, while T4 phage interferes less with EMCV. FIG. 23B shows in vivo assessment of different IRESes (mouse liver via LNP).

Figure 24:
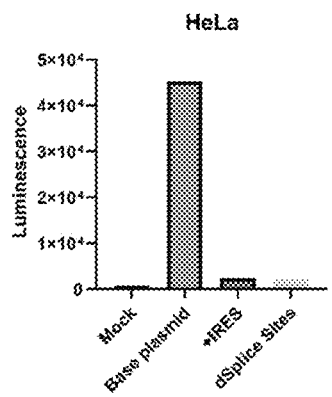
FIG. 24 shows expression of GLuc from a plasmid containing circRNA with 5' and 3' spacers and a CVB3 IRES in HeLa cells. Base plasmid does not contain the CVB3 IRES. dSplice Sites contains mutated splice sites to abrogate circularization after transcription.

The results for FIG. 24 show that show that plasmids that promote the transcription of circRNA precursor molecules in mammalian cells do not demonstrate enhanced protein translation compared to plasmids that promote the transcription of the same circRNA precursor molecules with deleted splice sites, suggesting that circularization does not occur in mammalian cells.

Figure 25A:
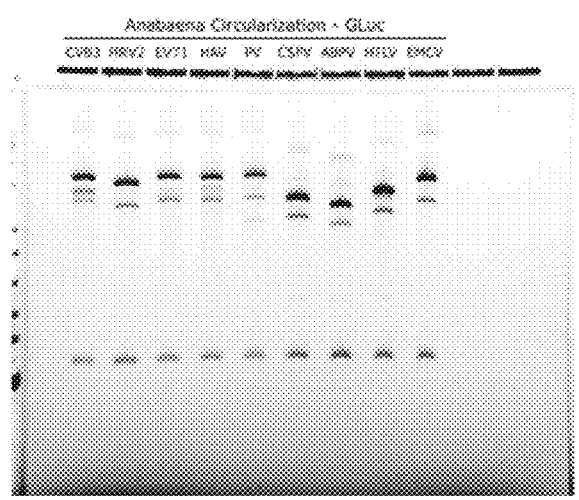
FIGS. 25A-25B.
Figure 25B:
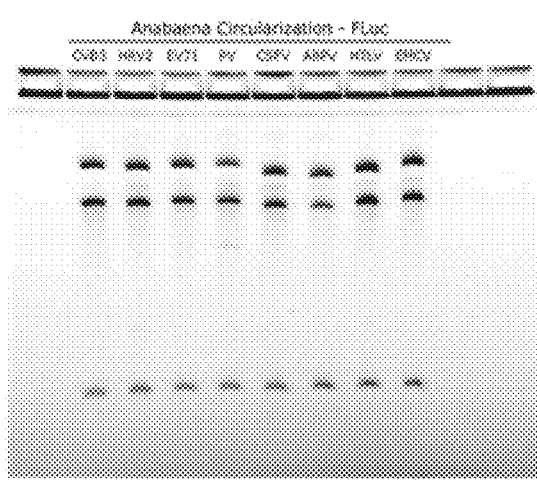

The results for FIGS. 25A and 25B show that circularization efficiency of constructs containing a panel of IRES sequences with either a gaussian or firefly luciferase coding region—efficiency is consistent despite varying inserts. These constructs all have the same splicing sequences (defined as spacers, homology arms, and internal homology (which is part of the spacers.

Figure 26A:
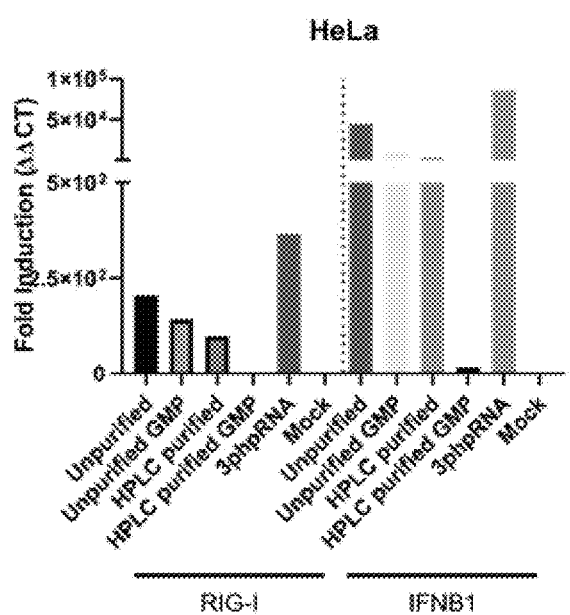
FIGS. 26A-26B.
Figure 26B:
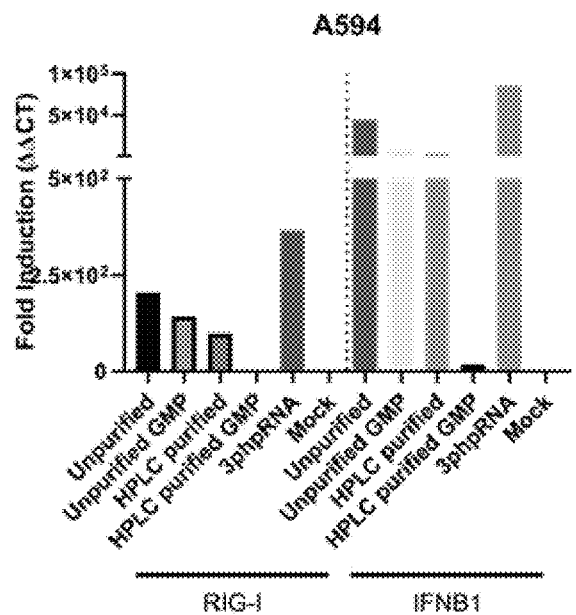

The results for FIGS. 26A and 26B show that spiking in guanosine monophosphate in the in vitro transcription reaction (in excess over guanosine triphosphate) reduces immunogenicity of circRNA preparations. Guanosine monophosphate is best used in combination with HPLC for sensitive cells.

Materials and Methods

Cloning and Mutagenesis

Protein coding, group I self-splicing intron, and IRES sequences were chemically synthesized (Integrated DNA Technologies) and cloned into a PCR-linearized plasmid vector containing a T7 RNA polymerase promoter by Gibson assembly using a NEBuilder HiFi DNA Assembly kit (New England Biolabs). Spacer regions, homology arms, and other minor alterations were introduced using a Q5 Site Directed Mutagenesis Kit (New England Biolabs).

circRNA Design, Synthesis, and Purification

RNA structure was predicted using RNAFold (Vicens, Q. et al., "Toward predicting self-splicing and protein-facilitated splicing of group I introns," *RNA*, 14(10):2013-2029 (2008)). Modified linear GLuc mRNA was obtained from Trilink Biotechnologies. Unmodified linear mRNA or circRNA precursors were synthesized by in-vitro transcription from a linearized plasmid DNA template using a T7 High Yield RNA Synthesis Kit (New England Biolabs). After in vitro transcription, reactions were treated with DNase I (New England Biolabs) for 20 minutes. After DNase treatment, unmodified linear mRNA was column purified using a MEGAclear Transcription Clean-up kit (Ambion). RNA was then heated to 70° C. for 5 minutes and immediately placed on ice for 3 minutes, after which the RNA was capped using mRNA cap-2'-O-methyltransferase (NEB) and Vaccinia capping enzyme (NEB) according to the manufacturer's instructions. Polyadenosine tails were added to capped linear transcripts using E. coli PolyA Polymerase (NEB) according to manufacturer's instructions, and fully processed mRNA was column purified. For circRNA, after DNase treatment additional GTP was added to a final concentration of 2 mM, and then reactions were heated at 55° C. for 15 minutes. RNA was then column purified. In some cases, purified RNA was re-circularized: RNA was heated to 70° C. for 5 minutes and then immediately placed on ice for 3 minutes, after which GTP was added to a final concentration of 2 mM along with a buffer including magnesium (50 mM Tris-HCl, 10 mM MgCl2, 1 mM DTT, pH 7.5; New England Biolabs). RNA was then heated to 55° C. for 8 minutes, and then column purified. To enrich for circRNA, 20 μg of RNA was diluted in water (86 uL final volume) and then heated at 65° C. for 3 minutes and cooled on ice for 3 minutes. 20U RNase R and 10 uL of 10× RNase R buffer (Epicenter) was added, and the reaction was incubated at 37° C. for 15 minutes; an additional 10U RNase R was added halfway through the reaction. RNase R-digested RNA was column purified. RNA was separated on precast 2% E-gel EX agarose gels (Invitrogen) on the E-gel iBase (Invitrogen) using the E-gel EX 1-2% program. Adequate circRNA separation using other agarose gel systems was not obtained. Bands were visualized using blue light transillumination and quantified using ImageJ. For gel extractions, bands corresponding to the circRNA were excised from the gel and then extracted using a Zymoclean Gel RNA Extraction Kit (Zymogen). For high-performance liquid chromatography, 30 μg of RNA was heated at 65° C. for 3 minutes and then placed on ice for 3 minutes. RNA was run through a 4.6×300 mm size-exclusion column with particle size of 5 μm and pore size of 200 Å (Sepax Technologies; part number: 215980P-4630) on an Agilent 1100 Series HPLC (Agilent). RNA was run in RNase-free TE buffer (10 mM Tris, 1 mM EDTA, pH:6) at a flow rate of 0.3 mL/minute. RNA was detected by UV absorbance at 260 nm, but was collected without UV detection. Resulting RNA fractions were precipitated with 5M ammonium acetate, resuspended in water, and then in some cases treated with RNase R as described above.

RNase H Nicking Analysis

Splicing reactions enriched for circRNA with RNase R and then column purified were heated at 65° C. for 5 minutes in the presence of a DNA probe (Table 1) at five-fold molar excess, and then annealed at room temperature. Reactions were treated with RNase H (New England Biolabs) in the provided reaction buffer for 15 minutes at 37C. RNA was column purified after digestion.

Reverse Transcription and cDNA Synthesis

For splice junction sequencing, splicing reactions enriched for circRNA with RNase R and then column purified were heated at 65° C. for 5 minutes and cooled on ice for 3 minutes to standardize secondary structure. Reverse transcription reactions were carried out with Superscript IV (Invitrogen) as recommended by the manufacturer using a primer specific for a region internal to the putative circRNA. PCR product for sequencing was synthesized using Q5 polymerase (New England Biolabs) and a pair of primers spanning the splice junction.

Tissue Culture and Transfections

HEK293, HEK293-GFP, HeLa, and A549 cells were cultured at 37° C. and 5% CO2 in Dulbecco's Modified Eagle's Medium (4500 mg/L glucose) supplemented with 10% heat-inactivated fetal bovine serum (hiFBS, Gibco) and penicillin/streptomycin. Min6 medium was additionally supplemented with 5% hiFBS, 20 mM HEPES (Gibco) and 50 μM beta-mercaptoethanol (BioRad). Cells were passaged every 2-3 days. For all circRNA data sets presented in FIG. 2 except Cas9, 40-100ng of RNase R-treated splicing reactions or HPLC-purified circRNAs were reverse transfected into 10,000 HEK293 cells/100 uL per well of a 96-well plate using Lipofectamine MessengerMax (Invitrogen) according to the manufacturer's instructions. For Cas9, 100ng of in vitro transcribed sgRNA was reverse transfected alone or cotransfected with 150 ng of RNase R-treated Cas9 splicing reaction into 50,000 HEK293-GFP cells/500 uL per well of a 24-well plate using MessengerMax. For all RNA data sets presented in FIG. 3, equimolar quantities of each RNA were reverse transfected into 10,000 HEK293, HeLa, or A549 cells/100 uL per well of a 96-well plate using MessengerMax. Min6 cells were transfected in 96-well plate format between 60-80% confluency.

Protein Expression Analysis

For luminescence assays, cells and media were harvested 24 hours post-transfection. To detect luminescence from Gaussia luciferase, 10-20 uL of tissue culture medium was transferred to a flat-bottomed white-walled plate (Corning). 25 uL of BioLux Gaussia Luciferase reagent including stabilizer (New England Biolabs) was added to each sample and luminescence was measured on an Infinite 200Pro Microplate Reader (Tecan) after 45 seconds. To detect luminescence from Firefly luciferase, 100 uL of Bright-Glo Luciferase reagent (Promega) was added to each well, mixed, and incubated for 5 minutes. 100 uL of the culture medium and luciferase reagent mix was then transferred to a flat-bottomed white-walled plate and luminescence was detected as described above. GFP fluorescence was detected 24 hours after transfection and images were taken using an EVOS FL cell imager (Invitrogen). Erythropoietin was detected by solid phase sandwich ELISA (R&D Systems) essentially according to the manufacturer's instructions except cell culture supernatant 24 hours post transfection was used, and samples were diluted 1:200 before use.

Flow Cytometry

CRISPR-Cas9-mediated GFP ablation was detected by flow cytometry 96 hours after transfection. HEK293-GFP and HEK293 control cells were trypsinized and suspended in Dulbecco's Modified Eagle's Medium (4500 mg/L glucose) supplemented with 10% fetal bovine serum and penicillin/streptomycin. Cells were then washed twice in FACS buffer (PBS, 5% heat-inactivated fetal bovine serum) and resuspended in FACS buffer containing Sytox Blue Dead Cell Stain (Thermo Fisher) according to the manufacturer's instructions, or FACS buffer alone for GFP and blank controls. Fluorescence was detected for 10,000 events on a BD FACSCelesta flow cytometer (BD Biosciences). Data was analyzed in Flowjo (Flowjo LLC).

Statistics

Statistical analysis of the results was performed by a two-tailed unpaired Welch's t-test, assuming unequal variances. Differences were considered significant when $p<0.05$. Statistical details of individual experiments are present in figure legends.

Example 2

Circular RNAs (circRNAs) are a class of single-stranded RNAs with a contiguous structure that have enhanced stability and a lack of end motifs necessary for interaction with various cellular proteins. Here, it is shown that unmodified exogenous circRNA is able to bypass cellular RNA sensors and thereby avoid provoking an immune response in RIG-I and toll-like receptor (TLR) competent cells and in mice. The immunogenicity and protein expression stability of circRNA preparations is found to be dependent on purity, with small amounts of contaminating linear RNA leading to robust cellular immune responses. Unmodified circRNA is less immunogenic than unmodified linear mRNA in vitro, in part due to evasion of TLR sensing, and provokes a cytokine response that is similar to that induced by uridine-modified linear mRNA. Additionally, it was found that uridine modification of circRNA disrupts internal ribosome entry site (IRES)-mediated translation and does not have a significant effect on cytokine response. Finally, the data shows the first demonstration of exogenous circRNA delivery and translation in vivo, and the data shows that circRNA translation is extended in adipose tissue in comparison to unmodified and uridine-modified linear mRNAs.

Introduction

CircRNAs are a class of RNAs with a range of protein-coding and non-coding functions (Legnini, I. et al. Circ-ZNF609 Is a Circular RNA that Can Be Translated and Functions in Myogenesis. *Mol. Cell* 66, 22-37.e9 (2017); Li, Z. et al. Exon-intron circular RNAs regulate transcription in the nucleus. *Nat. Struct. Mol. Biol.* 22, 256-264 (2015); Hansen, T. B. et al. Natural RNA circles function as efficient microRNA sponges. *Nature* 495, 384-388 (2013); and Barrett, S. P. & Salzman, J. Circular RNAs: analysis, expression and potential functions. Development 143, 1838-1847 (2016). Eukaryotic cells generate circRNAs through back-splicing, while the genomes of viral pathogens such as hepatitis D virus and plant viroids can also be circular (Chen, L.-L. & Yang, L. Regulation of circRNA biogenesis. RNA Biol. 12, 381-388 (2015); Jeck, W. R. & Sharpless, N. E. Detecting and characterizing circular RNAs. *Nat. Biotechnol.* 32, 453-461 (2014); Wang, Y. & Wang, Z. Efficient backsplicing produces translatable circular mRNAs. *RNA* 21, 172-179 (2014); Sanger, H. L., Klotz, G., Riesner, D., Gross, H. J. & Kleinschmidt, A. K. Viroids are single-stranded covalently closed circular RNA molecules existing as highly base-paired rod-like structures. *Proc. Natl. Acad. Sci. U.S.A* 73, 3852-3856 (1976); Kos, A., Dijkema, R., Arnberg, A. C., van der Meide, P. H. & Schellekens, H. The hepatitis delta (delta) virus possesses a circular RNA. *Nature* 323, 558-560 (1986); Chen, Y. G. et al. Sensing Self and Foreign Circular RNAs by Intron Identity. *Mol. Cell* 67, 228-238.e5 (2017)). It has recently been proposed that cells have evolved a splicing-dependent mechanism for the discrimination of endogenous and exogenous circRNA, using RIG-1 as a cytoplasmic sensor of exogenous circRNA (Chen, Y. G. et al. Sensing Self and Foreign Circular RNAs by Intron Identity. *Mol. Cell* 67, 228-238.e5 (2017)). While circRNA does not contain the triphosphate motif canonically required for RIG-I activation, it has been suggested that RIG-I may transiently interact with circRNA devoid of host nuclear proteins, leading to a canonical RIG-I mediated antiviral response (Chen, Y. G. et al. Sensing Self and Foreign Circular RNAs by Intron Identity. *Mol. Cell* 67, 228-238.e5 (2017); Loo, Y. M. & Gale, M., Jr. Immune signaling by RIG-I-like receptors.—PubMed—NCBI. Available at: https://www.ncbi.nlm.nih.gov/pubmed/21616437. (Accessed: 7 May 2018)). However, the mechanism of RIG-I-mediated recognition of circRNA remains unclear. In addition to RIG-I, it is also possible that circRNA interacts with other RNA sensors such as the endosomal TLRs 3, 7 and 8, which have been shown to activate signaling in response to linear ssRNA and dsRNA motifs as well as RNA degradation products such as uridine and guanosine-uridine rich fragments (Tanji, H. et al. Toll-like receptor 8 senses degradation products of single-stranded RNA. *Nat. Struct. Mol. Biol.* 22, 109-115 (2015); Zhang, Z. et al. Structural Analysis Reveals that Toll-like Receptor 7 Is a Dual Receptor for Guanosine and Single-Stranded RNA. *Immunity* 45, 737-748 (2016); Bell, J. K., Askins, J., Hall, P. R., Davies, D. R. & Segal, D. M. The dsRNA binding site of human Toll-like receptor 3. *Proc. Natl. Acad. Sci. U.S.A* 103, 8792-8797 (2006); and Tatematsu, M., Nishikawa, F., Seya, T. & Matsumoto, M. Toll-like receptor 3 recognizes incomplete stem structures in single-stranded viral RNA. *Nat. Commun.* 4, 1833 (2013)). To reduce an innate cellular immune response to exogenous RNA, nucleoside modifications such as pseudouridine ($\psi$), $N^1$-methylpseudouridine (m1$\psi$), and 5-methoxyuridine (5moU) have been developed for use in linear mRNA (Svitkin, Y. V. et al. $N^1$-methyl-pseudouridine in mRNA enhances translation through eIF2$\alpha$-dependent and independent mechanisms by increasing ribosome density. (*Nucleic Acids Res.* 45, 6023-6036 (2017); Karikó, K., Muramatsu, H., Ludwig, J. & Weissman, D. Generating the optimal mRNA for therapy: HPLC purification eliminates immune activation and improves translation of nucleoside-modified, protein-encoding mRNA. *Nucleic Acids Res.* 39, e142 (2011); Karikó, K. et al. Incorporation of Pseudouridine Into mRNA Yields Superior Nonimmunogenic With Increased Translational Capacity and Biological Stability. *Mol. Ther.* 16, 1833 (2008)). These modifications have been shown to prevent linear mRNA from activating TLRs and RIG-I (Karikó, K., Buckstein, M., Ni, H. & Weissman, D. Suppression of RNA recognition by Toll-like receptors: the impact of nucleoside modification and the evolutionary origin of RNA. Immunity 23, 165-175 (2005); Durbin, A. F., Wang, C., Marcotrigiano, J. & Gehrke, L. RNAs Containing Modified Nucleotides Fail To Trigger RIG-I Conformational Changes for Innate Immune Signaling. MBio 7, (2016)). RNA modification with $N^6$-methyladenosine (m6A) has been shown to mediate cap-independent translation in endogenous linear and circRNAs (Meyer et al. 2015; Yang et al. 2017). The contribution of TLRs to circRNA immunogenicity, and the effects of nucleoside modifications on exogenous circRNA translation, stability, and immunogenicity, have yet to be reported.

Recently, circRNA was developed for stable protein production in mammalian cells (Wesselhoeft, R. A., Kowalski, P. S. & Anderson, D. G. Engineering circular RNA for potent and stable translation in eukaryotic cells. *Nat. Commun.* 9, 2629 (2018)). As described herein, the immunogenicity and translatability of exogenous circRNA in vitro and in vivo was investigated to determine the potential utility of circRNA for protein production applications. It was demonstrated herein that exogenous circRNA does not stimulate a cellular immune response in RIG-I and TLR competent cells. Additionally, it is shown that unlike linear mRNA, IRES-dependent circRNA does not benefit from modification with m1$\psi$ in terms of protein expression and immunogenicity or modification with m6A in terms of protein expression. It was found that circRNA is compatible with lipid nanoparticle-mediated delivery and is effectively translated in vivo without provoking an RNA-mediated innate immune response, while protein expression from circRNA exhibits greater stability that that from uridine-modified linear mRNA in adipose tissue.

Results

Purification of Exogenous circRNA Ablates Immunogenicity

Using the optimized permuted intron-exon (PIE) splicing method previously reported, circRNA precursors were synthesized containing a coxsackievirus B3 internal ribosome entry site (CVB3 IRES), a *Gaussia* luciferase (GLuc) message, two designed spacer sequences, two short regions corresponding to exon fragments of the PIE construct, and the 3' and 5' intron segments of the permuted *Anabaena* pre-tRNA group I intron by run-off transcription (FIG. 7A-B) (Wesselhoeft, R. A., Kowalski, P. S. & Anderson, D. G. Engineering circular RNA for potent and stable translation in eukaryotic cells. *Nat. Commun.* 9, 2629 (2018); Puttaraju, M. & Been, M. Group I permuted intron-exon (PIE) sequences self-splice to produce circular exons. *Nucleic Acids Res.* 20, 5357-5364 (1992)). In the presence of GTP and $Mg^{2+}$, these precursor RNA molecules undergo the double transesterification reactions characteristic of group I catalytic introns, but because the exons are already fused, the region between the two intron segments is excised as a covalently 5' to 3' linked circle (FIG. 7A) (Puttaraju, M. & Been, M. Group I permuted intron-exon (PIE) sequences self-splice to produce circular exons. *Nucleic Acids Res.* 20, 5357-5364 (1992)). To confirm that circular products were obtained, the splicing reaction was treated with RNase R, a 3' to 5' RNA exonuclease, and observed enrichment of the putative circRNA band (FIG. 7C) (Suzuki, H. et al. Characterization of RNase R-digested cellular RNA source that consists of lariat and circular RNAs from pre-mRNA splicing. *Nucleic Acids Res.* 34, e63-e63 (2006)). Subsequent purification of the RNase R-treated splicing reaction by HPLC and then digestion with oligonucleotide-targeted RNase H produced a single major band in contrast to two major bands yielded by RNase H-digested linear precursor RNA that contains all of the same sequence elements as the circRNA precursor with the exception of the splice site nucleotides (FIG. 7C, αS), confirming circularity. Splicing reactions containing circRNA demonstrated improved protein production and expression stability of protein production in comparison to polyadenylated and phosphatase-treated linear precursor after transfection into 293 cells (FIG. 7. G-I).

Figures 7E, 7F:
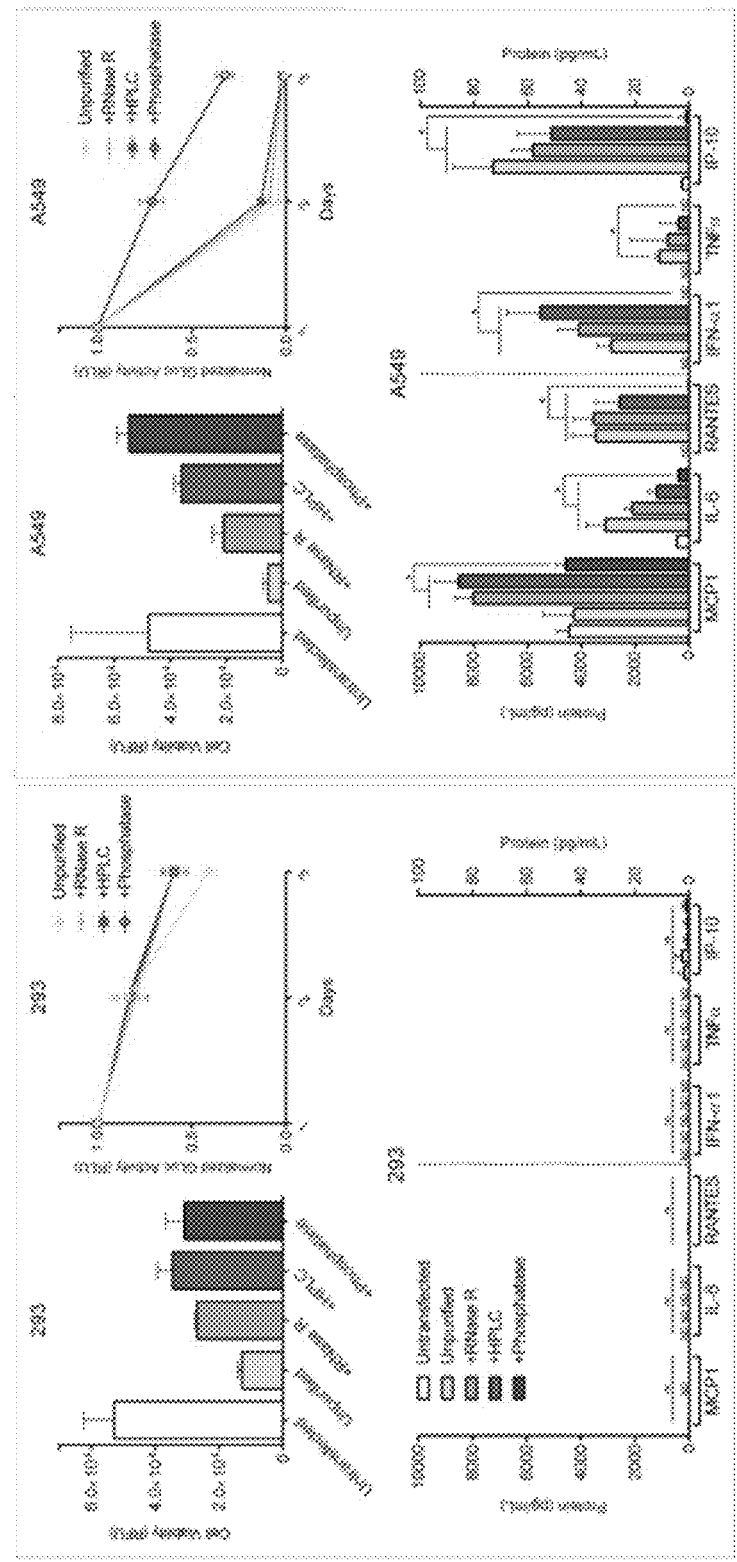

To probe the immunogenicity of circRNA, two cell lines (human embryonic kidney, 293; human lung carcinoma, A549) were selected that had been observed to elicit differential cell viability and GLuc expression stability responses upon transfection of unpurified circRNA splicing reactions (FIGS. 7E and F). After the circularization protocol, these splicing reactions are expected to contain circRNA, excised triphosphorylated introns, linear and circular concatenations, and degradation products of both linear RNA and circRNA, some of which is triphosphorylated. While the splicing reaction proceeds nearly to completion under the circularization conditions used herein, some triphosphorylated linear precursor RNA is also present. Several steps were then applied of purification to the unpurified splicing reactions and confirmed circRNA enrichment by gel electrophoresis: RNase R to enrich circRNA, HPLC to remove non-circular components, and phosphatase to remove residual triphosphates (FIG. 7D). To determine the extent of the innate cellular immune response to transfected RNA, the release of a wide range of cytokines and chemokines into the culture medium was monitored, as well as the protein expression stability from circRNA and cell viability.

Figures 8D, 8E, 8F:
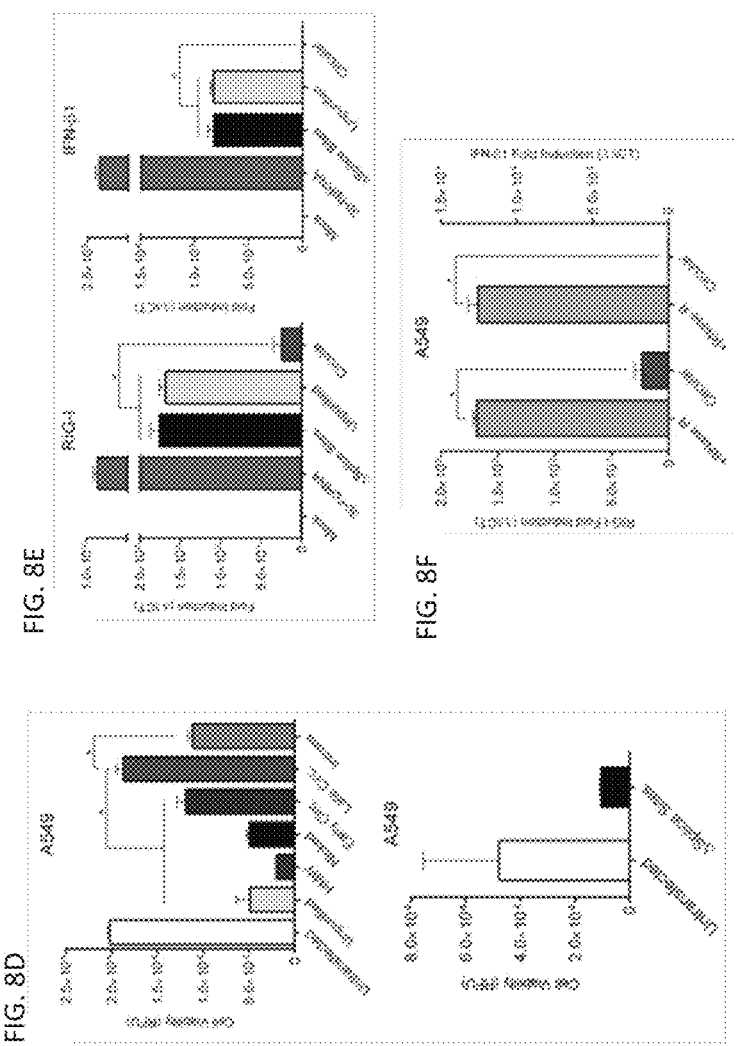
Figure 8G:
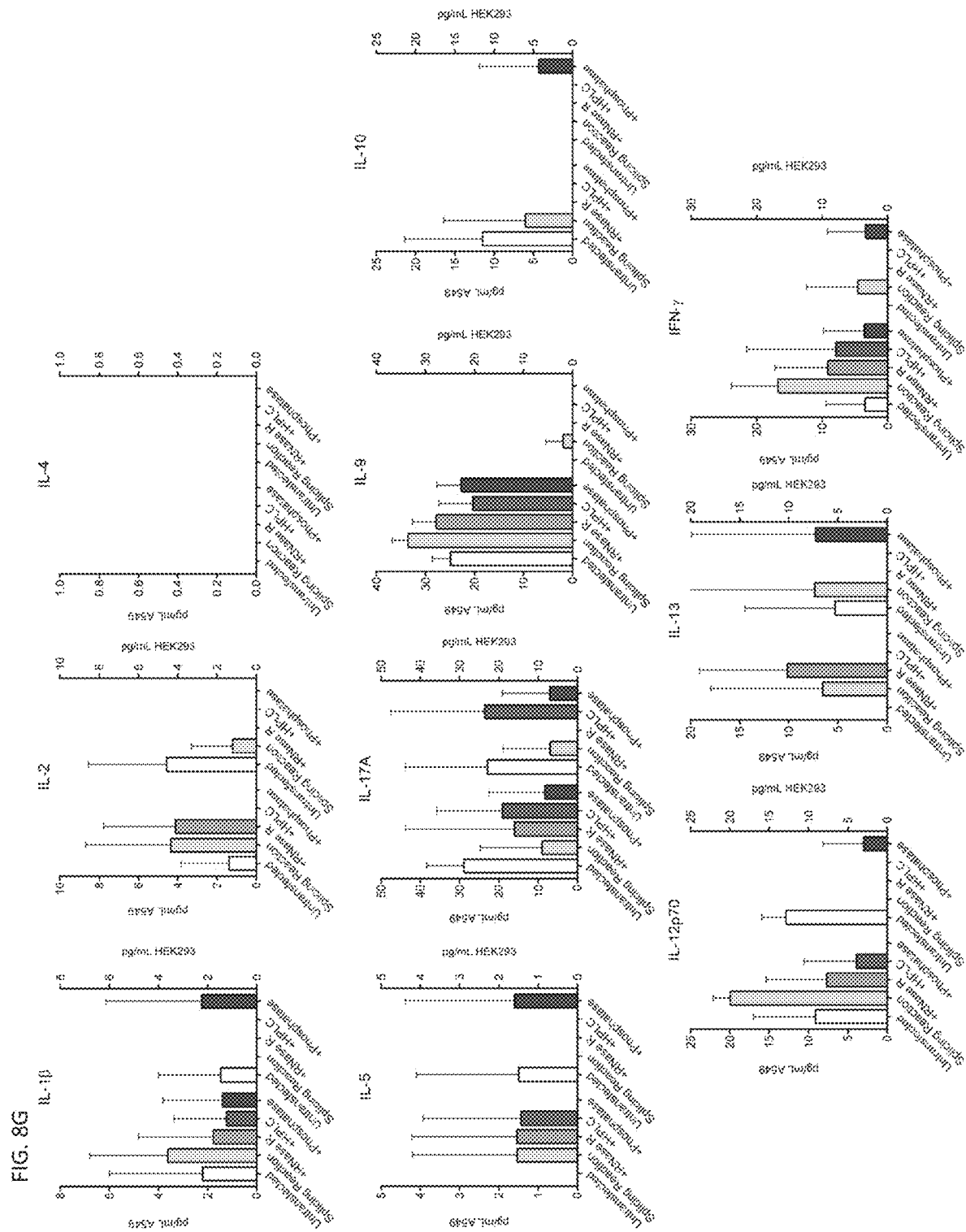

It was found that RNase R digestion of splicing reactions was insufficient to ablate cytokine release in A549 cells in comparison to untransfected controls (FIG. 7F, FIG. 8G). The addition of HPLC purification was furthermore insufficient to ablate cytokine release, although we did note a significant reduction in IL-6 and a significant increase in IFN-α1 compared to the unpurified splicing reaction, suggesting that combined RNase R and HPLC may have depleted some immunogenic RNA species while enriching others (FIG. 7F). The addition of HPLC purification was furthermore insufficient to ablate cytokine release, although a reduction in IL-6 compared to the unpurified splicing reaction (FIG. 7F) was noted. Interestingly, the addition of a phosphatase treatment after HPLC purification and before RNase R digestion dramatically reduced the expression of all upregulated cytokines that we assessed in A549 cells, with secreted MCP1, IL-6, IFN-α1, TNF-α, and IP-10 falling to undetectable or untransfected-baseline levels (FIG. 7F). Substantial cytokine release in 293 cells was not observed, consistent with the observation that the 3-day protein expression stability phenotype of these cells is relatively unaffected by the degree of circRNA purity and previous reports indicating that 293 cells do not express several key RNA sensors (FIG. 7E, FIG. 8G) (Hornung, V. et al. *Quantitative expression of toll-like receptor* 1-10 *mRNA in cellular subsets of human peripheral blood mononuclear cells and sensitivity to CpG oligodeoxynucleotides. J. Immunol.* 168, 4531-4537 (2002)). In contrast, increased circRNA purity improved GLuc expression stability in transfected A549 cells, with completely purified circRNA demonstrating a stability phenotype similar to that of transfected 293 cells (FIGS. 7E and F). Likewise, a trend of increased circRNA purity improved A549 cell viability 3 days post-transfection while 293 cell viabilities remained largely unaffected, consistent with a lack of inflammatory signaling in 293 cells and diminishing inflammatory signaling in A549 cells with increasing circRNA purity (FIGS. 7E and F). Together, these results demonstrate that circRNA purity strongly affects its immunogenic potential, and that fully purified circRNA is significantly less immunogenic than unpurified or incompletely purified splicing reactions. The stability of protein production from circRNA is also dependent on circRNA purity and the sensitivity of transfected cell types to contaminating RNA species. A time course experiment monitoring RIG-I, IFN-β1, IL-6 and RANTES transcript induction within the first 8 hours after transfection of A549 cells with splicing reactions or fully purified circRNA did not reveal a transient response to circRNA (Figure S2F). Purified circRNA similarly failed to induce pro-inflammatory transcripts in RAW264.7 murine macrophages (Figure S2G). To generalize these findings to another synthetic circRNA construct, we tested the induction of pro-inflammatory transcripts in response to transfection of A549 cells with purified circRNA containing an EMCV IRES and EGFP coding region, and again failed to observe substantial induction (Figure S2H). These data demonstrate that non-circular components of the splicing reaction are responsible for the immunogenicity observed in previous studies and that circRNA is not a natural ligand for RIG-I.

Non-Circular Components of the Splicing Reaction Contribute to Immunogenicity

To explore the source of immunogenicity in circRNA splicing reactions, each component of the splicing reaction was purified by HPLC and assessed cytokine release and cell viability upon transfection of A549 cells (FIGS. 8A and B). Because there was difficulty obtaining suitably pure linear precursor RNA from the splicing reaction, precursor RNA in the form of the splice site deletion mutant (ΔS) (FIG. 8B, bottom right) was separately synthesized and purified. Additionally, the circRNA peak was split into two fractions to control for nicked RNA peak overlap (FIG. 8B). Robust IL-6, RANTES, and IP-10 release was observed in response to most species present within the splicing reaction as well as precursor RNA (FIG. 8C, FIG. 9G). Early circRNA fractions elicited cytokine responses comparable to other non-circRNA fractions, indicating that even relatively small quantities of linear RNA contaminants are able to induce a substantial cellular immune response in A549 cells. Late circRNA fractions elicited no cytokine response in excess of that from untransfected controls. Consistent with cytokine release observations, A549 cell viability 36 hours post transfection was significantly greater for late circRNA fractions compared to all other fractions (FIG. 8D).

Because it has been previously reported that circRNA may induce RIG-I transcription in a self-regulatory feedback loop, RIG-I and IFN-β1 transcript induction was analyzed upon transfection of A549 cells with late circRNA HPLC fractions (Chen, Y. G. et al. Sensing Self and Foreign Circular RNAs by Intron Identity. *Mol. Cell* 67, 228-238.e5 (2017)). A significantly weaker induction of both RIG-I and IFN-β1 transcripts for late circRNA fractions was observed in comparison with precursor RNA and unpurified splicing reactions (FIG. 8E). Furthermore, it was found that RNase R treatment of splicing reactions alone was not sufficient to ablate this effect (FIG. 8F), while contamination of purified circRNA with very small quantities of the RIG-I ligand 3p-hpRNA induced substantial RIG-I transcription (FIG. 9I). In HeLa cells, transfection of RNase R-digested splicing reactions, but not purified circRNA, induced RIG-I and IFN-01, although it was found that HeLa cells to be less sensitive than A549 cells to contaminating RNA species (FIG. 9L). These data suggest that non-circular components of the splicing reaction are responsible for the immunogenicity observed in previous studies and that circRNA is not an endogenous ligand for RIG-I.

Nucleoside Modification of circRNA is Disruptive

Nucleoside modifications such as 5-methylcytidine (m5C), N$^6$-methyladenosine (m6A), and pseudouridine (ψ) have been reported to decrease the immunogenicity of linear mRNA in vitro and in some contexts in vivo by preventing ribonucleotides from interacting with cellular RNA sensors such as the endosomal TLRs 3, 7, and 8 and RIG-I (Karikó, K., Buckstein, M., Ni, H. & Weissman, D. Suppression of RNA recognition by Toll-like receptors: the impact of nucleoside modification and the evolutionary origin of RNA. *Immunity* 23, 165-175 (2005); Durbin, A. F., Wang, C., Marcotrigiano, J. & Gehrke, L. RNAs Containing Modified Nucleotides Fail To Trigger RIG-I Conformational Changes for Innate Immune Signaling. *MBio* 7, (2016)). N$^6$-methyladenosine (m6A) has been reported to mediate internal ribosome entry and translation on linear RNAs and separately on endogenous circRNAs (Meyer et al. 2015; Yang et al. 2017). The effects of these modifications on the utility of mRNA in vivo may be variable however, as ψ-mRNA delivered to the liver does not reduce immunogenicity or improve protein production (Kauffman, K. J. et al. Efficacy and immunogenicity of unmodified and pseudouridine-modified mRNA delivered systemically with lipid nanoparticles in vivo. *Biomaterials* 109, 78-87 (2016)). Recently, it was reported that incorporation of m1ψ diminishes mRNA immunogenicity and improves protein expression to a greater degree than incorporation of ψ (Svitkin, Y. V. et al. N1-methyl-pseudouridine in mRNA enhances translation through eIF2α-dependent and independent mechanisms by increasing ribosome density. *Nucleic Acids Res.* 45, 6023-6036 (2017) and Andries, O. et al. N(1)-methylpseudouridine-incorporated mRNA outperforms pseudouridine-incorporated mRNA by providing enhanced protein expression and reduced immunogenicity in mammalian cell lines and mice. *J. Control. Release* 217, 337-344 (2015)). The effects of nucleoside modifications on circRNA translation efficiency and immunogenicity have not been tested. Because of previous difficulties with circRNA purification, the immunogenicity of purified circRNA relative to that of unmodified linear mRNA has also not been assessed. Therefore, it was sought to evaluate the GLuc protein expression stability and cytokine release profile of purified unmodified and m1ψ-modified circRNA in comparison to unmodified and m1ψ-modified linear mRNA in A549 and 293 cells (FIG. 9A).

Initial attempts to circularize m1ψ-circRNA using the PIE method were unsuccessful, as complete replacement of uridine with m1ψ in PIE construct precursors abolished ribozyme activity while partial replacement dramatically reduced splicing efficiency (FIG. 9B). An alternative method of circRNA preparation using T4 RNA ligase I and splint oligonucleotides designed to bring the ends of the precursor RNA into proximity for ligation (FIG. 10G) (Sonj a Petkovic, S. M. RNA circularization strategies in vivo and in vitro. *Nucleic Acids Res.* 43, 2454 (2015)). Using optimized splint oligonucleotides and annealing conditions, 40% circularization efficiency of the 1.5 kb precursor RNA was obtained (FIGS. 10H and I). Complete replacement of uridine with m1ψ did not impede circularization using this method and fully modified circular products were obtained (FIG. 9C).

Figure 9E:
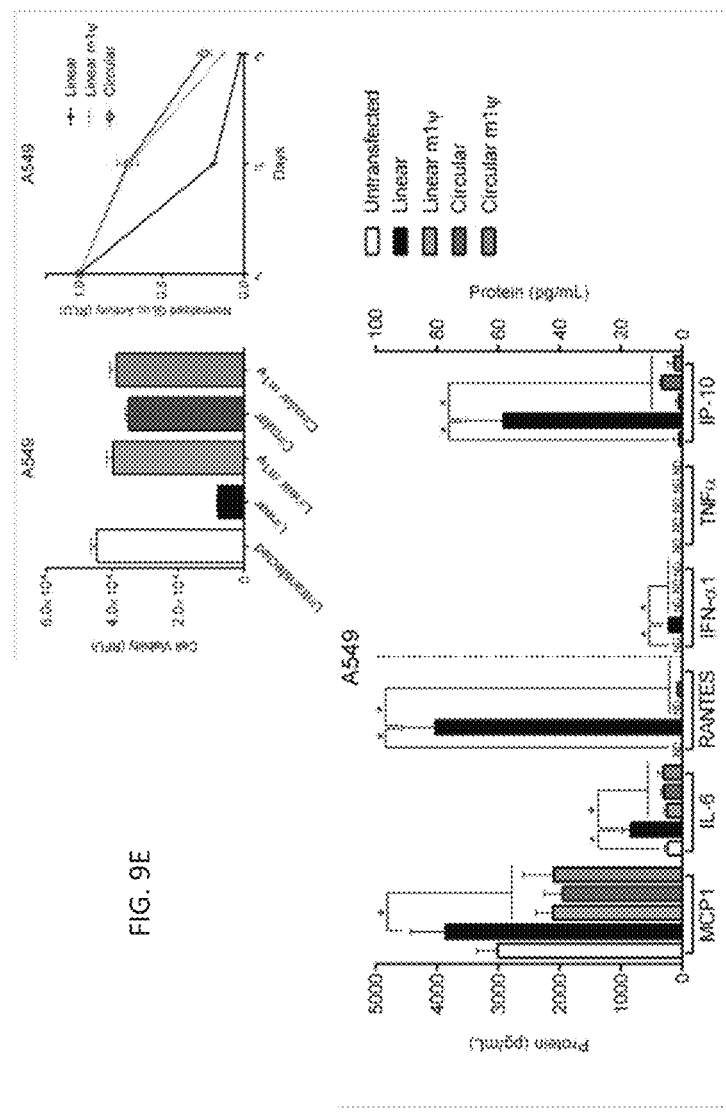
Figure 9G:
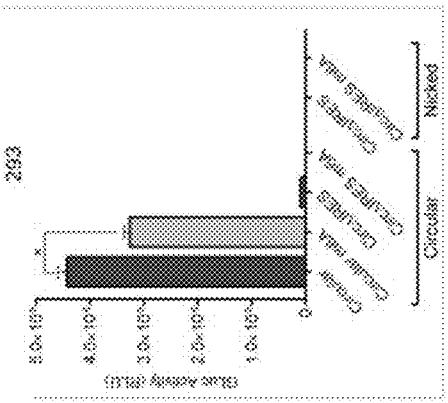
FIG. 9G) depicts GLuc activity (RLU).
Figure 9F:
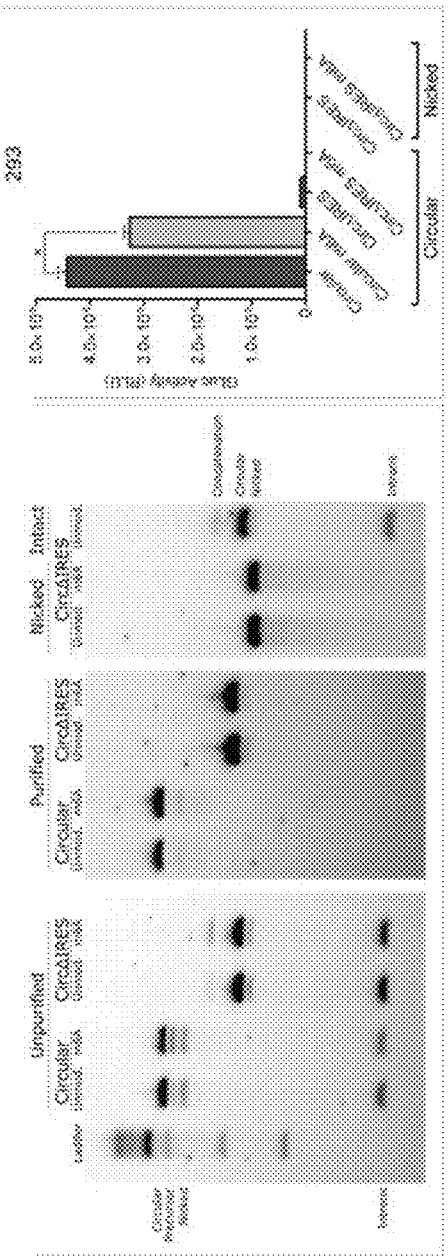
Figure 11E:
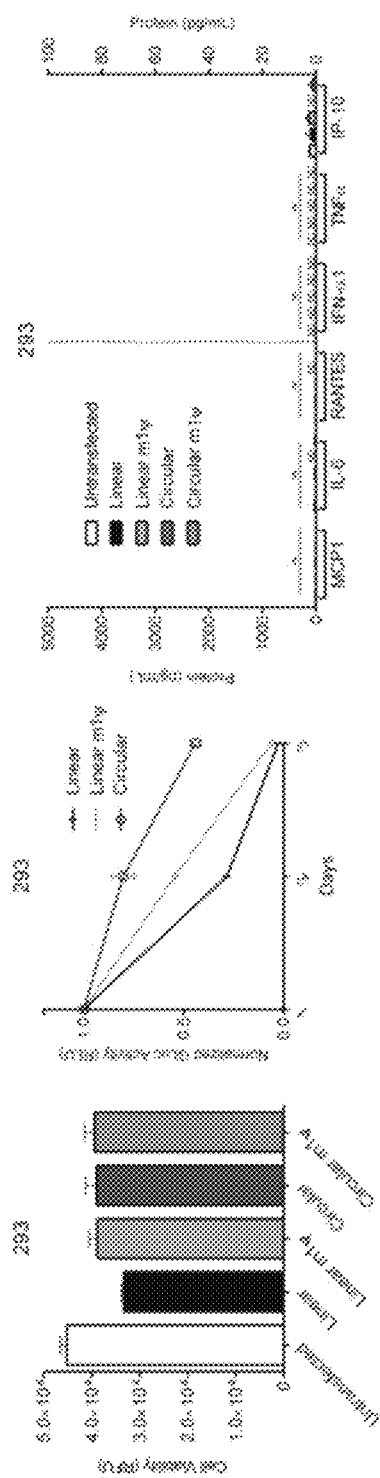
Figure 11F:
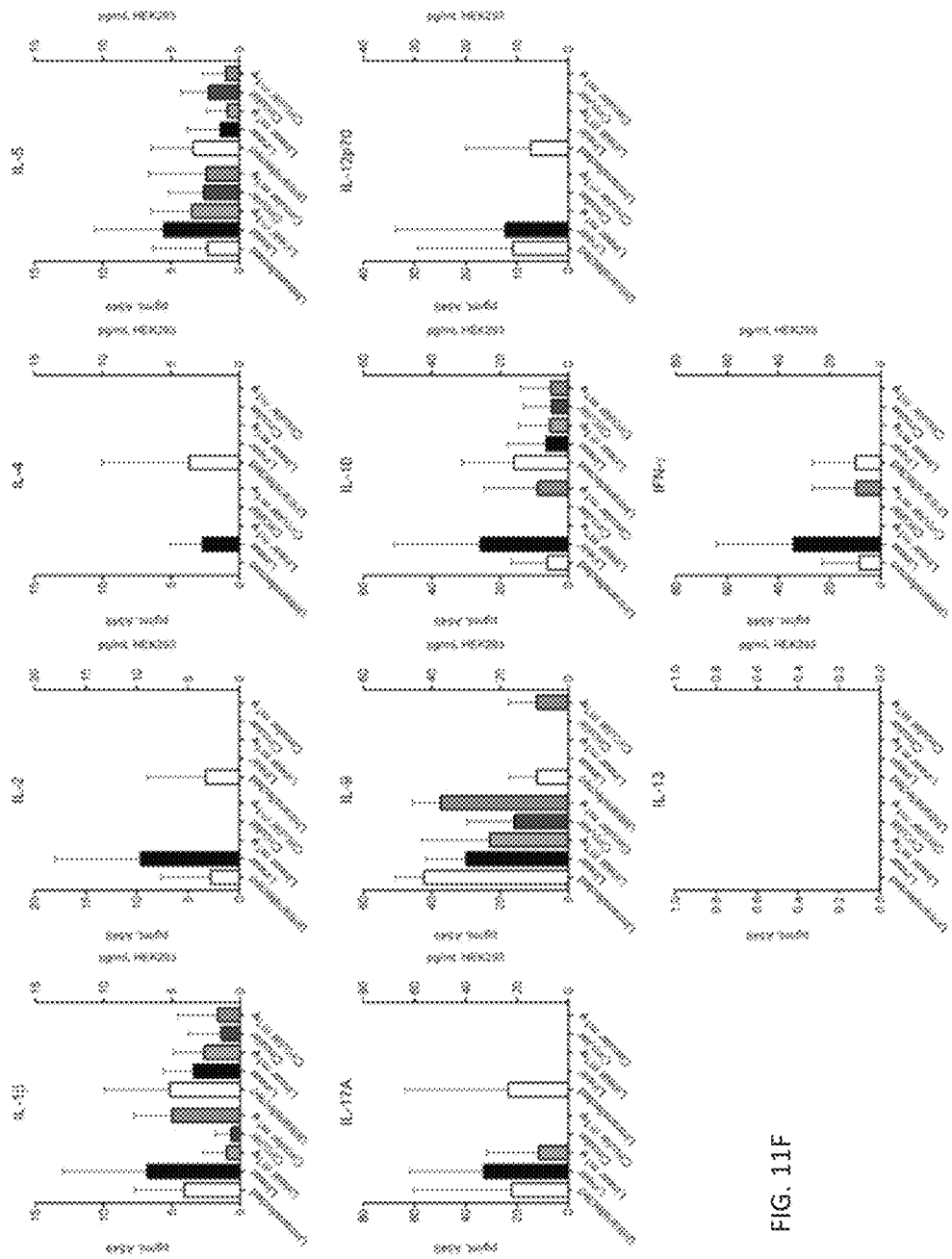

Upon transfection of 293 and A549 cells with m1ψ-circRNA, no protein expression was observed, and thus the stability of protein expression from modified circRNA was not determined (FIG. 9D). Unmodified circRNA displayed enhanced protein expression stability in HEK293 and A549 cells compared to both unmodified and modified linear mRNA (FIGS. 9E and F). Interestingly, it was found that unmodified linear mRNA provoked a greater cytokine response than unmodified circRNA in immunoresponsive A549 cells despite capping, phosphatase treatment, and HPLC purification to remove RIG-I ligands. In contrast, both m1ψ-circRNA and m1ψ-mRNA did not significantly alter cytokine release profiles (FIG. 9F, FIG. 11E). A549 cell viability was diminished upon transfection of unmodified linear mRNA, but not unmodified circRNA or either m1ψ-RNAs (FIG. 9F). Consistent with data from FIGS. 7A-F, significant differences in 293 cytokine release at 24 hours post-transfection and cell viability at 3 days post-transfection was not detected (FIG. 9E, FIG. 11E). These experiments indicate that circRNA is less immunogenic than capped and polyadenylated linear mRNA and that nucleoside modification of circRNA is unnecessary for protection against innate immune sensors.

CircRNA Evades Detection by Toll-Like Receptors

Because capped and polyadenylated linear mRNA was able to trigger cytokine secretion while circRNA did not, the ability of different RNAs to activate TLRs in reporter cell lines was investigated. TLRs 3, 7, and 8 are known to detect RNA in endosomes and initiate an inflammatory cascade (Takumi Kawasaki, T. K. Toll-Like Receptor Signaling Pathways. *Front. Immunol.* 5, (2014)). TLR3 binds to dsRNA and stem structures in viral ssRNA, while TLR7 and human TLR8 bind to ssRNA and nucleoside degradation products (guanosine for TLR7 and uridine for TLR8), with both ligands necessary for TLR activation (Tanji, H. et al.

Figure 10A:
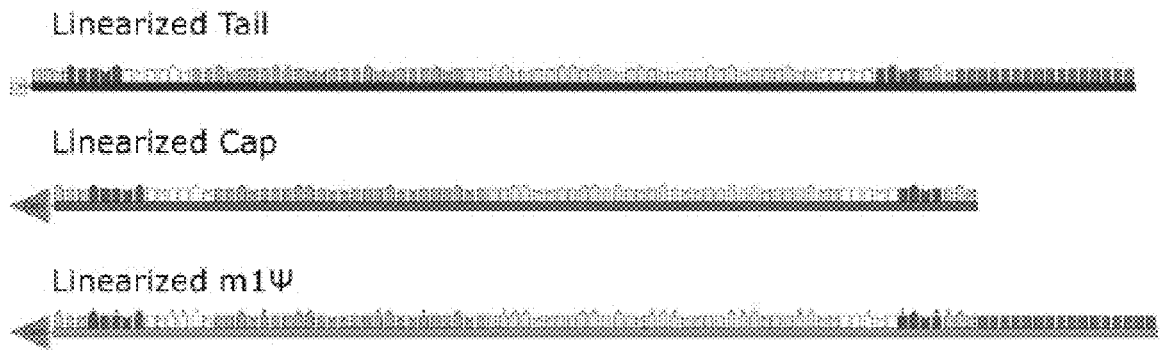
FIGS. 10A-I.
Figure 10B:
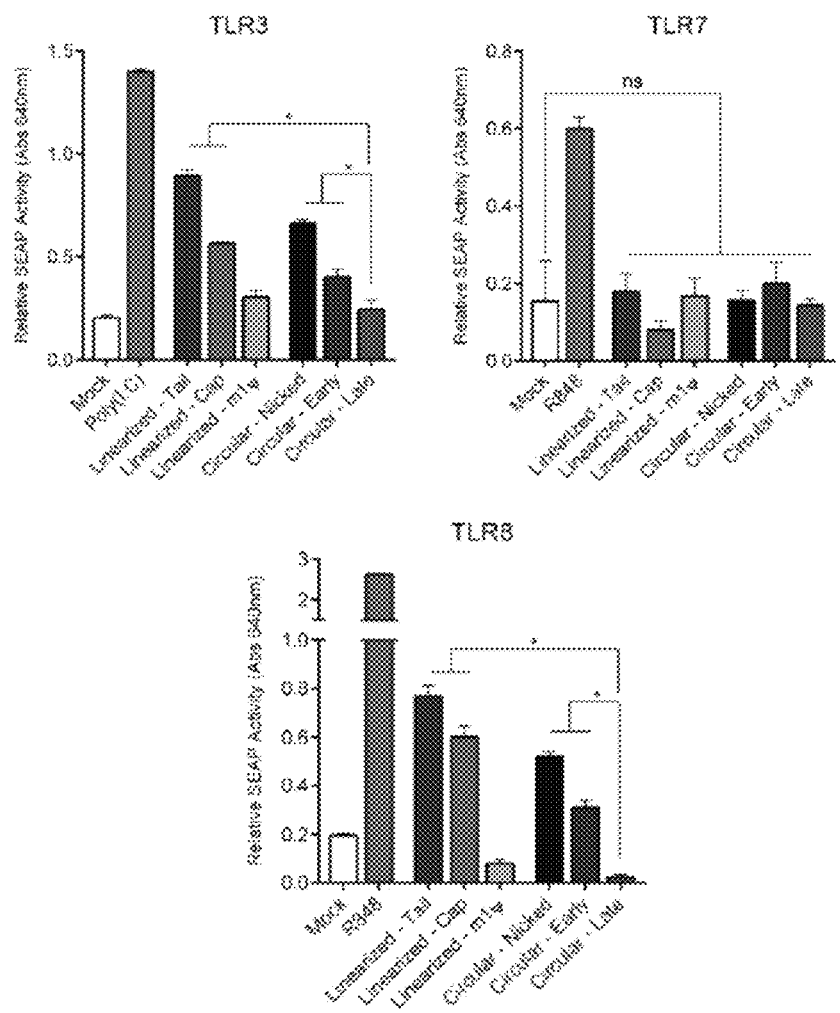
Figure 10C:
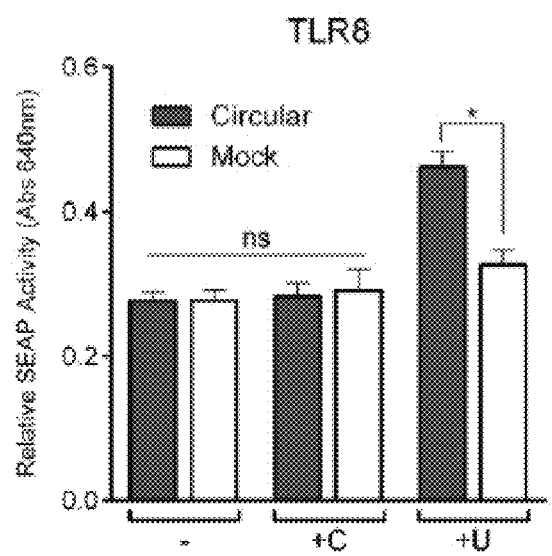

Toll-like receptor 8 senses degradation products of single-stranded RNA. *Nat. Struct. Mol. Biol.* 22, 109-115 (2015); Zhang, Z. et al. Structural Analysis Reveals that Toll-like Receptor 7 Is a Dual Receptor for Guanosine and Single-Stranded RNA. *Immunity* 45, 737-748 (2016); Bell, J. K., Askins, J., Hall, P. R., Davies, D. R. & Segal, D. M. The dsRNA binding site of human Toll-like receptor 3. *Proc. Natl. Acad. Sci. U.S.A* 103, 8792-8797 (2006); and Tatematsu, M., Nishikawa, F., Seya, T. & Matsumoto, M. Toll-like receptor 3 recognizes incomplete stem structures in single-stranded viral RNA. *Nat. Commun.* 4, 1833 (2013)). To control for structural and sequence differences between linear and circular RNAs, a linearized version of the circRNA was constructed. This construct contained all of the components of the spliced circRNA, and was created by deleting the intron and homology arm sequences (linearized RNA, FIG. 10A, FIG. 12G). All linearized RNAs were additionally treated with phosphatase (in the case of capped RNAs, after capping) and purified by HPLC. While a response to linearized or circular RNA in TLR7 reporter cells was not found, both TLR3 and TLR8 reporter cells were activated by capped linearized RNA, polyadenylated linearized RNA, the nicked circRNA fraction, and the early circRNA fraction (FIG. 10B). Interestingly, the late circRNA fraction did not provoke a TLR-mediated response in any cell line, similarly to m1ψ-mRNA (FIG. 10B). However, the addition of uridine, but not cytidine, to the media of TLR8 reporter cells transfected with circRNA partially reverted this effect and resulted in SEAP secretion, indicating that trans-addition of one of the two RNA degradation signals needed for TLR8 activation can compensate for the lack of circRNA detection by TLR8 (FIG. 10C, FIG. 12H).

Figure 10D:
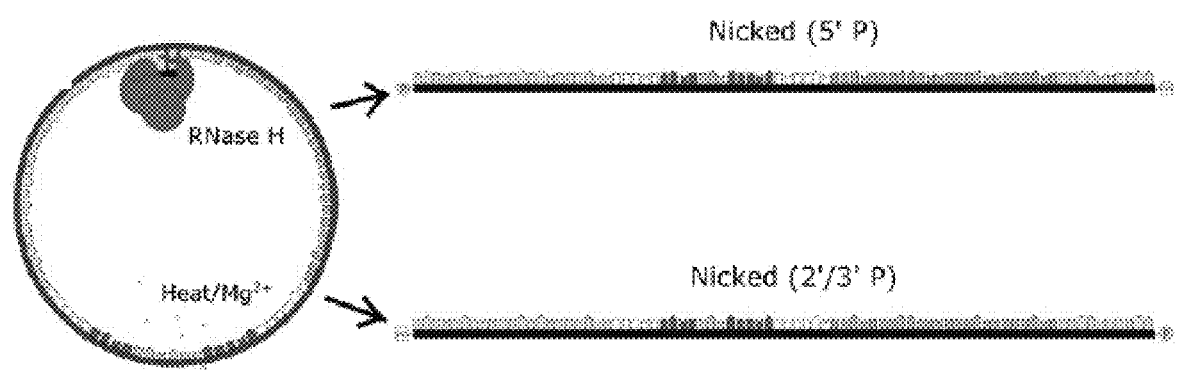
Figures 10E, 10F:
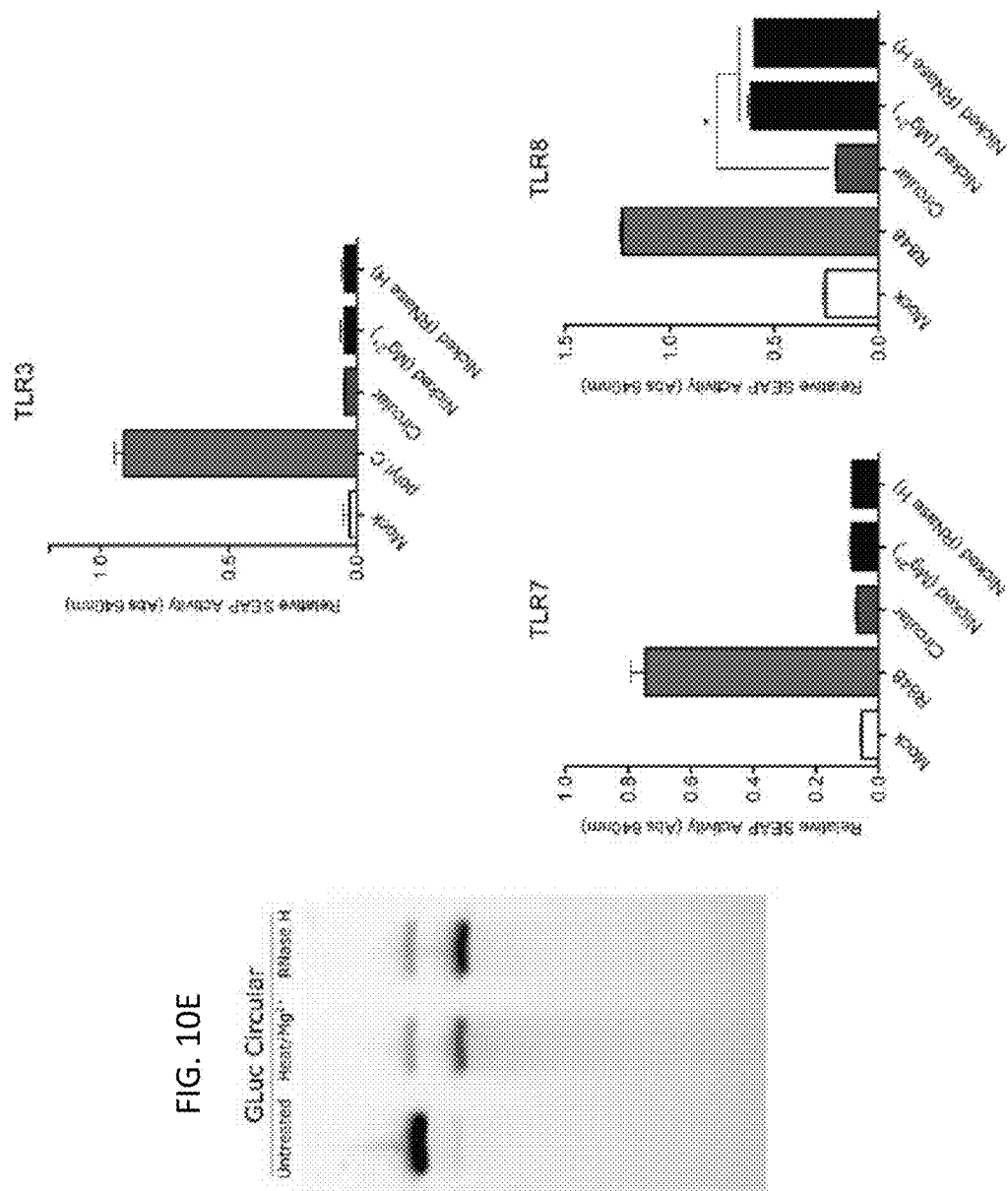
Figure 10G:
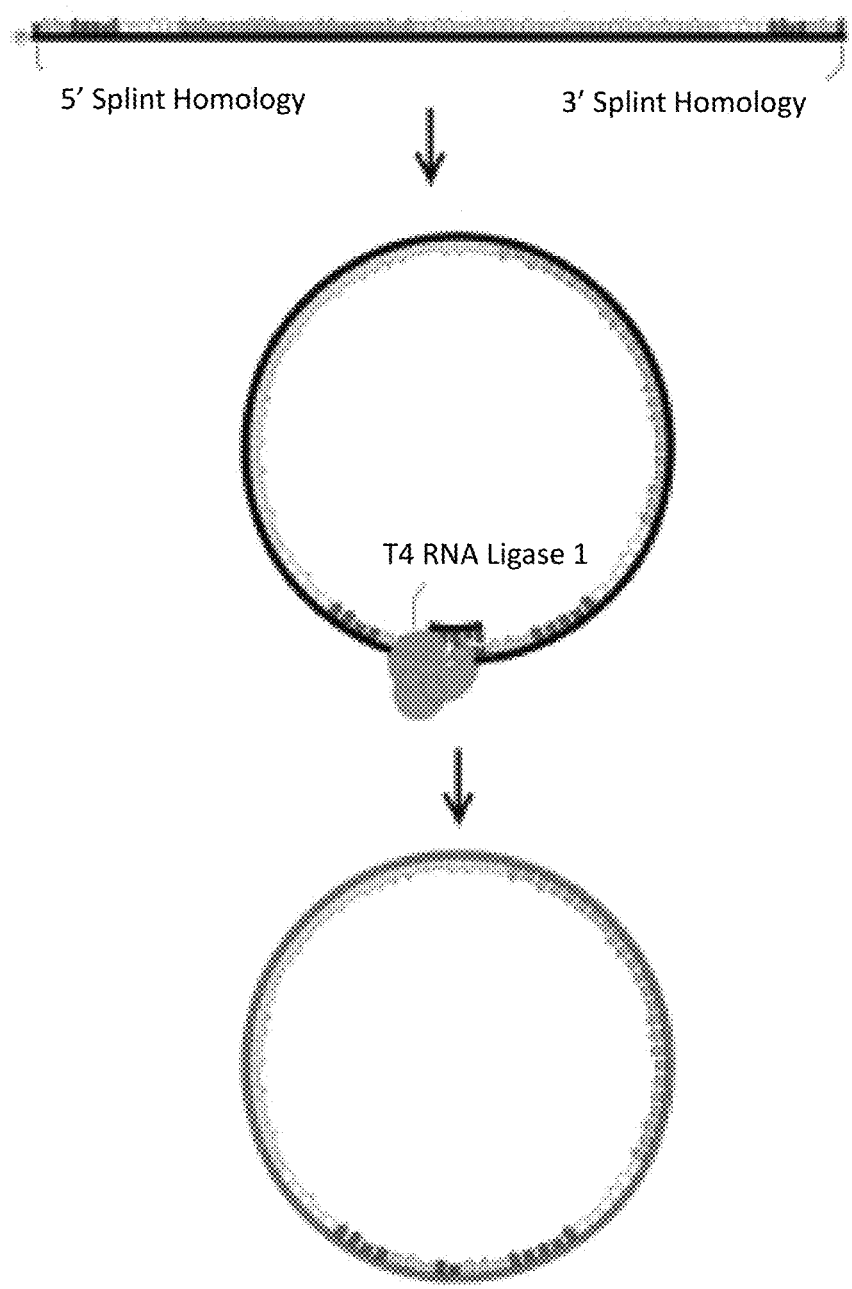
Figure 10H:
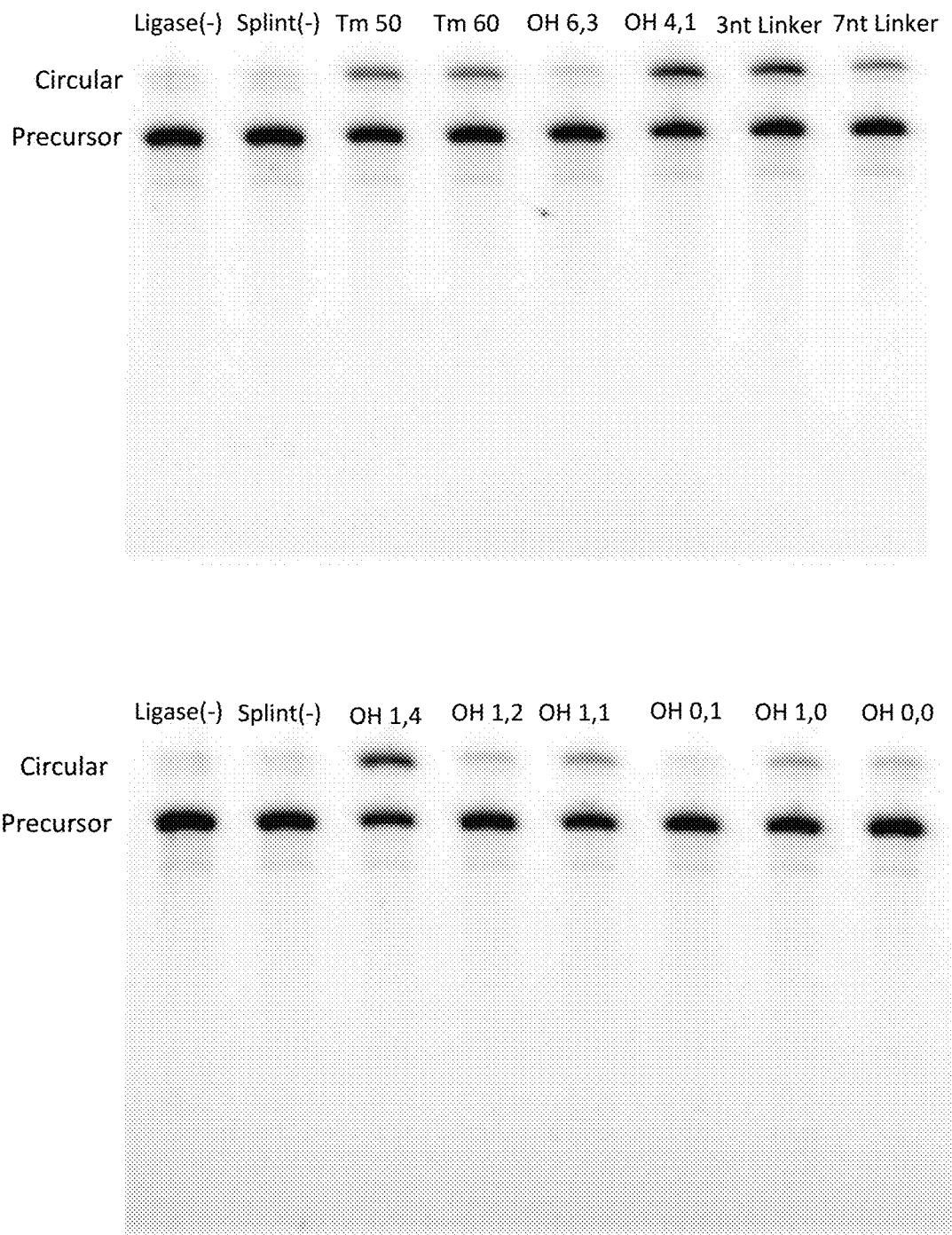
Figure 10I:
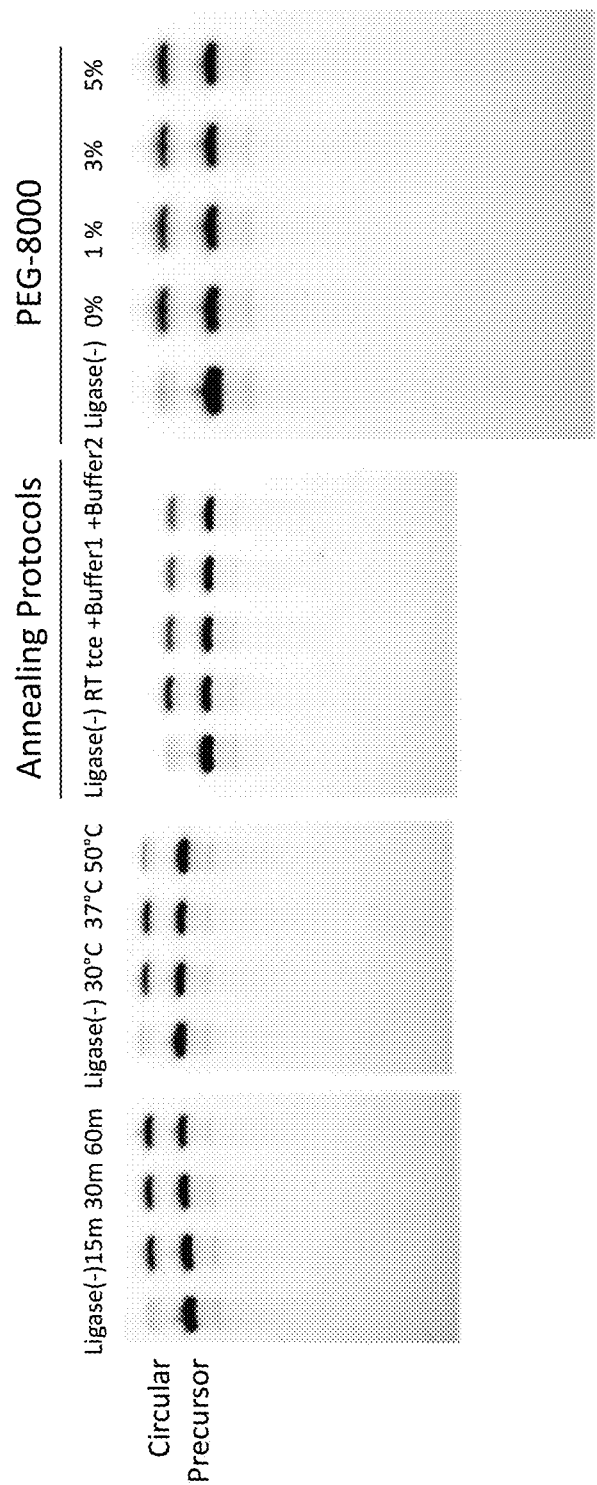

Next, purified circRNA was linearized using two methods: treatment of circRNA with heat in the presence of magnesium ions, and DNA oligonucleotide-guided RNase H digestion (FIG. 10D). Both methods yielded a majority of full-length linear RNA with small amounts of intact circRNA, although heat treatment resulted in a greater proportion of lower molecular weight linear RNA degradation products (FIG. 10E). Transfection of circRNA degraded by both heat and RNase H prompted SEAP secretion in TLR8 reporter cells (FIG. 4F). No activation was observed in TLR3 and TLR7 reporter cells for degraded or intact conditions despite activation of TLR3 by in vitro transcribed linearized RNA (FIG. 4F, FIG. 12I). These results indicate that circRNA is able to avoid detection by TLRs, and that TLR8 evasion is a result of circular conformation.

Exogenous circRNA is Translatable In Vivo

Figure 13:
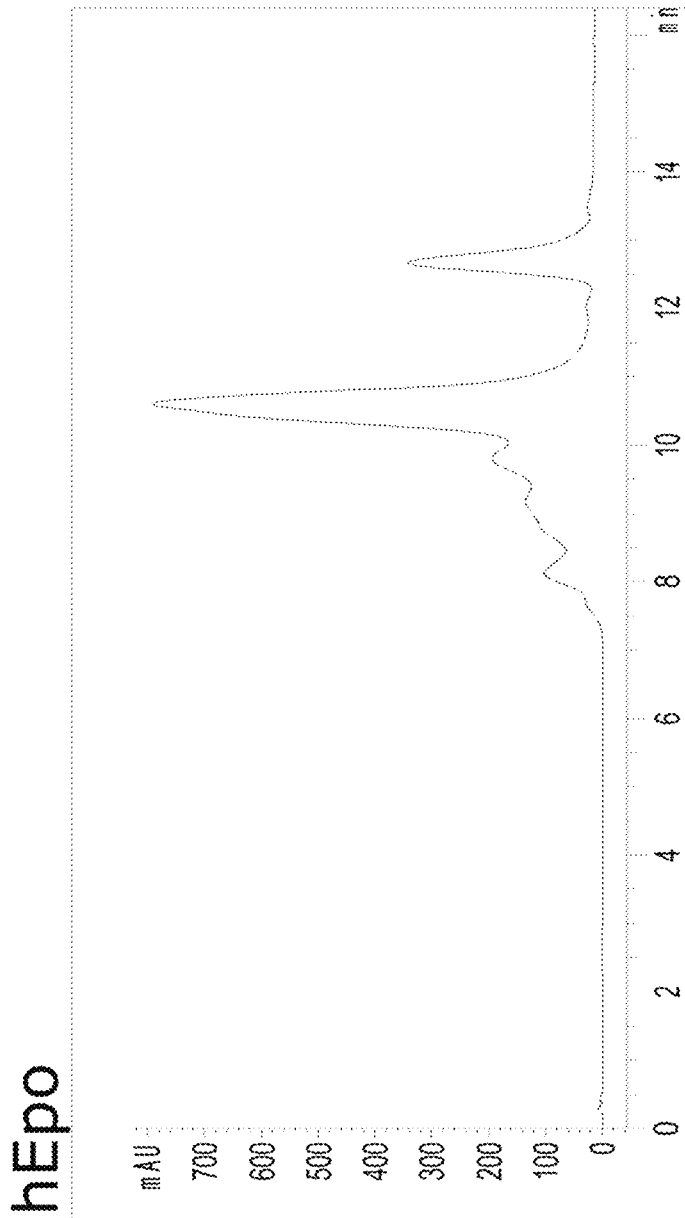
FIG. 13 shows a graph of HPLC chromatogram of an unpurified hEpo splicing reaction.
Figure 14A:
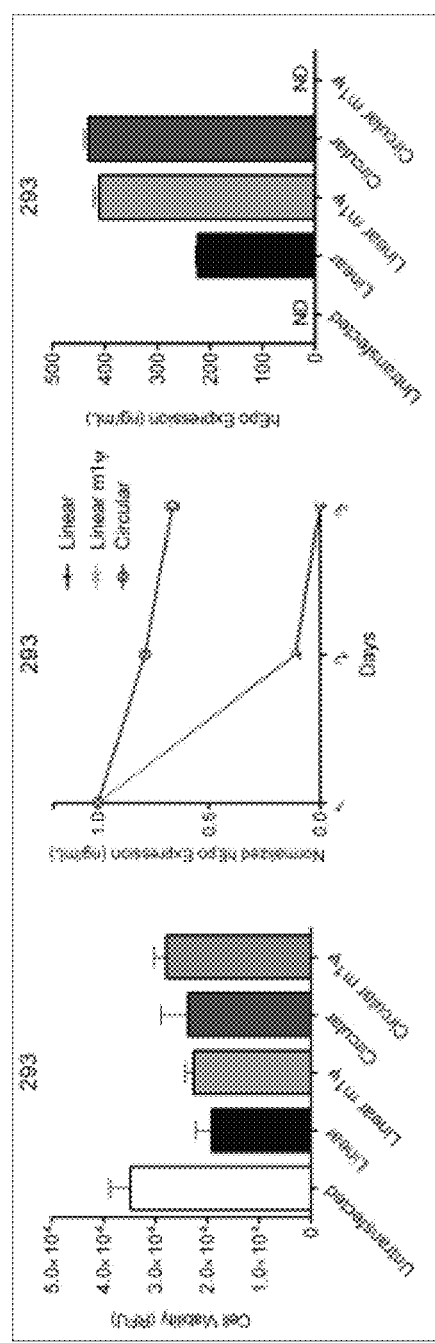
FIGS. 14A-D show hEpo circRNA characterization in vitro.
Figure 14B:
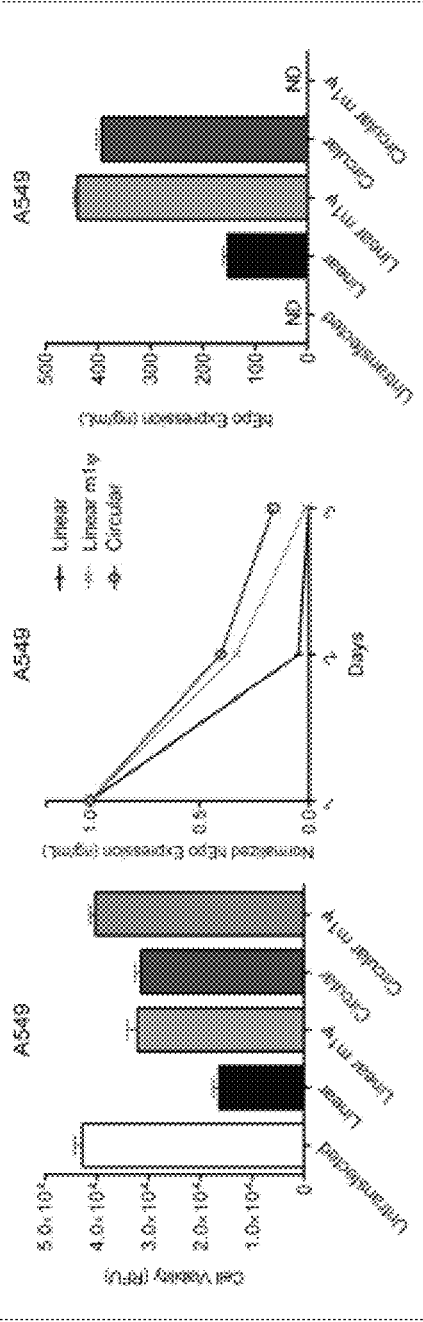
Figure 14C:
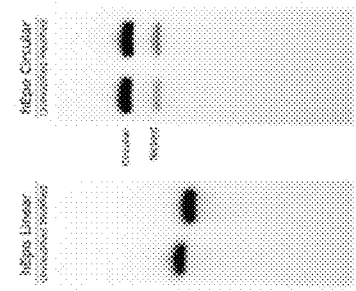
Figure 14D:
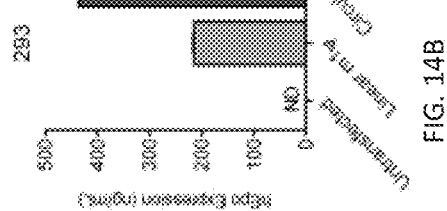
Figure 15:
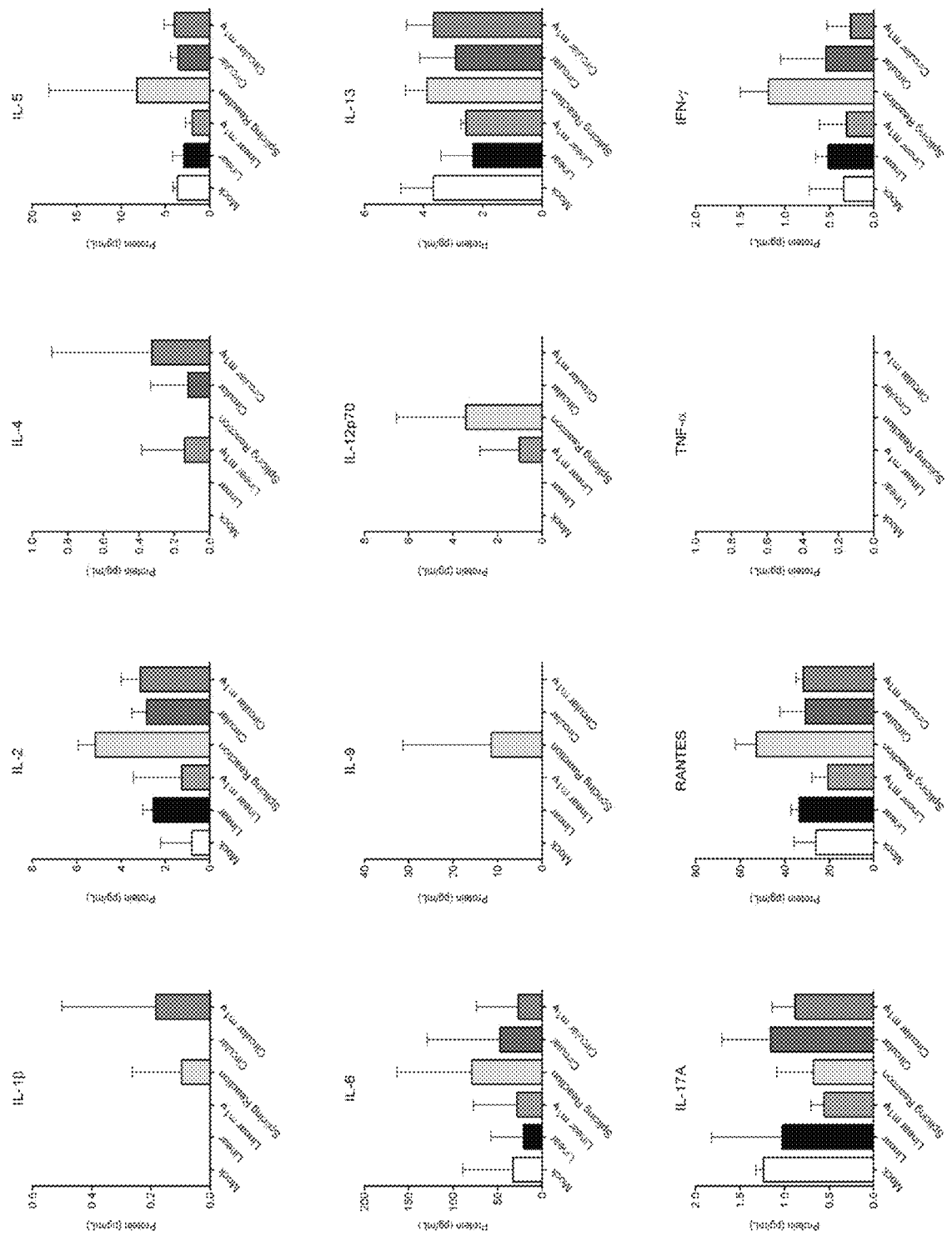
FIG. 15 shows additional cytokines detected in serum 6 hours after intraperitoneal injection of equal weights of the indicated RNAs (see FIG. 10F; data presented as mean+SD, n=3). In most cases, these analytes were detected at extremely low levels, precluding the observance of significant differences.

Translation and immunogenicity of unmodified and m1ψ-modified human erythropoietin (hEpo) linear mRNAs and circRNAs was first examined, with linear mRNAs identical to those depicted in FIG. 9A with the exception of the coding region (FIG. 13, FIG. 14A). Equimolar transfection of m1ψ-mRNA and unmodified circRNA resulted in robust protein expression in 293 cells (FIG. 14B). hEpo linear mRNA and circRNA displayed similar relative protein expression patterns and cell viabilities in comparison to GLuc linear mRNA and circRNA upon equal weight transfection of 293 and A549 cells (FIGS. 14C and D). In mice, hEpo was detected in serum after injection of hEpo circRNA or linear mRNA into visceral adipose (FIGS. 11A and D). hEpo detected after injection of unmodified circRNA decayed more slowly than that from unmodified or m1ψ-mRNA and was still present 42 hours post injection (FIG. 11B). A rapid decline in serum hEpo upon injection of unpurified circRNA splicing reactions or unmodified linear mRNA (FIG. 11B) was observed. Injection of unpurified splicing reactions furthermore produced a cytokine response detectable in serum that was not observe for the other RNAs, including purified circRNA (FIG. 11C, FIG. 15).

CircRNA is Compatible with Lipid Nanoparticles

Lipid nanoparticles have shown significant potential for use as delivery vehicles for therapeutic RNAs, including the delivery of mRNA to tissues (Oberli, M. A. et al. Lipid Nanoparticle Assisted mRNA Delivery for Potent Cancer Immunotherapy. *Nano Lett.* 17, 1326-1335 (2017); Yanez Arteta, M. et al. Successful reprogramming of cellular protein production through mRNA delivered by functionalized lipid nanoparticles. *Proc. Natl. Acad. Sci. U.S.A* 115, E3351-E3360 (2018); and Kaczmarek, J. C., Kowalski, P. S. & Anderson, D. G. Advances in the delivery of RNA therapeutics: from concept to clinical reality. *Genome Med.* 9, 60 (2017)). To assess the efficacy of lipid nanoparticles for circRNA delivery in vivo, purified circRNA was formulated into nanoparticles with the ionizable lipidoid cKK-E12 (Dong, Y. et al. Lipopeptide nanoparticles for potent and selective siRNA delivery in rodents and nonhuman primates. *Proc. Natl. Acad. Sci. U.S.A* 111, 3955-3960 (2014); and Kauffman, K. J. et al. Optimization of Lipid Nanoparticle Formulations for mRNA Delivery in Vivo with Fractional Factorial and Definitive Screening Designs. *Nano Lett.* 15, 7300-7306 (2015)). These particles formed uniform multilamellar structures with an average size, polydispersity index, and encapsulation efficiency similar to that of particles containing commercially available control linear mRNA modified with 5-methoxyuridine (5moU, FIG. 12A, Table 2). Purified hEpo circRNA encapsulated in LNPs displayed robust expression upon addition to 293 cells in comparison to 5moU-mRNA (FIG. 12B, left). This commercially available mRNA performed similarly to the m1ψ-mRNA that was used previously relative to circRNA (FIG. 14C). Protein expression stability from LNP-RNA in 293 cells was similar to that from RNA delivered by transfection reagent with the exception of a slight delay in decay for both 5moU-mRNA and circRNA (FIG. 12B, right). Encapsulation in LNPs did not alter RIG-I/IFN-β1 induction or TLR activation in vitro, with unmodified circRNA failing to activate immune sensors in a manner similar to 5moU-mRNA (FIGS. 12C and D).

Figure 16A:
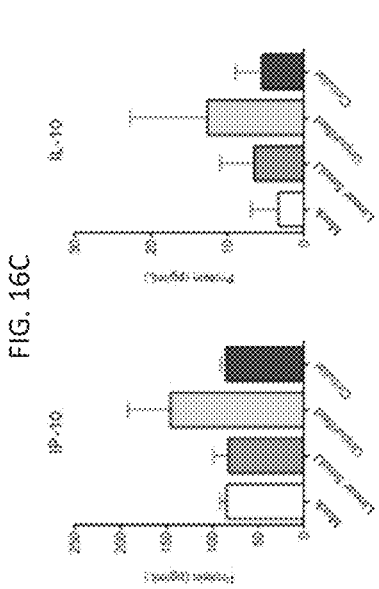
FIGS. 16A-D show LNP-RNA characterization in vivo.
Figure 16B:
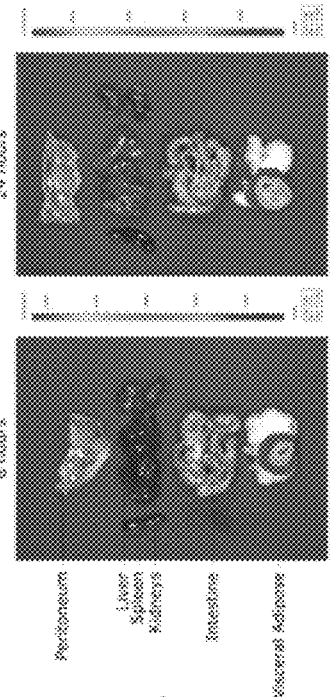
Figure 16C:
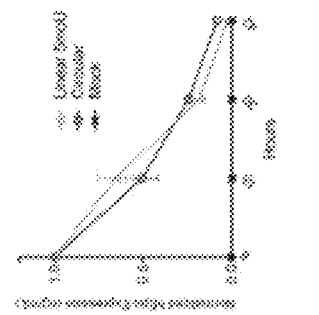
Figure 16D:
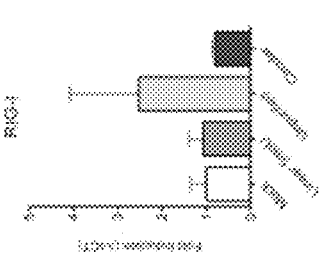
Figure 16E:
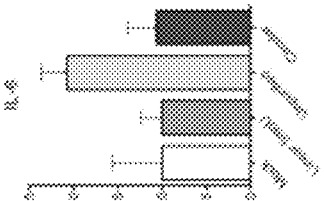
FIG. 16E) Serum hEpo expression from liver 6 hours after intravenous injection of 0.1 mg/kg 5moU-mRNA or unmodified circRNA (left) and relative hEpo expression over 42 hours (right; data presented relative to molecular weight, mean+SD, n=3).
Figure 16E:
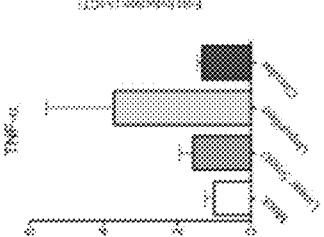

In mice, LNP-RNA was locally injected into visceral adipose tissue (FIG. 16B). Serum hEPo expression from circRNA was lower but comparable with that from 5moU-mRNA 6 hours after injection of LNP-RNAs into visceral adipose or intravenous delivery to liver (FIG. 12E, FIG. 16E). Serum hEpo detected after adipose injection of unmodified LNP-circRNA decayed more slowly than that from LNP-5moU-mRNA, with a delay in expression decay present in serum similar to that noted in vitro (FIG. 12F); however, serum hEpo detected after intravenous injection of LNP-circRNA decayed at the same rate as that from LNP-5moU-mRNA (FIG. 16E). An increase in serum cytokines was not observed, or local RIG-I, TNF-α, or IL-6 transcript induction after injection of LNP-5moU-mRNA or LNP-circRNA (FIGS. 16C and D).

TABLE 2

| Ckk-E12 Formulation | Polydispersity | Size Intensity Mean (nm) | Encapsulation Efficacy (%) |
|---|---|---|---|
| 5moU-mRNA | 0.14 ± 0.02 | 92 ± 6 | 75 ± 6 |
| Unpurified | 0.13 ± 0.04 | 87 ± 7 | 75 ± 13 |
| Circular | 0.12 ± 0.03 | 95 ± 7 | 77 ± 14 |

Physiochemical properties of LNP-RNAs (data presented as mean ± SD, n = 3).

DISCUSSION

In this work it was demonstrated that exogenous circRNA evades RNA sensors and that expression is extended relative to linear mRNA following injection into mouse adipose tissue. While previous studies examining circRNA immunogenicity have proposed that exogenous circRNA provokes a strong innate cellular immune response mediated by RIG-I, due to an absence of associated host splicing factors (Chen et al. 2017), it was found in this study that circRNA does not activate several known cellular RNA sensors including TLRs and RIG-I (Chen, Y. G. et al. Sensing Self and Foreign Circular RNAs by Intron Identity. *Mol. Cell* 67, 228-238.e5 (2017)). These discordant results are likely to be the result of impurities in circRNA preparations. Previous studies have used circRNA purified by RNase R (Chen, Y. G. et al. Sensing Self and Foreign Circular RNAs by Intron Identity. *Mol. Cell* 67, 228-238.e5 (2017)). This study found that treatment with RNase R is not sufficient to obtain pure circRNA and enriches multiple resistant RNA species, which include circRNA and linear RNAs with structured 3' ends. Furthermore, even small quantities of contaminating linear RNA, some of which may harbor triphosphates and may be present after HPLC purification, are sufficient to provoke robust cellular immune responses (FIG. 9C). HPLC purification of circRNA presents unique difficulties, as nicked circRNA and intact circRNA are equal in molecular weight and their respective peaks partly overlap. Degradation products of triphosphorylated precursor RNA will also separate within the circRNA peak, and therefore gentle circRNA preparation is required. Phosphatase treatment, minimizing heat exposure in the presence of divalent cations, and stringent HPLC peak selection can reduce these hazards. Using the purification protocol described here, it was found that circRNA does not elicit substantial innate immune responses from TLR and RIG-I competent cells, in contrast to other components of the splicing reaction, or from mouse adipose tissue, despite the absence of circRNA-associated host splicing factors. Using the purification protocol described here, it was found that circRNA does not elicit substantial innate immune responses from TLR and RIG-I competent cells, in contrast to other components of the splicing reaction, or from mouse adipose tissue. In addition, protein production from purified circRNA is significantly more stable than that from unpurified circRNA and transfection of purified circRNA results in greatly improved cell viability (FIG. 7F, FIG. 8D), both of which are indicators of an antiviral response resulting from non-circular contaminants (Loo, Y. M. & Gale, M., Jr. Immune signaling by RIG-I-like receptors.—PubMed—NCBI. Available at: https://www.ncbi.nlm.nih.gov/pubmed/21616437. (Accessed: 7 May 2018)). Nucleoside modifications, especially uridine modifications, have been reported to reduce linear mRNA immunogenicity by preventing detection by RNA sensors, which may be important for RNA function in some tissue types (Karikó, K., Buckstein, M., Ni, H. & Weissman, D. Suppression of RNA recognition by Toll-like receptors: the impact of nucleoside modification and the evolutionary origin of RNA. Immunity 23, 165-175 (2005); Durbin, A. F., Wang, C., Marcotrigiano, J. & Gehrke, L. RNAs Containing Modified Nucleotides Fail To Trigger RIG-I Conformational Changes for Innate Immune Signaling. MBio 7, (2016)). With the constructs described here, enhanced protein expression stability from m1ψ-mRNA compared to unmodified mRNA in vitro and in adipose tissue was observed (FIGS. 9E,11B). This may be a secondary outcome of immune evasion or an unrelated primary effect of modification. Modification of circRNA precursor molecules with m1ψ interfered with splicing in the PIE constructs and translation in the enzymatically circularized RNAs, suggesting that m1ψ significantly changes the folding of ribozyme and IRES structures.

Modification of RNA with m6A has been shown to promote cap-independent translation of endogenous linear and circular RNAs in living cells and exogenous linear RNAs in cell lysates (Meyer et al. 2015; Yang et al. 2017). We found that partial replacement of adenosine with m6A was not sufficient to drive translation from exogenous intact or linearized circRNA in living cells, consistent with previous reports indicating the involvement of nuclear RNA binding proteins in assisting m6A-dependent translation (FIGS. 9F,G) (Lin et al. 2016).

Unlike linear mRNA, circRNA relies heavily on folded RNA structures, including the permuted group I intron and IRES, for splicing and translation. Modification of circRNA precursor molecules with m1ψ and m6A interfered with splicing in the PIE constructs and translation in the enzymatically circularized RNAs, suggesting that modifications significantly change the folding of these structural elements (FIGS. 9B,D,F,G).

Incorporation of ψ has been shown to enhance base-stacking interactions, which may lead to structural alterations; however, it is possible that other nucleoside modifications may be more compatible with ribozyme and IRES structures and allow for the study of modified circRNA translation during stability (Davis, D. R. Stabilization of RNA stacking by pseudouridine. *Nucleic Acids Res.* 23, 5020 (1995)). While it is known that modified linear mRNA is able to avoid detection by TLRs, it was surprising to discover that unmodified circRNA exhibits the same property. Recently, the ligands of TLR7 and TLR8 have been reported as degradation products of RNA including short stretches of ssRNA and nucleosides (Tanji, H. et al. Toll-like receptor 8 senses degradation products of single-stranded RNA. *Nat. Struct. Mol. Biol.* 22, 109-115 (2015); Zhang, Z. et al. Structural Analysis Reveals that Toll-like Receptor 7 Is a Dual Receptor for Guanosine and Single-Stranded RNA. *Immunity* 45, 737-748 (2016)). These degradation products are presumably produced by nucleases in the endosome shortly after the RNA is internalized (Roers, A., Hiller, B. & Hornung, V. Recognition of Endogenous Nucleic Acids by the Innate Immune System. Immunity 44, 739-754 (2016)). The contiguous structure of circRNA may confer it with resistance to endosomal nucleases, resulting in evasion of these detectors. In this case, endosomal nucleases would be expected to be composed primarily of exonucleases, as the presence of endonucleases would be expected to lead to circRNA degradation. Consistent with this postulation, the addition of one of the two cooperative TLR8 ligands, uridine, to the media of TLR8 reporter cells was able to partially abrogate the immunoevasive properties of circRNA, suggesting that a lack of degradation products and therefore nuclease resistance may indeed be responsible for TLR8 evasion by circRNA. However, no degradation product has yet to be defined as a ligand for TLR3, which circRNA also appears to evade in the context of TLR3-overexpressing 293 cells despite containing the same dsRNA motifs as the TLR3-activating linearized circRNA. It may be possible that RNA degradation products bind to TLR3 at the dimerization interface in a similar manner to TLR8 (Roers, A., Hiller, B. & Hornung, V. Recognition of Endogenous Nucleic Acids by the Innate Immune System. Immunity 44, 739-754 (2016)). Differences in TLR3 activation by linearized circRNA was also observed, with in vitro transcribed linearized circRNA eliciting a TLR3-mediated response while linearized circRNA produced by degrading purified circRNA did not (FIGS. 10B and F). It is possible that degradation of circRNA by either heat or RNase H disrupts dsRNA structures required for robust TLR3 activation.

Intra-adipose injection of circRNA complexed with transfection reagent or within LNPs yielded hEpo expression that was more stable than that from m1ψ-mRNA or 5moU-mRNA (FIG. 11B and FIG. 12F). However, although hEpo production from circRNA was observed to be close to twofold higher than that from equimolar transfection of m1ψ-mRNA or 5moU-mRNA in 293 cells at 24 hours, hEpo expression from circRNA in vivo was relatively diminished. Several factors may have led to this result. The CVB3 IRES was originally selected for use in circRNA based on its ability to drive translation in human cell lines (Wesselhoeft, R. A., Kowalski, P. S. & Anderson, D. G. Engineering circular RNA for potent and stable translation in eukaryotic cells. *Nat. Commun.* 9, 2629 (2018)). Mouse adipose or liver tissue may therefore not be the ideal cell type for CVB3 IRES-mediated translation. IRES sequences must also compete for translation initiation factors with endogenous transcripts bearing m$^7$G caps. Accordingly, circRNA using viral IRES sequences to initiate translation could be more effective in cells with higher initiation factor density relative to transcript density. A comprehensive characterization of the ability of other IRES sequences to drive translation from circRNA in diverse tissues is needed.

Protein expression stability from circRNA delivered intravenously by LNP to liver was not enhanced compared to that from 5moU-mRNA, although the relative magnitude of expression from circRNA at 6 hours was comparable to that obtained from adipose tissue (FIG. 12E and FIG. 16E). This result highlights tissue specific stability that may be dependent on several factors, including general RNA turnover rate or endonuclease activity, sequence specific translation inhibition or degradation, and the presence or absence of RNA stabilizing proteins. Assessment and alteration of miRNA binding sites within circRNA or depletion of sequence-specific degradation motifs may further enhance circRNA stability and expression in select tissues.

An increase in serum cytokines was detected in mice injected with unpurified splicing reactions, but such a response in mice injected with unmodified mRNA, m1ψ-mRNA/5moU-mRNA, or circRNA was not detected. Consistent with in vitro results, a rapid decrease in hEpo expression upon injection of unmodified mRNA and unpurified splicing reactions was observed, while serum hEpo after injection of m1ψ-mRNA/5moU-mRNA and circRNA remained relatively stable, indicating that m1ψ-mRNA/5moU-mRNA and circRNA did not provoke a substantial immune response that would lead to RNA degradation in vivo. Formulation of circRNA into LNPs did not alter immune sensor interactions, and analysis of serum cytokines and local pro-inflammatory transcript levels after LNP-RNA injections did not reveal an immune response against LNP-delivered circRNA.

It is believed that the enhanced expression stability of circRNA in some tissues and the ability of circRNA to avoid immune sensors without the need for nucleoside modifications demonstrates the potential of circRNA as a vector for the expression of therapeutic proteins.

Methods:

RNA Design, Synthesis, and Purification

Linear mRNA or circRNA precursors were synthesized by runoff in-vitro transcription from a linearized plasmid DNA template using a T7 High Yield RNA Synthesis Kit (New England Biolabs (NEB)) with the complete replacement of uridine with N$^1$-methylpseudouridine (Trilink Biotechnologies) for modified linear or circular RNA. After in vitro transcription, reactions were treated with DNase I (NEB) for 15 minutes. After DNase treatment, RNA was column purified using a MEGAclear Transcription Clean-up kit (Ambion). RNA was then heated to 70° C. for 3 minutes and immediately placed on ice for 2 minutes, after which linear RNA was capped using mRNA cap-2'-O-methyltransferase (NEB) and Vaccinia capping enzyme (NEB) according to the manufacturer's instructions. Polyadenosine tails were added to capped linear transcripts using *E. coli* PolyA Polymerase (NEB) according to manufacturer's instructions, and fully processed mRNA was column purified. For circRNA, GTP was added to a final concentration of 2 mM along with a buffer including magnesium (50 mM Tris-HCl, 10 mM MgCl2, 1 mM DTT, pH 7.5; NEB), and then reactions were heated at 55° C. for 8 minutes. RNA was then column purified. In some cases, circRNA was digested with RNase R: 20 µg of RNA was diluted in water (86 uL final volume) and then heated at 70° C. for 3 minutes and cooled on ice for 2 minutes. 20U RNase R and 10 uL of 10× RNase R buffer (Applied Biological Materials) was added, and the reaction was incubated at 37° C. for 15 minutes; an additional 10U RNase R was added halfway through the reaction. RNase R-digested RNA was column purified. In some cases, RNA was treated with a phosphatase (CIP, NEB): 20 ug of RNA was diluted, heated and cooled as described above and then Cutsmart buffer (NEB) was added to a final concentration of 1X along with 20U of CIP. The reaction was incubated at 37° C. for 15 minutes. Phosphatase-treated RNA was column purified. RNA was diluted in 50% formamide, denatured at 70° C. for 3 minutes, and then cooled to room temperature. RNA was then separated on precast 2% E-gel EX agarose gels (Invitrogen) on the E-gel iBase (Invitrogen) using the E-gel EX 1-2% program; ssRNA Ladder (NEB) was used as a standard. Bands were visualized using blue light transillumination and quantified using ImageJ. For high-performance liquid chromatography, 30 µg of RNA was heated at 65° C. for 3 minutes and then placed on ice for 2 minutes. RNA was run through a 4.6×300 mm size-exclusion column with particle size of 5 µm and pore size of 2000 Å (Sepax Technologies; part number: 215980P-4630) on an Agilent 1100 Series HPLC (Agilent). RNA was run in RNase-free TE buffer (10 mM Tris, 1 mM EDTA, pH:6) at a flow rate of 0.3 mL/minute. RNA was detected by UV absorbance at 260 nm, but was collected without UV detection. Resulting RNA fractions were precipitated with 5M ammonium acetate, resuspended in water, and then in some cases subjected to further enzymatic treatment as described above. 5moU-modified Firefly Luciferase and hEpo mRNA was obtained from Trilink Biotechnologies.

Splint Ligation

Linear precursors for splint-mediated ligation were designed to have all of the same sequence features as PIE-circularized circRNA except for the addition of short adapter sequences onto the 5' and 3' ends of the precursor RNA. These adapter sequences shared homology with the splints used for circularization (Optimized splint: 5'-GTTTGTGGTTCGTGCGTCTCCGTGCTGTTCTGTT-GGTGTGGG-3' (SEQ ID NO: 33). Splint ligation precursor RNA was synthesized as described previously, except a 10-fold excess of GMP was added to in vitro transcription reactions. 25 ug of purified precursor RNA was heated to 70° C. for 5 minutes in the presence of DNA splint at a concentration of 5 uM in a 90 uL reaction. The reaction was allowed to cool to room temperature, and then T4 RNA Ligase I Buffer (NEB) was added to a final concentration of 1×. ATP was added to a final concentration of 1 mM. 50U of T4 RNA Ligase I (NEB) was added. Reactions were incubated at 37° C. for 30 minutes and then column purified.

RNase H Nicking

Splicing reactions enriched for circRNA with RNase R and then column purified, or purified by HPLC, were heated at 70° C. for 5 minutes in the presence of a DNA probe (5'-TTGAACCCAGGAATCTCAGG-3'(SEQ ID NO: 34)) at five-fold molar excess, and then annealed at room temperature. Reactions were treated with RNase H (New England Biolabs) in the provided reaction buffer for 15 minutes at 37° C. RNA was column purified after digestion.

Tissue Culture, Transfections, and Cell Viability 293 and A549 cells RAW264.7 cells (ATCC) and HEK-Blue mouse TLR3, mouse TLR7, human TLR8, Null1, and Null2 cells (Invivogen) were cultured at 37° C. and 5% CO2 in Dulbecco's Modified Eagle's Medium (4500 mg/L glucose) supplemented with 10% heat-inactivated fetal bovine serum (hiFBS, Gibco) and penicillin/streptomycin. HEK293 and HeLa cells tested negative for *mycoplasma*. Cells were passaged every 2-3 days. For 293 and A549 cells, 40 ng of RNA was reverse transfected into 10,000 cells/100 uL per well of a 96-well plate using Lipofectamine MessengerMax (Invitrogen) according to the manufacturer's instructions. For HEK-Blue cells, 100ng of RNA was reverse transfected into 40,000 cells/100 uL per well of a 96-well plate using Lipofectamine MessengerMax. For A549 cells transfected prior to RNA harvest and qPCR, 200 ng of RNA was reverse transfected into 100,000 cells per well of a 24-well plate using Lipofectamine MessengerMax. For experiments wherein protein expression was assessed at multiple time points, media was fully removed and replaced at each time point. For experiments wherein SEAP activity or cytokines were analyzed, media was not replaced between transfection and assessment. For all transfection experiments, RNA was heated to 70° C. for 3 minutes and immediately placed on ice for 2 minutes prior to complexation with transfection reagent. Cell viability 36-72 hours after transfection was assessed using a MultiTox kit (Promega). To detect SEAP secretion by TLR reporter and null cells, media was harvested 36-48 hours after transfection and combined with HEK-Blue Detection reagent (Invivogen) to a final concentration of 1×. Media and detection reagent were incubated overnight at 37° C. and then absorbance at 640 nm was measured on an Infinite 200Pro Microplate Reader (Tecan). R848, polyI:C, and 3p-hpRNA were obtained from Invivogen.

Protein Expression Analysis

For luminescence assays, media was harvested 24 hours post-transfection. To detect luminescence from *Gaussia* luciferase, 20 uL of tissue culture medium was transferred to a flat-bottomed white-walled plate (Corning). 25 uL of BioLux *Gaussia* Luciferase reagent including stabilizer (New England Biolabs) was added to each sample and luminescence was measured on an Infinite 200Pro Microplate Reader (Tecan) after 45 seconds. Human erythropoietin was detected by solid phase sandwich ELISA (R&D Systems) essentially according to the manufacturer's instructions. Cytokines in FIGS. 1, 3 and 5 were detected by Fireplex immunoassay (Abcam). Cytokines in FIGS. 2 and 6 were detected by individual or multiplex immunoassay (Eve Technologies).

Reverse Transcription and qPCR

Cells were washed and RNA was harvested and purified 24 hours after transfection using an RNeasy Mini Plus kit (Qiagen) or RNeasy Lipid Kit (Qiagen) for RNA extracted from mouse adipose tissue according to the manufacturer's instructions. Synthesis of first-strand cDNA from total RNA was performed with High-Capacity cDNA Reverse Transcription Kit using random hexamers (Thermo Fisher Scientific). Gene specific TaqMan primers were purchased as Assay-on-Demand (Thermo Fisher Scientific); human primers: GAPDH (Hs99999905_m1), DDX58 (Hs01061436_m1), IFN-β1 (Hs01077958_s1); mouse primers: Gapdh (Mm99999915_g1), Ddx58 (Mm01216853_m1), Il-6 (Mm00446190_m1), Tnf (Mm00443258_m1). The qPCR reaction was carried out using LightCycler 480 Probe Master Mix (Roche) and LightCycler 480 instrument (Roche). For each sample, threshold cycle values (Ct) were processed according to the comparative Ct method. Gene expression levels were normalized to the expression of the housekeeping gene GAPDH.

Animal Experiments

All animal experiments were performed under the guidelines of the MIT Animal Care and Use Committee. 30-35 g C57B1/6 female mice randomly assigned to treatment or control groups were injected into visceral fat through the lower right mammary fat pad and peritoneum with 350 ng of RNA complexed with MessengerMax or 1.5 picomoles of LNP-RNA in a total volume of 50 μL, or intravenously by tail vein injection with 0.1 mg/kg LNP-RNA. Blood samples were collected via tail bleed or cardiac puncture into BD Microtainer tubes at the indicated time points. To collect the serum, blood was allowed to coagulate for 15-30 min and was subsequently centrifuged at 2000×g for 5 min at room temperature. Human erythropoietin in 2 uL of serum was detected as described previously. To collect adipose tissue, mice were sacrificed and the entire lower visceral adipose tissue was removed and frozen in liquid nitrogen for subsequent RNA isolation.

Lipid Nanoparticle Formulation

LNPs were prepared by mixing ethanol and aqueous phase at a 1:3 volumetric ratio in a microfluidic device, using syringe pumps as previously described. In brief, ethanol phase was prepared by solubilizing a mixture of ionizable lipidoid cKK-E12, 1,2-dioleoyl-sn-glycero-3-phosphoethanolamine (DOPE, Avanti), cholesterol (Sigma), and 1,2-dimyristoyl-sn-glycero-3-phosphoethanolamine-N-[methoxy-(polyethyleneglycol)-2000] (ammonium salt) (C14-PEG 2000, *Avanti*) *at a molar ratio of* 35:16:46.5:2.5. The aqueous phase was prepared in 10 mM citrate buffer (pH 3) with linear mRNA or circRNA. LNPs were dialyzed against PBS in a Slide-A-Lyzer™ G2 Dialysis Cassettes, 20,000 MWCO (Thermo Fisher) for 2h at RT. The concentration of mRNA encapsulated into LNPs nanoparticles was analyzed using Quant-iT RiboGreen assay (Thermo Fisher) according to the manufacturer's protocol. The efficiency of mRNA encapsulation into LNPs was calculated by comparing measurements in the absence and presence of 1% (v/v) Triton X-100. Nanoparticle size, polydispersity (PDI), and ζ-potential were analyzed by dynamic light scattering (DLS) using Zetasizer Nano ZS (Malvern Instruments, Worcestershire, UK). LNP hydrodynamic diameters are reported in the volume weighting mode and are an average of three independent measurements.

CRYO-TEM

For Cryogenic Transmission Electron Microscopy (Cryo-TEM) samples were prepared on a Gatan Cryo Plunge III (Cp3). Briefly, 3 uL of the sample was dropped on a lacey copper grid coated with a continuous carbon film and frozen in liquid ethane. Subsequently the frozen grid was mounted on a Gatan 626 single tilt cryo-holder. Imaging was performed using JEOL 2100 FEG microscope operating at 200 kV with a magnification of 10,000-60,000. All Images were recorded under low-dose conditions with a Gatan 2kx2k UltraScan CCD camera.

Data Analysis and Statistics

For TLR data in FIGS. 10 and 12, absorbance measured in TLR reporter cells was normalized to absorbance measured in null reporter cells containing only the plasmid with SEAP under the control of the IFN-β1 minimal promoter fused to five NF-κB and AP-1 binding sites for mTLR3 and hTLR8, or null reporter cells containing only the plasmid with SEAP under the control of the IL-12p40 minimal promoter fused to five NF-κB and AP-1 binding sites for mTLR7 (Invivogen). For all multi-day GLuc and hEpo data, expression is presented relative to the first day of expression for each condition. Statistical analysis of the results was performed by a two-tailed unpaired Welch's t-test, assuming unequal variances. Differences were considered significant when $p<0.05$. For all studies, data presented is representative of one independent experiment.

STAR Methods:

| REAGENT or RESOURCE | SOURCE | IDENTIFIER |
|---|---|---|
| Chemicals, Peptides, and Recombinant Proteins | | |
| RNase R | Applied Biological Materials | Cat#E049 |
| 3p-hpRNA | Invivogen | Cat#tlrl-hprna |
| polyI:C | Invivogen | Cat#tlrl-pic |
| RNase H | New England Biolabs | Cat#M0297S |
| T4 RNA Ligase 1 | New England Biolabs | Cat#M0204S |
| Lipofectamine ™ MessengerMAX ™ Transfection Reagent | ThermoFisher Scientific | Cat#LMRNA003 |
| N1-Methylpseudouridine-5'-Triphosphate | Trilink Biotechnologies | Cat#N-1081 |
| CleanCap ™ EPO mRNA (5moU) | Trilink Biotechnologies | Cat#L-7209 |
| CleanCap ™ FLuc mRNA (5moU) | Trilink Biotechnologies | Cat#L-7202 |
| Alkaline Phosphatase, Calf Intestinal (CIP) | New England Biolabs | Cat#M0290S |
| Vaccinia Capping System | New England Biolabs | Cat#M2080S |
| mRNA Cap 2'-O-Methyltransferase | New England Biolabs | Cat#M0366S |
| *E. coli* Poly(A) Polymerase | New England Biolabs | Cat#M0276S |
| Uridine | Millipore Sigma | Cat#U6381 |
| Cytidine | Millipore Sigma | Cat#C4654 |
| 1,2-dioleoyl-sn-glycero-3-phosphoethanolamine | Avanti Polar Lipids | Cat#850725P |
| 1,2-dimyristoyl-sn-glycero-3-phosphoethanolamine-N-[methoxy-(polyethyleneglycol)-2000] | Avanti Polar Lipids | Cat#700100P |
| N6-Methyladenosine-5'-Triphosphate | Trilink Biotechnologies | Cat#N-1013 |
| Critical Commercial Assays | | |
| E-Gel ™ EX Agarose Gels, 2% | ThermoFisher Scientific | Cat# G401002 |
| HiScribe ™ T7 High Yield RNA Synthesis Kit | New England Biolabs | Cat#E2040S |

| REAGENT or RESOURCE | SOURCE | IDENTIFIER |
|---|---|---|
| MultiTox-Fluor Multiplex Cytotoxicity Assay | Promega | Cat#G9200 |
| RNeasy Mini Kit | Qiagen | Cat#74104 |
| Human Erythropoietin Quantikine IVD ELISA Kit | R & D Systems | Cat#DEP00 |
| BioLux ® Gaussia Luciferase Assay Kit | New England Biolabs | Cat#E3300 |
| hCCL5 TaqMan ® Gene Expression Assay | ThermoFisher Scientific | Cat#Hs00982282ml |
| hIFNB1 TaqMan ® Gene Expression Assay | ThermoFisher Scientific | Cat#Hs01077958sl |
| hGAPDH TaqMan ® Gene Expression Assay | ThermoFisher Scientific | Cat#Hs99999905ml |
| hDDX58 TaqMan ® Gene Expression Assay | ThermoFisher Scientific | Cat#Hs01061436ml |
| hIL6 TaqMan ® Gene Expression Assay | ThermoFisher Scientific | Cat#Hs00714131ml |
| mCcl5 TaqMan ® Gene Expression Assay | ThermoFisher Scientific | Cat#Mm01302427ml |
| mIfnB1 TaqMan ® Gene Expression Assay | ThermoFisher Scientific | Cat#Mm00439552sl |
| mGapdh TaqMan ® Gene Expression Assay | ThermoFisher Scientific | Cat#Mm99999915gl |
| mDdx58 TaqMan ® Gene Expression Assay | ThermoFisher Scientific | Cat#Mm01216853ml |
| mIl6 TaqMan ® Gene Expression Assay | ThermoFisher Scientific | Cat#Mm00446190ml |
| Tnf TaqMan ® Gene Expression Assay | ThermoFisher Scientific | Cat#Mm00443258_ml |
| Experimental Models: Cell Lines | | |
| HEK-Blue ™ Null1 Cells | Invivogen | Cat#hkb-null1 |
| HEK-Blue ™ Null2 cells | Invivogen | Cat#hkb-null2 |
| HEK-Blue ™ mTLR3 | Invivogen | Cat#hkb-mtlr3 |
| HEK-Blue ™ mTLR7 | Invivogen | Cat#hkb-mtlr7 |
| HEK-Blue ™ hTLR8 | Invivogen | Cat#hkb-htlr8 |
| 293 [HEK-293] | ATCC | Cat#CRL-1573 |
| A549 | ATCC | Cat#CCL-185 |
| RAW264.7 | ATCC | Cat#TIB-71 |
| HeLa | ATCC | Cat#CCL-2 |
| Experimental Models: Organisms/Strains | | |
| C57BL/6 Mice | Charles River | Cat#C57BL/6NCrl |
| Oligonucleotides | | |
| RNase H Probe: TTGAACCCAGGAATCTCAGG (SEQ ID NO. 34) | Described herein | N/A |
| Ligation Splint: GTTTGTGGTTCGTGCGTCTCCGTGCTGTTCTGTTGGTGTGGG (SEQ ID NO. 33) | Described herein | N/A |

| REAGENT or RESOURCE | SOURCE | IDENTIFIER |
|---|---|---|
| Recombinant DNA | | |
| Plasmid: GLuc APIE CVB3 pAC | Wesselhoeft et al., 2017 | N/A |
| Plasmid: hEpo APIE CVB3 pAC | Wesselhoeft et al., 2017 | N/A |
| Plasmid: EGFP APIE EMCV | Wesselhoeft et al., 2017 | N/A |
| Plasmid: GLuc APIE ΔIRES | Described herein | N/A |
| Plasmid: GLuc APIE CVB3 pAC dS | Wesselhoeft et al., 2017 | N/A |
| Plasmid: GLuc APIE CVB3 pAC dI | Wesselhoeft et al., 2017 | N/A |
| Plasmid: splintGLuc CVB3 | Described herein | N/A |
| Plasmid: splinthEpo CVB3 | Described herein | N/A |
| Plasmid: GLuc L | Described herein | N/A |
| Plasmid: hEpo L | Described herein | N/A |

TABLE 1

| | | |
|---|---|---|
| SEQ ID NO. 1 | GLuc T4PIE EMCV (Full) | GGGAGACCCTCGAGCCTAACGACTATCCCTTTGGGGAGTAGGGTCAAGTGACTCGAAACGATAG<br>ACAACTTGCTTTAACAAGTTGGAGATATAGTCTGCTCTGCATGGTGACATGCAGCTGGATATAAT<br>TCCGGGGTAAGATTAACGACCTTATCTGAACATAATGCTACCGTTTAATATTGCGTCACCCCCTC<br>TCCCTCCCCCCCTAACGTTACTGGCCGAAGCCGCTTGGAATAAGGCCGGTGTGCGTTTGTCTATAT<br>GTTATTTTCCACCATATTGCCGTCTTTTGGCAATGTGAGGGCCCGGAAACCTGGCCCTGTCTTCTT<br>GACGAGCATTCCTAGGGGTCTTTCCCCTCTCGCCAAAGGAATGCAAGGTCTGTTGAATGTCGTGA<br>AGGAAGCAGTTCCTCTGGAAGCTTCTTGAAGACAAACAACGTCTGTAGCGACCCTTTGCAGGCAG<br>CGGAACCCCCCACCTGGCGACAGGTGCCTCTGCGGCCAAAAGCCACGTGTATAAGATACACCTG<br>CAAAGGCGGCACAACCCCAGTGCCACGTTGTGAGTTGGATAGTTGTGGAAAGAGTCAAATGGCT<br>CTCCTCAAGCGTATTCAACAAGGGGCTGAAGGATGCCCAGAAGGTACCCCATTGTATGGGATCTG<br>ATCTGGGGCCTCGGTGCACATGCTTTACATGTGTTTAGTCGAGGTTAAAAAACGTCTAGGCCCCC<br>CGAACCACGGGGACGTGGTTTTCCTTTGAAAAACACGATGATAATATGGCCACAACCATGGGAG<br>TCAAAGTTCTGTTTGCCCTGATCTGCATCGCTGTGGCCGAGGCCAAGCCCACCGAGAACAACGAA<br>GACTTCAACATCGTGGCCGTGGCCAGCAACTTCGCGACCACGGATCTCGATGCTGACCGCGGAA<br>GTTGCCCGGCAAGAAGCTGCCGCTGGAGGTGCTCAAAGAGATGGAAGCCAATGCCCGGAAAGCT<br>GGCTGCACCAGGGGCTGTCTGATCTGCCTGTCCCACATCAAGTGCACGCCCAAGATGAAGAAGTT<br>CATCCCAGGACGCTGCCACACCTACGAAGGCGACAAAGAGTCCGCACAGGGCGGCATAGGCGAG<br>GCGATCGTCGACATTCCTGAGATTCCTGGGTTCAAGGACTTGGAGCCCATGGAGCAGTTCATCGC<br>ACAGGTCGATCTGTGTGTGGACTGCACAACTGGCTGCCTCAAAGGGCTTGCCAACGTGCAGTGTT<br>CTGACCTGCTCAAGAAGTGGCTGCCGCAACGCTGTGCGACCTTTGCCAGCAAGATCCAGGGCCAG<br>GTGGACAAGATCAAGGGGGCCGGTGGTGACTAACAGAGATGTTTTCTTGGGTTAATTGAGGCCTG<br>AGTATAAGGTGACTTATACTTGTAATCTATCTAAACGGGGAACCTCTCTAGTAGACAATCCCGTG<br>CTAAATTGTAGGACTAATTCCATTTATCAGATTTCTAG |
| SEQ ID NO. 2 | Weak homology arms 3' Intron | GGGAGACCCTCGAGGTTCTACATAAATGCCTAACGACTATCCCTTTGGGGAGTAGGGTCAAGTGA<br>CTCGAAACGATAGACAACTTGCTTTAACAAGTTGGAGATATAGTCTGCTCTGCATGGTGACATGC<br>AGCTGGATATAATTCCGGGGTAAGATTAACGACCTTATCTGAACATAATG |
| SEQ ID NO. 3 | Weak homology arms 5' Intron | TAATTGAGGCCTGAGTATAAGGTGACTTATACTTGTAATCTATCTAAACGGGGAACCTCTCTAGT<br>AGACAATCCCGTGCTAAATTGTAGGACTAATTCCATTTATCAGATTTCTAG |
| SEQ ID NO. 4 | Strong homology arms 3' Intron | GGGAGACCCTCGAATGGAATTGGTTCTACATAAATGCCTAACGACTATCCCTTTGGGGAGTAGGG<br>TCAAGTGACTCGAAACGATAGACAACTTGCTTTAACAAGTTGGAGATATAGTCTGCTCTGCATGG<br>TGACATGCAGCTGGATATAATTCCGGGGTAAGATTAACGACCTTATCTGAACATAATG |

TABLE 1-continued

| SEQ ID NO. 5 | Strong homology arms 5' Intron | TAATTGAGGCCTGAGTATAAGGTGACTTATACTTGTAATCTATCTAAACGGGGAACCTCTCTAGT<br>AGACAATCCCGTGCTAAATTGTAGGACTAATTCCATTTATCAGATTTCTAG |
|---|---|---|
| SEQ ID NO. 6 | T4 Disruptive spacer | ACTGCAAGTTGTCTATCGTTACGGTAAGTCACCTTATTTCA |
| SEQ ID NO. 7 | T41 5' Permissive spacer 1 | GGTAGTGGTGCTACTAACTTCAGCCTGCTGAAGCA |
| SEQ ID NO. 8 | T42 5' Permissive spacer 2 | GGTAGTAAACTACTAACTACAACCTGCTGAAGCA |
| SEQ ID NO. 9 | 2400 nt (Full) | GGGAGACCCTCGAATGGAATTGGTTCTACATAAATGCCTAACGACTATCCCTTTGGGGAGTAGGG<br>TCAAGTGACTCGAAACGATAGACAACTTGCTTTAACAAGTTGGAGATATAGTCTGCTCTGCATGG<br>TGACATGCAGCTGGATATAATTCCGGGGTAAGATTAACGACCTTATCTGAACATAATGCTACCGT<br>TTAATATTGCGTCAGGTAGTAAACTACTAACTACAACCTGCTGAAGCACCCCCCTCTCCCTCCCCC<br>CCTAACGTTACTGGCCGAAGCCGCTTGGAATAAGGCCGGTGTGCGTTTGTCTATATGTTATTTTCC<br>ACCATATTGCCGTCTTTTGGCAATGTGAGGGCCCGGAAACCTGGCCCTGTCTTCTTGACGAGCATT<br>CCTAGGGGTCTTTCCCCTCTCGCCAAAGGAATGCAAGGTCTGTTGAATGTCGTGAAGGAAGCAGT<br>TCCTCTGGAAGCTTCTTGAAGACAAACAACGTCTGTAGCGACCCTTTGCAGGCAGCGGAACCCCC<br>CACCTGGCGACAGGTGCCTCTGCGGCCAAAAGCCACGTGTATAAGATACACCTGCAAAGGCGGC<br>ACAACCCCAGTGCCACGTTGTGAGTTGGATAGTTGTGGAAAGAGTCAAATGGCTCTCCTCAAGCG<br>TATTCAACAAGGGGCTGAAGGATGCCCAGAAGGTACCCCATTGTATGGGATCTGATCTGGGGCCT<br>CGGTGCACATGCTTTACATGTGTTTAGTCGAGGTTAAAAAACGTCTAGGCCCCCCGAACCACGGG<br>GACGTGGTTTTCCTTTGAAAAACACGATGATAATATGGCCACAACCATGGAAGACGCCAAAAAC<br>ATAAAGAAAGGCCCGGCGCCATTCTATCCGCTGGAAGATGGAACCGCTGGAGAGCAACTGCATA<br>AGGCTATGAAGAGATACGCCCTGGTTCCTGGAACAATTGCTTTTACAGATGCACATATCGAGGTG<br>GACATCACTTACGCTGAGTACTTCGAAATGTCCGTTCGGTTGGCAGAAGCTATGAAACGATATGG<br>GCTGAATACAAATCACAGAATCGTCGTATGCAGTGAAAACTCTCTTCAATTCTTTATGCCGGTGTT<br>GGGCGCGTTATTTATCGGAGTTGCAGTTGCGCCCGCGAACGACATTTATAATGAACGTGAATTGC<br>TCAACAGTATGGGCATTTCGCAGCCTACCGTGGTGTTCGTTTCCAAAAAGGGGTTGCAAAAAATT<br>TTGAACGTGCAAAAAAAGCTCCCAATCATCCAAAAAATTTATTATCATGGATTCTAAAACGGATTA<br>CCAGGGATTTCAGTCGATGTACACGTTCGTCACATCTCATCTACCTCCCGGTTTTAATGAATACGA<br>TTTTGTGCCAGAGTCCTTCGATAGGGACAAGACAATTGCACTGATCATGAACTCCTCTGGATCTA<br>CTGGTCTGCCTAAAGGTGTCGCTCTGCCTCATAGAACTGCCTGCGTGAGATTCTCGCATGCCAGA<br>GATCCTATTTTTGGCAATCAAATCATTCCGGATACTGCGATTTTAAGTGTTGTTCCATTCCATCAC<br>GGTTTTGGAATGTTTACTACACTCGGATATTTGATATGTGGATTTTCGAGTCGTCTTAATGTATAGA<br>TTTGAAGAAGAGCTGTTTCTGAGGAGCCTTCAGGATTACAAGATTCAAAGTGCGCTGCTGGTGCC<br>AACCCTATTCTCCTTCTTCGCCAAAAGCACTCTGATTGACAAATACGATTTATCTAATTTACACGA<br>AATTGCTTCTGGTGGCGCTCCCCTCTCAAGGAAGTCGGGGAAGCGGTTGCCAAGAGGTTCCATC<br>TGCCCAGGTATCAGGCAAGGATATGGGCTCACTGAGACTACATCAGCTATTCTGATTACACCCGAG<br>GGGGATGATAAACCGGGCGCGGTCGGTAAAGTTGTTCCATTTTTTGAAGCGAAGGTTGTGGATCT<br>GGATACCGGGAAAACGCTGGGCGTTAATCAAAGAGGCGAACTGTGTGTGAGAGGTCCTATGATT<br>ATGTCCGGTATGGGAGTCAAAGTTCTGTTTGCCCTGATCTGCATCGCTGTGGCCGAGGCCAAGCC<br>CACCGAGAACAACGAAGACTTCAACATCGTGGCCGTGGCCAGCAACTTCGCGACCACGGATCTC<br>GATGCTGACCGCGGGAAGTTGCCCGGCAAGAAGCTGCCGCTGGAGGTGCTCAAAGAGATGGAAG<br>CCAATGCCCGGAAAGCTGGCTGCACCAGGGGCTGTCTGATCTGCCTGTCCCACATCAAGTGCACG<br>CCCAAGATGAAGAAGTTCATCCCAGGACGCTGCCACACCTACGAAGGCGACAAAGAGTCCGCAC<br>AGGGCGGCATAGGCGAGGCGATCGTCGACATTCCTGAGATTCCTGGGTTCAAGGACTTGGAGCC<br>CATGGAGCAGTTCATCGCACAGGTCGATCTGTGTGTGGACTGCACAACTGGCTGCCTCAAAGGGC<br>TTGCCAACGTGCAGTGTTCTGACCTGCTCAAGAAGTGGCTGCCGCAACGCTGTGCGACCTTTGCC<br>AGCAAGATCCAGGGCCAGGTGGACAAGATCAAGGGGGGCCGGTGGTGACTAACAGAGATGTTTTC<br>TTGGGTTAATTGAGGCCTGAGTATAAGGTGACTTATACTTGTAATCTATCTAAACGGGGAACCTC<br>TCTAGTAGACAATCCCGTGCTAAATTGTAGGACTAATTCCATTTATCAGATTTCTAG |
| SEQ ID NO. 10 | 4800 nt (Full) | GGGAGACCCTCGAATGGAATTGGTTCTACATAAATGCCTAACGACTATCCCTTTGGGGAGTAGGG<br>TCAAGTGACTCGAAACGATAGACAACTTGCTTTAACAAGTTGGAGATATAGTCTGCTCTGCATGG<br>TGACATGCAGCTGGATATAATTCCGGGGTAAGATTAACGACCTTATCTGAACATAATGCTACCGT<br>TTAATATTGCGTCAGGTAGTAAACTACTAACTACAACCTGCTGAAGCACCCCCCTCTCCCTCCCCC<br>CCTAACGTTACTGGCCGAAGCCGCTTGGAATAAGGCCGGTGTGCGTTTGTCTATATGTTATTTTCC<br>ACCATATTGCCGTCTTTTGGCAATGTGAGGGCCCGGAAACCTGGCCCTGTCTTCTTGACGAGCATT<br>CCTAGGGGTCTTTCCCCTCTCGCCAAAGGAATGCAAGGTCTGTTGAATGTCGTGAAGGAAGCAGT<br>TCCTCTGGAAGCTTCTTGAAGACAAACAACGTCTGTAGCGACCCTTTGCAGGCAGCGGAACCCCC<br>CACCTGGCGACAGGTGCCTCTGCGGCCAAAAGCCACGTGTATAAGATACACCTGCAAAGGCGGC<br>ACAACCCCAGTGCCACGTTGTGAGTTGGATAGTTGTGGAAAGAGTCAAATGGCTCTCCTCAAGCG<br>TATTCAACAAGGGGCTGAAGGATGCCCAGAAGGTACCCCATTGTATGGGATCTGATCTGGGGCCT<br>CGGTGCACATGCTTTACATGTGTTTAGTCGAGGTTAAAAAACGTCTAGGCCCCCCGAACCACGGG<br>GACGTGGTTTTCCTTTGAAAAACACGATGATAATATGGCCACAACCATGGAAGACGCCAAAAAC<br>ATAAAGAAAGGCCCGGCGCCATTCTATCCGCTGGAAGATGGAACCGCTGGAGAGCAACTGCATA<br>AGGCTATGAAGAGATACGCCCTGGTTCCTGGAACAATTGCTTTTACAGATGCACATATCGAGGTG<br>GACATCACTTACGCTGAGTACTTCGAAATGTCCGTTCGGTTGGCAGAAGCTATGAAACGATATGG |

TABLE 1-continued

```
              GCTGAATACAAATCACAGAATCGTCGTATGCAGTGAAAACTCTCTTCAATTCTTTATGCCGGTGTT
              GGGCGCGTTATTTATCGGAGTTGCAGTTGCGCCCGCGAACGACATTTATAATGAACGTGAATTGC
              TCAACAGTATGGGCATTTCGCAGCCTACCGTGGTGTTCGTTTCCAAAAAGGGGTTGCAAAAAATT
              TTGAACGTGCAAAAAAAGCTCCCAATCATCCAAAAAATTATTATCATGGATTCTAAAACGGATTA
              CCAGGGATTTCAGTCGATGTACACGTTCGTCACATCTCATCTACCTCCCGGTTTTAATGAATACGA
              TTTTGTGCCAGAGTCCTTCGATAGGGACAAGACAATTGCACTGATCATGAACTCCTCTGGATCTA
              CTGGTCTGCCTAAAGGTGTCGCTCTGCCTCATAGAACTGCCTGCGTGAGATTCTCGCATGCCAGA
              GATCCTATTTTTGGCAATCAAATCATTCCGGATACTGCGATTTTAAGTGTTGTTCCATTCCATCAC
              GGTTTTGGAATGTTTACTACACTCGGATATTTGATATGTGGATTTCGAGTCGTCTTAATGTATAGA
              TTTGAAGAAGAGCTGTTTCTGAGGAGCCTTCAGGATTACAAGATTCAAAGTGCGCTGCTGGTGCC
              AACCCTATTCTCCTTCTTCGCCAAAAGCACTCTGATTGACAAATACGATTTATCTAATTTACACGA
              AATTGCTTCTGGTGGCGCTCCCCTCTCTAAGGAAGTCGGGGAAGCGGTTGCCAAGAGGTTCCATC
              TGCCAGGTATCAGGCAAGGATATGGGCTCACTGAGACTACATCAGCTATTCTGATTACACCCGAG
              GGGGATGATAAACCGGGCGCGGTCGGTAAAGTTGTTCCATTTTTTGAAGCGAAGGTTGTGGATCT
              GGATACCGGGAAAACGCTGGGCGTTAATCAAAGAGGCGAACTGTGTGTGAGAGGTCCTATGATT
              ATGTCCGGTAGGTCTCATATCACCTTGGCTTTCGCCGTATTCACATGCTGGAACACATCATGCTAG
              CTTTAACATCGGGGAGTTACGATCCGTGAAAAGACGGATATATTGCCCTTGTATAGGACTATATT
              CCGGAGGGATTAGAATTTATAGTTGGAGAGCTTCATACCCCACTGAGCTTTTCACTGTATGCTAG
              TAATTATACTTCATTTGCTCGTTGGGTAGATGCGTTCTTCTCGCACAAGCCGATGATTTCCGAGTT
              TCTTTTCAGCGGCCGTAAAGCCTCGACACGTGACGCACTGTGAACCGCACCCGTATACCTAATAG
              AGGCAGTTAACTTCATTCAGCCACATAAGGGGTAGTAACGACTGCCCAAGTACGGAATTAA
              GAAAATGGATAATGAAGATTATGAGATCACCGCTACATTAGCAACGCTTGGTGCTTTAATTGGCA
              TGTATGACCAATCTACAACCTGGGGGAGGGTACCTCTTTGAGATGTACGATGCAGCCTAAAGGG
              TAACGTTATGCAAGTGGTCAAGAGCCTAGCATGCTTATGCGGTTTATCAAAATGTATCGCACTTT
              ATGCTAGGTAATGTGTGTTCTCCACGGTATCCATAAGCTTGCCTAAATACTGAAGTCTACGAGAA
              AACTATGGGATATTTGTGCATATATTACCCATAGTTATCCTGGAGCAGTCCGTTCCCACGTAGAAT
              GTAGCGAATTGCGTGGCTGGCTTCAAACATAGCACCGAACAGTAGATCTAGTTGCGCCCCTTCCA
              AGTTTACAGTTAGGTAAACCTTCACGATAGAAAGTTGGGAACAAGGCCGCATTCAACCTTTACGA
              TCACTTCCAGAAAGGGATTGTGGGTAGGAGACACCACGCCCTCAGATCACGTCGATCACTTGTTA
              TAAGGTCAAATGTGAGAAACGCGTCAGAAGGGAGTTGGTGCTTGCTTATTTCTTTTCCAGACTCG
              TCGTTGGATCAACCTATCTCATGACCCTAGCTCTAGTATGTCTGGTGGTAAAGGAGCTGCGCTGG
              ATGCATTTATTCTGCTGGGAGAAATAATCGCGGATATTATCCTTTTTCAAAGAGACGCCGAACTA
              ATGACTTGTCGAGAGGAATCGGCATGGTTTCGTACCTTGCCAGCATTCCCAATTTTTTTTATTTG
              CTTGGGTCTTATAAAGGAAATCGACAATTTGGGTAAAATGGTGCAAAGAATCTACCCGTTGGAAT
              ATTTTACTGGAGTCACCGGGGGAGCTTCGAGGACACACCTACCTGGTCTAACCCAGCCTACTTGT
              AAGATATGTTAACGTCGGCACCGTCATTGTAGTTATCTTATTTAAGGCGACACGAGACGTGAGAA
              CTTTTGCATTGCATATGTAACGGTCAATGTCGTACATGCGACACCATTGGATCGCTACCGTAAAA
              GTACACGTTACGGGGGTAGCTGGTGTACCTAAGCGCGACCCGGAACACCTACACCCGCTAGTTTA
              GCTTGTGAAAGTGCGGCGCTGCCTGTGATTCACGCGTTGTATGGACAACGTTGTACCATTCGTAG
              CAGACTTTGATCAATGATGTAGTTATGCCATGCCCGAAACAAACTATAGACATTTTCGAAAACGT
              TCCACTGAGTTAATCCTTAAGCCATGCAATTTTATGAAAATTTATTAGGCTAGCGGAAATTACGTT
              CCAAGTTCTGGAACCCTTATATCGATCAAGGCTGCAGACCTAATGGCTTGTGTTCCTGAAACATG
              TTACGTTGCCATTAACTCGGGAGTCGAGTACGTGCCATGTGTTGTGATGGGAGGTACTCGTTTGC
              GGAAAGGCATCTGCCCAAAAACACATTAGGTCATTAACGTCCCGTTACGGTAGATATGGCCACG
              GTCCACATAAACCGCTCATGGGTAAAAAGGATTCCTATACCTAACGGCTAGATGGCCAGGTATGT
              GCAATTTGGGCAGGATCCCGTTGGACGTGACATCTCAATGGCCTGAGAGGTCTGAGACCCCCGAT
              GGAGATAGTTTAATCAAACTTTTGAAATGCCAAGGCACAGCTAGATTTAGATAGTCAACGCCATC
              GACTTTGCATTTTCGACATATACTCTTGCCATTATGAGAGTGACGCGGATAAGAGGTAGGGATGC
              ATGAGTAAAAGAGAGCGGTTTTACGTTCAATATGTGGAAGGATGCTCTAGCCGGGAGTGAGGAC
              ACTAAACGCTTGTCATGCACAGTTACTGTGCGGTAGTAGTCAAACGGCCAGAAAATGTGTCTCATTTTGAATTCGCGATCTCAGATCTCCGTGAAATGATCTTCGGAA
              TTCAACTCTCATCGGGACAGCAGGACGCGTGCTAACTTAGGGCGTTTCAACTGTGATCCGAATAC
              GTATGGGAGTCAAAGTTCTGTTTGCCCTGATCTGCATCGCTGTGGCCGAGGCCAAGCCCACCGAG
              AACAACGAAGACTTCAACATCGTGGCCGTGGCCAGCAACTTCGCGACCACGGATCTCGATGCTG
              ACCGCGGGAAGTTGCCCGGCAAGAAGCTGCCGCTGGAGGTGCTCAAAGAGATGGAAGCCAATGC
              CCGGAAAGCTGGCTGCACCAGGGGCTGTCTGATCTGCCTGTCCCACATCAAGTGCACGCCCAAGA
              TGAAGAAGTTCATCCCAGGACGCTGCCACACCTACGAAGGCGACAAAGAGTCCGCACAGGGCGG
              CATAGGCGAGGCGATCGTCGACATTCCTGAGATTCCTGGGTTCAAGGACTTGGAGCCCATGGAGC
              AGTTCATCGCACAGGTCGATCTGTGTGTGGACTGCACAACTGGCTGCCTCAAAGGGCTTGCCAAC
              GTGCAGTGTTCTGACCTGCTCAAGAAGTGGCTGCCGCAACGCTGTGCGACCTTTGCCAGCAAGAT
              CCAGGGCCAGGTGGACAAGATCAAGGGGGCCGGTGGTGACTAACAGAGATGTTTTCTTGGGTTA
              ATTGAGGCCTGAGTATAAGGTGACTTATACTTGTAATCTATCTAAACGGGGAACCTCTCTAGTAG
              ACAATCCCGTGCTAAATTGTAGGACTAATTCCATTTATCAGATTTCTAG
SEQ ID      GGGAGACCCTCGACCGTCGATTGTCCACTGGTCAACAATAGATGACTTACAACTAATCGGAAGGT
NO. 11 (Full) GCAGAGACTCGACGGGAGCTACCCTAACGTCAAGACGAGGGTAAAGAGAGAGTCCAATTCTCAA
              AGCCAATAGGCAGTAGCGAAAGCTGCAAGAGAATGAAAATCCGTTGACCTTAAACGGTCGTGTG
              GGTTCAAGTCCCTCCACCCCCAGAAACCAACTTTATTACTATATTCCCCACAACCCCCCTCTCCCT
              CCCCCCCCTAACGTTACTGGCCGAAGCCGCTTGGAATAAGGCCGGTGTGCGTTTGTCTATATGTTAT
              TTTTCCACCATATTGCCGTCTTTTGGCAATGTGAGGGCCCGGAAACCTGGCCCTGTCTTCTTGACGA
              GCATTCCTAGGGGTCTTTCCCCTCTCGCCAAAGGAATGCAAGGTCTGTTGAATGTCGTGAAGGAA
              GCAGTTCCTCTGGAAGCTTCTTGAAGACAAACAACGTCTGTAGCGACCCCTTTGCAGGCAGCGGAA
              CCCCCCACCTGGCGACAGGTGCCTCTGCGGCCAAAAGCCACGTGTATAAGATACACCTGCAAAG
              GCGGCACAACCCCAGTGCCACGTTGTGAGTTGGATAGTTGTGGAAAGAGTCAAATGGCTCTCCTC
              AAGCGTATTCAACAAGGGGCTGAAGGATGCCCAGAAGGTACCCCATTGTATGGGATCTGATCTG
              GGGCCTCGGTGCACATGCTTTACATGTGTTTAGTCGAGGTTAAAAAACGTCTAGGCCCCCCGAAC
              CACGGGGACGTGGTTTTCCTTTGAAAAACACGATGATAATATGGCCACAACCATGGGAGTCAAA
              GTTCTGTTTGCCCTGATCTGCATCGCTGTGGCCGAGGCCAAGCCCACCGAGAACAACGAAGACTT
              CAACATCGTGGCCGTGGCCAGCAACTTCGCGACCACGGATCTCGATGCTGACCGCGGGAAGTTGC
              CCGGCAAGAAGCTGCCGCTGGAGGTGCTCAAAGAGATGGAAGCCAATGCCCGGAAAGCTGGCTG
```

TABLE 1-continued

| | |
|---|---|
| | CACCAGGGGCTGTCTGATCTGCCTGTCCCACATCAAGTGCACGCCCAAGATGAAGAAGTTCATCC<br>CAGGACGCTGCCACACCTACGAAGGCGACAAAGAGTCCGCACAGGGCGGCATAGGCGAGGCGA<br>TCGTCGACATTCCTGAGATTCCTGGGTTCAAGGACTTGGAGCCCATGGAGCAGTTCATCGCACAG<br>GTCGATCTGTGTGTGGACTGCACAACTGGCTGCCTCAAAGGGCTTGCCAACGTGCAGTGTTCTGA<br>CCTGCTCAAGAAGTGGCTGCCGCAACGCTGTGCGACCTTTGCCAGCAAGATCCAGGGCCAGGTG<br>GACAAGATCAAGGGGGCCGGTGGTGACTAAAGACGCTACGGACTTAAATAATTGAGCCTTAAAG<br>AAGAAATTCTTTAAGTGGATGCTCTCAAACTCAGGGAAACCTAAATCTAGTTATAGACAAGGCAA<br>TCCTGAGCCAAGCCGAAGTAGTAATTAGTAAGACCAGTGGACAATCGACGGATAACAGCATATC<br>TAG |
| SEQ ID<br>NO. 12 | Ana2.0<br>(Full) | GGGAGACCCTCGACCGTCGATTGTCCACTGGTCAACAATAGATGACTTACAACTAATCGGAAGGT<br>GCAGAGACTCGACGGGAGCTACCCTAACGTCAAGACGAGGGTAAAGAGAGAGTCCAATTCTCAA<br>AGCCAATAGGCAGTAGCGAAAGCTGCAAGAGAATGAAAATCCGTTGACCTTAAACGGTCGTGTG<br>GGTTCAAGTCCCTCCACCCCCATGATCTGAAACCAACTTTATTACTATATTCCCCACAACCCCCCT<br>CTCCCTCCCCCCCCTAACGTTACTGGCCGAAGCCGCTTGGAATAAGGCCGGTGTGCGTTTGTCTATA<br>TGTTATTTTCCACCATATTGCCGTCTTTTGGCAATGTGAGGGCCCGGAAACCTGGCCCTGTCTTCT<br>TGACGAGCATTCCTAGGGGTCTTTCCCCTCTCGCCAAAGGAATGCAAGGTCTGTTGAATGTCGTG<br>AAGGAAGCAGTTCCTCTGGAAGCTTCTTGAAGACAAACAACGTCTGTAGCGACCCTTTGCAGGCA<br>GCGGAACCCCCCACCTGGCGACAGGTGCCTCTGCGGCCAAAAGCCACGTGTATAAGATACACCT<br>GCAAAGGCGGCACAACCCCAGTGCCACGTTGTGAGTTGGATAGTTGTGGAAAGAGTCAAATGGC<br>TCTCCTCAAGCGTATTCAACAAGGGGCTGAAGGATGCCCAGAAGGTACCCCATTGTATGGGATCT<br>GATCTGGGGCCTCGGTGCACATGCTTTACATGTGTTTAGTCGAGGTTAAAAAACGTCTAGGCCCC<br>CCGAACCACGGGGACGTGGTTTTCCTTTGAAAAACACGATGATAATATGGCCACAACCATGGGA<br>GTCAAAGTTCTGTTTGCCCTGATCTGCATCGCTGTGGCCGAGGCCAAGCCCACCGAGAACAACGA<br>AGACTTCAACATCGTGGCCGTGGCCAGCAACTTCGCGACCACGGATCTCGATGCTGACCGCGGGA<br>AGTTGCCCGGCAAGAAGCTGCCGCTGGAGGTGCTCAAAGAGATGGAAGCCAATGCCCGGAAAGC<br>TGGCTGCACCAGGGGCTGTCTGATCTGCCTGTCCCACATCAAGTGCACGCCCAAGATGAAGAAGT<br>TCATCCCAGGACGCTGCCACACCTACGAAGGCGACAAAGAGTCCGCACAGGGCGGCATAGGCGA<br>GGCGATCGTCGACATTCCTGAGATTCCTGGGTTCAAGGACTTGGAGCCCATGGAGCAGTTCATCG<br>CACAGGTCGATCTGTGTGTGGACTGCACAACTGGCTGCCTCAAAGGGCTTGCCAACGTGCAGTGT<br>TCTGACCTGCTCAAGAAGTGGCTGCCGCAACGCTGTGCGACCTTTGCCAGCAAGATCCAGGGCCA<br>GGTGGACAAGATCAAGGGGGCCGGTGGTGACTAAAGACGCTACGGACTTAAATAATTGAGCCTT<br>AAAGAAGAAATTCTTTAAGTGGATGCTCTCAAACTCAGGGAAACCTAAATCTAGTTATAGACAA<br>GGCAATCCTGAGCCAAGCCGAAGTAGTAATTAGTAAGACCAGTGGACAATCGACGGATAACAGC<br>ATATCTAG |
| SEQ ID<br>NO. 13 | Ana3.0<br>(Full) | GGGAGACCCTCGACCGTCGATTGTCCACTGGTCAACAATAGATGACTTACAACTAATCGGAAGGT<br>GCAGAGACTCGACGGGAGCTACCCTAACGTCAAGACGAGGGTAAAGAGAGAGTCCAATTCTCAA<br>AGCCAATAGGCAGTAGCGAAAGCTGCAAGAGAATGAAAATCCGTTGACCTTAAACGGTCGTGTG<br>GGTTCAAGTCCCTCCACCCCACGCCGGAAACGCAATAGCCGAAAAACAAAAAACAAAAAAACC<br>CCCCTCTCCCTCCCCCCCTAACGTTACTGGCCGAAGCCGCTTGGAATAAGGCCGGTGTGCGTTTGT<br>CTATATGTTATTTTCCACCATATTGCCGTCTTTTGGCAATGTGAGGGCCCGGAAACCTGGCCCTGT<br>CTTCTTGACGAGCATTCCTAGGGGTCTTTCCCCTCTCGCCAAAGGAATGCAAGGTCTGTTGAATGT<br>CGTGAAGGAAGCAGTTCCTCTGGAAGCTTCTTGAAGACAAACAACGTCTGTAGCGACCCTTTGCA<br>GGCAGCGGAACCCCCCACCTGGCGACAGGTGCCTCTGCGGCCAAAAGCCACGTGTATAAGATAC<br>ACCTGCAAAGGCGGCACAACCCCAGTGCCACGTTGTGAGTTGGATAGTTGTGGAAAGAGTCAAA<br>TGGCTCTCCTCAAGCGTATTCAACAAGGGGCTGAAGGATGCCCAGAAGGTACCCCATTGTATGGG<br>ATCTGATCTGGGGCCTCGGTGCACATGCTTTACATGTGTTTAGTCGAGGTTAAAAAACGTCTAGG<br>CCCCCCGAACCACGGGGACGTGGTTTTCCTTTGAAAAACACGATGATAATATGGCCACAACCATG<br>GGAGTCAAAGTTCTGTTTGCCCTGATCTGCATCGCTGTGGCCGAGGCCAAGCCCACCGAGAACAA<br>CGAAGACTTCAACATCGTGGCCGTGGCCAGCAACTTCGCGACCACGGATCTCGATGCTGACCGCG<br>GAAGTTGCCCGGCAAGAAGCTGCCGCTGGAGGTGCTCAAAGAGATGGAAGCCAATGCCCGGAA<br>AGCTGGCTGCACCAGGGGCTGTCTGATCTGCCTGTCCCACATCAAGTGCACGCCCAAGATGAAGA<br>AGTTCATCCCAGGACGCTGCCACACCTACGAAGGCGACAAAGAGTCCGCACAGGGCGGCATAGG<br>CGAGGCGATCGTCGACATTCCTGAGATTCCTGGGTTCAAGGACTTGGAGCCCATGGAGCAGTTCA<br>TCGCACAGGTCGATCTGTGTGTGGACTGCACAACTGGCTGCCTCAAAGGGCTTGCCAACGTGCAG<br>TGTTCTGACCTGCTCAAGAAGTGGCTGCCGCAACGCTGTGCGACCTTTGCCAGCAAGATCCAGGG<br>CCAGGTGGACAAGATCAAGGGGGCCGGTGGTGACTAAAAAAAACAAAAACAAAACGGCTATT<br>ATGCGTTACCGGCGAGACGCTACGGACTTAAATAATTGAGCCTTAAAGAAGAAATTCTTTAAGTG<br>GATGCTCTCAAACTCAGGGAAACCTAAATCTAGTTATAGACAAGGCAATCCTGAGCCAAGCCGA<br>AGTAGTAATTAGTAAGACCAGTGGACAATCGACGGATAACAGCATATCTAG |
| SEQ ID<br>NO. 14 | hEpo | ATGGGAGTGCATGAATGTCCTGCCTGGCTGTGGCTTCTCCTGTCACTGCTGTCTCTCCCTCTGGGC<br>CTCCCAGTGCTGGGCGCACCACCAAGACTCATCTGTGACAGCAGAGTGCTGGAGAGGTATCTCTT<br>GGAGGCCAAGGAGGCTGAGAACATTACCACAGGCTGTGCTGAACACTGCAGCTTGAATGAGAAT<br>ATCACTGTCCCAGACACCAAAGTTAATTTCTATGCCTGGAAGAGGATGGAGGTTGGGCAACAAG<br>CAGTTGAAGTGTGGCAAGGCCTGGCCCTGCTGTCTGAAGCTGTCCTGAGGGGCCAGGCACTGTTG<br>GTCAACTCTTCCCAGCCTTGGGAGCCCCTGCAACTGCATGTGGATAAAGCAGTGAGTGGCCTTAG<br>AAGCCTCACCACTCTGCTTCGGGCTCTGGGAGCACAGAAGGAAGCCATCTCCCCTCCAGATGCAG<br>CCTCAGCAGCTCCACTCAGAACAATTACTGCTGACACTTTTAGAAAACTCTTTAGGGTGTACTCC<br>AATTTCCTCCGGGGAAAGCTGAAGCTGTACACAGGTGAGGCATGTAGGACAGGGGACAGATAA |
| SEQ ID<br>NO. 15 | EGFP | ATGGTGAGCAAGGGCGAGGAGCTGTTCACCGGGGTGGTGCCCATCCTGGTCGAGCTGGACGGCG<br>ACGTAAACGGCCACAAGTTCAGCGTGTCTGGCGAGGGCGAGGGCGATGCCACCTACGGCAAGCT<br>GACCCTGAAGTTCATCTGCACCACCGGCAAGCTGCCCGTGCCCTGGCCCACCCTCGTGACCACCC<br>TGACCTACGGCGTGCAGTGCTTCAGCCGCTACCCCGACCACATGAAGCAGCACGACTTCTTCAAG<br>TCCGCCATGCCCGAAGGCTACGTCCAGGAGCGCACCATCTTCTTCAAGGACGACGGCAACTACAA<br>GACCCGCGCCGAGGTGAAGTTCGAGGGCGACACCCTGGTGAACCGCATCGAGCTGAAGGGCATC<br>GACTTCAAGGAGGACGGCAACATCCTGGGGCACAAGCTGGAGTACAACTACAACAGCCACAACG<br>TCTATATCATGGCCGACAAGCAGAAGAACGGCATCAAGGCGAACTTCAAGATCCGCCACAACAT |

TABLE 1-continued

|  |  |
|---|---|
|  | CGAGGACGGCAGCGTGCAGCTCGCCGACCACTACCAGCAGAACACCCCCATCGGCGACGGCCCC<br>GTGCTGCTGCCCGACAACCACTACCTGAGCACCCAGTCCGCCCTGAGCAAAGACCCCAACGAGA<br>AGCGCGATCACATGGTCCTGCTGGAGTTCGTGACCGCCGCCGGGATCACTCTCGGCATGGACGAG<br>CTGTACAAGTAA |
| SEQ ID<br>NO. 16 FLuc | ATGGAAGACGCCAAAAACATAAAGAAAGGCCCGGCGCCATTCTATCCGCTGGAAGATGGAACCG<br>CTGGAGAGCAACTGCATAAGGCTATGAAGAGATACGCCCTGGTTCCTGGAACAATTGCTTTTACA<br>GATGCACATATCGAGGTGGACATCACTTACGCTGAGTACTTCGAAATGTCCGTTCGGTTGGCAGA<br>AGCTATGAAACGATATGGGCTGAATACAAATCACAGAATCGTCGTATGCAGTGAAAACTCTCTTC<br>AATTCTTTATGCCGGTGTTGGGCGCGTTATTTATCGGAGTTGCAGTTGCGCCCGCGAACGACATTT<br>ATAATGAACGTGAATTGCTCAACAGTATGGGCATTTCGCAGCCTACCGTGGTGTTCGTTTCCAAA<br>AAGGGGTTGCAAAAAATTTTGAACGTGCAAAAAAAGCTCCCAATCATCCAAAAAATTATTATCAT<br>GGATTCTAAAACGGATTACCAGGGATTTCAGTCGATGTACACGTTCGTCACATCTCATCTACCTCC<br>CGGTTTTAATGAATACGATTTTGTGCCAGAGTCCTTCGATAGGGACAAGACAATTGCACTGATCA<br>TGAACTCCTCTGGATCTACTGGTCTGCCTAAAGGTGTCGCTCTGCCTCATAGAACTGCCTGCGTGA<br>GATTCTCGCATGCCAGAGATCCTATTTTTGGCAATCAAATCATTCCGGATACTGCGATTTTAAGTG<br>TTGTTCCATTCCATCACGGTTTTGGAATGTTTACTACACTCGGATATTTGATATGTGGATTTCGAG<br>TCGTCTTAATGTATAGATTTGAAGAAGAGCTGTTTCTGAGGAGCCTTCAGGATTACAAGATTCAA<br>AGTGCGCTGCTGGTGCCAACCCTATTCTCCTTCTTCGCCAAAAGCACTCTGATTGACAAATACGAT<br>TTATCTAATTTACACGAAATTGCTTCTGGTGGCGCTCCCCTCTCTAAGGAAGTCGGGGAAGCGGT<br>TGCCAAGAGGTTCCATCTGCCAGGTATCAGGCAAGGATATGGGCTCACTGAGACTACATCAGCTA<br>TTCTGATTACACCCGAGGGGGATGATAAACCGGGCGCGGTCGGTAAAGTTGTTCCATTTTTTGAA<br>GCGAAGGTTGTGGATCTGGATACCGGGAAAACGCTGGGCGTTAATCAAAGAGGCGAACTGTGTG<br>TGAGAGGTCCTATGATTATGTCCGGTTATGTAAACAATCCGGAAGCGACCAACGCCTTGATTGAC<br>AAGGATGGATGGCTACATTCTGGAGACATAGCTTACTGGGACGAAGACGAACTTCTTCATCGT<br>TGACCGCCTGAAGTCTCTGATTAAGTACAAAGGCTATCAGGTGGCTCCCGCTGAATTGGAATCCA<br>TCTTGCTCCAACACCCCAACATCTTCGACGCAGGTGTCGCAGGTCTTCCCGACGATGACGCCGGT<br>GAACTTCCCGCCGCCGTTGTTGTTTTGGAGCACGGAAAGACGATGACGGAAAAAGAGATCGTGG<br>ATTACGTCGCCAGTCAAGTAACAACCGCGAAAAAGTTGCGCGGAGGAGTTGTGTTTGTGGACGA<br>AGTACCGAAAGGTCTTACCGGAAAACTCGACGCAAGAAAAATCAGAGAGATCCTCATAAAGGCC<br>AAGAAGGGCGGAAAGATCGCCGTGTAA |
| SEQ ID<br>NO. 17 Cas9 | ATGGCCCCAAAGAAGAAGCGGAAGGTCGGTATCCACGGAGTCCCAGCAGCCGACAAGAAGTAC<br>AGCATCGGCCTGGACATCGGCACCAACTCTGTGGGCTGGGCCGTGATCACCGACGAGTACAAGG<br>TGCCCAGCAAGAAATTCAAGGTGCTGGGCAACACCGACCGGCACAGCATCAAGAAGAACCTGAT<br>CGGAGCCCTGCTGTTCGACAGCGGCGAAACAGCCGAGGCCACCCGGCTGAAGAGAACCGCCAGA<br>AGAAGATACACCAGACGGAAGAACCGGATCTGCTATCTGCAAGAGATCTTCAGCAACGAGATGG<br>CCAAGGTGGACGACAGCTTCTTCCACAGACTGGAAGAGTCCTTCCTGGTGGAAGAGGATAAGAA<br>GCACGAGCGGCACCCCATCTTCGGCAACATCGTGGACGAGGTGGCCTACCACGAGAAGTACCCC<br>ACCATCTACCACCTGAGAAAGAAACTGGTGGACAGCACCGACAAGGCCGACCTGCGGCTGATCT<br>ATCTGGCCCTGGCCCACATGATCAAGTTCCGGGGCCACTTCCTGATCGAGGGCGACCTGAACCCC<br>GACAACAGCGACGTGGACAAGCTGTTCATCCAGCTGGTGCAGACCTACAACCAGCTGTTCGAGG<br>AAAACCCCATCAACGCCAGCGGCGTGGACGCCAAGGCCATCCTGTCTGCCAGACTGAGCAAGAG<br>CAGACGGCTGGAAAATCTGATCGCCCAGCTGCCCGGCGAGAAGAAGAATGGCCTGTTCGGAAAC<br>CTGATTGCCCTGAGCCTGGGCCTGACCCCCAACTTCAAGAGCAACTTCGACCTGGCCGAGGATGC<br>CAAACTGCAGCTGAGCAAGGACACCTACGACGACGACCTGGACAACCTGCTGGCCCAGATCGGC<br>GACCAGTACGCCGACCTGTTTCTGGCCGCCAAGAACCTGTCCGACGCCATCCTGCTGAGCGACAT<br>CCTGAGAGTGAACACCGAGATCACCAAGGCCCCCCTGAGCGCCTCTATGATCAAGAGATACGAC<br>GAGCACCACCAGGACCTGACCCTGCTGAAAGCTCTCGTGCGGCAGCAGCTGCCTGAGAAGTACA<br>AAGAGATTTTCTTCGACCAGAGCAAGAACGGCTACGCCGGCTACATTGACGGCGGAGCCAGCCA<br>GGAAGAGTTCTACAAGTTCATCAAGCCCATCCTGGAAAAGATGGACGGCACCGAGGAACTGCTC<br>GTGAAGCTGAACAGAGAGGACCTGCTGCGGAAGCAGCGGACCTTCGACAACGGCAGCATCCCCC<br>ACCAGATCCACCTGGGAGAGCTGCACGCCATTCTGCGGCGGCAGGAAGATTTTTACCCATTCCTG<br>AAGGACAACCGGGAAAAGATCGAGAAGATCCTGACCTTCCGCATCCCCTACTACGTGGGCCCTCT<br>GGCCAGGGGAAACAGCAGATTCGCCTGGATGACCAGAAAGAGCGAGGAAACCATCACCCCCTGG<br>AACTTCGAGGAAGTGGTGGACAAGGGCGCTTCCGCCCAGAGCTTCATCGAGCGGATGACCAACT<br>TCGATAAGAACCTGCCCAACGAGAAGGTGCTGCCCAAGCACAGCCTGCTGTACGAGTACTTCACC<br>GTGTATAACGAGCTGACCAAAGTGAAATACGTGACCGAGGGAATGAGAAAGCCCGCCTTCCTGA<br>GCGGCGAGCAGAAAAAGGCCATCGTGGACCTGCTGTTCAAGACCAACCGGAAAGTGACCGTGAA<br>GCAGCTGAAAGAGGACTACTTCAAGAAAATCGAGTGCTTCGACTCCGTGGAAATCTCCGGCGTG<br>GAAGATCGGTTCAACGCCTCCCTGGGCACATACCACGATCTGCTGAAAATTATCAAGGACAAGG<br>ACTTCCTGGACAATGAGGAAAACGAGGACATTCTGGAAGATATCGTGCTGACCCTGACACTGTTT<br>GAGGACAGAGAGATGATCGAGGAACGGCTGAAAACCTATGCCCACCTGTTCGACGACAAAGTGA<br>TGAAGCAGCTGAAGCGGCGGAGATACACCGGCTGGGGCAGGCTGAGCCGGAAGCTGATCAACG<br>GCATCCGGGACAAGCAGTCCGGCAAGACAATCCTGGATTTCCTGAAGTCCGACGGCTTCGCCAAC<br>AGAAACTTCATGCAGCTGATCCACGACGACAGCCTGACCTTTAAAGAGGACATCCAGAAAGCCC<br>AGGTGTCCGGCCAGGGCGATAGCCTGCACGAGCACATTGCCAATCTGGCCGGCAGCCCCGCCATT<br>AAGAAGGGCATCCTGCAGACAGTGAAGGTGGTGGACGAGCTCGTGAAAGTGATGGGCCGGCACA<br>AGCCCGAGAACATCGTGATCGAAATGGCCAGAGAGAACCAGACCACCCAGAAGGGACAGAAGA<br>ACAGCCGCGAGAGAATGAAGCGGATCGAAGAGGGCATCAAAGAGCTGGGCAGCCAGATCCTGA<br>AAGAACACCCCGTGGAAAACACCCAGCTGCAGAACGAGAAGCTGTACCTGTACTACCTGCAGAA<br>TGGGCGGGATATGTACGTGGACCAGGAACTGGACATCAACCGGCTGTCCGACTACGATGTGGAC<br>CATATCGTGCCTCAGAGCTTTCTGAAGGACGACTCCATCGACAACAAGGTGCTGACCAGAAGCG<br>ACAAGAACCGGGGCAAGAGCGACAACGTGCCCTCCGAAGAGGTCGTGAAGAAGATGAAGAACT<br>ACTGGCGGCAGCTGCTGAACGCCAAGCTGATTACCCAGAGAAAGTTCGACAATCTGACCAAGGC<br>CGAGAGAGGCGGCCTGAGCGAACTGGATAAGGCCGGCTTCATCAAGAGACAGCTGGTGGAAACC<br>CGGCAGATCACAAAGCACGTGGCACAGATCCTGGACTCCCGGATGAACACTAAGTACGACGAGA<br>ATGACAAGCTGATCCGGGAAGTGAAAGTGATCACCCTGAAGTCCAAGCTGGTGTCCGATTTCCGG<br>AAGGATTTCCAGTTTTACAAAGTGCGCGAGATCAACAACTACCACCACGCCCACGACGCCTACCT<br>GAACGCCGTCGTGGGAACCGCCCTGATCAAAAAGTACCCTAAGCTGGAAAGCGAGTTCGTGTAC |

TABLE 1-continued

|  |  |  |
|---|---|---|
|  |  | GGCGACTACAAGGTGTACGACGTGCGGAAGATGATCGCCAAGAGCGAGCAGGAAATCGGCAAG<br>GCTACCGCCAAGTACTTCTTCTACAGCAACATCATGAACTTTTTCAAGACCGAGATTACCCTGGC<br>CAACGGCGAGATCCGGAAGCGGCCTCTGATCGAGACAAACGGCGAAACCGGGGAGATCGTGTGG<br>GATAAGGGCCGGGATTTTGCCACCGTGCGGAAAGTGCTGAGCATGCCCCAAGTGAATATCGTGA<br>AAAAGACCGAGGTGCAGACAGGCGGCTTCAGCAAAGAGTCTATCCTGCCCAAGAGGAACAGCGA<br>TAAGCTGATCGCCAGAAAGAAGGACTGGGACCCTAAGAAGTACGGCGGCTTCGACAGCCCCACC<br>GTGGCCTATTCTGTGCTGGTGGTGGCCAAAGTGGAAAAGGGCAAGTCCAAGAAACTGAAGAGTG<br>TGAAAGAGCTGCTGGGGATCACCATCATGGAAAGAAGCAGCTTCGAGAAGAATCCCATCGACTT<br>TCTGGAAGCCAAGGGCTACAAAGAAGTGAAAAAGGACCTGATCATCAAGCTGCCTAAGTACTCC<br>CTGTTCGAGCTGGAAAACGGCCGGAAGAGAATGCTGGCCTCTGCCGGCGAACTGCAGAAGGGAA<br>ACGAACTGGCCCTGCCCTCCAAATATGTGAACTTCCTGTACCTGGCCAGCCACTATGAGAAGCTG<br>AAGGGCTCCCCCGAGGATAATGAGCAGAAACAGCTGTTTGTGGAACAGCACAAGCACTACCTGG<br>ACGAGATCATCGAGCAGATCAGCGAGTTCTCCAAGAGAGTGATCCTGGCCGACGCTAATCTGGA<br>CAAAGTGCTGTCCGCCTACAACAAGCACCGGGATAAGCCCATCAGAGAGCAGGCCGAGAATATC<br>ATCCACCTGTTTACCCTGACCAATCTGGGAGCCCCTGCCGCCTTCAAGTACTTTGACACCACCATC<br>GACCGGAAGAGGTACACCAGCACCAAAGAGGTGCTGGACGCCACCCTGATCCACCAGAGCATCA<br>CCGGCCTGTACGAGACACGGATCGACCTGTCTCAGCTGGGAGGCGACAAAAGGCCGGCGGCCAC<br>GAAAAAGGCCGGCCAGGCAAAAAAGAAAAAGTAA |
| SEQ ID<br>NO. 18 | sgGFP | GGGCGAGGAGCGCACCGGGGGUUUUAGAGCUAGAAAUAGCAAGUUAAAAUAAGGCUAGUCCG<br>UUAUCAACUUGAAAAAGUGGCACCGAGUCGGUGCUUUUUU |
| SEQ ID<br>NO. 19 | RNase H<br>Probe | CATGGTTGTGGCCATATTATCATCG |
| SEQ ID<br>NO. 20 | Splice<br>Junction<br>PCR F | CGATCGTCGACATTCCTGAG |
| SEQ ID<br>NO. 21 | Splice<br>Junction<br>PCR R | ATGCTCGTCAAGAAGACAGG |
| SEQ ID<br>NO. 22 | ABPV | TTTGGGAATCGCAACACAACATGGTTACCCATAGATTGAGGAAATTTCCAATAAACTCAATCTTA<br>AGGCTTGTTGTGTTGGACAAGGTGCCCTATTTAGGGTGAGGAGCCTTGCTGGCAGCCCCAGTGAA<br>TCCTCTATTGGATAGGAACAGCTATATTGGGTAGTTGTAGCAGTTGTATTCAAACGAATGCAGCG<br>TTCCGAAATACCATACCT |
| SEQ ID<br>NO. 23 | CSFV | GTATACGAGGTTAGTTCATTCTCGTATACACGATTGGACAAATCAAAATTATAATTTGGTTCAGG<br>GCCTCCCTCCAGCGACGGCCGAACTGGGCTAGCCATGCCCATAGTAGGACTAGCAAACGGAGGG<br>ACTAGCCGTAGTGGCGAGCTCCCTGGGTGGTCTAAGTCCTGAGTACAGGACAGTCGTCAGTAGTT<br>CGACGTGAGCAGAAGCCCACCCTGAGATGCTACGTGGACGAGGGCATGCCCAAGCACACCTTA<br>ACCCTAGCGGGGGTCGCTAGGGTGAAATCACACCACGTGATGGGAGTACGACCTGATAGGGCGC<br>TGCAGAGGCCCACTATTAGGCTAGTATAAAAATCTCTGCTGTACATGGCAC |
| SEQ ID<br>NO. 24 | CVB3 | TTAAAACAGCCTGTGGGTTGATCCCACCCACAGGCCCATTGGGCGCTAGCACTCTGGTATCACGG<br>TACCTTTGTGCGCCTGTTTTATACCCCCTCCCCCAACTGTAACTTAGAAGTAACACACACCGATCA<br>ACAGTCAGCGTGGCACACCAGCCACGTTTTGATCAAGCACTTCTGTTACCCCGGACTGAGTATCA<br>ATAGACTGCTCACGCGGTTGAAGGAGAAAGCGTTCGTTATCCGGCCAACTACTTCGAAAAACCTA<br>GTAACACCGTGGAAGTTGCAGAGTGTTTCGCTCAGCACTACCCCAGTGTAGATCAGGTCGATGAG<br>TCACCGCATTCCCCACGGGCGACCGTGGCGGTGGCTGCGTTGGCGGCCTGCCCATGGGGAAACCC<br>ATGGGACGCTCTAATACAGACATGGTGCGAAGAGTCTATTGAGCTAGTTGGTAGTCCTCCGGCCC<br>CTGAATGCGGCTAATCCTAACTGCGGAGCACACACCCTCAAGCCAGAGGGCAGTGTGTCGTAAC<br>GGGCAACTCTGCAGCGGAACCGACTACTTTGGGTGTCCGTGTTTCATTTTATTCCTATACTGGCTG<br>CTTATGGTGACAATTGAGAGATCGTTACCATATAGCTATTGGATTGGCCATCCGGTGACTAATAG<br>AGCTATTATATATCCCTTTGTTGGGTTTATACCACTTAGCTTGAAAGAGGTTAAAACATTACAATT<br>CATTGTTAAGTTGAATACAGCAAA |
| SEQ ID<br>NO. 25 | EMCV2 | TTGCCAGTCTGCTCGATATCGCAGGCTGGGTCCGTGACTACCCACTCCCCCTTTCAACGTGAAGG<br>CTACGATAGTGCCAGGGCGGGTACTGCCGTAAGTGCCACCCCAAACAACAACAACAAAACAAAC<br>TCCCCCTCCCCCCCCTTACTATACTGGCCGAAGCCACTTGGAATAAGGCCGGTGTGCGTTTGTCTA<br>CATGCTATTTTCTACCGCATTACCGTCTTATGGTAATGTGAGGGTCCAGAACCTGACCCTGCTTC<br>TTGACGAACACTCCTAGGGGTCTTTCCCCTCTCGACAAAGGAGTGTAAGGTCTGTTGAATGTCGT<br>GAAGGAAGCAGTTCCTCTGGAAGCTTCTTAAAGACAAACAACGTCGTAGCGACCCTTTGCAGGC<br>AGCGGAACCCCCACCTGGTGACAGGTGCCTCTGCGGCCAAAAGCCACGTGTATAAGATACACC<br>TGCAAAGGCGGCACAACCCCAGTGCCACGTTGTGAGTTGGATAGTTGTGGAAAGAGTCAAATGG<br>CTCTCCTCAAGCGTATTCAACAAGGGGCTGAAGGATGCCCAGAAGGTACCCATTGTATGGGATC<br>TGATCTGGGGCCTCGGTGCACGTGCTTTACACGTGTTGAGTCGAGGTGAAAAAACGTCTAGGCCC<br>CCCGAACCACGGGGACGTGGTTTTCCTTTGAAAACCACGATTACAAT |
| SEQ ID<br>NO. 26 | EV71 | TTAAAACAGCTGTGGGTTGTCACCCACCCACAGGGTCCACTGGGCGCTAGTACACTGGTATCTCG<br>GTACCTTTGTACGCCTGTTTTATACCCCCTCCCCTGATTTGCAACTTAGAAGCAACGCAAACCAGAT<br>CAATAGTAGGTGTGACATACCAGTCGCATCTTGATCAAGCACTTCTGTATCCCCGGACCGAGTAT<br>CAATAGACTGTGCACACGGTTGAAGGAGAAAACGTCCGTTACCCGGCTAACTACTTCGAGAAGC<br>CTAGTAACGCCATTGAAGTTGCAGAGTGTTTCGCTCAGCACTCCCCCGTGTAGATCAGGTCGAT<br>GAGTCACCGCATTCCCCACGGGCGACCGTGGCGGTGGCTGCGTTGGCGGCCTGCCTATGGGGTAA<br>CCCATAGGACGCTCTAATACGGACATGGCGTGAAGAGTCTATTGAGCTAGTTAGTAGTCCTCCGG<br>CCCCTGAATGCGGCTAATCCTAACTGCGGAGCACATACCCTTAATCCAAAGGGCAGTGTGTCGTA |

TABLE 1-continued

| | | |
|---|---|---|
| | | ACGGGCAACTCTGCAGCGGAACCGACTACTTTGGGTGTCCGTGTTTCTTTTTATTCTTGTATTGGC<br>TGCTTATGGTGACAATTAAAGAATTGTTACCATATAGCTATTGGATTGGCCATCCAGTGTCAAAC<br>AGAGCTATTGTATATCTCTTTGTTGGATTCACACCTCTCACTCTTGAAACGTTACACACCCTCAAT<br>TACATTATACTGCTGAACACGAAGCG |
| SEQ ID<br>NO. 27 | HAV | TTCAAGAGGGGTTTCCGGAGTTTTCCGGAGCCCCTCTTGGAAGTCCATGGTGAGGGGACTTGATA<br>CCTCACCGCCGTTTGCCTAGGCTATAGGCTAAATTTCCCTTTCCCTGTCCTTCCCTTATTTCCCTTT<br>ATCTTGTTTGTAAATATTAATTCCTGCAGGTTCAGGGTTCTTTAATCTGTTTCTCTATAAGAACACT<br>CAATTTTCACGCTTTCTGTCTTCTTTCTTCCAGGGCTCTCCCCTTGCCCTAGGCTCTGGCCGTTGCG<br>CCCCGGCGGGGTCAACTCCATGATTAGCATGGAGCTGTAGGAGTCTAAATTGGGGACGCAGATGTT<br>TGGGACGTCGCCTTGCAGTGTTAACTTGGCTCTCATGAACCTCTTTGATCTTTCACAAGGGGTAGG<br>CTACGGGTGAAACCCCTTAGGCTAATACTTCTATGAAGAGATGCCTTGGATAGGGTAACAGCGGC<br>GGATATTGGTGAGTGTTAAGACAAAAACCATTCAACGCCGGAGGACTGGCTCTCATTCAGTGGA<br>TGCATTGAGTGAATTGATTGTCAGGGCTGTCTTTAGGTTTAATCTCAGACCTCTCTGTGCTTAGGG<br>CAAACACTATTTGGCCTTAAATGGGATCCTGTGAGAGGGGTCCCTCCATTGACAGCTGGACTGT<br>TCTTTGGGGCCTTATGTAGTGTTTGCCTCTGAGGTACTCAGGGGCATTTAGGTTTTTCCTCACTCTT<br>AAACAATA |
| SEQ ID<br>NO. 28 | HRV2 | TTAAAACTGGATCCAGGTTGTTCCCACCTGGATTTCCCACAGGGAGTGGTACTCTGTTATTACGGT<br>AACTTTGTACGCCAGTTTTATCTCCCTTCCCCCATGTAACTTAGAAGTTTTTCACAAAGACCAATA<br>GCCGGTAATCAGCCAGATTACTGAAGGTCAAGCACTTCTGTTTCCCCGGTCAATGTTGATATGCT<br>CCAACAGGGCAAAAACAACTGCGATCGTTAACCGCAAAGCGCCTACGCAAAGCTTAGTAGCATC<br>TTTGAAATCGTTTGGCTGGTCGATCCGCCATTTCCCTGGTAGACCTGGCAGATGAGGCTAGAAA<br>TACCCCACTGGCGACAGTGTTCTAGCCTGCGTGGCTGCCTGCACACCCTATGGGTGTGAAGCCAA<br>ACAATGGACAAGGTGTGAAGAGCCCCGTGTGCTCGCTTTGAGTCCTCCGGCCCCTGAATGTGGCT<br>AACCTTAACCCTGCAGCTAGAGCACGTAACCCAATGTGTATCTAGTCGTAATGAGCAATTGCGGG<br>ATGGGACCAACTACTTTGGGTGTCCGTGTTTCACTTTTTCCTTTATATTTGCTTATGGTGACAATAT<br>ATACAATATATATATTGGCACCATGG |
| SEQ ID<br>NO. 29 | HTLV | GGCTCGCATCTCTCCTTCACGCGCCCGCCGCCCTACCTGAGGCCGCCATCCACGCCGGTTGAGTC<br>GCGTTCTGCCGCCTCCCGCTGTGGTGCCTCCTGAACTGCGTCCGCCGTCTAGGTAAGTTTAGAGC<br>TCAGGTCGAGACCGGGCCTTTGTCCGGCGCTCCCTTGGAGCCTACCTAGACTCAGCCGGTCTCTCC<br>ACGCTTTGCCTGACCCTGCTTGTTCAACTCTGCGTCTTTGTTTCGTTTTCTGTTCTGCGCCGCTACA<br>GATCGAAAGTTCCACCCCTTTCCCTTTCATTCACGACTGACTGCCGGCTTGGCCCACGGCCAAGTA<br>CCGGCGACTCCGTTGCTCGGAGCCAGCGACAGCCCATCCTATAGCACTCTCCAGGAGAGAAACT<br>TAGTACACAGTTGGGGGCTCGTCCGGGATACGAGCGCCCCTTTATTCCCTAGGCA |
| SEQ ID<br>NO. 30 | PV | TTAAAACAGCTCTGGGGTTGTACCCACCCCAGAGGCCCACGTGGCGGCTAGTACTCCGGTATTGC<br>GGTACCCTTGTACGCCTGTTTTATACTCCCTTCCCGTAACTTAGACGCACAAAACCAAGTTCAATA<br>GAAGGGGGTACAAACCAGTACCACCACGAACAAGCACTTCTGTTTCCCCGGTGATGTCGTATAGA<br>CTGCTTGCGTGGTTGAAAGCGACGGATCCGTTATCCGCTTATGTACTTCGAGAAGCCCAGTACCA<br>CCTCGGAATCTTCGATGCGTTGCGCTCAGCACTCAACCCCAGAGTGTAGCTTAGGCTGATGAGTC<br>TGGACATCCCTCACCGGTGACGGTGGTCCAGGCTGCGTTGGCGGCCTACCTATGGCTAACGCCAT<br>GGGACGCTAGTTGTGAACAAGGTGTGAAGAGCCTATTGAGCTACATAAGAATCCTCCGGCCCCTG<br>AATGCGGCTAATCCCAACCTCGGAGCAGGTGGTCACAAACCAGTGATTGGCCTGTCGTAACGCGC<br>AAGTCCGTGGCGGAACCGACTACTTTGGGTGTCCGTGTTTCCTTTTATTTTATTGTGGCTGCTTAT<br>GGTGACAATCACAGATTGTTATCATAAAGCGAATTGGATTGGCCATCCGGTGAAAGTGAGACTCA<br>TTATCTATCTGTTTGCTGGATCCGCTCCATTGAGTGTGTTTACTCTAAGTACAATTTCAACAGTTAT<br>TTCAATCAGACAATTGTATCATA |
| SEQ ID<br>NO. 31 | CVB3-<br>GLuc-<br>pAC<br>(Full) | GGGAGACCCTCGACCGTCGATTGTCCACTGGTCAACAATAGATGACTTACAACTAATCGGAAGGT<br>GCAGAGACTCGACGGGAGCTACCCTAACGTCAAGACGAGGGTAAAGAGAGAGTCCAATTCTCAA<br>AGCCAATAGGCAGTAGCGAAAGCTGCAAGAGAATGAAAATCCGTTGACCTTAAACGGTCGTGTG<br>GGTTCAAGTCCCTCCACCCCACGCCGGAAACGCAATAGCCGAAAACAAAAACAAAAAAAAAC<br>AAAAAAAAAACCAAAAAAACAAAACACATTAAAACAGCCTGTGGGTTGATCCCACCCACAGGCC<br>CATTGGGCGCTAGCACTCTGGTATCACGGTACCTTTGTGCGCCTGTTTTATACCCCTCCCCCAAC<br>TGTAACTTAGAAGTAACACACCGATCAACAGTCAGCGTGGCACACCAGCCACGTTTTGATCAA<br>GCACTTCTGTTACCCCGGACTGAGTATCAATAGACTGCTCACGCGGTTGAAGGAGAAAGCGTTCG<br>TTATCCGGCCAACTACTTCGAAAAACCTAGTAACACCGTGGAAGTTGCAGAGTGTTTCGCTCAGC<br>ACTACCCCAGTGTAGATCAGGTCGATGAGTCACCGCATTCCCACGGGCGACCGTGGCGGTGGCT<br>GCGTTGGCGGCCTGCCCATGGGGAAACCCATGGGACGCTCTAATACAGACATGGTGCGAAGAGT<br>CTATTGAGCTAGTTGGTAGTCCTCCGGCCCCTGAATGCGGCTAATCCTAACTGCGGAGCACACAC<br>CCTCAAGCCAGAGGGCAGTGTGTCGTAACGGGCAACTCTGCAGCGGAACCGACTACTTTGGGTGT<br>CCGTGTTTCATTTTATTCCTATACTGGCTGCTTATGGTGACAATTGAGAGATCGTTACCATATAGC<br>TATTGGATTGGCCATCCGGTGACTAATAGAGCTATTATATATCCCTTTGTTGGGTTTATACCACTT<br>AGCTTGAAAGAGGTTAAAACATTACAATTCATTGTTAAGTTGAATACAGCAAAATGGGAGTCAA<br>AGTTCTGTTTGCCCTGATCTGCATCGCTGTGGCCGAGGCCAAGCCCACCGAGAACAACGAAGACT<br>TCAACATCGTGGCCGTGGCCAGCAACTTCGCGACCACGGATCTCGATCTGACCGCGGGAAGTTG<br>CCCGGCAAGAAGCTGCCGCTGGAGGTGCTCAAAGAGATGGAAGCCAATGCCCGGAAAGCTGGCT<br>GCACCAGGGGCTGTCTGATCTGCCTGTCCCACATCAAGTGCACGCCCAAGATGAAGAAGTTCATC<br>CCAGGACGCTGCCACACCTACGAAGGCGACAAAGAGTCCGCACAGGGCGGCATAGGCGAGGCG<br>ATCGTCGACATTCCTGAGATTCCTGGGTTCAAGGACTTGGAGCCCATGGAGCAGTTCATCGCACA<br>GGTCGATCTGTGTGTGGACTGCACAACTGGCTGCCTCAAAGGGCTTGCCAACGTGCAGTGTTCTG<br>ACCTGCTCAAGAAGTGGCTGCCGCAACGCTGTGCGACCTTTGCCAGCAAGATCCAGGGCCAGGT<br>GGACAAGATCAAGGGGCCGGTGGTGACTAAAAAAACAAAAACAAAACGGCTATTATGCGTT<br>ACCGGCGAGACGCTACGGACTTAAATAATTGAGCCTTAAAGAAGAAATTCTTTAAGTGGATGCTC<br>TCAAACTCAGGGAAACCTAAATCTAGTTATAGACAAGGCAATCCTGAGCCAAGCCGAAGTAGTA<br>ATTAGTAAGACCAGTGGACAATCGACGGATAACAGCATATCTAG |

TABLE 1-continued

| SEQ ID NO. 32 | Unmodified Linear GLuc (Full) | GGGAGACCCTCGAATGGGAGTCAAAGTTCTGTTTGCCCTGATCTGCATCGCTGTGGCCGAGGCCA<br>AGCCCACCGAGAACAACGAAGACTTCAACATCGTGGCCGTGGCCAGCAACTTCGCGACCACGGA<br>TCTCGATGCTGACCGCGGGAAGTTGCCCGGCAAGAAGCTGCCGCTGGAGGTGCTCAAAGAGATG<br>GAAGCCAATGCCCGGAAAGCTGGCTGCACCAGGGGCTGTCTGATCTGCCTGTCCCACATCAAGTG<br>CACGCCCAAGATGAAGAAGTTCATCCCAGGACGCTGCCACACCTACGAAGGCGACAAAGAGTCC<br>GCACAGGGCGGCATAGGCGAGGCGATCGTCGACATTCCTGAGATTCCTGGGTTCAAGGACTTGG<br>AGCCCATGGAGCAGTTCATCGCACAGGTCGATCTGTGTGTGGACTGCACAACTGGCTGCCTCAAA<br>GGGCTTGCCAACGTGCAGTGTTCTGACCTGCTCAAGAAGTGGCTGCCGCAACGCTGTGCGACCTT<br>TGCCAGCAAGATCCAGGGCAGGTGGACAAGATCAAGGGGGCCGGTGGTGACTAATCTAG |
| --- | --- | --- |
| SEQ ID NO. 35 | HCV | gccagcccctgatgggggcgacactccaccatgaatcactcccctgtgaggaactactgtcttc<br>acgcagaaaagcgtctagccatggcgttagtatgagtgtcgtgcagcctccaggaccccccctccc<br>gggagagccatagtggtctgcggaaccggtgagtacaccggaattgccaggacgaccgggtcctt<br>tcttggataaacccgctcaatgcctggagatttgggcgtgccccgcaagactgctagccgag |
| SEQ ID NO. 36 | EMCV | cccccctctccctccccccctaacgttactggccgaagccgcttggaataaggccggtgtgcgtt<br>tgtctatatgttattttccaccatattgccgtcttttggcaatgtgagggcccggaaacctggcc<br>ctgtcttcttgacgagcattcctaggggtctttcccctctcgccaaaggaatgcaaggtctgttg<br>aatgtcgtgaaggaagcagttcctctggaagcttcttgaagacaaacaacgtctgtagcgaccct<br>ttgc |
| SEQ ID NO. 37 | NRF | CAGAGTAATGACATGGTTCCTTCCATCCTCCAAAGGTGACCAATAATAGTTTGTAAGTATCATTA<br>TGAACTAATGAATTTTCAACATATTTGATATATTTCAATCCATTGCCATCATTGTTCTTATCGATAT<br>TTGAGTTGGCTCACTTTGCCAGTAAGAGTCTATTCAAATTGGCTTCTGAGTCCATTTGACACAACA<br>CCT |
| SEQ ID NO. 38 | CRPV | AAAGCAAAAATGTGATCTTGCTTGTAAATACAATTTTGAGAGGTTAATAAATTACAAGTAGTGCT<br>ATTTTTGTATTTAGGTTAGCTATTTAGCTTTACGTTCCAGGATGCCTAGTGGCAGCCCCACAATAT<br>CCAGGAAGCCCTCTCTGCGGTTTTTCAGATTAGGTAGTCGAAAAACCTAAGAAATTTACCTGCTA<br>CAT |
| SEQ ID NO. 39 | GTX | TTCTGACATCCGGCGGGTATTTCAGAACCGGCGGGTAGTACTGTACCGGCGGGTTTCTGACATCC<br>GGCGGGTTACAGTCATCCGGCGGGTTACTACAGTCCGGCGGGTTACTCAGAACCGGCGGGTTAG<br>AATTCCTCCGGCGGGTGACTCACAACCCCAGAAACAGAGCC |
| SEQ ID NO. 40 | Rbm3 | TTTATAATTTCTTCTTCCAGAAGAATTTGTTGGTAAAGCCACC |
| SEQ ID NO. 41 | TMEV | CAATCTTTGATGTCGTCTGCGGTGAATACGCTAATCGTGTTTTCACCATCCTTGGCAAAGAGAAC<br>GGTCTCCTGACTGTTGAACAAGCCGTGCTTGGCTTGCCGGGTATGGATCCCATGGAGAAAGACAC<br>CTCCCCTGGATTGCCCTACACCCAACAAGGACTCAGACGAACTG |
| SEQ ID NO. 42 | PPV | CTAGGGCGCGCCAGTCCTCCAAACACTCAACACACAGACCCGGAGGCTGTCGCTTCAGGTGTGTC<br>ATCTATCACAGGTCCCATGTCGACATTTATGGCATCACCCACTGTTGAGGAACTTGCCGGAGACA<br>CATCAGATAGGTTGTTCCAGCTAATTGCAGGTAACTCATCCCTTATTACCCAGGAGTCAGCACGA<br>CT |
| SEQ ID NO. 43 | Ana1 5' | Gaaaccaactttattactatattccccacaa |
| SEQ ID NO. 44 | Ana2 5' (internal homology) | cgccggaaacgcaatagccgaaaaacaaaaaacaaaaaaA |
| SEQ ID NO. 45 | Ana2 3' (internal homology) | aaaaaacaaaaaacaaaacggctattatgcgttaccggcg |
| SEQ ID NO. 46 | Ana3 5' | cgccggaaacgcaatagccgaaaaacaaaaaacaaaaaaAacaaaaaaaaaaccaaaaaaacaaa<br>acaca |
| SEQ ID NO. 47 | Ana4 5' | cgccggaaacgcaatagccgaaaaacaaaaaacaaaaaaAaaaaaaaaaaaaaaaaaaaaaaaaa<br>aaaaa |
| SEQ ID NO. 48 | Ana5 5' (internal homology) | TGATCTGaaaccaactttattactatattccccacaA |
| SEQ ID NO. 49 | Ana6 5' (PolioV) | Gaaaccaactttattactatattcctcttaa |
| SEQ ID NO. 50 | Ana7 5' | Gaaaccaactttattactggcatatccgtccccacaa |
| SEQ ID NO. 51 | Ana pA 5' | aaaaaaaaaaaaaaaaaaaaaaaaaaaaaa |
| SEQ ID NO. 52 | Ana pA 3' | aaaaaaaaaaaaaaaaaaaaaaaaaaaaaa |

TABLE 1-continued

| SEQ ID NO. 53 | Ana pAC 5' | acaaaaaaaaaaccaaaaaaaacaaaacaca |
|---|---|---|
| SEQ ID NO. 54 | Ana pT 5' | tttttttttttttttttttttttttttttttt |
| SEQ ID NO. 55 | Ana pT 3' | tttttttttttttttttttttttttttttttt |
| SEQ ID NO. 56 | Ana pC 5' | cccccccccccccccccccccccccccccccc |
| SEQ ID NO. 57 | Ana pC 3' | cccccccccccccccccccccccccccccccc |
| SEQ ID NO. 58 | Ana pG 3' | gggggggggggggggggggggggggggggggg |
| SEQ ID NO. 59 | BG 5' | ACATTTGCTTCTGACACAACTGTGTTCACTAGCAACCTCAAACAGACACC |
| SEQ ID NO. 60 | BG 3' | gctcgctttcttgctgtccaatttctattaaaggttcctttgttccctaagtccaactactaaact<br>gggggatattatgaagggccttgagcatctggattctgcctaataaaaaacatttattttcattgc |
| SEQ ID NO. 61 (also known simply as '5' UTR') | 5' HHV | GGACAGATCGCCTGGAGACGCCATCCACGCTGTTTTGACCTCCATAGAAGACACCGGGACCGATC<br>CAGCCTCCGCGGCCGGGAACGGTGCATTGGAACGCGGATTCCCCGTGCCAAGAGTGACTCACCG<br>TCCTTGACACG |
| SEQ ID NO. 62 (also known simply as '3' UTR') | 3' HGH | CGGGTGGCATCCCTGTGACCCCTCCCCAGTGCCTCTCCTGGCCCTGGAAGTTGCCACTCCAGTGCC<br>CACCAGCCTTGTCCTAATAAAATTAAGTTGCATCAAGCT |
| SEQ ID NO. 63 | AL 5' | ctagcttttctcttctgtcaaccccacacgcctttggcaca |
| SEQ ID NO. 64 | AL 3' | CATCACATTTAAAAGCATCTCAGCCTACCATGAGAATAAGAGAAAGAAAATGAAGATCAAAAGC<br>TTATTCATCTGTTTTTCTTTTTCGTTGGTGTAAAGCCAACACCCTGTCTAAAAAACATAAATTTC<br>TTTAATCATTTTGCCTCTTTTCTCTGTGCTTCAATTAATAAAAAATGGAAAGAATCG |
| SEQ ID NO. 65 | Ana1 5' | ccgtcgattgtccactggtc |
| SEQ ID NO. 66 | Ana1 3' | gaccagtggacaatcgacgg |
| SEQ ID NO. 67 inherent | T4 5' | aatctgataaat |
| SEQ ID NO. 68 inherent | T4 3' | atttatcagatt |
| SEQ ID NO. 69 | T41 5' | agcctacgatcgggctaacagctcgaatctgataaat |
| SEQ ID NO. 70 | T41 3' | atttatcagattcgagctgttagcccgatcgtaggct |
| SEQ ID NO. 71 | T42 5' | GAatggaattggttctaca |
| SEQ ID NO. 72 | T42 3' | TGTAGGACTAATTCCATTT |
| SEQ ID NO. 73 Weak | T4 5' | ggttctaca |
| SEQ ID NO. 74 Weak | T4 3' | TGTAGGACT |
| SEQ ID NO. 75 | Ana2 5' | ggtaactgtccgtcgattgtccactggtc |
| SEQ ID NO. 76 | Ana2 3' | gaccagtggacaatcgacggacagttacc |

Wesselhoeft, R. A., et al., "RNA Circularization Diminishes Immunogenicity and Can Extend Translation Duration In Vivo," *Molecular Cell*, vol. 74, pages 508-520 (2019) is incorporated herein by reference in its entirety.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A vector for making circular RNA, comprising:
   a) at least one spacer sequence that increases splicing efficiency compared to a vector without the at least one spacer sequence,
   b) a 3' Group I self-splicing intron fragment containing a 3' splice site dinucleotide,
   c) an internal ribosome entry site (IRES),
   d) a protein coding region, and
   e) a 5' Group I self-splicing intron fragment containing a 5' splice site dinucleotide, wherein the vector allows production of a circular RNA that is translatable or biologically active inside eukaryotic cells.

2. The vector of claim 1, wherein the 3' Group I intron fragment and the 5' Group I intron fragment are from a *Cyanobacterium Anabeana* sp. pre-tRNA-Leu gene or a T4 phage Td gene.

3. The vector of claim 1, further comprising an RNA polymerase promoter positioned at the 5' end of the vector.

4. The vector of claim 3, wherein the RNA polymerase promoter is an RNA polymerase promoter from a T7 virus, T6 virus, SP6 virus, T3 virus, or T4 virus.

5. The vector of claim 1, comprising the following elements operably connected to each other and arranged in the following sequence:
   a) the 3' Group I self-splicing intron fragment containing the 3' splice site dinucleotide,
   b) the at least one spacer sequence, wherein the at least one spacer sequence is a 5' spacer sequence,
   c) the IRES,
   d) the protein coding region, and
   e) the 5' Group I self-splicing intron fragment containing the 5' splice site dinucleotide.

6. The vector of claim 5, further comprising a 5' internal homology region positioned between (a) and (b) and a 3' internal homology region positioned between (d) and (e).

7. The vector of claim 1, comprising the following elements operably connected to each other and arranged in the following sequence:
   a) the 3' Group I self-splicing intron fragment containing the 3' splice site dinucleotide,
   b) the IRES,
   c) the protein coding region,
   d) the at least one spacer sequence, wherein the at least one spacer sequence is a 3' spacer sequence, and
   e) the 5' Group I self-splicing intron fragment containing the 5' splice site dinucleotide.

8. The vector of claim 7, further comprising a 5' internal homology region positioned between (a) and (b) and a 3' internal homology region positioned between (d) and (e).

9. The vector of claim 1, comprising the following elements operably connected to each other and arranged in the following sequence:
   a) the 3' Group I self-splicing intron fragment containing the 3' splice site dinucleotide,
   b) the at least one spacer sequence, wherein the at least one spacer sequence is a 5' spacer sequence
   c) the IRES,
   d) the protein coding region,
   e) a 3' spacer sequence that increases splicing efficiency compared to a vector without the 3' spacer sequence, and
   f) the 5' Group I self-splicing intron fragment containing the 3' splice site dinucleotide.

10. The vector of claim 9, further comprising a 5' internal homology region positioned between (a) and (b) and a 3' internal homology region positioned between (e) and (f).

11. The vector of claim 1, wherein the protein coding region encodes a human protein, a non-human protein, or a synthetic protein for therapeutic use.

12. The vector of claim 1, wherein the protein coding region encodes a chimeric antigen receptor (CAR).

13. The vector of claim 1, wherein the at least one spacer sequence is about 10-60 nucleotides in length.

14. The vector of claim 1, wherein the at least one spacer sequence comprises a polyA sequence or a polyA-C sequence.

15. The vector of claim 1, wherein the vector produces a circular RNA having a size of at least 500 nucleotides.

16. The vector of claim 1, wherein the at least one spacer sequence is designed using an RNA folding computer software.

17. The vector of claim 16, wherein RNA folding computer software is RNAFold software.

18. The vector of claim 1, wherein the at least one spacer sequence is at least 7 nucleotides in length.

19. The vector of claim 1, wherein the at least one spacer sequence is no more than 100 nucleotides in length.

* * * * *